United States Patent
McPhee et al.

(10) Patent No.: US 7,173,004 B2
(45) Date of Patent: Feb. 6, 2007

(54) MACROCYCLIC ISOQUINOLINE PEPTIDE INHIBITORS OF HEPATITIS C VIRUS

(75) Inventors: Fiona McPhee, Wallingford, CT (US); Jeffrey Allen Campbell, Glen Gardner, NJ (US); Stanley D'Andrea, Meriden, CT (US); Zhizhen Barbara Zheng, Cheshire, CT (US); Andrew Charles Good, Wallingford, CT (US); David J. Carini, Wallingford, CT (US); Barry L. Johnson, Wallingford, CT (US); Paul Michael Scola, Glastonbury, CT (US); Kenneth M. Boy, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 130 days.

(21) Appl. No.: 10/825,693

(22) Filed: Apr. 16, 2004

(65) Prior Publication Data

US 2005/0090432 A1  Apr. 28, 2005

Related U.S. Application Data

(60) Provisional application No. 60/463,423, filed on Apr. 16, 2003.

(51) Int. Cl.
*A61K 38/00* (2006.01)

(52) U.S. Cl. ..................................................... 514/10
(58) Field of Classification Search ............... None
See application file for complete search history.

(56) References Cited

U.S. PATENT DOCUMENTS

| | | | |
|---|---|---|---|
| 6,534,523 B1 | 3/2003 | Llinas-Brunet et al. | |
| 6,608,027 B1 | 8/2003 | Tsantrizos et al. | |
| 2004/0038872 A1 | 2/2004 | Campbell et al. | |

FOREIGN PATENT DOCUMENTS

WO    WO 00/59929    * 10/2000

OTHER PUBLICATIONS

Lauer, Georg M. et al., "Hepatitis C Virus Infection", New England Journal of Medicine, vol. 345, No. 1, pp. 41-52 (2001).
Poynard, Thierry et al., "Randomized trial of interferon α2b plus ribavirin for 48 weeks or for 24 weeks versus interferon α2b plus placebo for 48 weeks for treatment of chronic infection with hepatitis C virus", The Lancet, vol. 352, pp. 14226-1432, (1998).
Zeuzem, Stefan et al., "Peginterferon Alfa-2a in Patents with Chronic Hepatitis C", New England Journal of Medicine, vol. 343, pp. 1666-1672, (2000).

* cited by examiner

*Primary Examiner*—Bruce R. Campell
*Assistant Examiner*—Thomas S. Heard
(74) *Attorney, Agent, or Firm*—Pamela A. Mingo

(57) ABSTRACT

Macrocyclic isoquinoline peptides are disclosed having the general formula:
A compound of formula I:

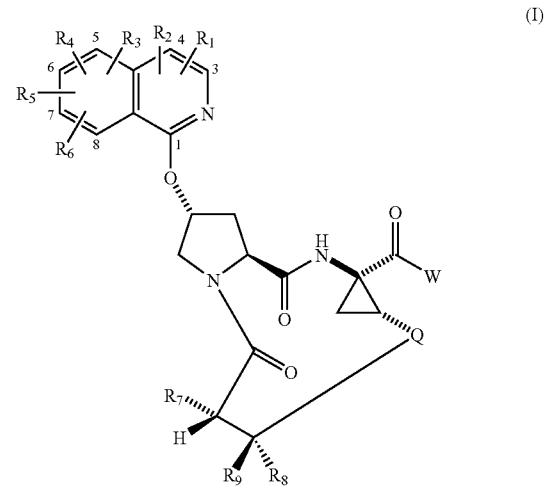

wherein $R_1$ to $R_9$, Q and W are described in the description. Compositions comprising the compounds and methods for using the compounds to inhibit HCV are also disclosed.

44 Claims, No Drawings

MACROCYCLIC ISOQUINOLINE PEPTIDE INHIBITORS OF HEPATITIS C VIRUS

CROSS REFERENCE TO RELATED APPLICATION

The non-provisional application claims priority from the provisional application U.S. Ser. No. 60/463,423 filed Apr. 16, 2003.

FIELD OF THE INVENTION

The present invention is generally directed to antiviral compounds, and more specifically directed to compounds which inhibit the functioning of the NS3 protease (also referred to herein as "serine protease") encoded by Hepatitis C virus (HCV), compositions comprising such compounds, and methods for inhibiting the functioning of the NS3 protease.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. (Lauer, G. M.; Walker, B. D. *N. Engl. J. Med.* (2001), 345, 41–52).

Presently, the most effective HCV therapy employs a combination of alpha-interferon and ribavirin, leading to sustained efficacy in 40% of patients. (Poynard, T. et al. *Lancet* (1998), 352, 1426–1432). Recent clinical results demonstrate that pegylated alpha-interferon is superior to unmodified alpha-interferon as monotherapy (Zeuzem, S. et al. *N. Engl. J. Med.* (2000), 343, 1666–1672). However, even with experimental therapeutic regimens involving combinations of pegylated alpha-interferon and ribavirin, a substantial fraction of patients do not have a sustained reduction in viral load. Thus, there is a clear and unmet medical need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. Complex formation between the NS3 protease domain and its cofactor, NS4A, is essential for efficient proteolytic cleavage of the four respective sites. The NS3 protein also exhibits nucleoside triphosphatase and RNA helicase activities. NS5B is a RNA-dependent RNA polymerase that is involved in the replication of HCV.

Among the compounds that have demonstrated efficacy in inhibiting HCV replication, as selective HCV serine protease inhibitors, are the macrocyclic peptide compounds disclosed in International Application PCT/CA00/00353 (Publication No. WO 00/59929).

SUMMARY OF THE INVENTION

The present invention provides macrocyclic isoquinoline compounds of the following formula:

A compound of formula I:

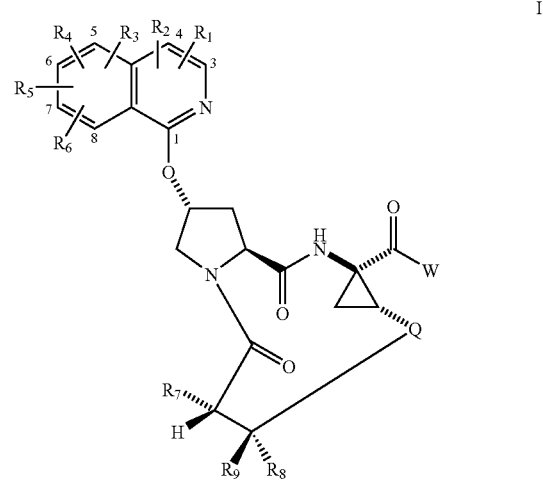

wherein:
(a) $R_1$, $R_2$, $R_3$, $R_4$, $R_5$ and $R_6$ are each independently H; $C_{1-6}$ alkyl; $C_{3-7}$ cycloalkyl; $C_{1-6}$ alkoxy; $C_{3-7}$ cycloalkoxy; halo-$C_{1-6}$ alkoxy; halo-$C_{1-6}$ alkyl; cyano; halo; hydroxyl; $C_{1-6}$ alkanoyl; nitro; amino; mono or di-$(C_{1-6})$ alkyl amine; mono or di-$(C_{3-7})$ cycloalkyl amine; mono or di-$C_{1-6}$ alkylamide; mono or di-$(C_{3-7})$ cycloalkyl amide; carboxyl; $(C_{1-6})$ carboxyester; thiol; $C_{1-6}$ thioalkyl; $C_{1-6}$ alkylsulfoxide; $C_{1-6}$ alkylsulfone; $C_{1-6}$ alkylsulfonamide; $C_{6-10}$ aryl optionally substituted with Het; $C_{7-14}$ alkylaryl; $C_{6-10}$ aryloxy; $C_{7-14}$ alkylaryloxy; 5–7 membered monocyclic heteroaryloxy; or Het; said $R_1$ to $R_6$ optionally attached to the isoquinoline group by a $C_{1-6}$ alkyl linking group;
(b) $R_7$ is $NH_2$ or $-NR_{10}R_{11}$; wherein $R_{10}$ is $C_{1-6}$ alkyl, $C_{1-6}$ haloalkyl, $C(O)-NR_{12}R_{13}$, $C(O)-OR_{14}$, $C(O)-SR_{15}$, or $-C(O)-R_{16}$; $R_{11}$ is H, $C_{1-6}$ alkyl or $C_{1-6}$ haloalkyl, provided that if either $R_{12}$ or $R_{13}$ is H then $R_{11}$ is H; $R_{12}$ and $R_{13}$ are each independently H; $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; or aryl; and wherein $R_{12}$ and $R_{13}$ together with the nitrogen to which they are bonded can form a 4–7 membered heterocycle; $R_{14}$ and $R_{15}$ are each independently $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; aryl or Het; $R_{16}$ is H; $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; aryl or Het;

(c) $R_8$ and $R_9$ are each independently H or $C_{1-3}$ alkyl optionally substituted with halo, or $C_{1-3}$ alkoxy, or $C_{1-3}$ haloalkoxy;

(d) Q is a $C_{3-9}$ saturated or unsaturated chain optionally containing one to three heteroatoms independently selected from O, $S(O)_m$; wherein m is 0, 1 or 2, or $NR_{17}$, wherein $R_{17}$ is H; $C_{1-6}$ alkyl or $C_{1-6}$ cycloalkyl, each optionally substituted with halo, $C_{1-6}$ alkoxy, cyano or $C_{1-6}$ haloalkoxy; —C(O)—$R_{18}$, C(O)—$OR_{19}$, C(O)—$NR_{20}R_{21}$ or —$SO_2R_{22}$; $R_{18}$, $R_{20}$, and $R_{21}$ are each independently H; $C_{1-6}$ alkyl or $C_{1-6}$ cycloalkyl, each optionally substituted with halo, $C_{1-6}$ alkoxy, cyano or $C_{1-6}$ haloalkoxy; $R_{19}$ is $C_{1-6}$ alkyl or $C_{1-6}$ cycloalkyl, each optionally substituted with halo, $C_{1-6}$ alkoxy, cyano or $C_{1-6}$ haloalkoxy; $R_{22}$ is aryl, $C_{1-6}$ alkyl or $C_{1-6}$ cycloalkyl, each optionally substituted with halo, $C_{1-6}$ alkoxy, cyano or $C_{1-6}$ haloalkoxy; and (e) W is OH, —NH—$SO_n$—$R_{23}$, or NH—$SO_n$—$R_{24}$; wherein n is 1 or 2, $R_{23}$ is $C_{1-8}$ alkyl, $C_{4-10}$ alkylcycloalkyl, unsubstituted $C_{3-7}$ cycloalkyl, or cyclopropyl or cyclobutyl optionally substituted with $C_{7-9}$ alkylaryl or $C_{1-4}$ alkyl optionally substituted with halo, $C_{1-3}$ alkoxy, cyano, amine, mono or di-$C_{1-6}$ alkylamine, mono or di-$C_{1-6}$ alkylamide or carboxylate; and $R_{24}$ is $C_{6-10}$ aryl or Het;

or a pharmaceutically acceptable enantiomer, diastereomer, salt, solvate or prodrug thereof.

The present invention also provides compositions comprising the compounds or pharmaceutically acceptable salts, solvates or prodrugs thereof and a pharmaceutically acceptable carrier. In particular, the present invention provides pharmaceutical compositions useful for inhibiting HCV NS3 protease comprising a therapeutically effective amount of a compound of the present invention, or a pharmaceutically acceptable salt, solvate or prodrug thereof, and a pharmaceutically acceptable carrier.

The present invention further provides methods for treating patients infected with HCV, comprising administering to the patient a therapeutically effective amount of a compound of the present invention, or a pharmaceutically acceptable salt, solvate or prodrug thereof. Additionally, the present invention provides methods of inhibiting HCV NS3 protease by contacting the NS3 protease with a compound of the present invention.

By virtue of the present invention, it is now possible to provide improved drugs comprising the compounds of the invention which can be effective in the treatment of patients infected with HCV. Specifically, the present invention provides peptide compounds that can inhibit the functioning of the NS3 protease, e.g., in combination with the NS4A protease. Further, the present invention makes it possible to administer combination therapy to a patient whereby a compound in accordance with the present invention, which is effective to inhibit the HCV NS3 protease, can be administered with another compound having anti-HCV activity, e.g., a compound which is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection.

DETAILED DESCRIPTION OF THE INVENTION

Stereochemical definitions and conventions used herein generally follow McGraw-Hill Dictionary of Chemical Terms, S. P. Parker, Ed., McGraw-Hill Book Company, New York (1984) and Stereochemistry of Organic Compounds, Eliel, E. and Wilen, S., John Wiley & Sons, Inc., New York (1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory and (+) or d, meaning the compound, is dextrorotatory. For a given chemical structure, these compounds, called stereoisomers, are identical except that they are mirror images of one another. A specific stereoisomer of a mirror image pair may also be referred to as an enantiomer, and a mixture of such isomers is often called an enantiomeric mixture. With reference to the instances where (R) or (S) is used, it is to designate the absolute configuration of a substituent in context to the whole compound and not in context to the substituent alone.

Unless otherwise specifically noted herein, the terms set forth below will have the following definitions.

The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical composition, but differ with regard to the arrangement of the atoms or groups in space.

The term "diastereomer" refers to a stereoisomer which is not an enantiomer, e.g., a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

The term "enantiomers" refers to two stereoisomers of a compound which are non-superimposable mirror images of one another.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "compounds of the invention", and equivalent expressions, are meant to embrace compounds of formula I, and pharmaceutically acceptable enantiomer, diastereomer salts, and solvates, e.g. hydrates and prodrugs. Similarly, references to intermediates, are meant to embrace their salts, and solvates, where the context so permits. References to the compound of the invention also include the preferred compounds, e.g. formula II and A–M.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like.

The term "prodrug" as used herein means derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner with a functional group of the compounds such as with an amino, hydroxy or carboxy group when present. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine.

The term "patient" includes both human and other mammals.

The term "pharmaceutical composition" means a composition comprising a compound of the invention in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, e.g., the compounds and their enantiomers, diastereomers, salts, solvates or prodrugs, and/or dosage forms which are, within the scope of sound medical judgment, suitable for use in contact with the tissues of patients for treatment without excessive toxicity, irritation, allergic response, or other problem or complication commensurate with a reasonable risk/benefit ratio.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

The term "substituted" as used herein includes substitution at from one to the maximum number of possible binding sites on the core, e.g., organic radical, to which the subsitutent is bonded, e.g., mono-, di-, tri- or tetra-substituted, unless otherwise specifically stated.

The nomenclature used to describe organic radicals, e.g., hydrocarbons and substituted hydrocarbons, generally follows standard nomenclature known in the art, unless otherwise specifically defined. Combinations of groups, e.g., alkylalkoxyamine or arylalkyl, include all possible stable configurations, unless otherwise specifically stated. Thus, an alkylaryl substituent can be bonded to a core segment by either the alkyl portion or the aryl portion of the alkylaryl substituent, provided the resulting compound is stable. Certain radicals and combinations are defined below for purposes of illustration.

The term "halo" as used herein means a halogen substituent selected from bromo, chloro, fluoro or iodo. The term "haloalkyl" means an alkyl group that in substituted with one or more halo substituents.

The term "alkyl" as used herein means acyclic, straight or branched chain hydrocarbon substituents having the specified number of carbon atoms and includes, for example, methyl, ethyl, propyl, butyl, tert-butyl, hexyl, 1-methylethyl, 1-methylpropyl, 2-methypropyl, 1,1-dimethylethyl. Thus, $C_{1-6}$ alkyl refers to an alkyl group having from one to six carbon atoms. The term "lower alkyl" means an alkyl group having from one to six, preferably from one to four carbon atoms. The term "alkylester" means an alkyl group additionally containing on ester group. Generally, a stated carbon number range, e.g., $C_{2-6}$ alkylester, includes all of the carbon atoms in the radical.

The term "alkenyl" as used herein means an alkyl radical containing at least one double bond, e.g., ethenyl (vinyl) and alkyl.

The term "alkoxy" as used herein means an alkyl group with the indicated number of carbon atoms attached to an oxygen atom. Alkoxy includes, for example, methoxy, ethoxy, propoxy, 1-methylethoxy, butoxy and 1,1-dimethylethoxy. The latter radical is referred to in the art as tert-butoxy. The term "alkoxycarbonyl" means an alkoxy group additionally containing a carbonyl group.

The term "cycloalkyl" as used herein means a cyclic hydrocarbon substituent containing the indicated number of carbon atoms and includes, for example, cyclopropyl, cyclobutyl, cyclopentyl, cyclohexyl, cycloheptyl and spiro cyclic groups such as spirocyclopropyl and spirocyclobutyl. The term "cycloalkoxy" as used herein means a cycloalkyl group linked to an oxygen atom, such as, for example, cyclobutyloxy or cyclopropyloxy. The term "alkylcycloalkyl" means a cycloalkyl group linked to an alkyl group. The stated carbon number range includes the total number of carbons in the radical, unless otherwise spec fically stated. Thus a $C_{4-10}$ alkylcycloalkyl may contain from 1–7 carbon atoms in the alkyl group and from 3–9 carbon atoms in the ring, e.g., cyclopropylmethyl or cyclohexylethyl.

The term "aryl" as used herein means an aromatic moiety containing the indicated number of carbon atoms, such as, but not limited to phenyl, indanyl or naphthyl. For example, $C_{6-10}$ aryl refers to an aromatic moiety having from six to ten carbon atoms which may be in the form of a monocyclic or bicyclic structure. The term "haloaryl" as used herein refers to an aryl mono, di or tri substituted with one or more halogen atoms. The terms "alkylaryl", "arylalkyl" and "aralkyl" mean an aryl group substituted with one or more alkyl groups. Unless the carbon range of each group is specified, the stated range applies to the entire substituent. Thus, a $C_{7-14}$ alkylaryl group many have from 1–8 carbon atoms in the alkyl group for a monocyclic aromatic and from 1–4 carbon atoms in the alkyl group for a fused aromatic. The attachment of the group to bonding site on the molecule can be either at the aryl group or the alkyl group. Unless a specific aryl radical is specified, e.g., fluoro-phenyl, or the radical is stated to be unsubstituted, the aryl radicals, e.g., in an aryl substituent or an alkylaryl substituent, include those substituted with typical substituents known to those skilled in the art, e.g., halogen, hydroxy, carboxy, carbonyl, nitro, sulfo, amino, cyano, dialkylamino haloalkyl, $CF_3$, haloalkoxy, thioalkyl, alkanoyl, SH, alkylamino, alkylamide, dialkylamide, carboxyester, alkylsulfone, alkylsulfonamide and alkyl(alkoxy)amine. Examples of alkylaryl groups include benzyl, butylphenyl and 1-naphthylmethyl.

The term "alkanoyl" as used herein means straight or branched 1-oxoalkyl radicals containing the indicated number of carbon atoms and includes, for example, formyl, acetyl, 1-oxopropyl (propionyl), 2-methyl-1-oxopropyl, 1-oxohexyl and the like.

The term "alkylamide" as used herein means an amide mono-substituted with an alkyl, such as

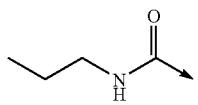

The term "heterocycle", also referred to as "Het", as used herein means 7–12 membered bicyclic heterocycles and 4–7 membered monocyclic heterocycles.

Preferred bicyclic heterocycles are 7–12 membered fused bicyclic ring systems (both rings share an adjacent pair of atoms) containing from one to four heteroatoms selected from nitrogen, oxygen and sulfur, wherein both rings of the heterocycle are fully unsaturated. The nitrogen and sulfur heteroatoms atoms may be optionally oxidized. The bicyclic heterocycle may contain the heteroatoms in one or both rings. Unless a specific heterocycle is specified, e.g., a fluorinated 7–12 membered bicyclic heterocycle, or the heterocycle is stated to be unsubstituted, the heterocycles include those substituted with typical substituents known to those skilled in the art. For example, the bicyclic heterocycle may also contain substituents on any of the ring carbon atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfonamide, $C_{1-6}$ alkylsulfoxide, di ($C_{1-6}$) alkyl(alkoxy)amine, $C_{6-10}$ aryl, $C_{7-14}$ alkylaryl, and a 4–7 membered monocyclic heterocycle. When two substituents are attached to vicinal carbon atoms of the bicyclic heterocycle, they can join to form a ring, e.g., a five, six or seven membered ring system containing up to two heteroatoms selecting from oxygen and nitrogen. The bicyclic heterocycle may be attached to the molecule, e.g. $R_1$ in formula I, at any atom in the ring and preferably carbon.

Examples of bicyclic heterocycles include, but are not limited to, the following ring systems:

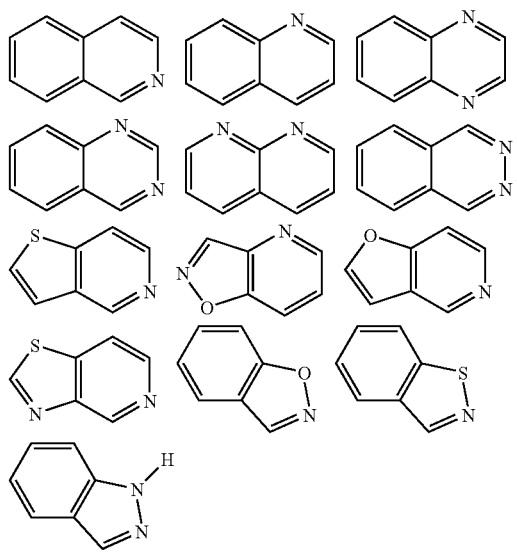

Preferred monocyclic heterocycles are 4–7 membered saturated, partially saturated or fully unsaturated ring system (this latter subset also herein referred to as unsaturated heteroaromatic) containing in the ring from one to four heteroatoms selected from nitrogen, oxygen and sulfur, wherein the sulfur and nitrogen heteroatoms may be optionally oxidized. Unless a specific heterocycle is specified, e.g., a $C_{1-6}$ alkoxy substituted 4–7 membered monocyclic heterocycle, or the heterocycle is stated to be unsubstituted, the heterocycles include those substituted with typical substituents known to those skilled in the art. For example, the monocyclic heterocycle may also contain substituents on any of the ring atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfoxide, $C_{1-6}$ alkylsulfonamide, di ($C_{1-6}$) alkyl(alkoxy)amine, $C_{6-10}$ aryl, $C_{7-14}$ alkylaryl and an additional 4–7 membered monocyclic heterocycle. The monocyclic heterocycle may be attached to the molecule, e.g. $R_1$ in formula I, at any atom in the ring.

Examples of monocyclic heterocycles include, but are not limited to, the following (and their tautomers):

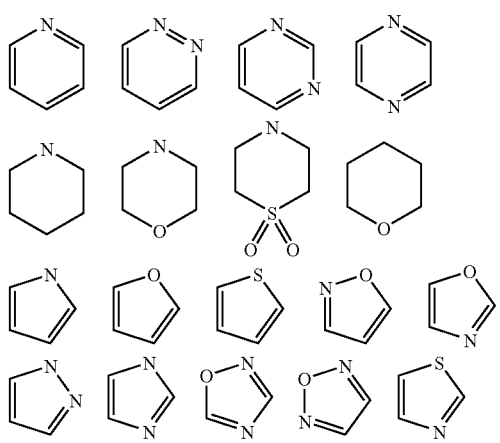

-continued

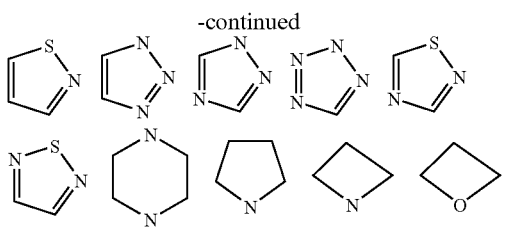

Those skilled in the art will recognize that the heterocycles used in the compounds of the present invention should be stable. Generally, stable compounds are those which can be synthesized, isolated and formulated using techniques known the those skilled in the art without degradation of the compound.

The term "substituent" with reference to an amino acid or amino acid derivative means a radical derived from the corresponding α-amino acid. For instance, the substituents methyl, iso-propyl, and phenyl represent the amino acids alanine, valine, and phenyl glycine, respectively.

Where used in naming compounds of the present invention, the designations "P1', P1, P2, P3 and P4", as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend towards the C-terminus. For example, P1' refers to the first position away from the right hand end of the C-terminus of the cleavage site (ie. N-terminus first position); whereas P1 starts the numbering from the left hand side of the C-terminus cleavage site, P2: second position from the C-terminus, etc.)[see Berger A. & Schechter I., Transactions of the Royal Society London series (1970), B257, 249–264].

In accordance with the present invention, there are provided compounds of formula I:

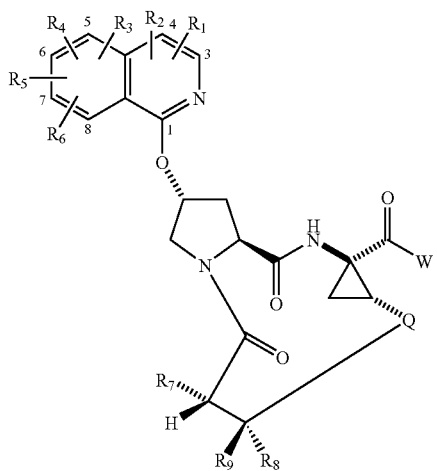

I wherein:
(a) $R_1$, $R_2$, $R_3$, $R_4$, $R_5$ and $R_6$ are each independently H; $C_{1-6}$ alkyl; $C_{3-7}$ cycloalkyl; $C_{1-6}$ alkoxy; $C_{3-7}$ cycloalkoxy; halo-$C_{1-6}$ alkoxy; halo-$C_{1-6}$ alkyl; cyano; halo; hydroxyl; $C_{1-6}$ alkanoyl; nitro; amino; mono or di-($C_{1-6}$) alkyl amine; mono or di-($C_{3-7}$) cycloalkyl amine; mono or di-$C_{1-6}$ alkylamide; mono or di-($C_{3-7}$) cycloalkyl amide; carboxyl; ($C_{1-6}$) carboxyester; thiol; $C_{1-6}$ thioalkyl; $C_{1-6}$ alkylsulfoxide; $C_{1-6}$ alkylsulfone; $C_{1-6}$ alkyl sulfonamide; $C_{6-10}$ aryl optionally substituted with Ret; $C_{7-14}$ alkylaryl; $C_{6-10}$ aryloxy; $C_{7-14}$ alkylaryloxy; 4–7 membered monocyclic heteroaryloxy; or Het; said $R_1$ to $R_6$ optionally attached to the isoquinoline group by a $C_{1-6}$ alkyl linking group;

(b) $R_7$ is $NH_2$ or —$NR_{10}R_{11}$; wherein $R_{10}$ is $C_{1-6}$ alkyl, $C_{1-6}$ haloalkyl, C(O)—$NR_{12}R_{13}$, C(O)—$OR_{14}$, C(O)—$SR_{15}$, or —C(O)—$R_{16}$; $R_{11}$ is H, $C_{1-6}$ alkyl or $C_{1-6}$ haloalkyl, provided that if either $R_{12}$ or $R_{13}$ is H then $R_{11}$ is H; $R_{12}$ and $R_{13}$ are each independently H; $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; or aryl; and wherein $R_{12}$ and $R_{13}$ together with the nitrogen to which they are bonded can form a 4–7 membered heterocycle; $R_{14}$ and $R_{15}$ are each independently $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; aryl or Het; $R_{16}$ is H; $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; aryl or Het;

(c) $R_8$ and $R_9$ are each independently H or $C_{1-3}$ alkyl optionally substituted with halo, or $C_{1-3}$ alkoxy, or $C_{1-3}$ haloalkoxy;

(d) Q is a $C_{3-9}$ saturated or unsaturated chain optionally containing one to three heteroatoms independently selected from O, S(O)$_m$; wherein m is 0, 1 or 2, or $NR_{17}$, wherein $R_{17}$ is H; $C_{1-6}$ alkyl or $C_{1-6}$ cycloalkyl, each optionally substituted with halo, $C_{1-6}$ alkoxy, cyano or $C_{1-6}$ haloalkoxy; —C(O)—$R_{18}$, C(O)—$OR_{19}$, C(O)—$NR_{20}R_{21}$ or —$SO_2R_{22}$; $R_{18}$, $R_{20}$, and $R_{21}$ are each independently H; $C_{1-6}$ alkyl or $C_{1-6}$ cycloalkyl, each optionally substituted with halo, $C_{1-6}$ alkoxy, cyano or $C_{1-6}$ haloalkoxy; $R_{19}$ is $C_{1-6}$ alkyl or $C_{1-6}$ cycloalkyl, each optionally substituted with halo, $C_{1-6}$ alkoxy, cyano or $C_{1-6}$ haloalkoxy; $R_{22}$ is aryl, $C_{1-6}$ alkyl or $C_{1-6}$ cycloalkyl, each optionally substituted with halo, $C_{1-6}$ alkoxy, cyano or $C_{1-6}$ haloalkoxy; and (e) W is OH, —NH—SO$_n$—$R_{23}$, or NH—SO$_n$—$R_{24}$; wherein n is 1 or 2, $R_{23}$ is $C_{1-8}$ alkyl, $C_{4-10}$ alkylcycloalkyl, unsubstituted $C_{3-7}$ cycloalkyl, or cyclopropyl or cyclobutyl optionally substituted with $C_{7-9}$ alkylaryl or $C_{1-4}$ alkyl optionally substituted with halo, $C_{1-3}$ alkoxy, cyano, amine, mono or di-$C_{1-6}$ alkylamine, mono or di-$C_{1-6}$ alkylamide or carboxylate; and $R_{24}$ is $C_{6-10}$ aryl or Het;

or a pharmaceutically acceptable enantiomer, diastereomer, salt, solvate or prodrug thereof.

Preferably, $R_1$ is bonded to the $C_3$ position and is selected from H; $C_{1-6}$ alkyl; $C_{3-7}$ cycloalkyl; $C_{1-6}$ alkoxy; $C_{3-7}$ cycloalkoxy; halo-$C_{1-6}$ alkoxy; halo-$C_{1-6}$ alkyl; cyano; halo; $C_{1-6}$ alkanoyl; mono or di-($C_{1-6}$) alkyl amine; mono or di-$C_{1-6}$ alkylamide; carboxyl; $C_{6-10}$ aryl optionally substituted with Het; $C_{7-14}$ alkylaryl; $C_{6-10}$ aryloxy or Het. Preferably, $R_2$, $R_3$, and $R_4$ are bonded to the $C_4$, $C_5$ and $C_6$ positions, respectively, and are each independently selected from H; $C_{1-6}$ alkyl; $C_{3-7}$ cycloalkyl; $C_{1-6}$ alkoxy; $C_{3-7}$ cycloalkoxy; halo-$C_{1-6}$ alkoxy; halo-$C_{1-6}$ alkyl; cyano; halo; hydroxyl; $C_{1-6}$ alkanoyl; mono or di-($C_{1-6}$) alkyl amine; mono or di-($C_{3-7}$) cycloalkyl amine; mono or di-$C_{1-6}$ alkylamide; mono or di-($C_{3-7}$) cycloalkyl amide; carboxyl; $C_{6-10}$ aryl optionally substituted with Het; $C_{7-14}$ alkylaryl; $C_{6-10}$ aryloxy; or Het. Preferably, $R_5$ and $R_6$ are bonded to the $C_7$ and $C_8$ positions, respectively, and are each independently selected from H; $C_{1-3}$ alkyl; $C_{3-4}$ cycloalkyl; $C_{1-3}$ alkoxy; $C_{3-4}$ cycloalkoxy; halo-$C_{1-3}$ alkoxy; halo-$C_{1-3}$ alkyl; cyano; halo; hydroxyl; $C_{1-3}$ alkanoyl; mono or di-($C_{1-3}$) alkyl amine; mono or di-($C_{3-4}$) cycloalkyl amine; mono or di-$C_{1-3}$ alkylamide; mono or di-($C_{3-4}$) cycloalkyl amide; or carboxyl. If desired, one or more of the $R_1$ $R_2$, $R_3$, $R_4$, $R_5$ and $R_6$ substituents can be attached to the isoquinoline group by a $C_{1-6}$ alkyl linking group, e.g., a methylene group.

Preferably, Q is a $C_{3-9}$ saturated or unsaturated chain optionally containing one to three heteroatoms independently selected from O, $S(O)_m$; wherein m is 0, 1 or 2, or $NR_{17}$, wherein $R_{17}$ is H; $C_{1-6}$ alkyl, $C_{1-6}$ cycloalkyl, —C(O)—$R_{18}$, C(O)—$OR_{19}$, C(O)—$NR_{20}R_{21}$ or —$SO_2R_{22}$. Preferably, $R_{18}$, $R_{20}$, and $R_{21}$ are each independently H; $C_{1-6}$ alkyl or $C_{1-6}$ cycloalkyl; $R_{19}$ is $C_{1-6}$ alkyl or $C_{1-6}$ cycloalkyl; and $R_{22}$ is aryl, $C_{1-6}$ alkyl or $C_{1-6}$ cycloalkyl, each optionally substituted with halo.

Preferably, W is OH, —NH—$SO_n$—$R_{23}$, or NH—SO—$R_{24}$ wherein n is 1 or 2, $R_{23}$ is unsubstituted $C_{3-7}$ cycloalkyl, cyclopropyl, or cyclobutyl optionally substituted with $C_{7-9}$ alkylaryl or $C_{1-4}$ alkyl; and $R_{24}$ is $C_{6-10}$ aryl or Het.

In accordance with one aspect of the present invention, there are provided compounds of formula II:

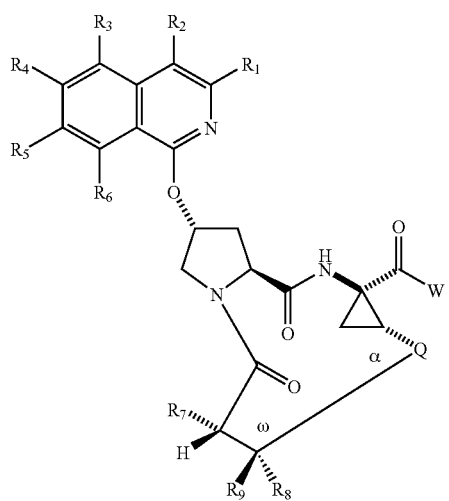

wherein:
(a) $R_1$ is H; $C_{1-6}$ alkyl; $C_{3-7}$ cycloalkyl; $C_{1-6}$ alkoxy; $C_{3-7}$ cycloalkoxy; halo-$C_{1-6}$ alkoxy; halo-$C_{1-6}$ alkyl; cyano; halo; $C_{1-6}$ alkanoyl; mono or di-($C_{1-6}$) alkyl amine; mono or di-$C_{1-6}$ alkylamide; carboxyl; $C_{6-10}$ aryl optionally substituted with Het; $C_{7-14}$ alkylaryl; $C_{6-10}$ aryloxy or Het; said $R_1$ optionally attached to the isoquinoline group by a $C_{1-6}$ alkyl linking group; $R_2$, $R_3$, and $R_4$ are each independently H; $C_{1-6}$ alkyl; $C_{3-7}$ cycloalkyl; $C_{1-6}$ alkoxy; $C_{3-7}$ cycloalkoxy; halo-$C_{1-6}$ alkoxy; halo-$C_{1-6}$ alkyl; cyano; halo; hydroxyl; $C_{1-6}$ alkanoyl; mono or di-($C_{1-6}$) alkyl amine; mono or di-($C_{3-7}$) cycloalkyl amine; mono or di-$C_{1-6}$ alkylamide; mono or di-($C_{3-7}$) cycloalkyl amide; carboxyl; $C_{6-10}$ aryl optionally substituted with Het; $C_{7-14}$ alkylaryl; $C_{6-10}$ aryloxy; or Het; said $R_2$ to $R_4$ optionally attached to the isoquinoline group by a $C_{1-3}$ alkyl linking group; $R_5$ and $R_6$ are each independently H; $C_{1-3}$ alkyl; $C_{3-4}$ cycloalkyl; $C_{1-3}$ alkoxy; $C_{3-4}$ cycloalkoxy; halo-$C_{1-3}$ alkoxy; halo-$C_{1-3}$ alkyl; cyano; halo; hydroxyl; $C_{1-3}$ alkanoyl; mono or di-($C_{1-3}$) alkyl amine; mono or di-($C_{3-4}$) cycloalkyl amine; mono or di-$C_{1-3}$ alkylamide; mono or di-($C_{3-4}$) cycloalkyl amide; or carboxyl;

(b) $R_7$ is $NH_2$ or —$NR_{10}R_{11}$; wherein $R_{10}$ is $C_{1-6}$ alkyl, $C_{1-6}$ haloalkyl, C(O)—$NR_{12}R_{13}$, C(O)—$OR_{14}$, or —C(O)—$R_{16}$; $R_{11}$ is H, $C_{1-6}$ alkyl or $C_{1-6}$ haloalkyl, provided that if either $R_{12}$ or $R_{13}$ is H then $R_{11}$ is H; $R_{12}$ and $R_{13}$ are each independently H; $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; and wherein $R_{12}$ and $R_{13}$ together with the nitrogen to which they are bonded can form a 4–7 membered heterocycle; $R_{14}$ and $R_{15}$ are each independently $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; $R_{16}$ is H; $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; aryl or Het;

(c) $R_8$ and $R_9$ are each independently H or $C_{1-3}$ alkyl optionally substituted with halo, or $C_{1-3}$ alkoxy, or $C_{1-3}$ haloalkoxy;

(d) Q is a $C_{3-9}$ saturated or unsaturated chain optionally containing one to three heteroatoms independently selected from O, $S(O)_m$; wherein m is 0, 1 or 2, or $NR_{17}$, wherein $R_{17}$ is H; $C_{1-6}$ alkyl, $C_{1-6}$ cycloalkyl, —C(O)—$R_{18}$, C(O)—$OR_{19}$, C(O)—$NR_{20}R_{21}$ or —$SO_2R_{22}$; $R_{18}$, $R_{20}$, and $R_{21}$ are each independently H; $C_{1-6}$ alkyl or $C_{1-6}$ cycloalkyl; $R_{19}$ is $C_{1-6}$ alkyl or $C_{1-6}$ cycloalkyl; $R_{22}$ is aryl, $C_{1-6}$ alkyl or $C_{1-6}$ cycloalkyl, each optionally substituted with halo; and (e) W is OH, —NH—$SO_n$—$R_{23}$ or NH—$SO_n$—$R_{24}$, wherein n is 1 or 2, $R_{23}$ is unsubstituted $C_{3-7}$ cycloalkyl, or cyclopropyl or cyclobutyl optionally substituted with $C_{7-9}$ alkylaryl or $C_{1-4}$ alkyl; and $R_{24}$ is $C_{6-10}$ aryl or Het;

or a pharmaceutically acceptable enantiomer, diastereomer, salt, solvate or prodrug thereof.

Preferably, $R_1$ is H; $C_{1-3}$ alkoxy; mono or di-($C_{1-6}$) alkyl amine; a 5 or 6 membered monocyclic heterocycle; or $C_{6-10}$ aryl optionally substituted with a 5 or 6 membered monocyclic heterocycle. Preferably, $R_2$, $R_3$, $R_4$ and $R_5$ are each independently H; $C_{1-6}$ alkoxy; halo-$C_{1-6}$ alkoxy; hydroxyl; or mono or di-($C_{1-6}$) alkyl amine.

Preferably, $R_7$ is $NH_2$ or —$NHR_{10}$; wherein $R_{10}$ is C(O)—$NR_{12}R_{13}$, or C(O)—$OR_{14}$; and $R_{12}$ and $R_{13}$ are $C_{1-6}$ alkyl optionally substituted with halo; and $R_{14}$ is $C_{1-6}$ alkyl or $C_{3-7}$ cycloalkyl optionally substituted with halo.

Preferably, Q is a $C_{5-7}$ membered chain having one double bond optionally containing one heteroatom independently selected from O, $S(O)_m$; wherein m is 0, 1 or 2, or $NR_{17}$, wherein $R_{17}$ is H; $C_{1-6}$ alkyl or $C_{1-6}$ cycloalkyl. In a preferred aspect of the invention, Q has the following structure:

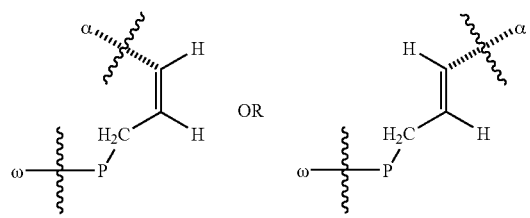

wherein P is a C₃ saturated chain optionally containing one heteroatom independently selected from O, S(O)$_m$; wherein m is 0, 1 or 2, or NR$_{17}$ (as defined in the compound of Formula II).

In one aspect of the invention, W is preferably —NH—SO$_n$—R$_{23}$, wherein n is 1 or 2 and R$_{23}$ is unsubstituted C$_{3-7}$ cycloalkyl, or cyclopropyl or cyclobutyl optionally substituted with C$_{7-9}$ alkylaryl or C$_{1-4}$ alkyl. In another aspect of the invention, W is NH—SO$_n$—R$_{24}$, wherein n is 1 or 2 and R$_{24}$ is Het.

Preferably, when R$_{24}$ is Het, the Het is selected from the group consisting of:

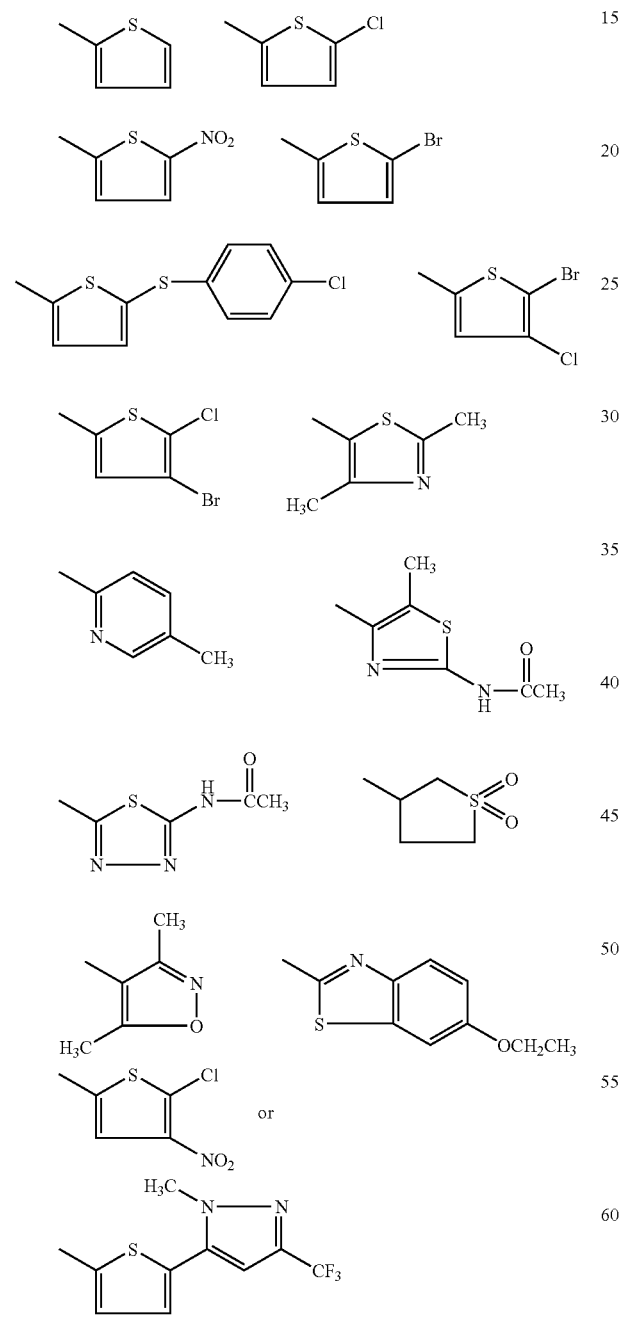

In accordance with another aspect of the present invention, there are provided compounds of formula III:

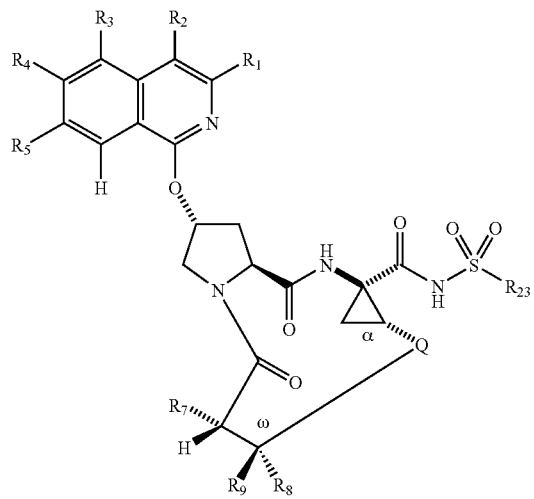

wherein:

(a) R$_1$ is H; C$_{1-3}$ alkoxy; di-(C$_{1-6}$) alkyl amine; a 5 or 6 membered monocyclic heterocycle; or C$_{6-10}$ aryl optionally substituted with a 5 or 6 membered monocyclic heterocycle;

R$_2$, R$_3$, R$_4$ and R$_5$ are each independently H; C$_{1-3}$ alkoxy; halo; or di-(C$_{1-6}$) alkyl amine;

(b) R$_7$ is —NHR$_{10}$; wherein R$_{10}$ is C(O)—NHR$_{13}$, or C(O)—OR$_{14}$; R$_{13}$ and R$_{14}$ are C$_{1-6}$ alkyl;

(c) Q is a C$_{5-7}$ membered chain having one double bond optionally containing one heteroatom independently selected from O, S(O)$_m$; wherein m is 0, 1 or 2, or NR$_{17}$, wherein R$_{17}$ is H; C$_{1-6}$ alkyl or C$_{1-6}$ cycloalkyl; and (d) R$_{23}$ is unsubstituted C$_{3-7}$ cycloalkyl, or cyclopropyl or cyclobutyl optionally substituted with C$_{7-9}$ alkylaryl or C$_{1-4}$ alkyl;

or a pharmaceutically acceptable enantiomer, diastereomer, salt, solvate or prodrug thereof.

Preferably, R$_1$ is selected from the group consisting of pyridine, pyrrolidine, morpholine, piperazine, oxazole, isoxazole, thiazole, imidazole, pyrrole and pyrazole. In one preferred aspect, R$_1$ is phenyl optionally substituted with one or more members selected from the group consisting of selected from the group consisting of C$_{1-3}$ alkoxy, halo, carboxyl, di-(C$_{1-3}$) alkyl amine, C$_{1-3}$ haloalkyl, trifluoromethyl, trifluoromethoxy and hydroxy. In another preferred aspect, R$_1$ is di-(C$_{1-3}$) alkyl amine. In another preferred aspect, R$_1$ is piperazine substituted with one or more members selected from the group consisting of C$_{1-3}$ alkyl, C$_{5-7}$ cycloalkyl or pyridine. Preferably, R$_2$ is chloro or fluoro. In one preferred aspect, R$_2$ is di-(C$_{1-3}$) alkyl amine or methoxy.

In one preferred aspect, Q has a structure selected from the following:

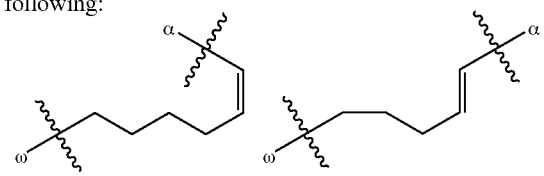

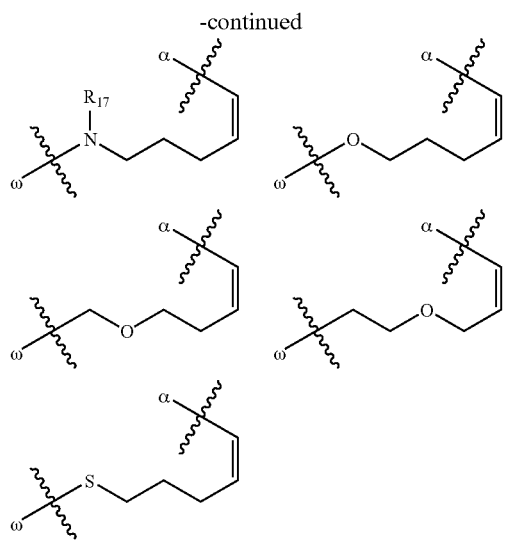
In another preferred aspect, Q has a structure selected from the following:
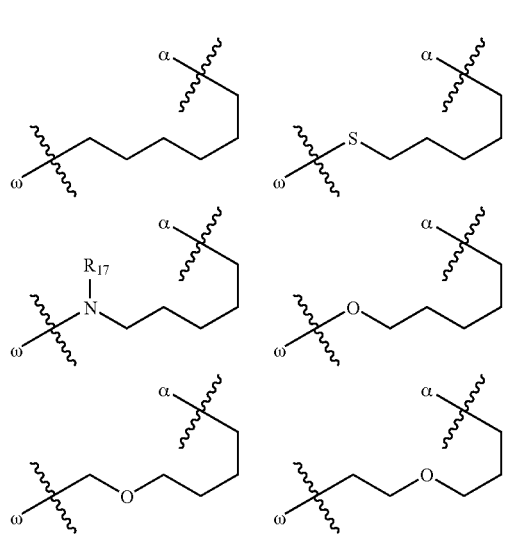
Examples of preferred compounds in accordance with the invention are selected from the group consisting of
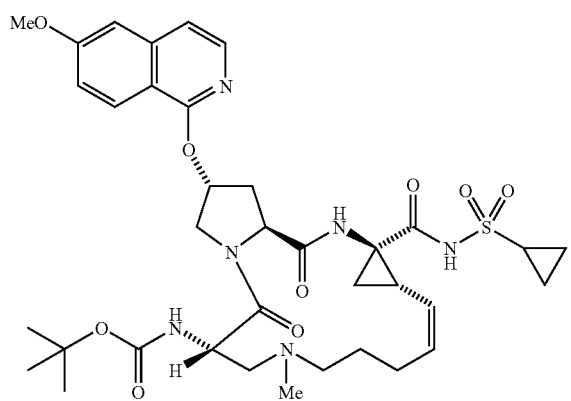
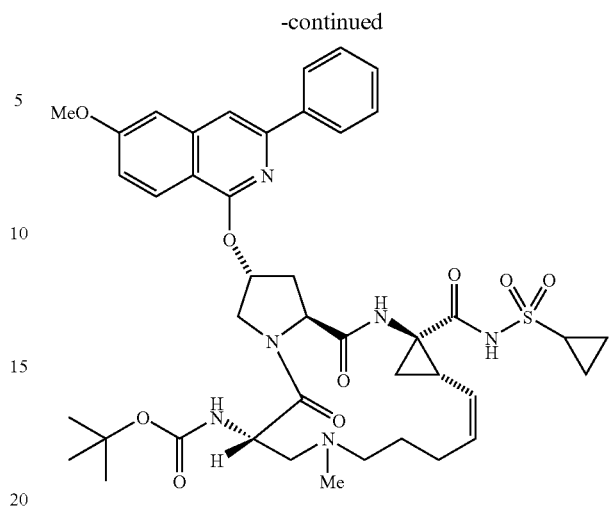
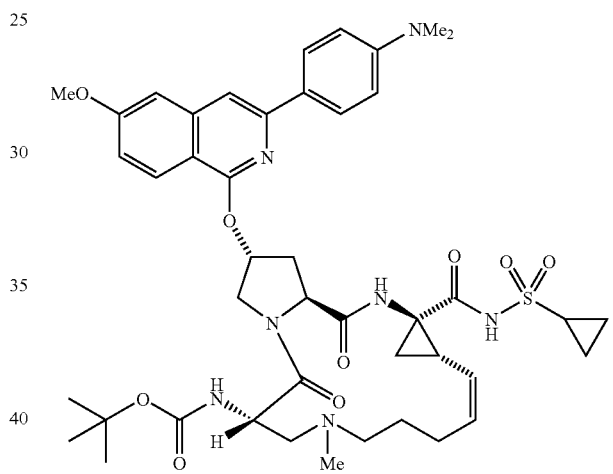
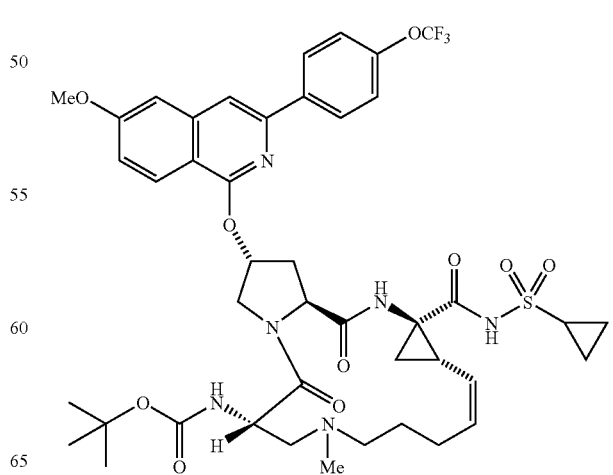

-continued
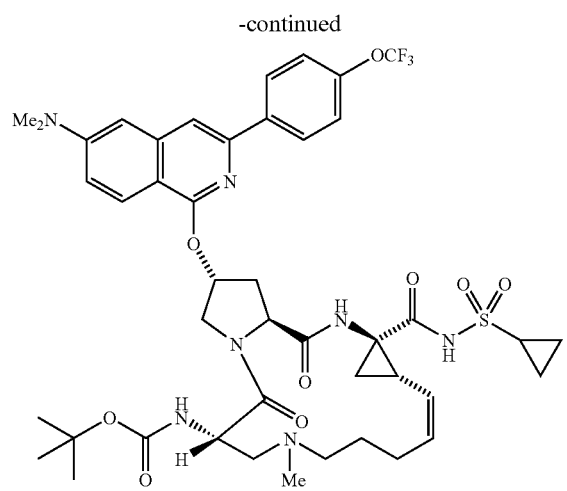
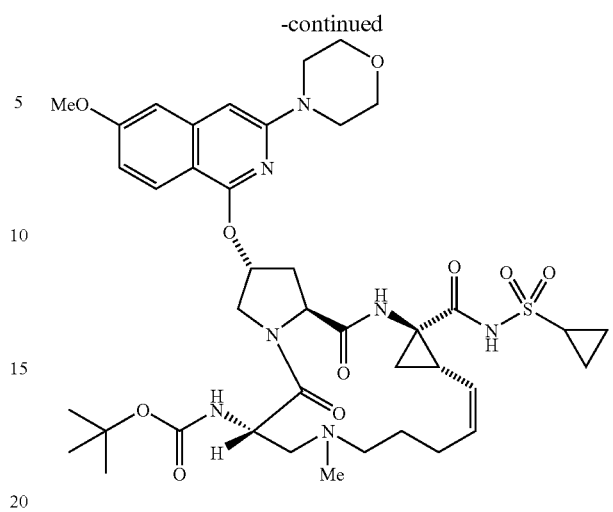
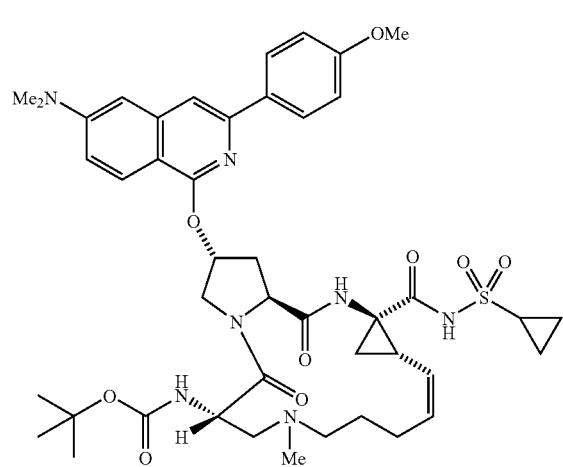
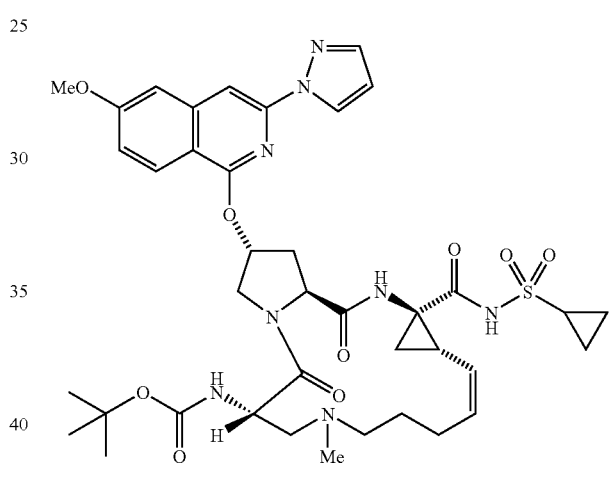
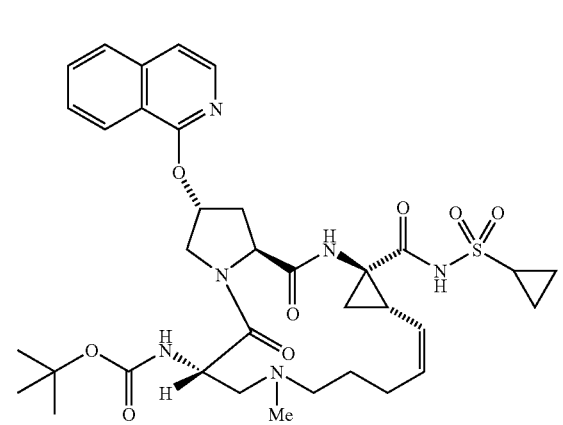
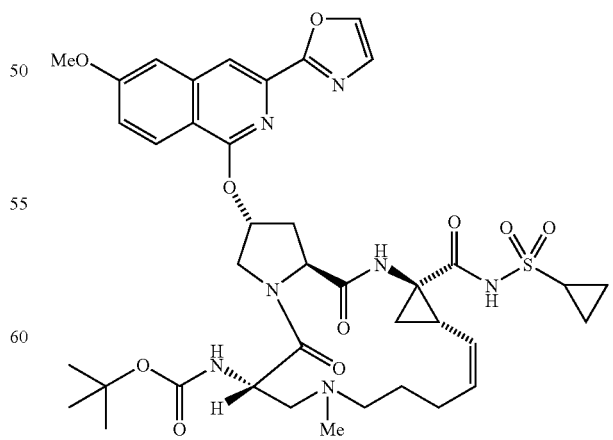

-continued
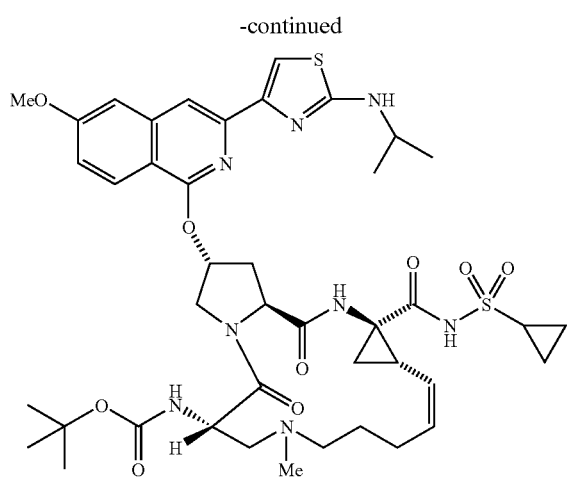
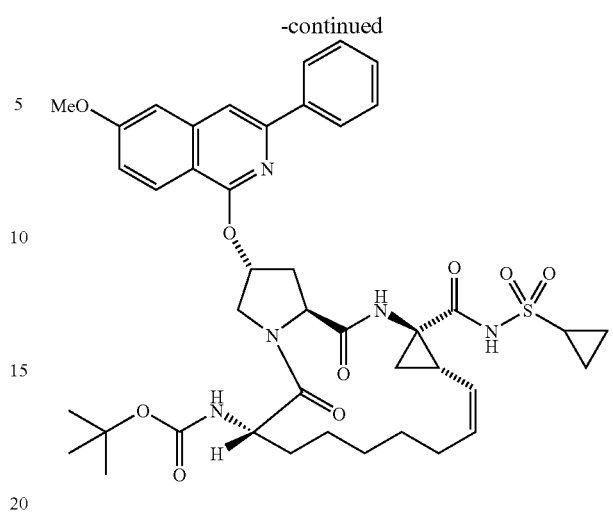
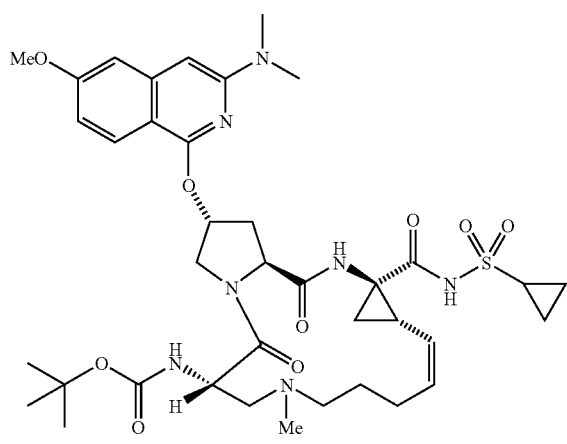
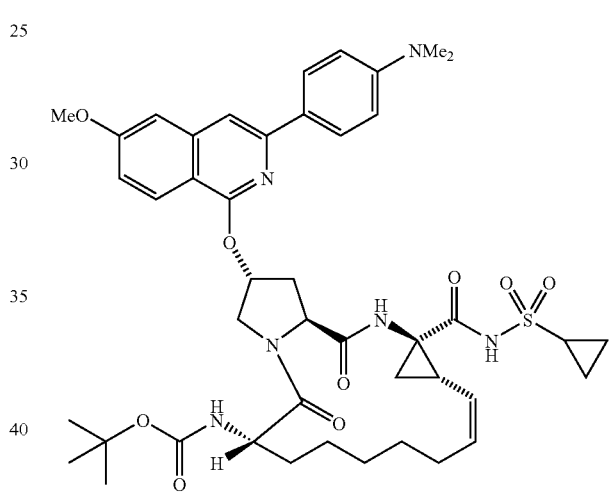
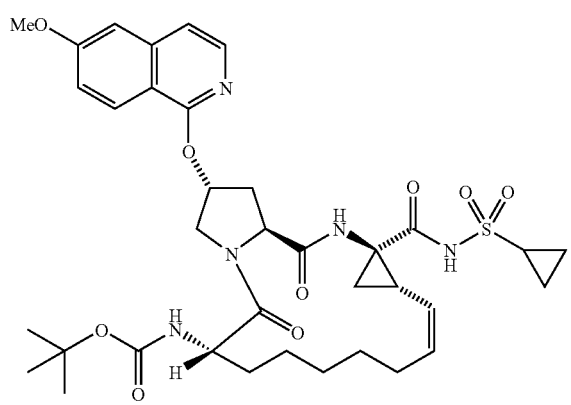
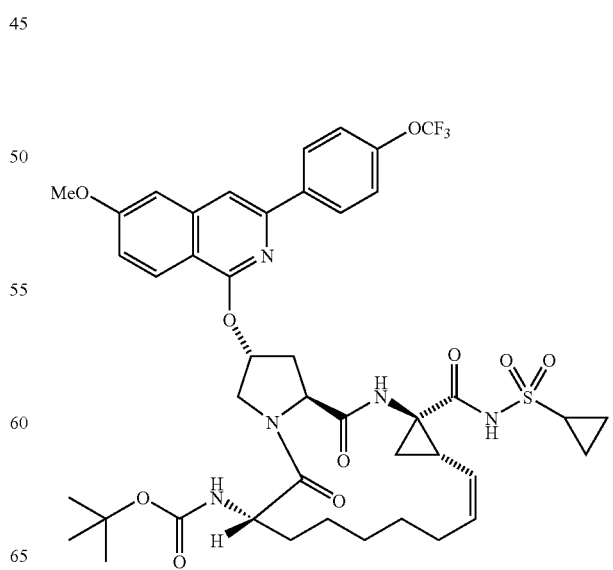

21
-continued
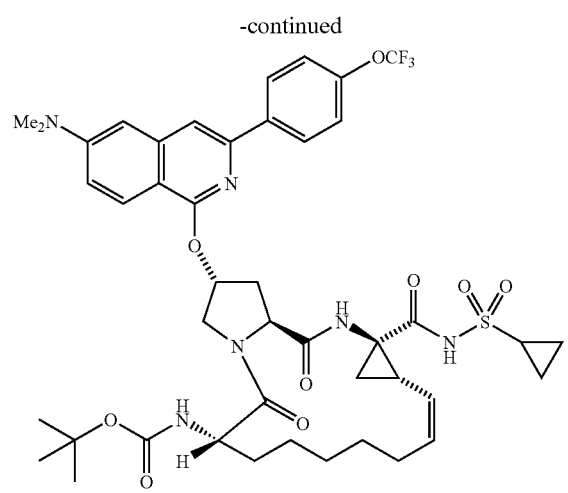
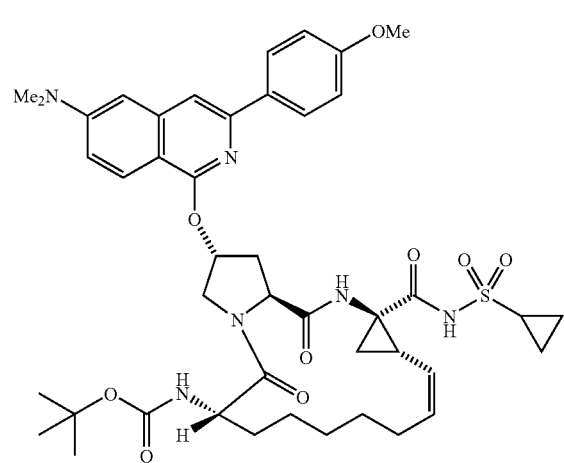
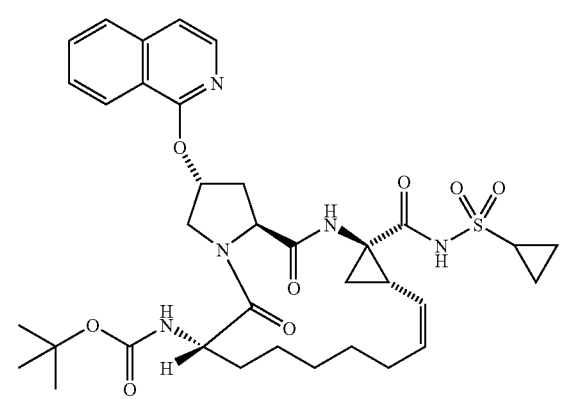
22
-continued
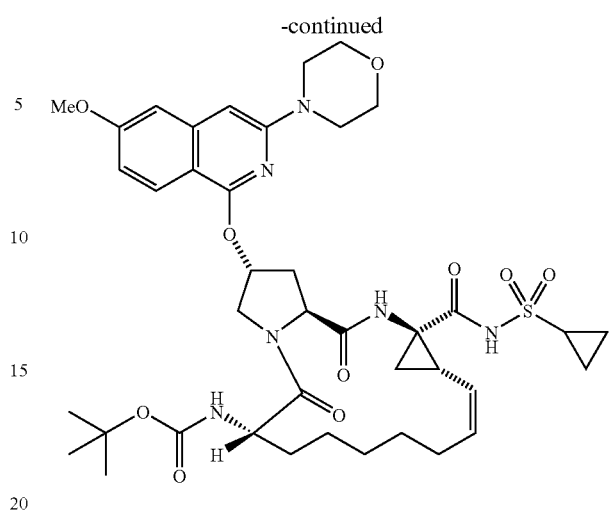
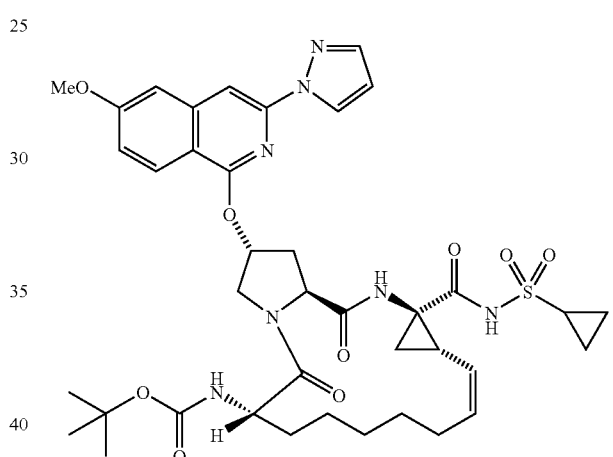
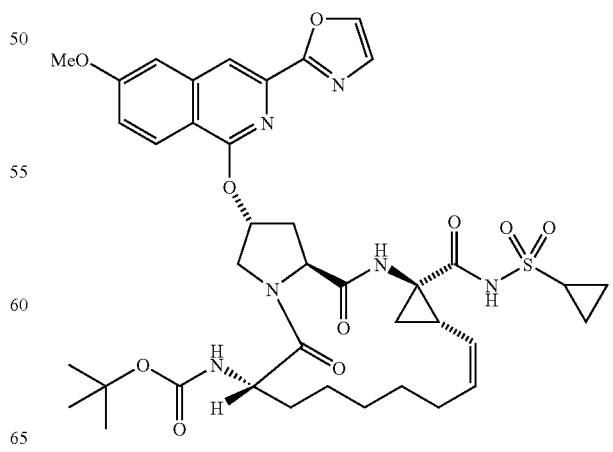

-continued
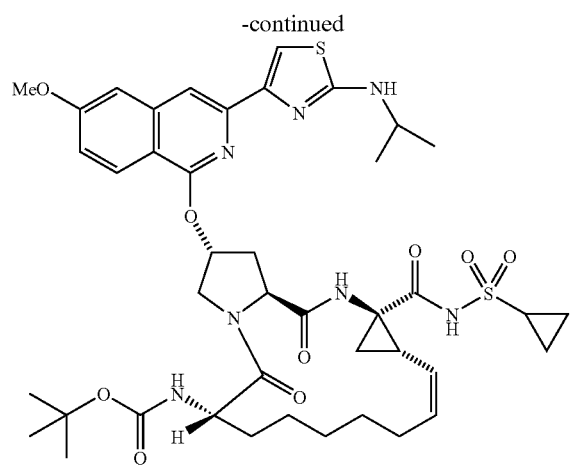
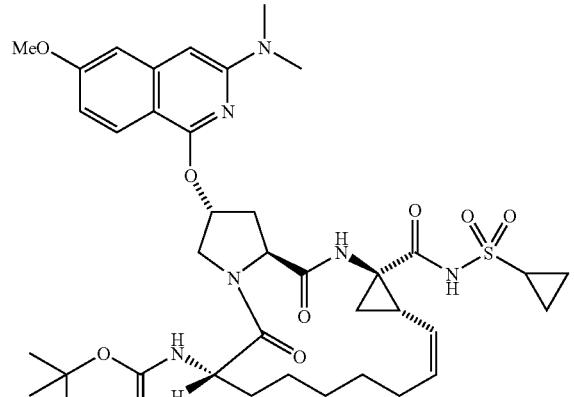
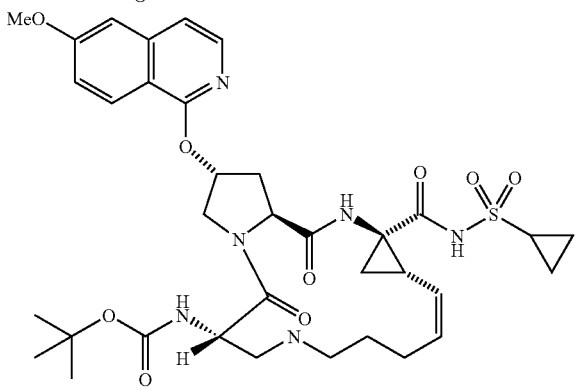
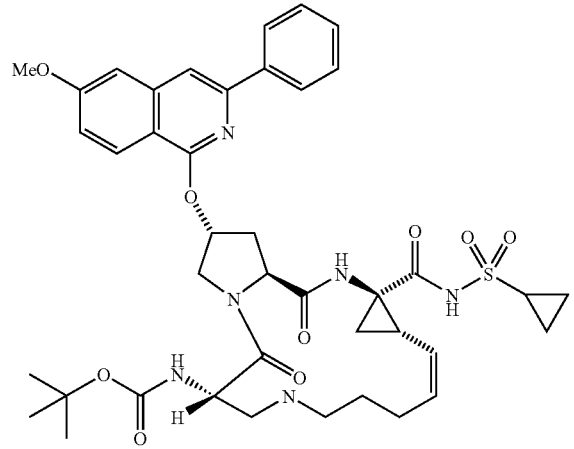
-continued
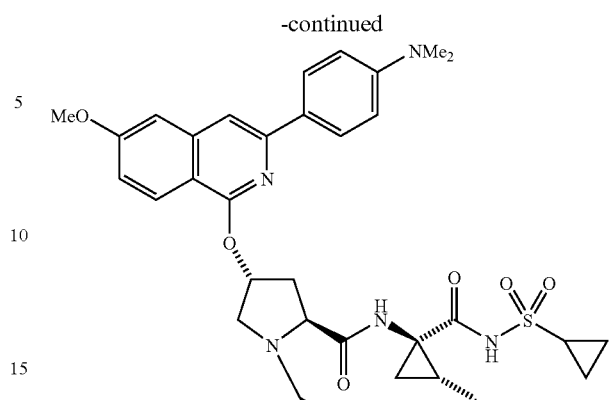
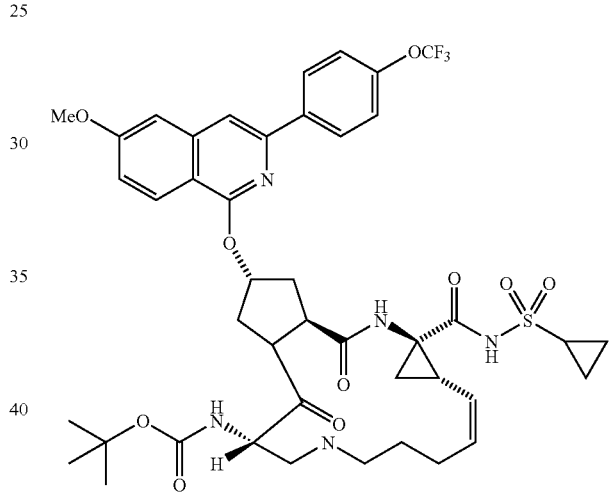
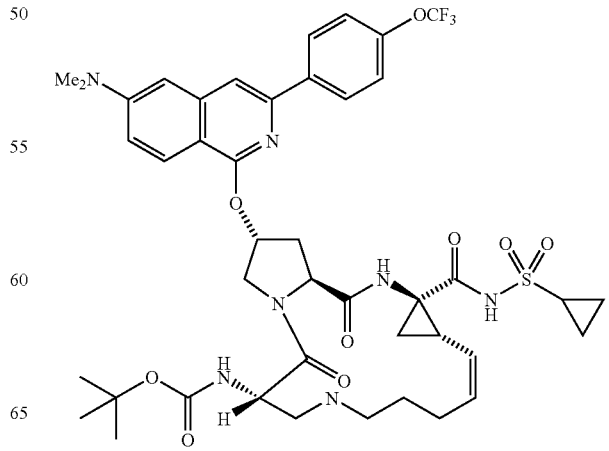

-continued
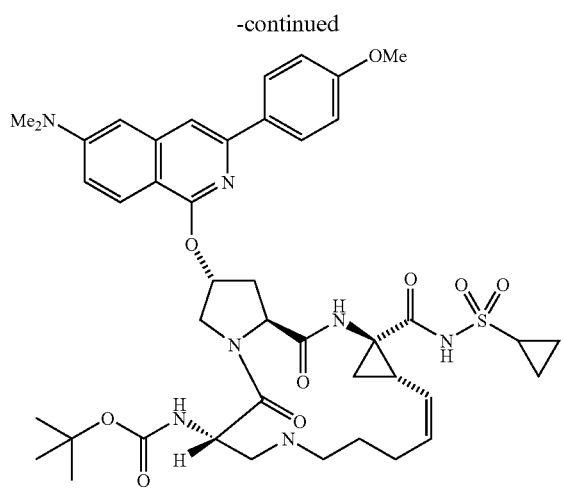
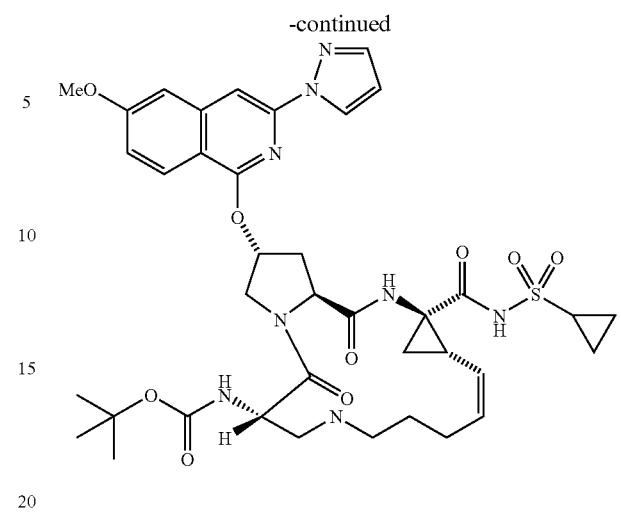
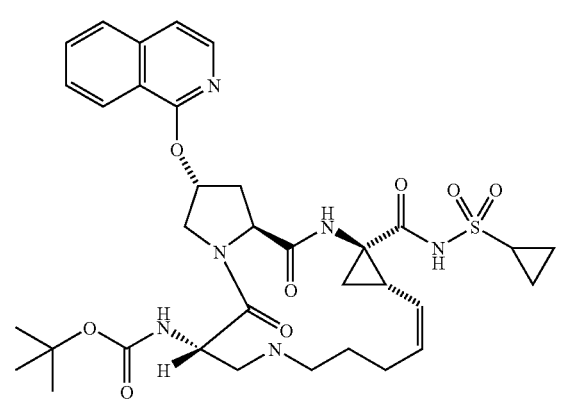
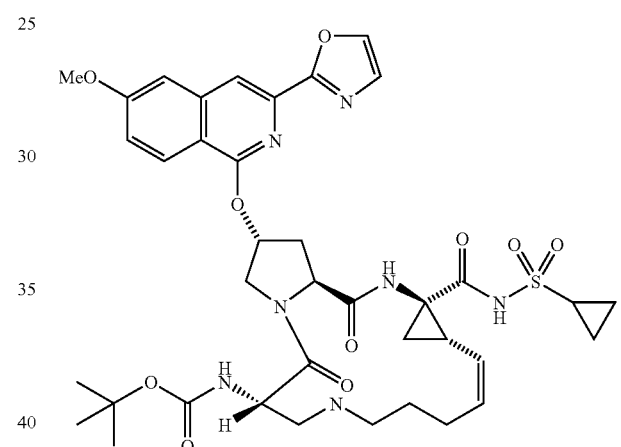
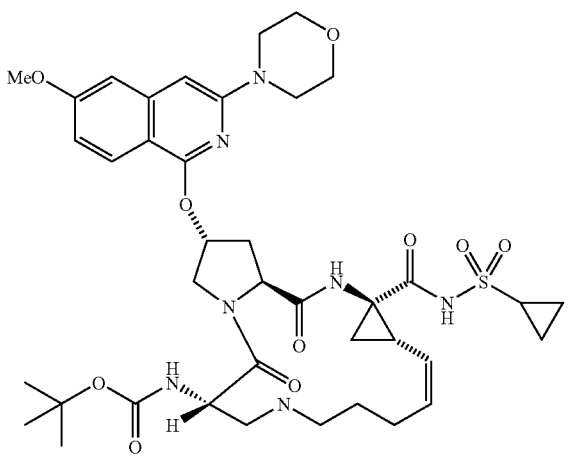
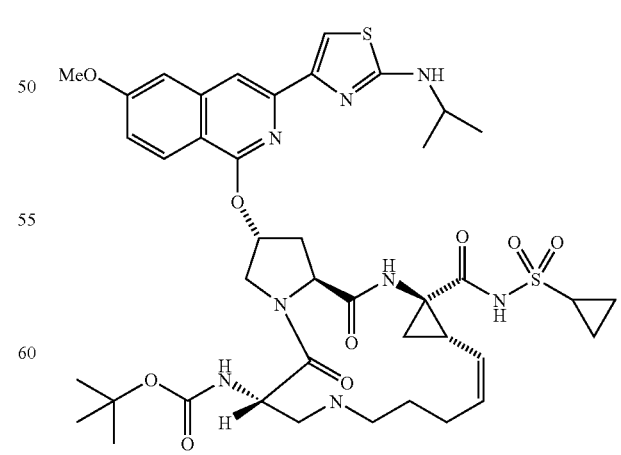

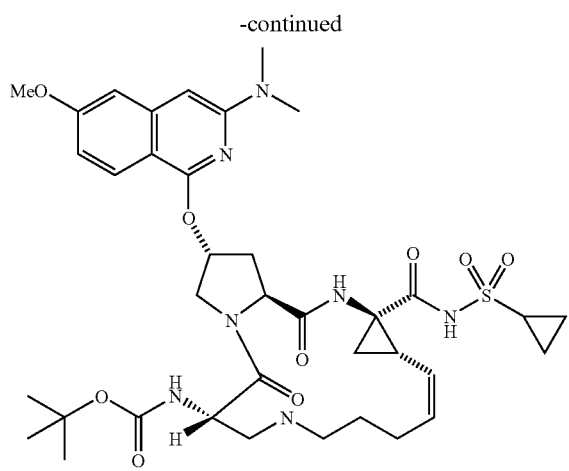
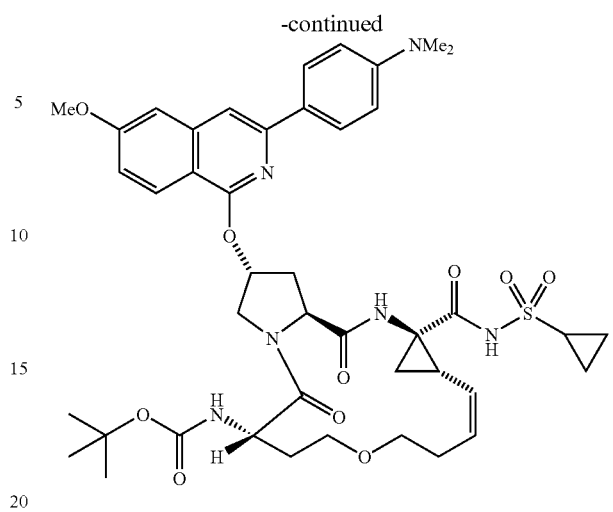
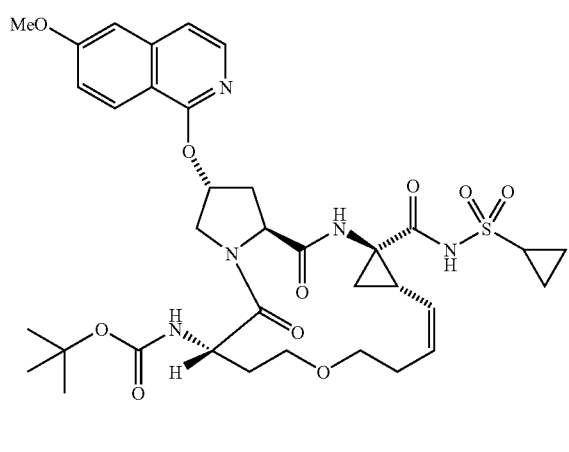
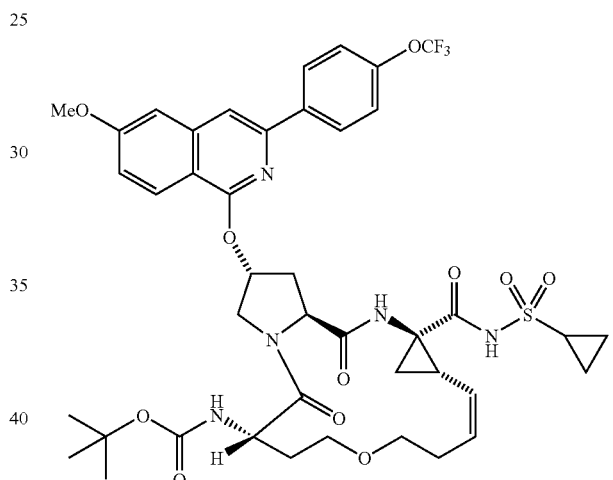
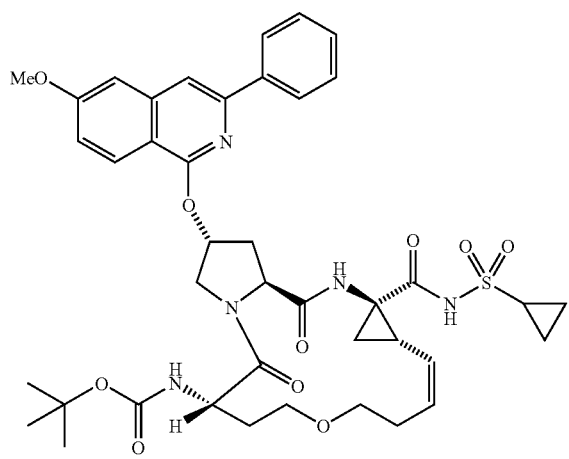
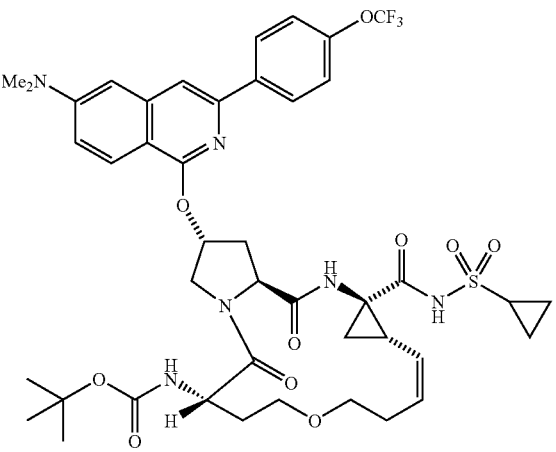

-continued
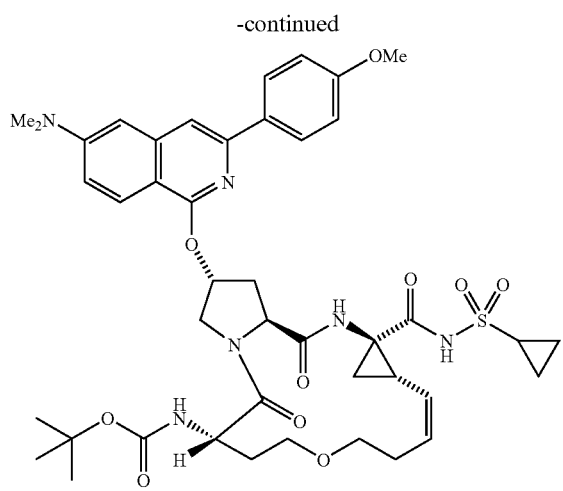
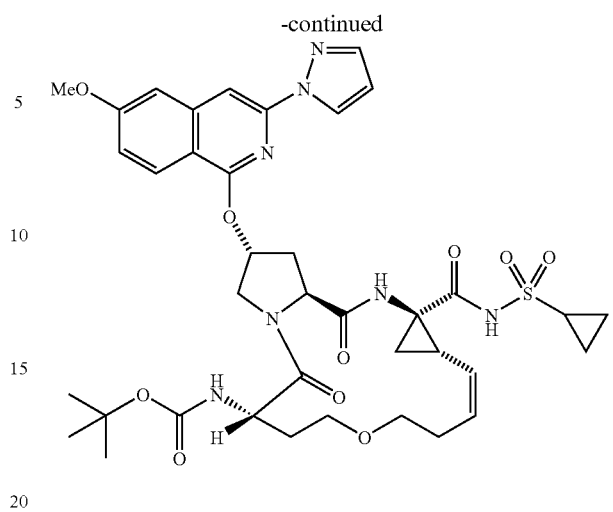
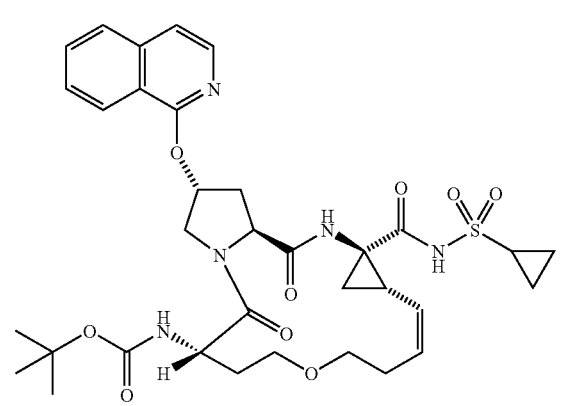
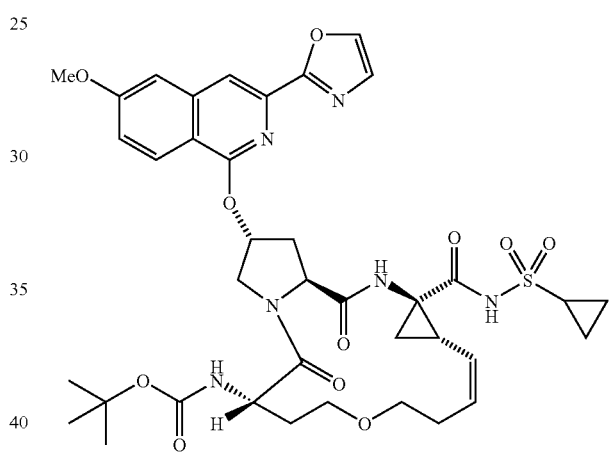
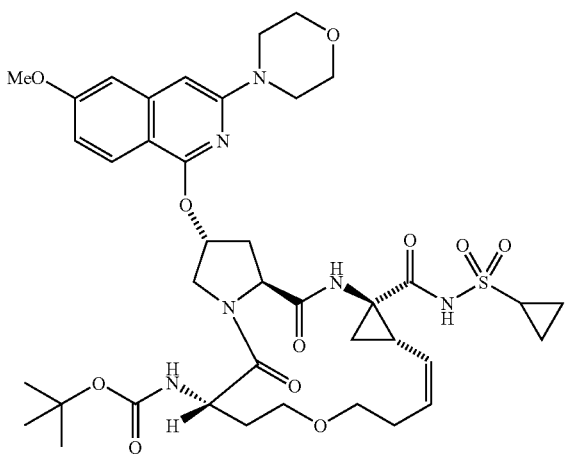
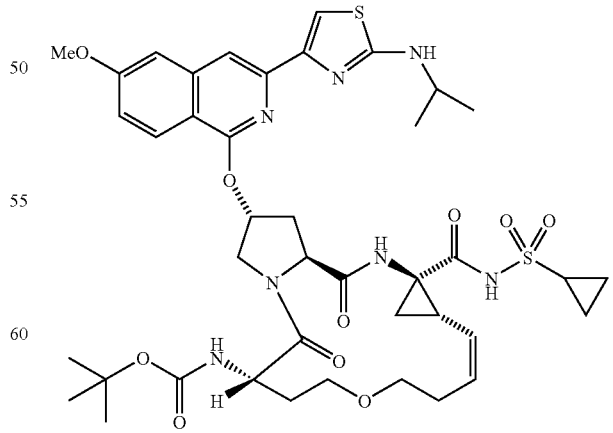

-continued
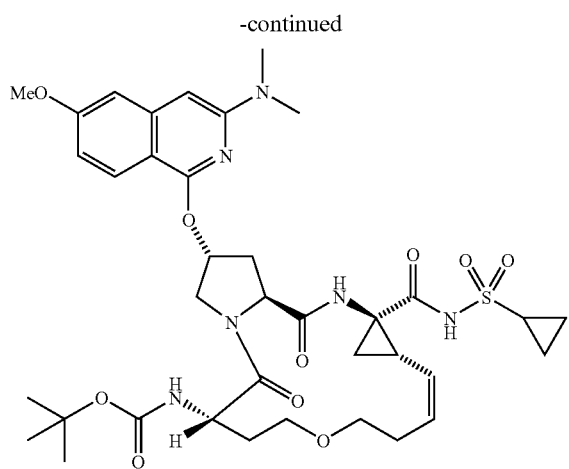
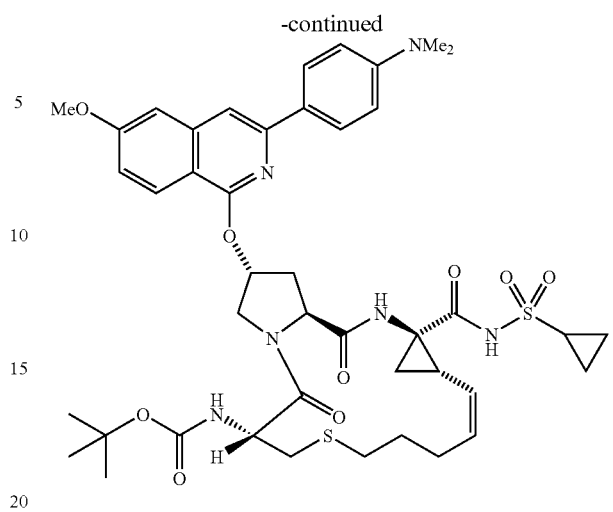
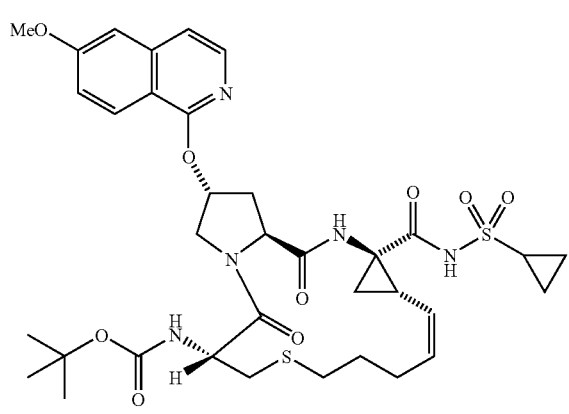
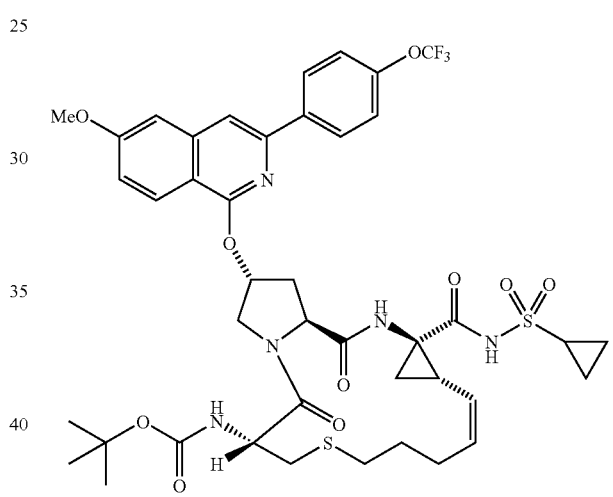
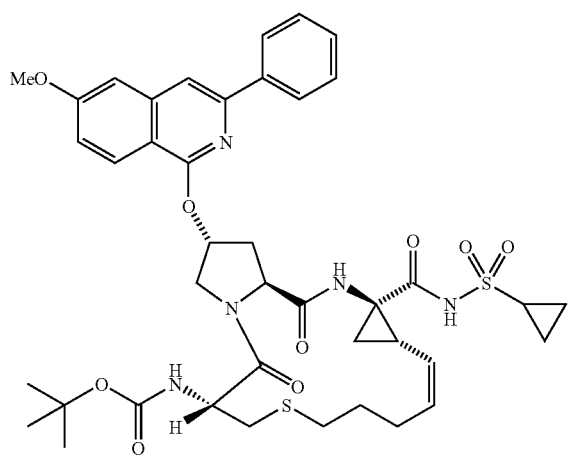
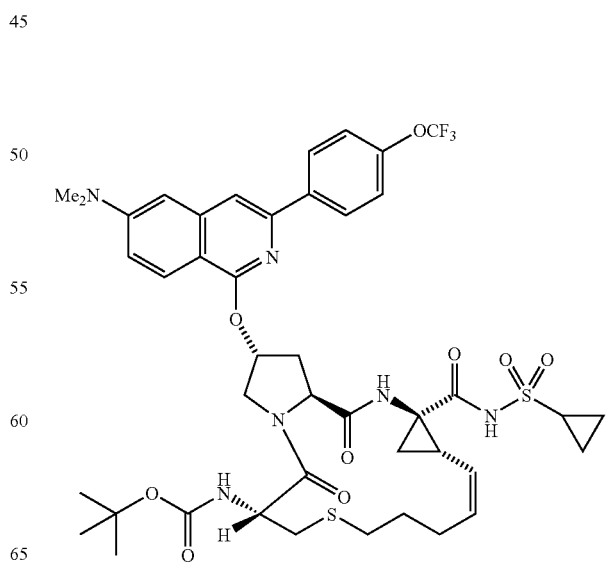

-continued
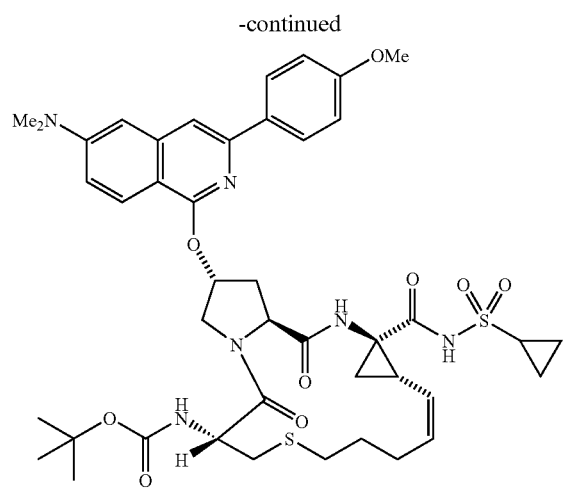
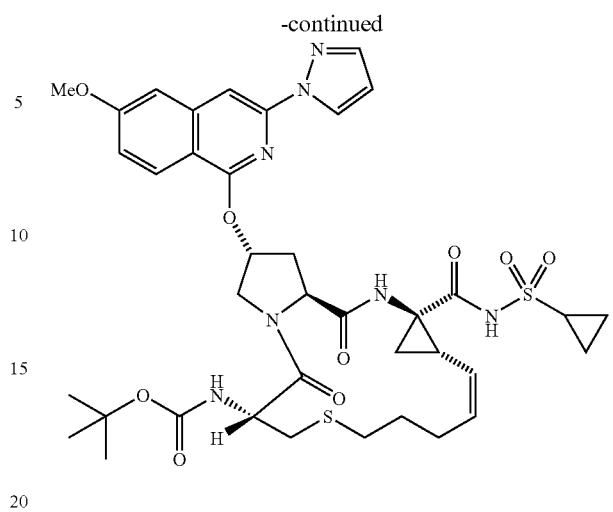
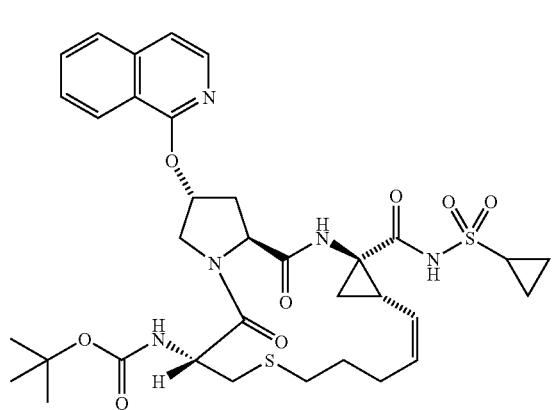
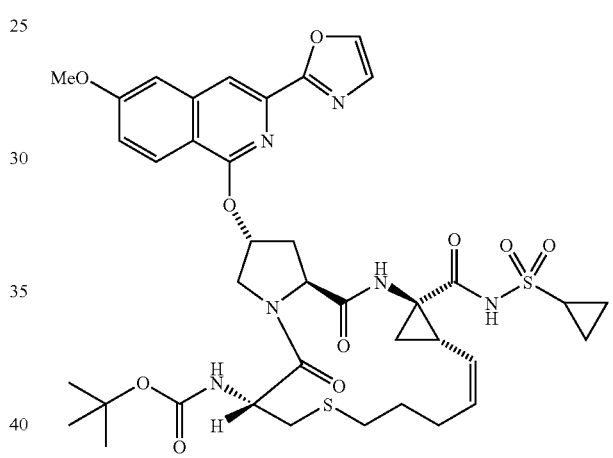
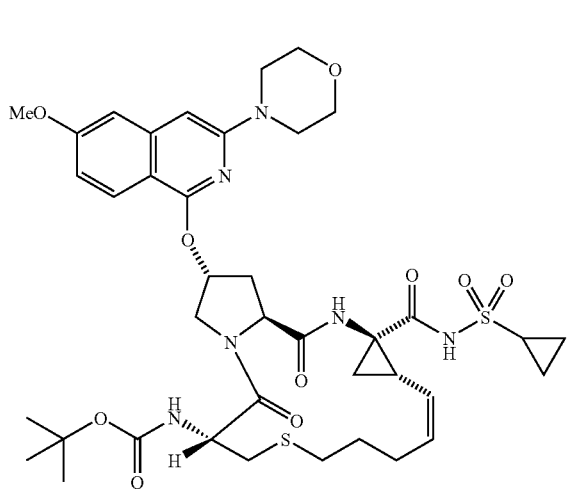
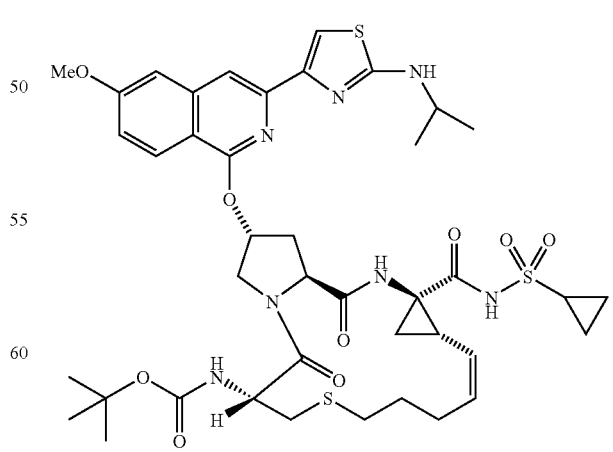

35
-continued
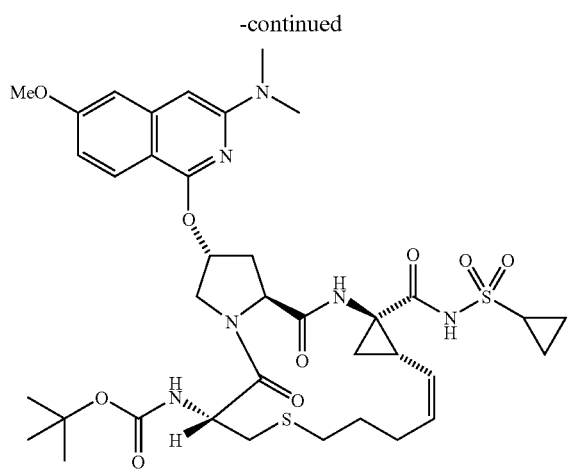
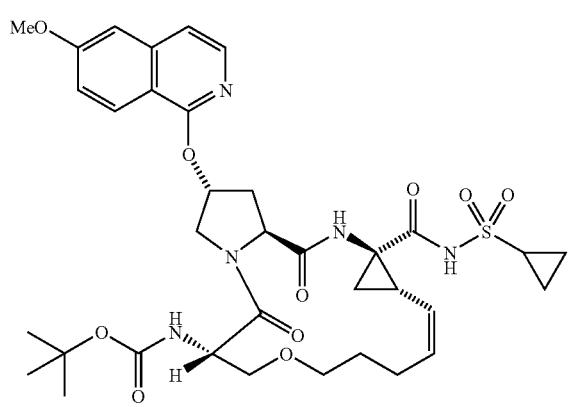
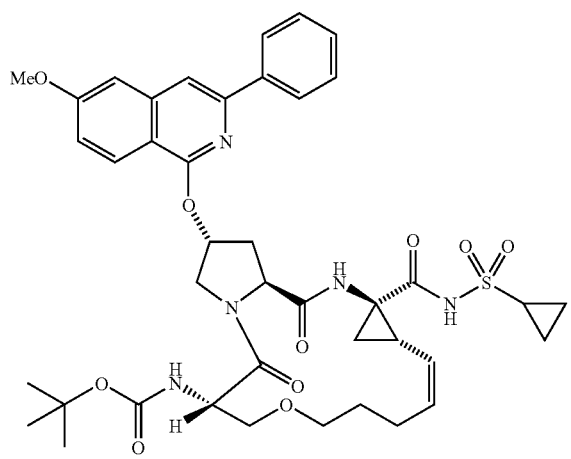
36
-continued
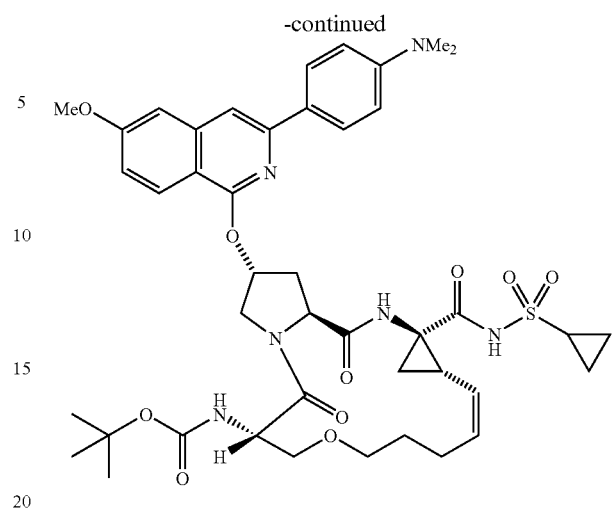
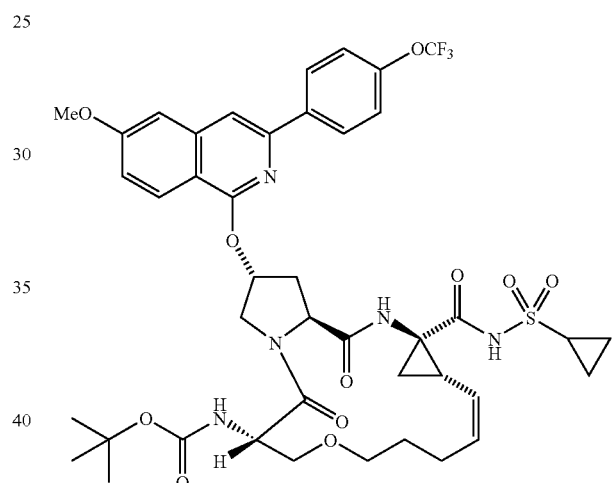
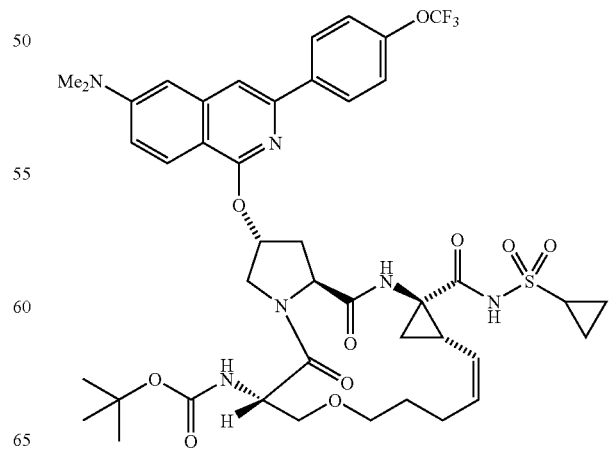

-continued
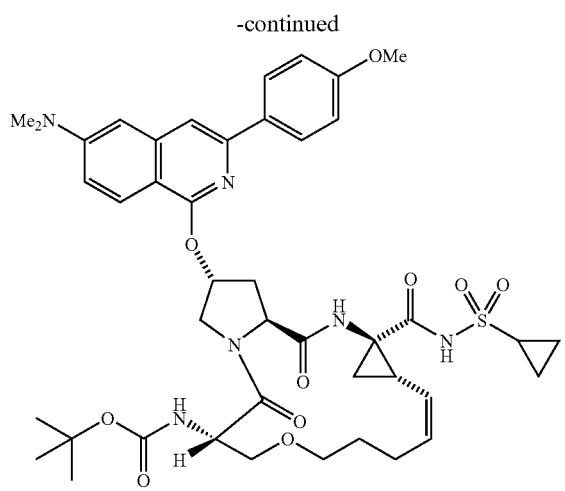
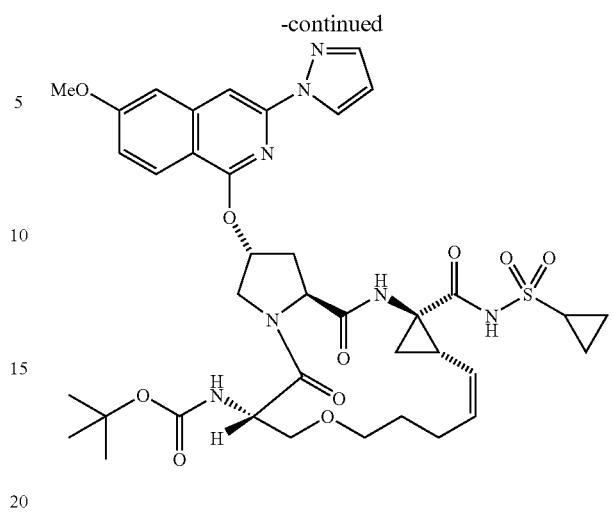
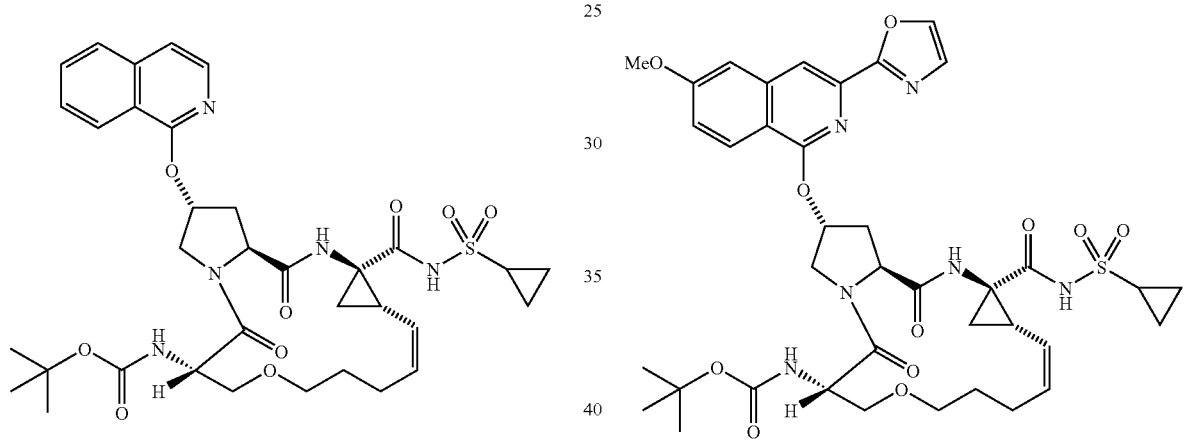
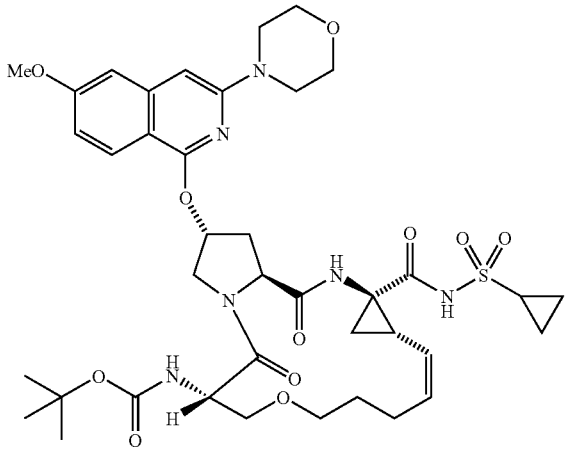
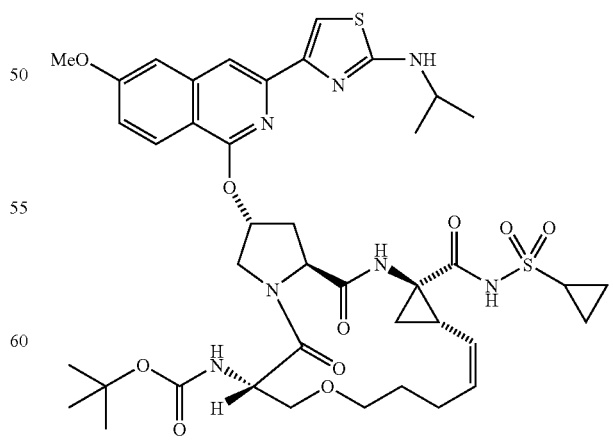

39
-continued
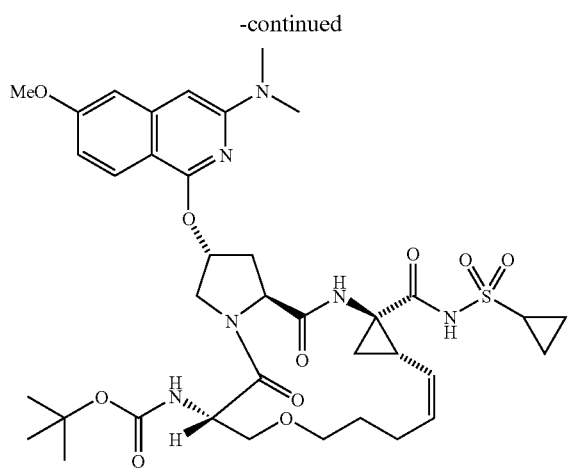
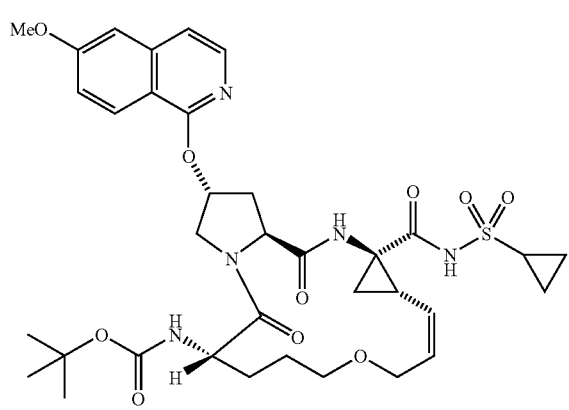
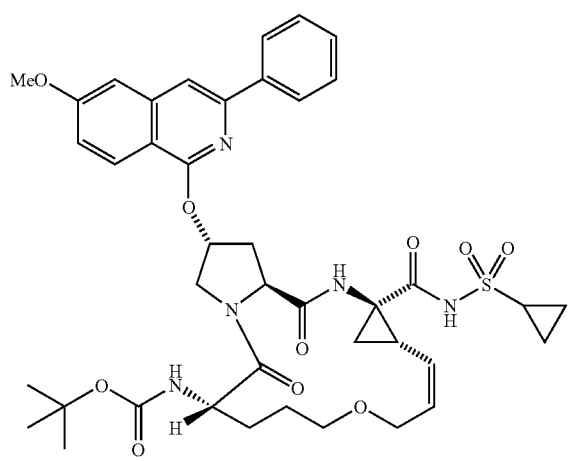
40
-continued
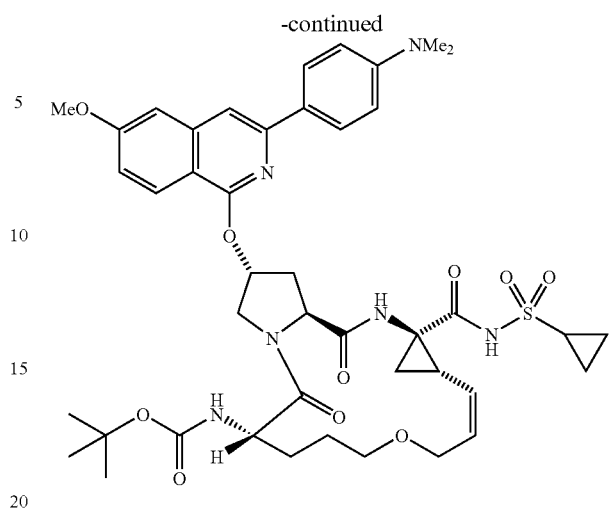
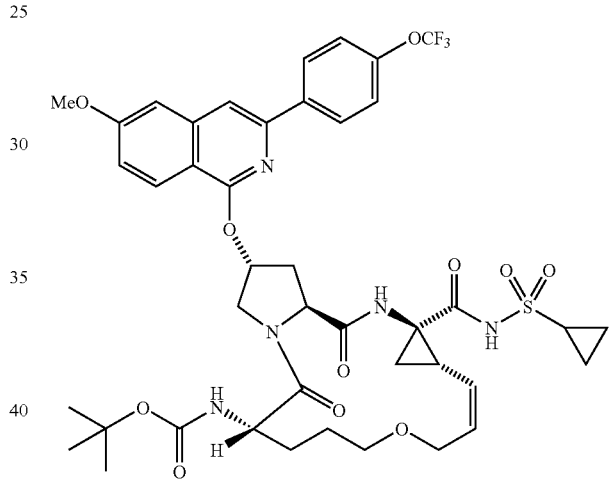
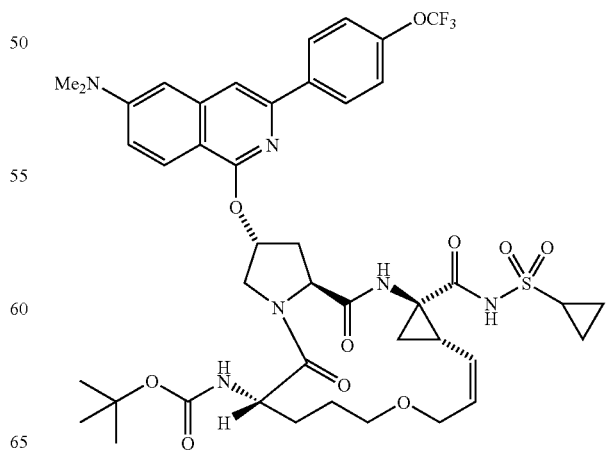

-continued
41
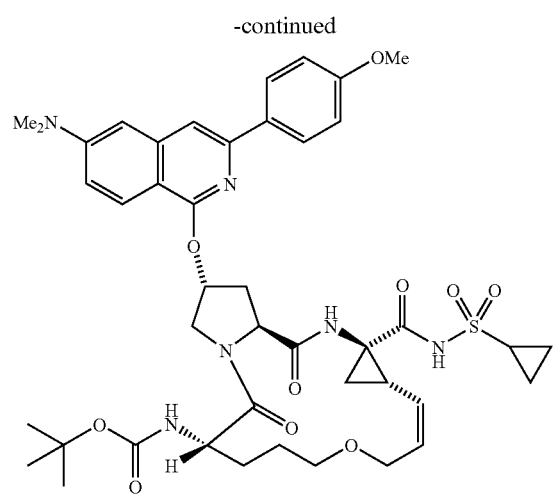
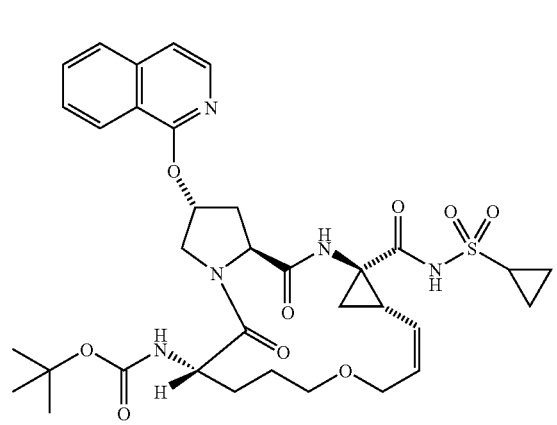
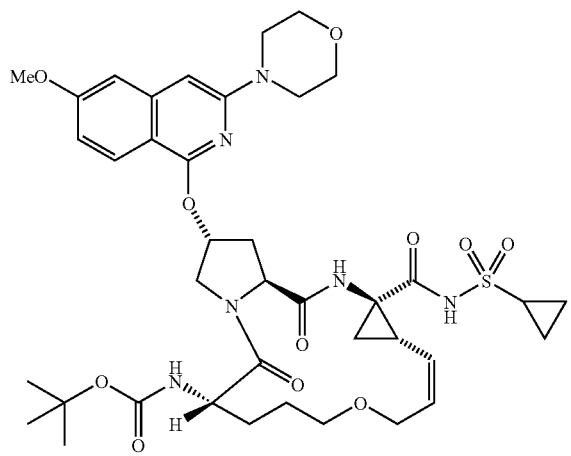
42
-continued
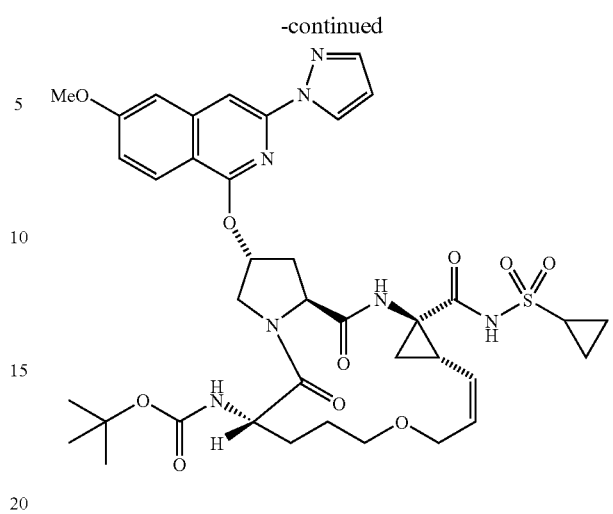
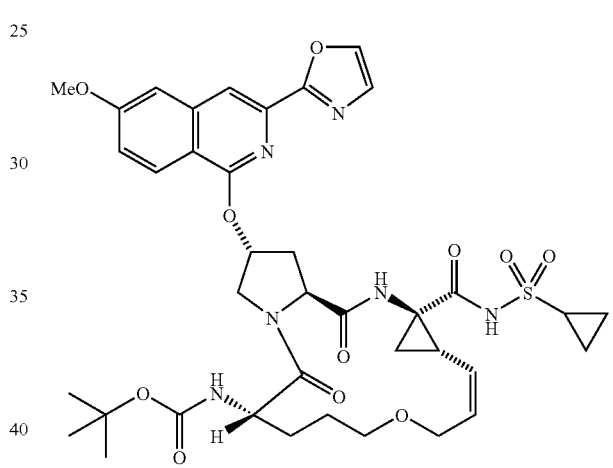
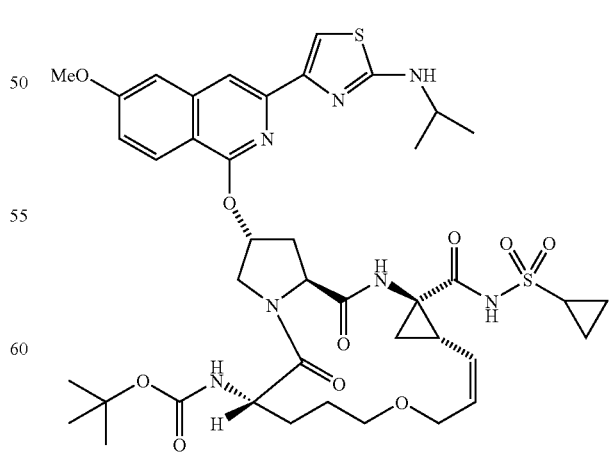

-continued

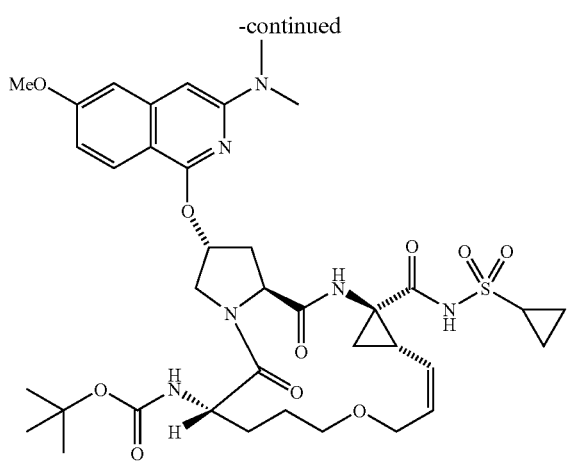

The compounds of the present invention, which contain a basic moiety, can form salts by the addition of a pharmaceutically acceptable acid. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Salts of an amine group may also comprise quaternary ammonium salts in which the amino nitrogen carries a suitable organic group such as an alkyl, alkenyl, alkynyl or aralkyl moiety.

Compounds of the present invention, which are substituted with an acidic group, may exist as salts formed through base addition. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino acids such as lysine, arginine and N-methylglutamine. These salts may be prepared by methods known to those skilled in the art.

Lists of suitable salts are found, for example, in *Remington's Pharmaceutical Sciences*, 18th ed., Mack Publishing Company, Easton, Pa., 1990, p. 1445.

Certain compounds of the present invention, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

In addition, compounds of the present invention, or a salt or solvate thereof, may exhibit polymorphism. The present invention also encompasses any such polymorphic form.

Compounds of the present invention (Formula I, II or III) also contain two or more chiral centers and exist in different optically active forms. For example, compounds of Formula I may include a cyclopropyl group as represented in the P1 fragment below:

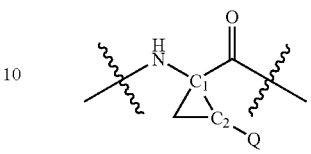

wherein $C_1$ and $C_2$ each represent an asymmetric carbon atom at positions 1 and 2 of the cyclopropyl ring. Notwithstanding other possible asymmetric centers at other segments of the compounds of the invention, the presence of these two asymetric centers means that the compounds can exist as mixtures of diastereomers, such as the diastereomers of compounds of Formula III wherein Q is configured either syn to the amide or syn to the carbonyl as shown below.

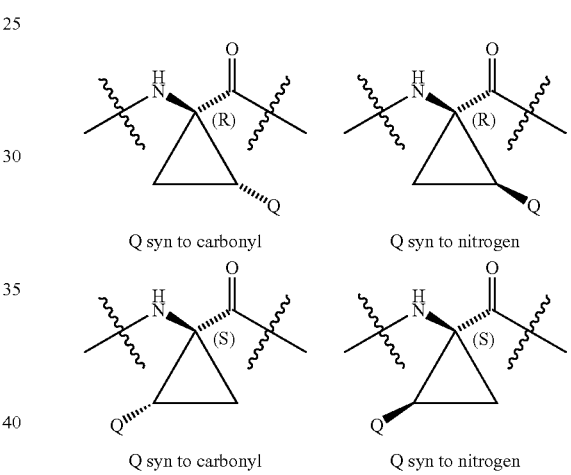

The present invention includes both enantiomers and mixtures of enantiomers of the compunds, such as racemic mixtures.

The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Certain compounds of the present invention may exist in zwitterionic form and the present invention includes each zwitterionic form of these compounds and mixtures thereof.

The starting materials useful to synthesize the compounds of the present invention are known to those skilled in the art and can be readily manufactured or are commercially available.

The compounds of the present invention can be manufactured by methods known to those skilled in the art. The following methods set forth below are provided for illustrative purposes and are not intended to limit the scope of the claimed invention. For example, compounds of the present invention having the structure of Formula I, II or III can be synthesized, as shown in the following scheme, from compounds of Formula IV, Formula VIIA or VIIB. It will be recognized that it may be preferred or necessary to prepare such a compound in which a functional group is protected using a conventional protecting group then to remove the protecting group to provide a compound of the present invention. The details concerning the use of protecting groups in accordance with the present invention are known to those skilled in the art.

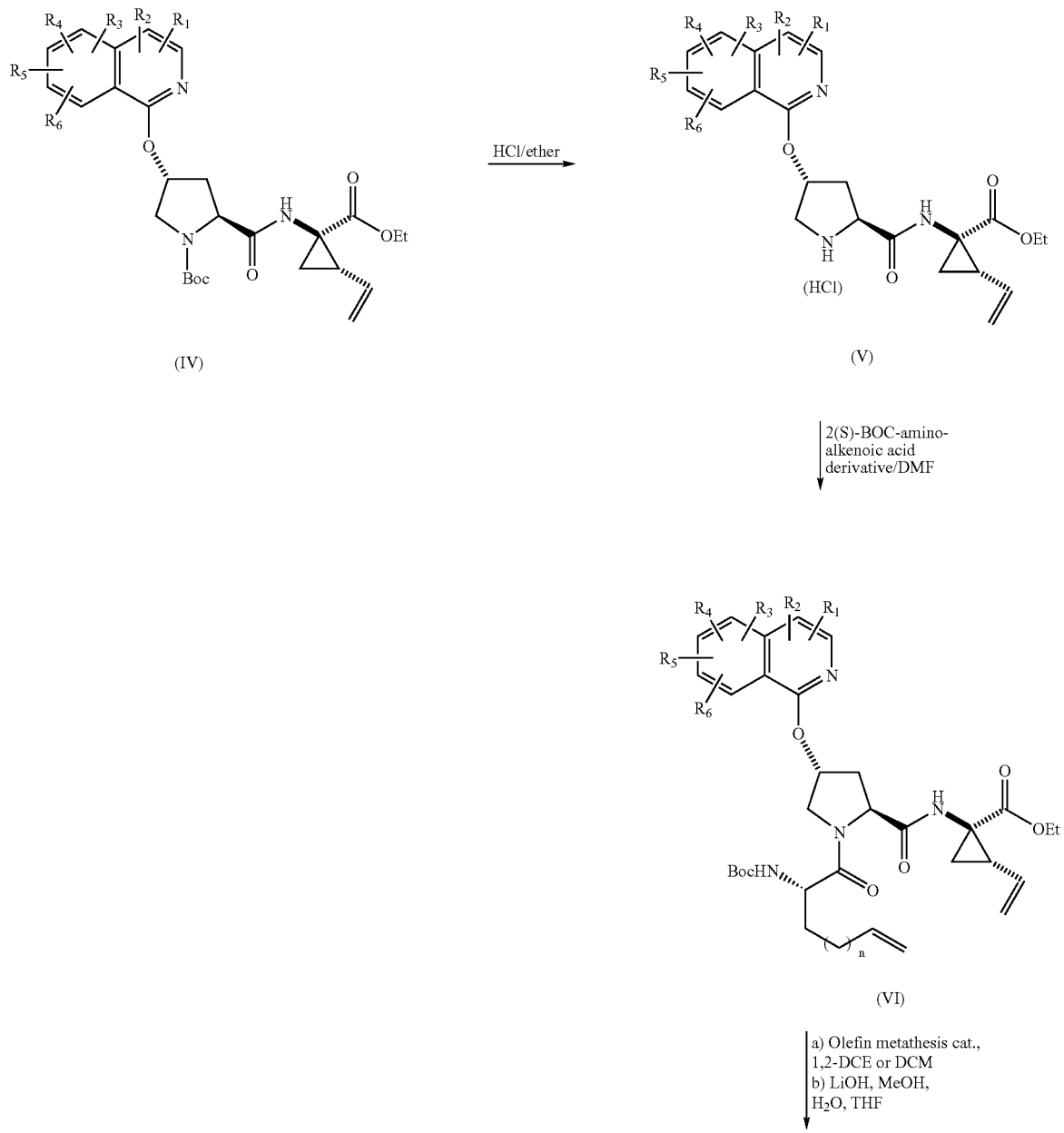

-continued
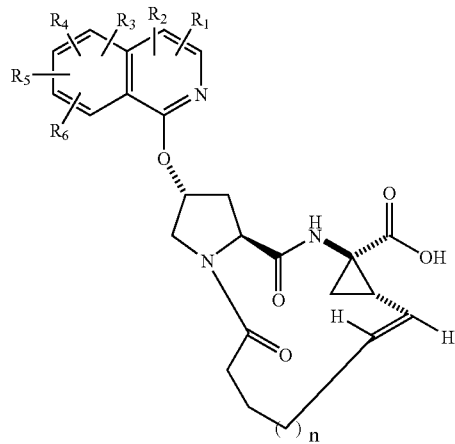
(VIIA)
and
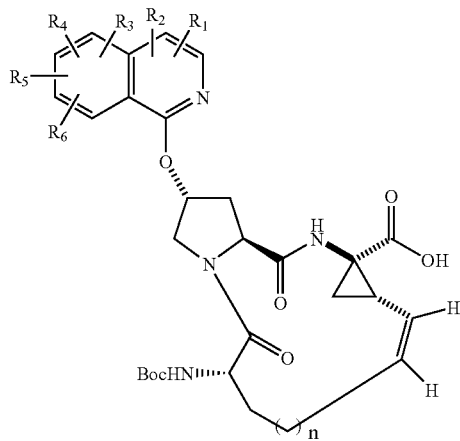
(VIIB)
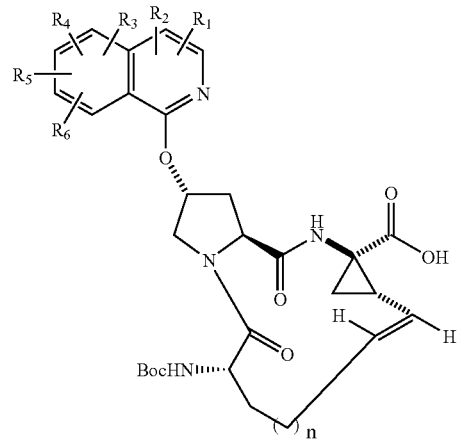
(VIIA)
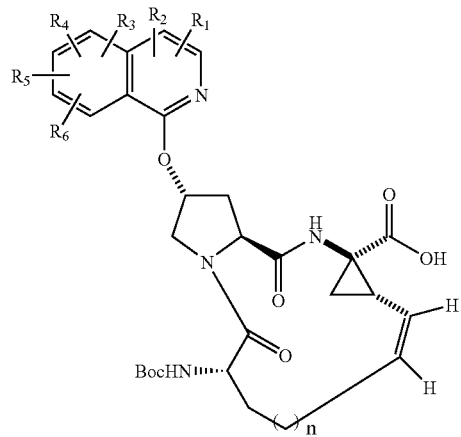
(VIIB)
↓ $R_{23}SO_2NH_2$
↓ $R_{23}SO_2NH_2$
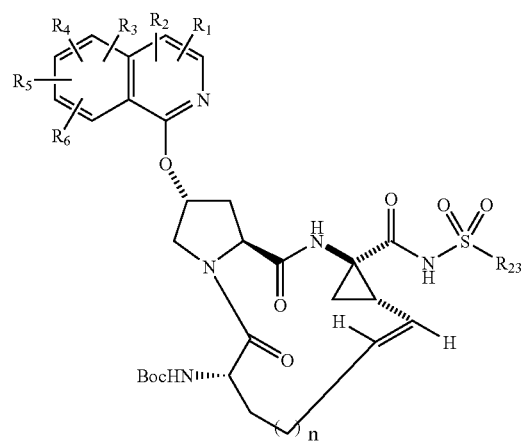
(IIIA)
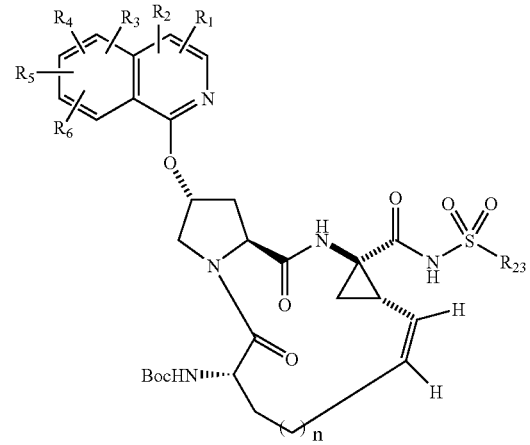
(IIIB)

The α-carboxylic acid of a compound of Formula VIIA or VIIB is coupled with $R_{23}SO_2NH_2$ ($R_{23}$ as defined above) in the presence of peptide coupling agent, such as CDI or EDAC, and in the presence of a base, such as 4-dimethylaminopyridine (4-DMAP) and/or 1,8-diazabicyclo [5.4.0] undec-7-ene (DBU), to form a compound of Formula I, II or III.

In the construction of compounds of Formula I, the P1' terminus is incorporated into the molecules using one of the general processes outlined above and described in more detail below. In some examples the P1' elements, that is the cycloalkylsulfonamides, alkyl sulfonamides or heteroarylsulfonamides are commercially available or can be prepared from the corresponding alkyl- or cycloalkyl-sulfonyl chloride by treating said sulfonyl chloride with ammonia. Alternatively, these sulfonamides can be synthesized using the general process outline in the following Scheme. Therein commercially available 3-chloropropylsulfonyl chloride (1) is converted to a suitable protected sulfonamide as for example by treatment with tert-butyl amine. The sulfonamide obtained (2) is then converted to the corresponding cycloalkylsulfonamide by treatment with two equivalents of a base such as butyl lithium in a solvent such as THF at low temperature. The resulting cycloalkylsulfonamide can be deprotected by treatment with an acid to provide the desired unprotected cycloalkylsulfoamide. Said P1' fragment can be incorporated into compounds of Formula I.

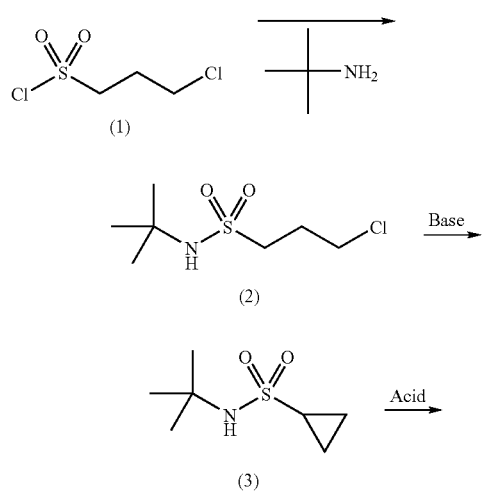

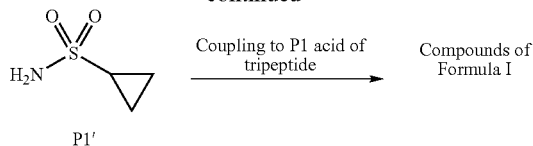

Compounds having the structure of Formula IV, VI, VIIA or VIIB can be prepared, for example, as described herein, and in International Application Number PCT/US01/45145, Publication No. WO 02/060926, published Aug. 8, 2002; International Application Number PCT/CA00/00353, Publication No. WO 00/59929, published Oct. 12, 2000; and U.S. Pat. No. 6,323,180 granted Nov. 27, 2001.

Compounds having the structure of Formula IV can also be prepared by coupling chemical precursor A with chemical precursor B as shown below.

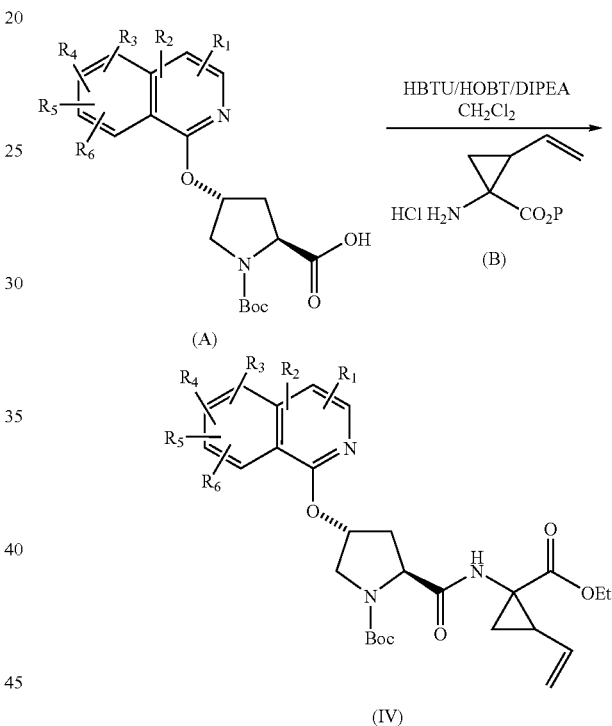

Chemical precursor B, which is also shown above, may for example, be synthesized as follows.

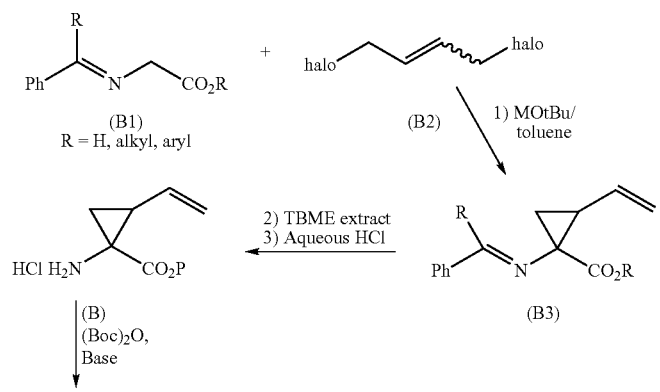

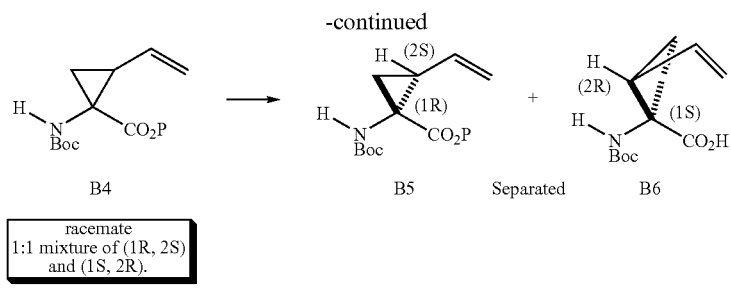

B4
racemate
1:1 mixture of (1R, 2S) and (1S, 2R).

B5 Separated B6

Treatment of commercially available or readily synthesized imine (B1) with 1,4-dihalobutene (B2) in presence of a base provides the imine (B3). Acid hydrolysis of B3 then provides B, which has a vinyl substituent syn to the carboxyl group. It is preferred that for compounds B3 and B that the vinyl group is syn to the ester. The amine moiety of B can protected using a Boc group to provide the fully protected amino acid B4. This intermediate is a racemate which can be resolved by an enzymatic process wherein the ester moiety of B4 is cleaved to provide the corresponding carboxylic acid. Without being bound to any particular theory, it is believed that this reaction is selective in that one of the enantiomers B4 (1S,2R) undergoes the reaction at a much greater rate than its mirror image B4 (1R,2S) providing for a kinetic resolution of the intermediate racemate. In the example cited above, the more preferred stereoisomer for integration into the tripeptdes is B4 (1R,2S). In the presence of the enzyme, this enantiomer does not undergo ester cleavage and thereby this enantiomer B5 is recovered from the reaction mixture. However, the less preferred enantiomer B4 (1S,2R) undergoes ester cleavage, i.e., enzyme catalyzed hydrolysis, to provide the free acid B6. The ester (B5) can be separated from the acid product (B6) by routine methods such as, for example, aqueous extraction methods or chromatography.

Compounds of Formula I can also be converted into other compounds of Formula I as described herein. An example of such a process is the Scheme below, wherein a compound of Formula I (1) which bears a Boc group at the P4 position is converted into a compound of Formula I (3) wherein said compound bears a urea group at the P4 position. The conversion of (1) to (3) can be carried out in a two step process the first of which is the conversion of (1) to amine (2) by treatment of (1) with an acid such as TFA in a solvent such as methylene chloride. The resulting amine TFA salt can be treated with an isocyanate in the presence of one equivalent of base to provide a compound of Formula I (3) wherein the P3 moiety is capped with a urea. As previously noted one skilled in the art will recognize that intermediate (2) can be used as starting materials for the preparation of compounds of Formula I wherein the P3 group is capped with an amide or a carbamate. The construction of said compounds of Formula I can be achieved using standard conditions for the formation of said P4 functionalities from amines.

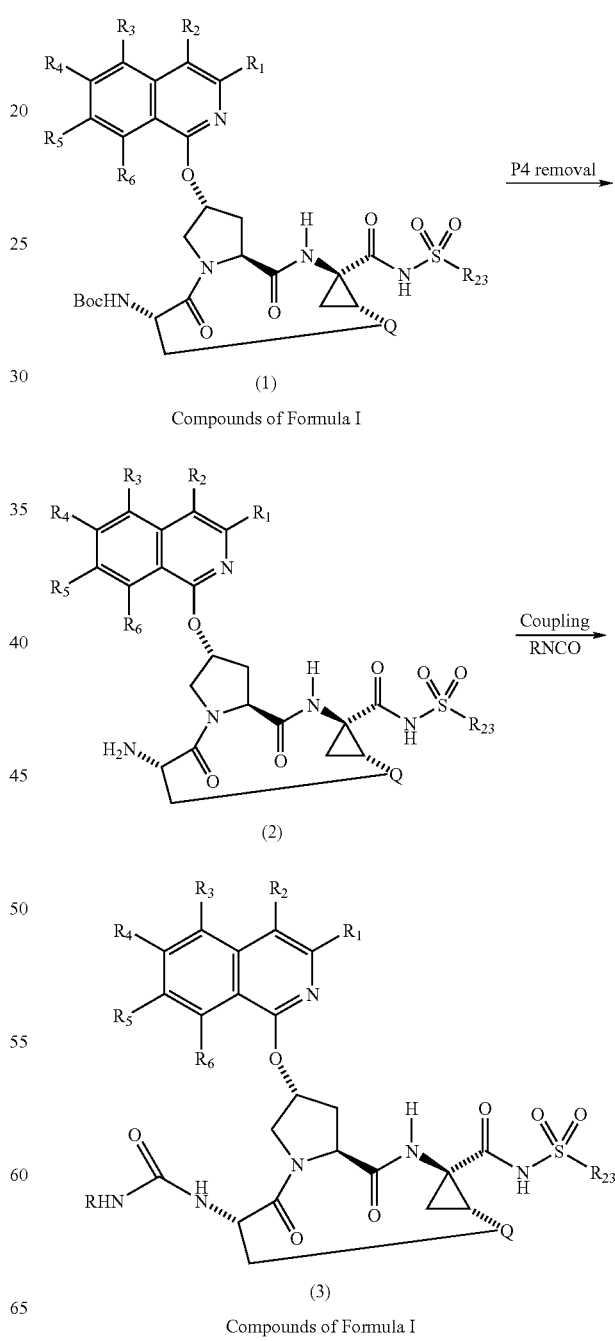

Compounds of Formula I

Procedures for making P2 intermediates and compounds of Formula I are shown in the Schemes below. It should be noted that in many cases reactions are depicted for only one position of an intermediate. However, it is to be understood that such reactions could be used to impart modifications to other positions within this intermediate. Moreover, said intermediates, reaction conditions and methods given in the specific examples are broadly applicable to compounds with other substitution patterns. The general Schemes outlined below are followed with examples herein. Both general and specific examples are non-limiting.

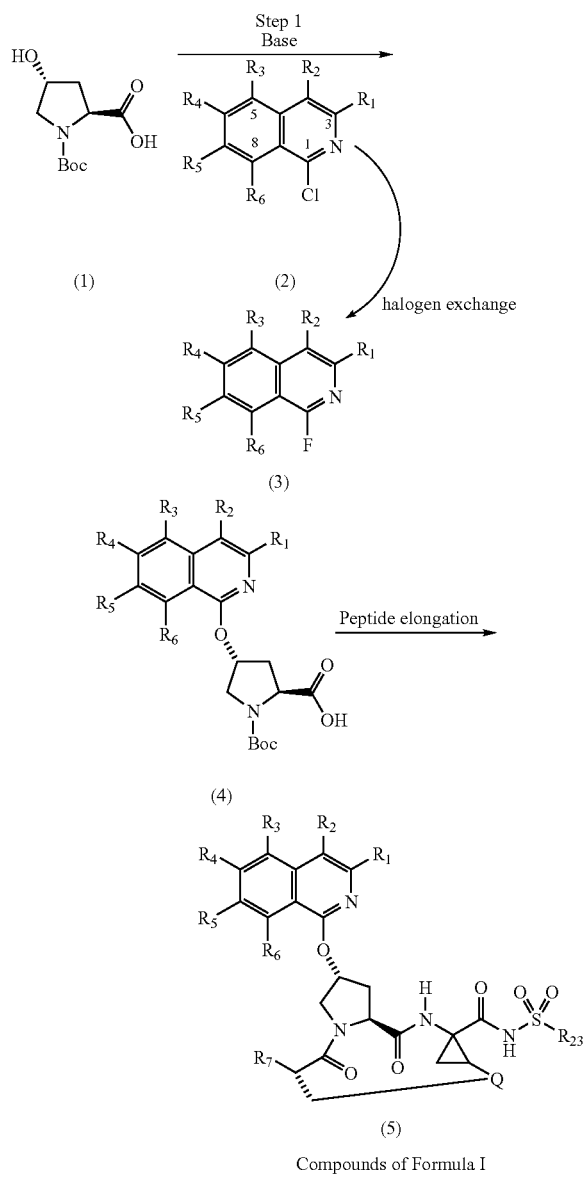

Compounds of Formula I

The above Scheme shows the coupling of an N-protected C4-hydroxyproline moiety with an isoquinoline heterocycle to form intermediate (4) and the subsequent modification of said intermediate (4) to a compound of Formula I by the process of peptide elongation and a ring-closing olefin metathesis reaction as described herein. It should be noted that in the first step, that is the coupling of the C4-hydroxy proline group with the isoquinoline element, a base is employed. One skilled in the art would recognize that this coupling can be done using bases such as potassium tert-butoxide, or sodium hydride, in solvent such as DMF or DMSO or THF. This coupling to the isoquinoline ring system occurs at the C1 position (numbering for isoquinoline ring system shown in intermediate 2) and is directed by the chloro group which is displaced in this process. It should be noted that alternative leaving groups can be utilized at this position such as a fluoro as shown in the Scheme. Said fluoro intermediates (3) are available from the corresponding chloro compound using literature procedures described herein.

In a subset of examples herein, isoquinolines are incorporated into the final compounds and specifically into the P2 region of said compounds. One skilled in the art would recognize that a number of general methods are available for the synthesis of isoquinolines. Moreoever, said isoquinolines generated by these methods can be readily incorporated into final compounds of Formula I using the processes described herein. One general methodology for the synthesis of isoquinolines is shown in the scheme below, wherein cinnamic acid derivatives, shown in general form as structure (2) are

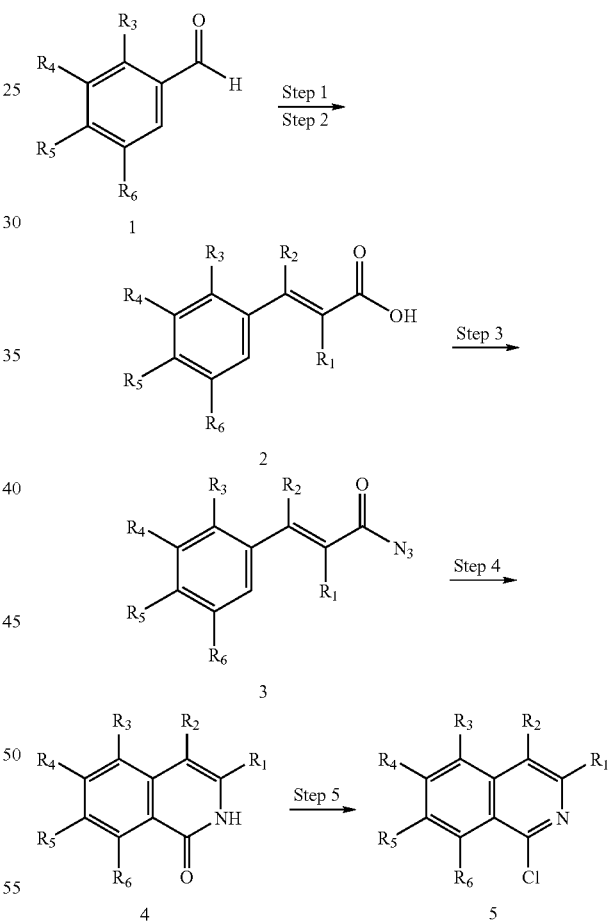

Reference: N. Briet at al, *Tetrahedron*, 2002, 5761 converted to 1-chloroisoquinolines in a four step process. Said chloroisoquinolines can be subsequently used in coupling reactions to C4-hydroxyproline derivatives as described herein. The conversion of cinnamic acids to chloroquinolines begins with the treatment of cinnamic acid with an alkylcholorformate in the presence of a base. The resulting anhydride is then treated with sodium azide which results in the formation of an acylazide (3) as shown in the Scheme. Alternate methods are available for the formation of acylazides from carboxylic acids as for example said carboxylic acid can be treated with diphenylphosphorylazide (DPPA) in an aprotic solvent such as methylene chloride in the presence of a base. In the next step of the reaction sequence the acylazide (3) is coverted to the corresponding isoquinolone (4) as shown in the Scheme. In the event the acylazide is heated to a temperature of approximately 190 degress celcius in a high boiling solvent such a diphenylmethane. This reaction is general and provides moderate to good yields of substituted isoquinolone from the corresponding cinnamic acid derivatives. It should be noted that said cinnamic acid derivatives are available commercially or can be obtained from the corresponding benzaldehyde (1) derivative by direct condensation with malonic acid or derivatives thereof and also by employing a Wittig reaction. The intermediate isoquinolones (4) can be converted to the corresponding 1-chloroisoquinoline by treatment with phosphorous oxychloride. This reaction is general and can be applied to any of the isoquinolones shown herein to covert a hydroxy substituent to the corresponding chloro compound.

An alternative method for the synthesis of the isoquinoline ring system is the Pomeranz-Fritsh procedure. This general method is outlined below. The process begins with the conversion of a benzaldehyde derivative (1) to a functionalized imine (2). Said imine is then converted to the isoquinoline ring system by treatment with acid at elevated

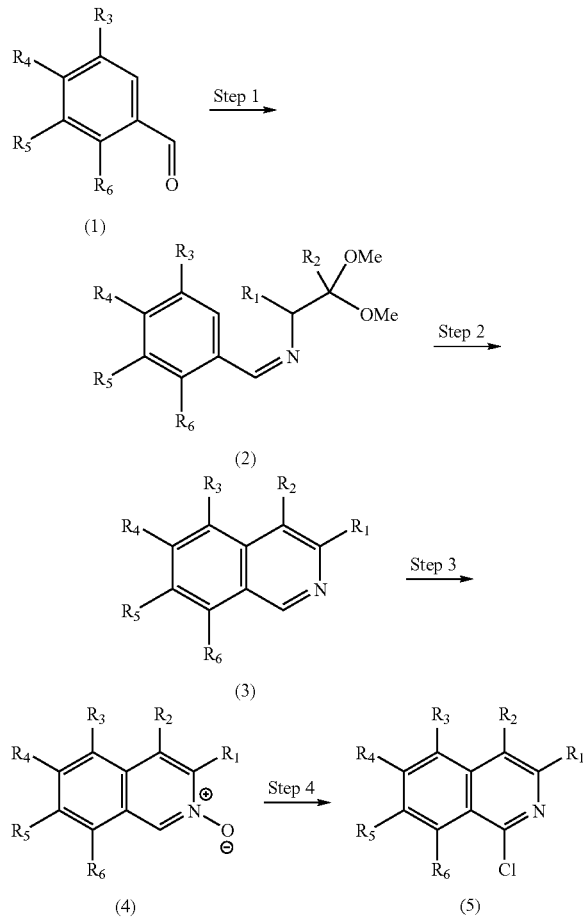

Pomeranz-Fritsch synthesis
K. Hirao, R. Tsuchiya, Y. Yano, H. Tsue, *Heterocycles 42(1)* 1996, 415–422 temperature. This isoquinoline synthesis as outlined above is general, and it should be noted that this process is particularly useful in procuring isoquinoline intermediates that are substituted at the C8 position (note: in intermediate (3) of the above Scheme the C8 position of the isoquinoline ring is substituted with substutuent $R_6$). The intermediate isoquinolines (3) can be converted to the corresponding 1-chloroquinolines (5) in a two step process as shown. The first step in this sequence is the formation of the isoquinoline N-oxide (4) by treatment of isoquinoline (3) with meta-chloroperbenzoic acid in an aprotic solvent such as dichloromethane. Intermediate (4) can be converted to the corresponding 1-chloroisoquinoline by treatment with phosphorous oxychloride in refluxing chloroform.

Another method for the synthesis of the isoquinoline ring system is shown below. In this process an ortho-alkylbenzamide derivative (1) is treated with a strong

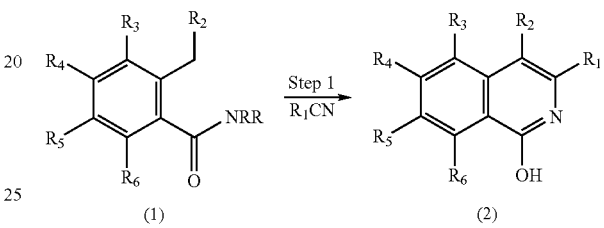

base such as tert-butyl lithium in a solvent such as THF at low temperature. To this reaction mixture is then added a nitrile derivative, which undergoes an addition reaction with the anion derived from deprotonation of (1), resulting in the formation of (2). This reaction is general and can be used for the formation of substituted isoquinolines. Intermediate (2) of the above scheme can be converted to the corresponding 1-chloroisoquinoline by the methods described herein. An additional method for the synthesis of isoquinolines is shown below. The deprotonation of intermediate (1) using tert-butyl lithium is described above. In the present method however, said intermediate anion is trapped by an ester, resulting in the formation of intermediate (2) as shown below. In a subsequent reaction ketone (2) is condensed with ammonium acetate at elevated temperature providing for the formation of quinolone (3). This reaction is general and can be applied for the construction of substituted isoquinolones which can then be converted to the corresponding 1-chloroisoquinolines as described herein.

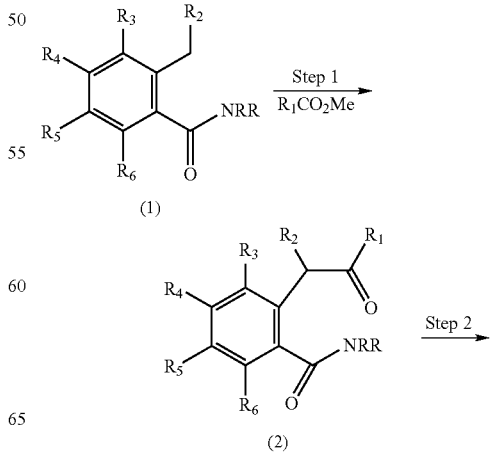

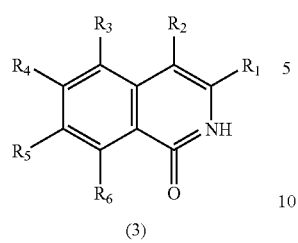

(3)

Yet an additional method for the construction of isoquinolines is found in the scheme below. In the first step of this process an ortho-alkylarylimine derivative such as (1) is subjected to deprotonation conditions (sec-butyl lithium, THF) and the resulting anion is quenched by

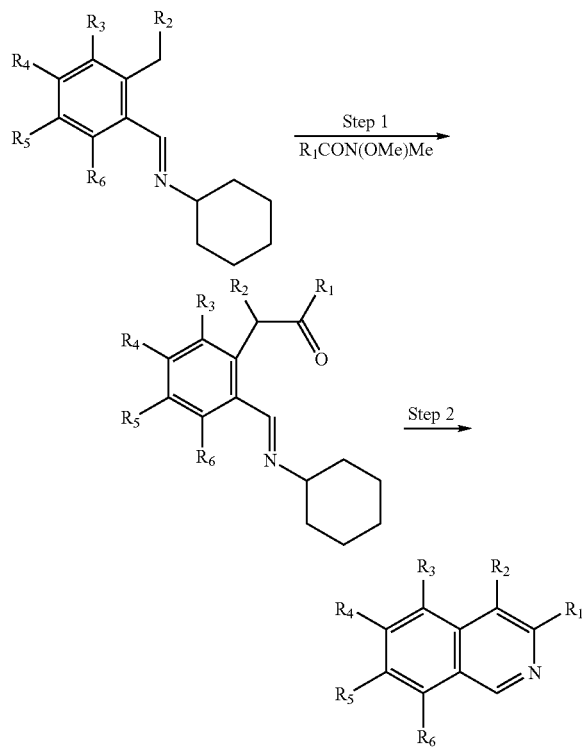

L. Flippin, J. Muchowski, *JOC*, 1993, 2631–2632 the addition of an activated carboxylic acid derivative such as a Weinreb amide. The resulting keto imine (2) can be converted to the corresponding isoquinoline by condensation with ammonium acetate at elevated temperatures. This method is general and can be used for the synthesis of substituted isoquinolines. Said isoquinolines can be converted to the corresponding 1-chloroisoquinoline by the methods described herein.

The construction of functionalized isoquinoline ring systems is also possible employing [4+2] cycloaddition reactions. For example as shown below the use of vinyl isocyantes (1) in cycloaddition reactions with benzyne precursors (2) provides functionalized isoquinolones (3). Said isoquinolines can be incorporated into compounds of Formula I using the methods described herein.

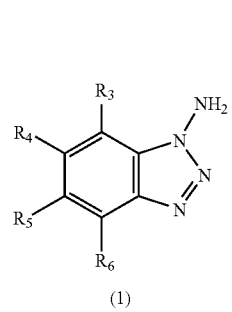

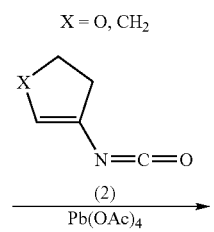

The isoquinolines described herein, and which are incorporated into the compounds of Formula I can be further functionalized. It is obvious to one skilled in the art that additional functionalization of said heterocycles can be done either before or after incorporation of these functionalities into compounds of Formula I. The following schemes illustrate this point. For example the scheme below shows the conversion of a 1-chloro-

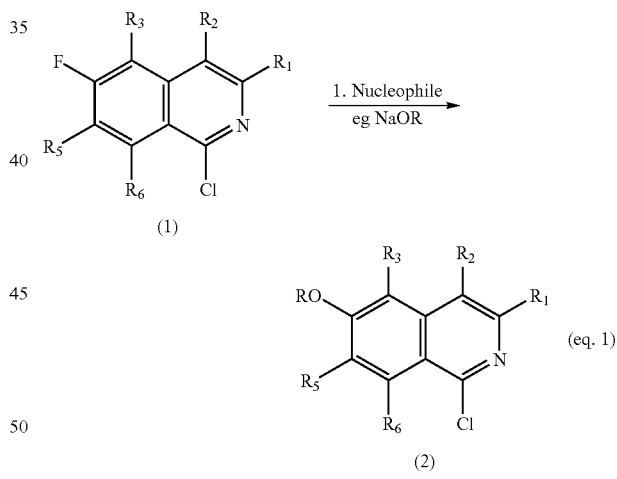

(eq. 1)

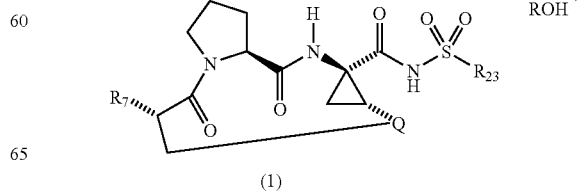

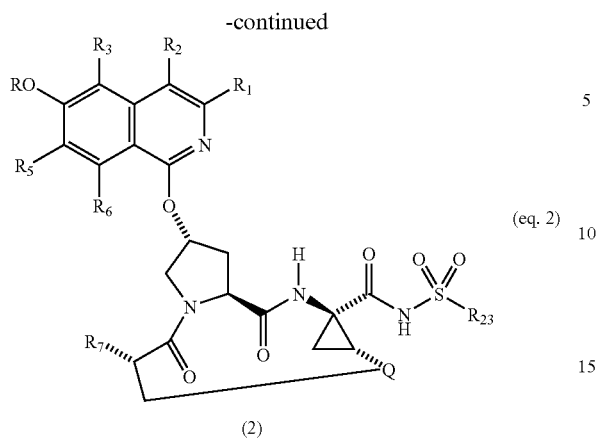

(eq. 2)

(2)

6-fluoro-isoquinoline to the corresponding 1-chloro-6-alkoxy-isoquinoline species, by treatment of (1) of (eq. 1) with a sodium or potassium alkoxide species in the alcohol solvent from which the alkoxide is derived at room temperature. In some cases it may be necessary to heat the reaction to drive it to completion. Intermediate (2) of equation 1 can be incorporated into compounds of Formula I by the teachings herein. As shown in equation 2 the analogous reaction can also be conducted on a substrate wherein the 6-fluoro-isoquinoline element has been incorporated into the macrocycle. Therein treatment of intermediate 2 of equation 2 with a sodium or potassium alkoxide species in the alcohol solvent from which the alkoxide is derived can provide compounds of Formula I.

The scheme below provides a general example for the modification of isoquinolines as defined herein by employing palladium mediated coupling reactions. Said couplings can be employed to functionalize an isoquinoline at each position of the ring system providing said ring is suitably activated or functionalized, as for example with a chloride as shown in the scheme. This sequence begins with 1-chloroisoquinoline (1) which upon treatment with metachloroperbenzoic acid can be converted to the corresponding N-oxide (2). Said intermediate (2) can be converted to the corresponding 1,3-dichloroisoquinoline (3) by treatment with phosphorous oxychloride in refluxing chloroform. Intermediate (3) can be coupled with N-Boc-4-hydroxyproline by the methods described herein to provide intermediate (5) as shown in the Scheme. Intermediate (5) can undergo a Suzuki coupling with an aryl boronic acid, in the presence of a palladium reagent and base, and in a solvent such as THF or toluene or DMF to provide the C3-arylisoquinoline intermediate (6). Heteroarylboronic acids can also be employed in this Pd mediated coupling process to provide C3-heteroarylisoquinolines. Intermediate (6) can be converted into final compounds of Formula I by the methods described herein.

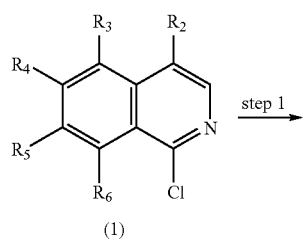

(1)

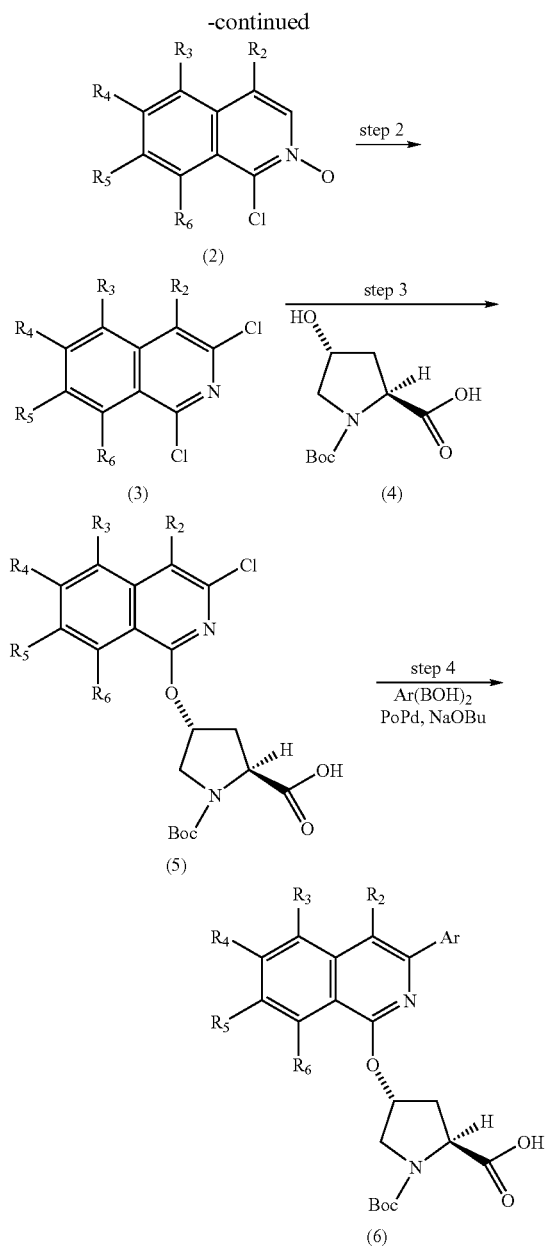

Palladium mediated couplings of heteroaryl systems with aryl or heteroaryl elements can also be employed at a later synthetic stage in the construction of compounds of Formula I as shown below. Therein macrocycle tripeptide acylsulfonamide intermediate (1) is coupled to a 1-chloro-3-bromoisoquinoline (2) using the previously described process of alkoxide displacement of an heteroarylhalo moiety to provide intermediate (3). The coupling of (1) and (2) can be executed in the presence of a catalyst such as lanthanum chloride. The isoquinoline ring system of intermediate (3) can be further functionalized by employing either Suzuki couplings (Process 1: subjecting (3) to heteroaryl or aryl boronic acids in the presence of a palladium catalyst such as palladium tetrakis(triphenylphosphine) and a base such as cesium carbonate in solvents such as DMF) or Stille couplings (Process 2: subjecting (3) to heteraryl or aryl tin dervatives in the presence of palladium catalyst such as palladium tetrakis(triphenylphosphine in solvents such as toluene).

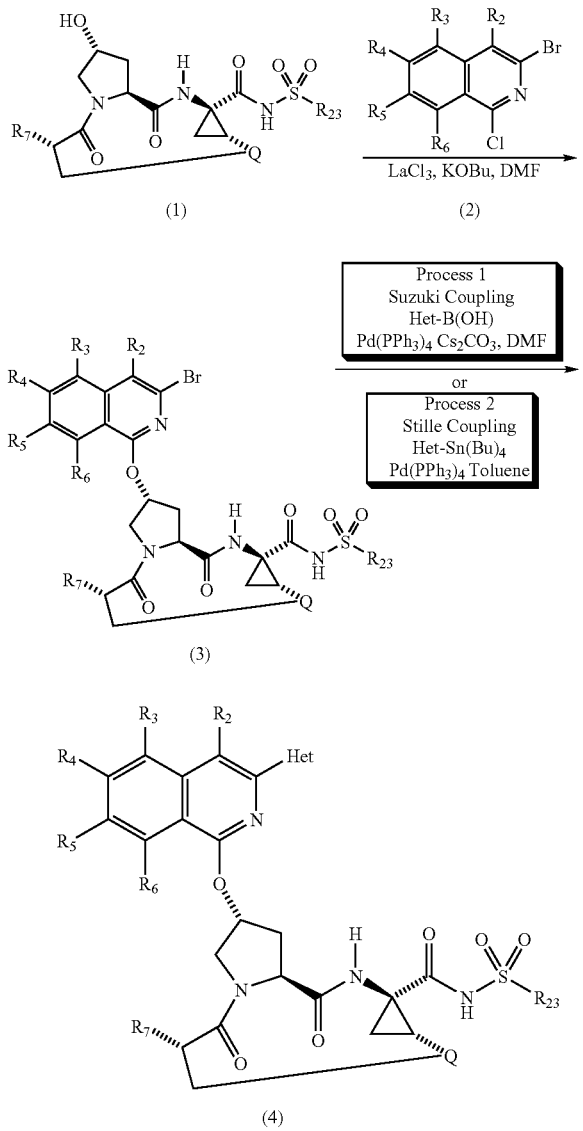

The present invention also provides compositions comprising a compound of the present invention, or a pharmaceutically acceptable enantiomer, diastereomer, salt, solvate or prodrug thereof, and a pharmaceutically acceptable carrier. Pharmaceutical compositions of the present invention comprise a therapeutically effective amount of a compound of the invention, or a pharmaceutically acceptable enantiomer, diastereomer, salt, solvate or prodrug thereof, and a pharmaceutically acceptable carrier, with a pharmaceutically acceptable carrier, e.g., excipient, or vehicle diluent.

The active ingredient, i.e., compound, in such compositions typically comprises from 0.1 weight percent to 99.9 percent by weight of the composition, and often comprises from about 5 to 95 weight percent.

Thus, in one aspect of the invention, there is provided a composition comprising the compound of formula I and a pharmaceutically acceptable carrier. Preferably, the composition further comprises a compound having anti-HCV activity. As used herein, the term "anti-HCV activity" means the compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection. Often, the other compound having anti-HCV activity is effective to inhibit the function of target in the HCV life cycle other than the HCV NS3 protease protein.

In one preferred aspect, the compound having anti-HCV activity is an interferon. Preferably, the interferon is selected from the group consisting of interferon alpha 2B, pegylated interferon alpha, consensus interferon, interferon alpha 2A, lymphoblastiod interferon tau.

In another aspect of the invention, the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In one preferred aspect of the invention, the composition comprises a compound of the invention, an interferon and ribavirin.

In another preferred aspect of the invention, the compound having anti-HCV activity is a small molecule compound. As used herein, the term "small molecule compound" means a compound having a molecular weight of less than 1,500 daltons, preferably less than 1000 daltons. Preferably, the small molecule compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, inosine monophophate dehydrogenase ("IMPDH") and a nucleoside analog for the treatment of an HCV infection.

Certain illustrative HCV inhibitor compounds which can be administered with the compounds of the present invention include those disclosed in the following publications: WO 02/04425 A2 published Jan. 17, 2002, WO 03/007945 A1 published Jan. 30, 2003, WO 03/010141 A2 published Feb. 6, 2003, WO 03/010142 A2 published Feb. 6, 2003, WO 03/010143 A1 published Feb. 6, 2003, WO 03/000254 A1 published Jan. 3, 2003, WO 01/32153 A2 published May 10, 2001, WO 00/06529 published Feb. 10, 2000, WO 00/18231 published Apr. 6, 2000, WO 00/10573 published Mar. 2, 2000, WO 00/13708 published Mar. 16, 2000, WO 01/85172 A1 published Nov. 15, 2001, WO 03/037893 A1 published May 8, 2003, WO 03/037894 A1 published May 8, 2003, WO 03/037895 A1 published May 8, 2003, WO 02/100851 A2 published Dec. 19, 2002, WO 02/100846 A1 published Dec. 19, 2002, EP 1256628 A2 published Nov. 13, 2002, WO 99/01582 published Jan. 14, 1999, WO 00/09543 published Feb. 24, 2000.

Table 1 below lists some illustrative examples of compounds that can be administered with the compounds of this invention. The compounds of the invention can be administered with other anti-HCV activity compounds in combination therapy, either jointly or separately, or by combining the compounds into a composition.

TABLE 1

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/ immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/Eli Lilly and Co. Inc., Indianapolis, IN |

TABLE 1-continued

| Brand Name | Type of Inhibitor or Target | Source Company |
|---|---|---|
| Omniferon | natural IFN-α | Viragen Inc., Plantation, FL |
| XTL-002 | monoclonal antibody | XTL Biopharmaceuticals Ltd., Rehovot, Isreal |

The pharmaceutical compositions of this invention may be administered orally, parenterally or via an implanted reservoir. Oral administration or administration by injection are preferred. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intrasynovial, intrasternal, intrathecal, and intralesional injection or infusion techniques.

When orally administered, the pharmaceutical compositions of this invention may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Other suitable carriers for the above noted compositions can be found in standard pharmaceutical texts, e.g. in "Remington's Pharmaceutical Sciences", 19th ed., Mack Publishing Company, Easton, Pa., 1995.

The pharmaceutical compositions can be prepared by known procedures using well-known and readily available ingredients. The compositions of this invention may be formulated so as to provide quick, sustained or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like. Further details concerning the design and preparation of suitable delivery forms of the pharmaceutical compositions of the invention are known to those skilled in the art.

Dosage levels of between about 0.01 and about 1000 milligram per kilogram ("mg/kg") body weight per day, preferably between about 0.5 and about 250 mg/kg body weight per day of the compounds of the invention are typical in a monotherapy for the prevention and treatment of HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of the invention and one or more additional therapeutic or prophylactic agent, both the compound and the additional agent are usually present at dosage levels of between about 10 to 100%, and more preferably between about 10 and 80% of the dosage normally administered in a monotherapy regimen.

When these compounds or their pharmaceutically acceptable enantiomers, diastereomers, salts, solvates or prodrugs are formulated together with a pharmaceutically acceptable carrier, the resulting composition may be administered in vivo to mammals, such as man, to inhibit HCV NS3 protease or to treat or prevent HCV virus infection.

Accordingly, another aspect of this invention provides methods of inhibiting HCV NS3 protease activity in patients by administering a compound of the present invention or a pharmaceutically acceptable enantiomer, diastereomer, salt or solvate thereof.

In one aspect of the invention, there is provided a method of treating an HCV infection in a patient, comprising administering to the patient a therapeutically effective amount of the compound of the invention, or a pharmaceutically acceptable enantiomer, diastereomer, solvate, prodrug or salt thereof.

Preferably, the method of administering the compound is effective to inhibit the function of the HCV NS3 protease protein. In a preferred aspect, the method further comprises administering another compound having anti-HCV activity (as described above) prior to, after or concurrently with a compound of the invention.

The compounds of the invention may also be used as laboratory reagents. Compounds may be instrumental in providing research tools for designing of viral replication assays, validation of animal assay systems and structural biology studies to further enhance knowledge of the HCV disease mechanisms. Further, the compounds of the present invention are useful in establishing or determining the binding site of other antiviral compounds, for example, by competitive inhibition.

The compounds of this invention may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

Further, the compounds and compositions of the invention can be used for the manufacture of a medicament for treating HCV infection in a patient.

The present invention also provides processes for resolving a mixture of alkyl ester enantiomers comprising contacting the mixture with an enzyme effective to preferentially promote the hydrolysis of one of the enantiomers; characterized in that the contacting is conducted in the presence of a buffer. Such a mixture of alkyl ester enantiomers can result from the preparation of chemical precursor B, described above.

Preferably, the alkyl ester has the following Formula

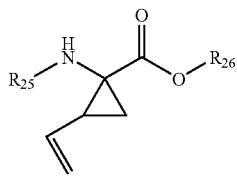

VIII wherein:

$R_{25}$ is an amino protecting group, such as, for example carbamates, e.g., BOC imines, or amides; and $R_{26}$ is selected from the group consisting of $C_{1-10}$ alkyl, $C_{6-14}$ aryl, $C_{7-16}$ alkylaryl, $C_{3-7}$ cycloalkyl or $C_{3-10}$ alkyl cycloalkyl.

The particular buffer used in the processes of the present invention is not critical. Typically, the buffer will have a pKa of ±1 of the pH at which the hydrolysis is conducted, e.g., pH from about 7.0 to 11. Thus, if the hydrolysis is conducted, e.g., at a pH of 8.0, a buffer with a pKa of from about 7.0 to 9.0 can be used. Preferred buffers are phosphates, borates and carbonates. Examples of suitable buffers include: 2-[(2-amino-2-oxoethyl)amino]ethanesulphonic acid, N-(2-acetamido)-2-iminodiacetic acid, n,n-bis(2-hydroxyethyl)glycine, 1,3-bis[tris(hydroxymethyl)methylamino]propane, o-Boric acid, carbonic acid, 2-(cyclohexylamino)ethanesulphonic acid, Diethylmalonic acid, Glycylglycine, N-2-hydroxyethylpiperazine-N'-2-ethanesulphonic acid (HEPES), N-2-hydroxyethylpiperazine-N'-3-propane-sulphonic acid, imidazole, 3-(N-morpholino)propanesulphonic acid, o-phosphoric acid, piperazine-N-N'-bis(2-ethanesulphonic acid), piperazine-1,4-bis(2-hydroxypropanesulfonic acid), 3-[tris(hydroxymethyl)methyl]amino propanesulphonic acid, 2-[tris(hydroxymothyl)methyl]amino ethanesulphonic acid, N-[tris(hydroxymethyl)methyl]glycine, and tris(hydroxylmethyl)aminomethane.

Any enzyme effective to preferentially hydrolyze the desired alkyl estes enantiomer can be used in accordance with the present invention. Proteases, lipases and esterases are often used for hydrolysis of carboxylic ester bonds. The enzymes suitable for use in accordance with the present invention, regardless of origin or purity, may be employed in the free state, either liquid or dry forms, or immobilized on a support such as, for example, by physical adsorption or entrapment. Examples of lipases include lipases from *Candida rugosa*, Wheat Germ, Porcine Pancreas, *Rhizopus arrhizus, Candida antarctica, Mucor miehei, Aspergillus niger, Pseudomonas* species, *Candida lipolytica, Humicola langinosa* and *Mucor javanicus*. Examples of esterase include pig liver esterase (PLE), horse liver esterase (HLE), acetylcholine esterase (ACE), cholesterol esterase, esterase from *Bacillus subtilis* (carboxyl esterase NP). Proteases are generally defined as hydrolases acting on peptide bonds as their natural substrates, but they are capable of cleaving a carboxylic ester bond since an ester bond is much weaker than a peptide (amide) bond. Examples of proteases include α-chymotrypsin, thermolysin, papain, proteases from *Aspergillus* sp., *Bacillus* sp., *Rhizopus* sp., *Penicillum* sp., *Streptomyces griseus*.

In the ester of Formula VIII, the chiral center in the acid moiety is fully substituted. This represents a difficult target for hydralitic enzymes since their natural substrates (such as natural amino acids) usually contain at least one α-hydrogen. Quite surprisingly, it was found in accordance with the present invention that certain proteases were highly effective for the enantioselective hydrolysis of ester VIII. Preferred proteases include proteases from strains selected from the group consisting of *Bacillus globigii, Bacillus licheniformis, Bacillus halodurans, Bacillus clausii* and *Aspergillus oryzae*. Examples of suitable enzymes include those selected from the group consisting of Alcalase® (subtilisin, alkaline protease, Novozymes North America Inc., Franklington, N.C.), Savinase® (substilisin, alkaline protease, Novozymes), ChiroCLEC™-BL (subtilisin, alkaline protease, Altus Biologics, Inc.), Protease N (subtilisin, alkaline protease, Amano) and Flavourzyme™ (fungal protease/peptidase, Novozymes). Further details of such enzymes are known in the art. Such enzymes are commercially available. These enzymes can be employed alone or used as mixtures thereof.

The ester hydrolysis leads to the release of an alcohol and a carboxylic acid, which can lower the pH significantly if no buffer is present. In accordance with the present invention, it has been found that including buffer in the reaction mixture can stabilize the pH in the course of hydrolysis, thus contributing to higher enzyme activity and stability.

Futhermore, by virtue of the present invention, it is possible to conduct the hydrolysis at elevated temperatures, preferably about 30 to 60° C., and for short time periods, preferably less than about seven days, more preferably from about two hours to three days.

EXAMPLES

The specific examples that follow illustrate the syntheses of the compounds of the present invention, and are not to be construed as limiting the scope of the claims which follow. The methods may be adapted to variations in order to produce compounds embraced by this invention but not specifically disclosed. Further, variations of the methods to produce the same compounds in somewhat different manner will also be evident to one skilled in the art.

Chemical abbreviations commonly used to identify chemical compounds disclosed herein include Bn: benzyl; Boc: tert-butyloxycarbonyl {Me₃COC(O)}; BSA: bovine serum albumin; CDI: carbonyldiimidazole; DBU: 1,8-diazabicyclo[5.4.0]-undec-7-ene; CH₂Cl₂=DCM: methylene chloride; TBME: tert-butyl methyl ether; DEAD: diethylazodicarboxylate; DIAD: diisopropylazodicarboxylate; DIEA: diisopropylethylamine; DIPEA: diisopropylethylamine; 4-DMAP: 4-dimethylaminopyridine; DCC: 1,3-dicyclohexylcarbodiimide; DMF: dimethylformamide; DMSO: dimethylsulfoxide; DPPA: diphenylphosphoryl azide; Et: ethyl; EtOH: ethanol; EtOAc: ethyl acetate; Et$_2$O: diethyl ether; Grubb's Catalyst: bis(tricyclohexylphosphine) benzylidene ruthenium (IV) dichloride; Grubb's 2$^{nd}$ Generation Catalyst: tricyclohexylphosphine[1,3-bis(2,4,6-trimethylphenyl)-4,5-dihydroimidazol-2-ylidene][benzylidene] ruthenium (IV) dichloride; HATU: [O-(7-azabenzotriazol-1-yl)-N,N,N',N'-tetramethyluronium hexafluorophosphate; HBTU: [O-(1H-benzotriazol-1-yl)-N,N,N',N'-tetramethyluronium hexafluorophosphate; HOBT, 1-hydroxybenzotriazole; HOAT, 1-hydroxy-7-azabenzotriazole; HPLC: high performance liquid chromatography; MS: mass spectrometry; Me: methyl; MeOH: methanol; NMM: N-methylmorpholine; NMP: N-methylpyrrolidine; Pr: propyl; PPA: polyphosphoric acid; TBAF: tetra-n-butylammonium fluoride; 1,2-DCE or DCE: 1,2-dichloroethane; TFA: trifluoroacetic acid; THF: tetrahydrofuran.

Solution percentages express a weight to volume relationship, and solution ratios express a volume to volume relationship, unless stated otherwise. Nuclear magnetic resonance (NMR) spectra were recorded either on a Bruker 300, 400 or 500 megahertz (MHz) spectrometer; the chemical shifts (δ) are reported in parts per million. Flash chromatography was carried out on silica gel (SiO$_2$) evident to one skilled in the art. All Liquid Chromatography (LC) data were recorded on a Shimadzu LC-10AS liquid chromatograph using a SPD-10AV UV-Vis detector and Mass Spectrometry (MS) data were determined with a Micromass Platform for LC in electrospray mode (ES+).

Unless otherwise noted, each compound was analyzed, by LC/MS, using one of three methodologies, having the following conditions.

Columns: Method A)—YMC Xterra ODS S7 micrometer ("μm") 3.0×50 millimeter ("mm") i.e., 3.0 mm diameter by 50 mm length.
Gradient: 100% Solvent A/0% Solvent B to
 0% Solvent A/100% Solvent B
Gradient time: 4 min (A)
Hold time: 1 min (A); 2 min
Flow rate: 4 mL/min
Detector Wavelength: 220 nanometer ("run")
Solvent A: 10% MeOH/90% H$_2$O/0.1% TFA
Solvent B: 10% H$_2$O/90% MeOH/0.1% TFA.
Columns: Method B)—YMC Xterra ODS S7 3.0×50 mm
 Gradient: 100%
 Solvent A/0% Solvent B to
 0% Solvent A/100% Solvent B
 Gradient time: 2 min
 Hold time: 1 min
Flow rate: 5 mL/min
Detector Wavelength: 220 run
Solvent A: 10% MeOH/90% H$_2$O/0.1% TFA
Solvent B: 10% H$_2$O/90% MeOH/0.1% TFA.
Columns: Method D)—YMC Xterra C18 5 μM 3.0×50 mm
 Gradient: 100% Solvent A/0% Solvent B to 0% Solvent
 A/100% Solvent B
Gradient time: 3 min
Hold time: 1 min
Flow rate: 5 mL/min
Detector Wavelength: 220 nm
Solvent A: 10% MeOH/90% H$_2$O/0.1% TFA
Solvent B: 10% H$_2$O/90% MeOH/0.1% TFA.
Unless otherwise noted, preparative HPLC was carried out under the following conditions.
Gradient time: 10 min
Hold time: 2 min
Flow rate: 25 mL/min
Detector wavelength: 220 nM
Solvent A: 10% MeOH/90% H$_2$O/0.1% TFA
Solvent B: 10% H$_2$O/90% MeOH/0.1% TFA The pure fractions were combined and 0.1N NaOH was used to bring the pH up to 7. The solution was concentrated in vacuo, and then the pH was carefully lowered to pH 3–4 using 0.1N HCl. The mixture was quickly extracted with ethyl acetate (3×). The combined extracts were dried (MgSO$_4$) and concentrated in vacuo to give the purified products.

The compounds and chemical intermediates of the present invention, described in the following examples, were prepared according to the following methods.

Example 1

Preparation of Representative Intermediates

Preparation of P2 Isoquinoline Intermediates for Incorporation into Compounds of Formula I Method A

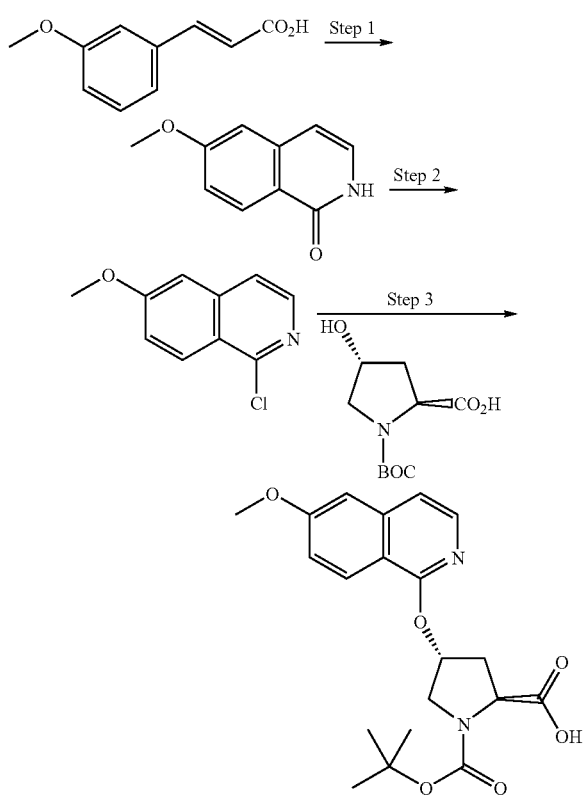

Step 1:
To a solution of 3-methoxy cinnamic acid (11.04 g, 62 mmol) and triethylamine (12.52 g, 124 mmol) in acetone (80 mL) was added ethyl chloroformate (approximately 1.5 equivalents) dropwise at 0° C. After stirring at this temperature for 1 h, aqueous NaN$_3$ (6.40 g, 100 mmol in 35 mL H$_2$O; appropriate precautions must be taken when using sodium azide) was added dropwise and the reaction mixture was stirred for 16 h at the ambient temperature. Water (100 mL) was added to the mixture and the volatile was removed in vacuo. The resulting slurry was extracted with toluene (3×50 mL) and the combined organic layers were dried over MgSO$_4$. This dried solution was added dropwise to a heated solution of diphenylmethane (50 mL) and tributylamine (30 mL) at 190° C. The toluene was distilled off as added. After complete addition, the reaction temperature was raised to 210° C. for 2 h. After cooling, the precipitated product was collected by filtration, washed with hexane (2×50 mL), and dried to yield the desired product as a white solid (5.53 g, 51%) (Nicolas Briet et al, Tetrahedron, 2002, 5761–5766).

LC-MS (retention time: 0.82 min, method B), MS m/z 176 (M$^+$+H).

An altenative procedure to the above employs diphenylphosphoryl azide for the conversion of the carboxylic acid to the corresponding acylazide. In a one pot procedure then the acid is converted to the corresponding quinolone. The process is described below for the prepapration of 4-methyl-2H-isoquinolin-1-one from 3-phenyl-but-2-enoic acid:

A solution of 3-phenyl-but-2-enoic acid (16.2 g), diphenylphosphoryl azide (27.5 g), and triethylamine (10.1 g) in benzene (100 mL) was stirred for 1 h. After filtration through a silica gel plug washing with benzene and concentration, the residue was dissolved in diphenylmethane (80 mL) and refluxed for 3 h. After cooling to rt, solids were collected through a plug washing with benzene and dried to give 10 g (63%) of the desired 4-methyl-2H-isoquinolin-1-one as a solid. $^1$H NMR (400 MHz, CD$_3$OD) δ ppm 2.30 (s, 3H), 7.00 (s, 1H), 7.54 (m, 1H), 7.77 (m, 2H), 8.33 (d, J=7.34 Hz, 1H).

Step 2:

6-Methoxy-2H-isoquinolin-1-one (5.0 g, 28.4 mmol) in POCl$_3$ (10 mL) was heated to gentle reflux for 3 h the evaporated in vacuo (Nicolas Briet et al, Tetrahedron, 2002, 5761–5766). The residue was poured into iced water (20 mL) and neutralized to pH 10 with 10 M NaOH. Extracted with CHCl$_3$. The organic layer was washed with brine, dried over MgSO$_4$, filtered, evaporated. The residue was purified by flash chromatography (1:1 hexane-EtOAc) to afford 4.41 g (80%) of the desired product as a white solid.

$^1$H NMR (CD$_3$OD) δ 3.98 (s, 3H), 7.34–7.38 (m, 2H), 7.69 (d, J=5.5 Hz, 1H), 8.10 (d, J=6.0 Hz, 1H), 8.23 (d, J=9.5 Hz, 1H);

LC-MS (retention time: 1.42 min, method B), MS m/z 194 (M$^+$+H).

Step 3:

To a solution of N-BOC-3-(R)-hydroxy-L-proline (892 mg, 3.89 mmol) in DMSO (40 mL) at the ambient temperature was added potassium tert-butoxide (1.34 g, 12.0 mmol) in one portion. The formed suspension was stirred at this temperature for 30 min before being cooled to 10° C. 1-chloro-6-methoxy-isoquinoline (example 11, Step 2) (785 mg, 4.05 mmol) was added as solid in one portion and the final mixture was stirred at the ambient temperature for 12 h. Quenched with iced 5% citric acid (aq), extracted with EtOAC (100 mL). The aqueous phase was extracted with EtOAC again. The combined organic layers were washed with 5% citric acid (aq) and brine respectively, dried over MgSO$_4$, filtered. The filtrate was evaporated in vacuo to dryness to yield 1.49 g (99%) of the desired product as an off-white foam. This material was used in the next step reaction as crude without further purification.

$^1$H NMR (CD$_3$OD) δ 1.42, 1.44 (rotamers, 9H), 2.38–2.43 (m, 1H), 2.66–2.72 (m, 1H), 3.80–3.87 (m, 2H), 3.92 (s, 3H), 4.44–4.52 (m, 1H), 5.73 (b, 1H), 7.16–7.18 (m, 2H), 7.24–7.25 (m, 1H), 7.87–7.88 (m, 1H), 8.07 (d, J=8.5 Hz, 1H);

LC-MS (retention time: 1.62 min, method B), MS m/z 389 (M$^+$+H).

The following intermediates were prepared as described herein and can be incorporated into compounds of Formula I

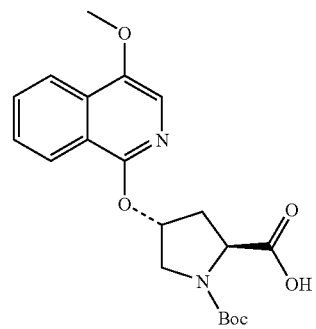

Step 1:

Modifications: 15 g 3-methoxy-3-phenyl-acrylic acid used, 250 mg product obtained (2% yield).

Product:

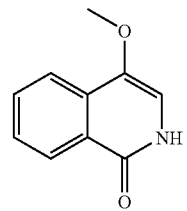

$^1$H NMR (400 MHz, CD$_3$COCD$_3$) δ ppm 3.85 (s, 3H), 6.96 (s, 1H), 7.54 (m, 1H), 7.71 (m, 1H), 7.86 (d, J=8.07 Hz, 1H), 8.31 (d, J=8.07 Hz, 1H).

Step 2:

Modifications: 200 mg 4-methoxy-2H-isoquinolin-1-one used, 150 mg product obtained (68% yield).

Product:

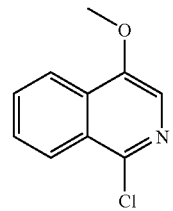

$^1$H NMR (400 MHz, CDCl$_3$) δ ppm 4.05 (s, 2H), 7.71 (m, 1H), 7.72 (m, 2H), 7.80 (s, 1H), 8.23 (dd, J=18.71, 7.70 Hz, 2H).

Step 3:

Modifications: 122 mg 1-chloro-4-methoxy-isoquinoline used, 218 mg product obtained (89% yield).

Product:

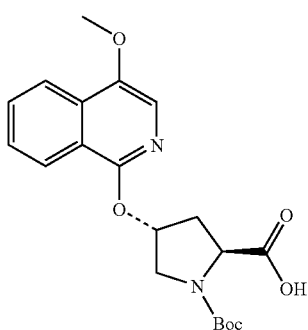

MS: (M+Na)⁺ 411.

The following intermediates were prepared as described herein and can be incorporated into compounds of Formula I

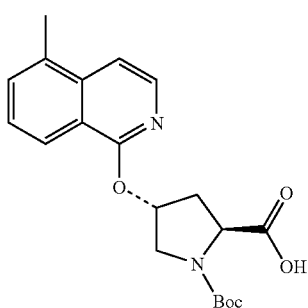

Step 1:

Modifications: 20 g 2-methylcinnamic acid used, 14.3 g product obtained (72% yield)

Product:

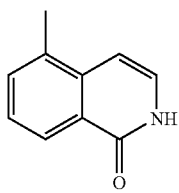

Data: ¹H NMR (400 MHz, CD₃OD) δ ppm 2.54 (s, 1H), 6.69 (d, J=7.3 Hz, 1H), 7.23 (d, J=7.3 Hz, 1H), 7.39 (t, J=7.8 Hz, 1H), 7.50 (d, J=7.1 Hz, 1H), 8.30 (d, J=8.1 Hz, 1H), 11.62 (s, 1H); MS: (M+H)⁺ 160.

Step 2:

Modifications: 14.4 g 5-methyl-2H-isoquinolin-1-one used, 10.6 g product obtained (66% yield).

Product:

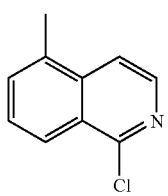

Data: ¹H NMR (400 MHz, CDCl₃) δ ppm 2.67 (s, 3H), 7.55 (m, 2H), 7.70 (dd, J=5.9, 1.0 Hz, 1H), 8.19 (m, 1H), 8.28 (d, J=5.9 Hz, 1H); MS: (M+H)⁺ 178.

Step 3:

Modifications: 533 mg 1-chloro-5-methyl-isoquinoline used, 1116 mg product obtained (100% yield).

Product:

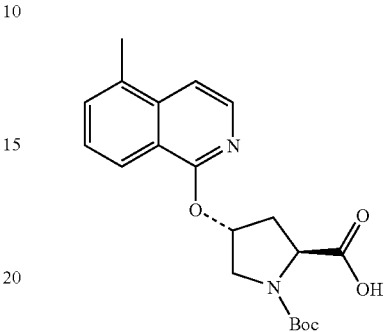

Data: MS: (M+H)⁺ 373.

The following intermediates were prepared as described herein and can be incorporated into compounds of Formula I

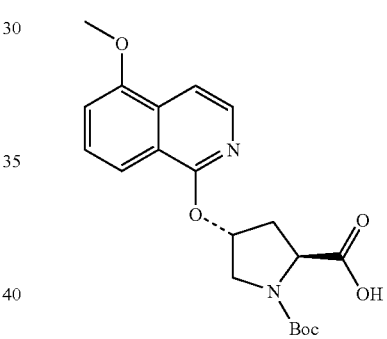

Step 1:

Modifications: 10 g 2-methoxy cinnamic acid used, 5.3 g product obtained (53% yield).

Product:

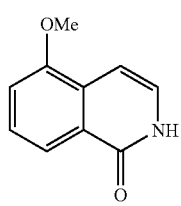

Data: ¹H NMR (400 MHz, CD₃OD) δ ppm 3.95 (s, 3H), 6.94 (d, J=7.3 Hz, 1H), 7.08 (d, J=8.1 Hz, 1H), 7.14 (d, J=7.3 Hz, 1H), 7.43 (t, J=8.1 Hz, 1H), 7.99 (d, J=8.1 Hz, 1H), 10.92 (s, 1H); MS: (M+H)⁺ 176.

Step 2:

Modifications: 5.3 g 5-methoxy-2H-isoquinolin-1-one used, 5.38 g product obtained (92% yield).

Product:

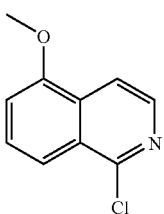

Data: $^1$H NMR (400 MHz, CDCl$_3$) δ ppm 4.01 (s, 3H), 7.04 (d, J=7.8 Hz, 1H), 7.57 (t, J=8.1 Hz, 1H), 7.88 (d, J=8.6 Hz, 1H), 7.97 (d, J=5.9 Hz, 1H), 8.25 (d, J=5.9 Hz, 1H); MS: (M+H)$^+$ 194.

Step 3:
Modifications: 581 mg 1-chloro-5-methoxy-isoquinoline used, 1163 mg product obtained (100% yield).

Product:

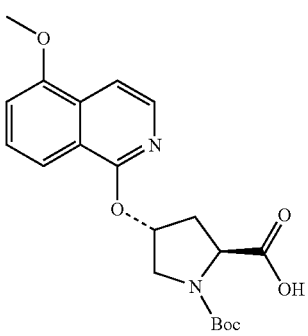

Data: MS: (M+H)$^+$ 389.

The following intermediates were prepared as described herein and can be incorporated into compounds of Formula I

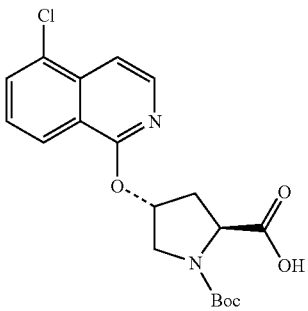

Step 1:
Modifications: 25 g 2-chlorocinnamic acid used, 14.6 g product obtained (59% yield).

Product:

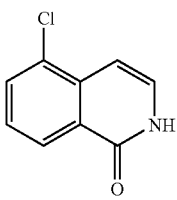

Data: $^1$H NMR (400 MHz, CD$_3$OD) δ ppm 7.22 (d, J=7.3 Hz, 1H), 7.42 (t, J=7.8 Hz, 1H), 7.73 (d, J=7.8 Hz, 1H), 8.34 (d, J=8.1 Hz, 1H), 10.61 (s, 1H); MS: (M+H)$^+$ 180.

Step 2:
Modifications: 14.2 g 5-chloro-2H-isoquinolin-1-one used, 8.28 g product obtained (53% yield).

Product:

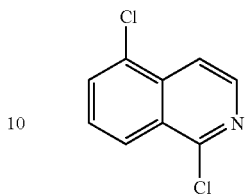

Data: $^1$H NMR (400 MHz, CDCl$_3$) δ ppm 7.60 (dd, J=8.6, 7.6 Hz, 1H), 7.83 (m, 1H), 8.00 (d, J=5.9 Hz, 1H), 8.29 (dt, J=8.9, 1.0 Hz, 1H), 8.38 (d, J=5.9 Hz, 1H); MS: (M+H)$^+$ 198.

Step 3:
Modifications: 594 mg 1,5-dichloro-isoquinoline used, 1174 mg product obtained (100% yield).

Product:

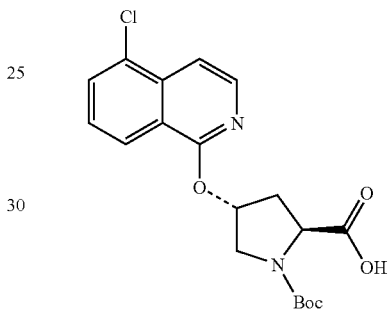

Data: MS: (M+H)$^+$ 393.

The following intermediates were prepared as described herein and can be incorporated into compounds of Formula I

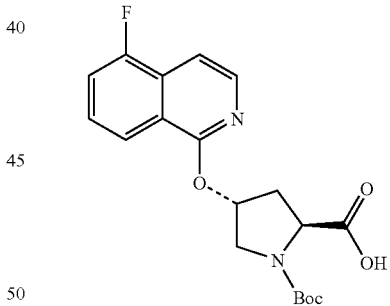

Step 1:
Modifications: 16.6 g 2-fluorocinnamic acid used, 8.55 g product obtained (51% yield).

Product:

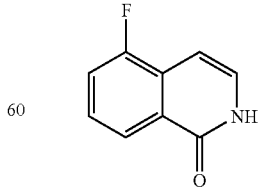

Data: $^1$H NMR (400 MHz, CD$_3$COCD$_3$) δ ppm 6.62 (d, J=7.3 Hz, 1H), 7.32 (d, J=7.3 Hz, 1H), 7.47 (m, 2H), 8.09 (m, 1H).

Step 2:

Modifications: 8.4 g 5-fluoro-2H-isoquinolin-1-one used, 7.5 g product obtained (80% yield).

Product:

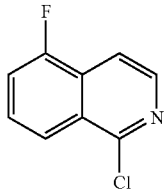

Data: ¹H NMR (400 MHz, CDCl₃) δ ppm 7.43 (ddd, J=9.7, 7.8, 0.9 Hz, 1H), 7.62 (td, J=8.2, 5.4 Hz, 1H), 7.84 (d, J=5.6 Hz, 1H), 8.14 (d, J=8.6 Hz, 1H), 8.33 (d, J=5.9 Hz, 1H); MS: (M+H)⁺ 182.

Step 3:

Modifications: 203 mg 1-chloro-5-fluoro-isoquinoline used, 384 mg product obtained (90% yield).

Product:

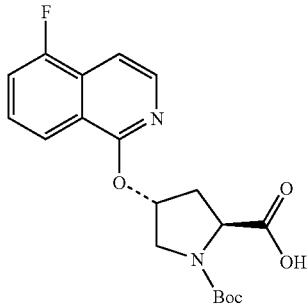

Data: ¹H NMR (400 MHz, CD₃SOCD₃) δ ppm 1.34, 1.36 (2s, 9H, rotamers), 2.35 (m, 1H), 2.61 (m, 1H), 3.65 (d, J=12.23 Hz, 1H), 3.80 (m, 1H), 4.35 (m, 1H), 5.70 (s, 1H), 7.48 (d, J=6.11 Hz, 1H), 7.63 (m, 2H), 7.99 (m, 1H), 8.10 (d, J=5.87 Hz, 1H); MS: (M+Na)⁺ 399.

The following intermediates were prepared as described herein and can be incorporated into compounds of Formula I

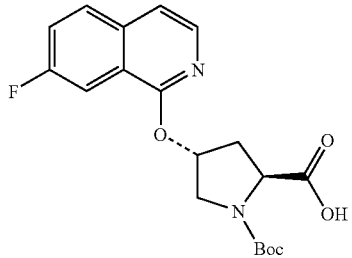

Step 1:

Modifications: 16.6 g 4-fluorocinnamic acid used, 8.2 g product obtained (49% yield).

Product:

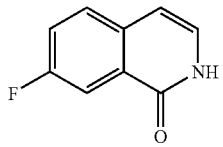

Data: ¹H NMR (400 MHz, CD₃COCD₃) δ ppm 6.57 (d, J=7.09 Hz, 1H), 7.21 (d, J=7.09 Hz, 1H), 7.50 (m, 1H), 7.72 (dd, J=8.68, 5.26 Hz, 1H), 7.90 (dd, J=9.54, 2.93 Hz, 1H).

Step 2:

Modifications: 8.15 g 7-fluoro-2H-isoquinolin-1-one used, 7.6 g product obtained (84% yield).

Product:

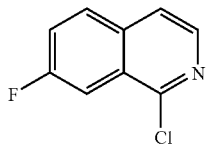

Data: ¹H NMR (400 MHz, CDCl₃) δ ppm 7.52 (td, J=8.6, 2.6 Hz, 1H), 7.59 (d, J=5.6 Hz, 1H), 7.86 (dd, J=9.1, 5.4 Hz, 1H), 7.95 (dd, J=9.5, 2.5 Hz, 1H), 8.26 (d, J=5.6 Hz, 1H); MS: (M+H)⁺ 182.

Step 3:

Modifications: 191 mg 1-chloro-7-fluoro-isoquinoline used, 350 mg product obtained (93% yield).

Product:

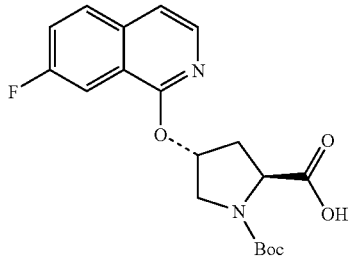

Data: MS: (M+Na)⁺ 399.

The following intermediates were prepared as described herein and can be incorporated into compounds of Formula I

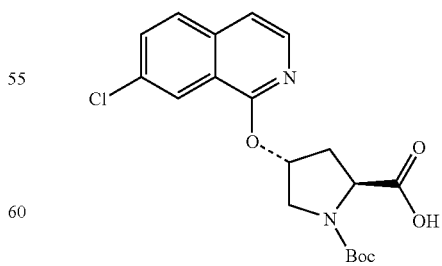

Step 1:

Modifications: 9.13 g 4-chlorocinnamic acid used, 4 g product obtained (44% yield).

Product:

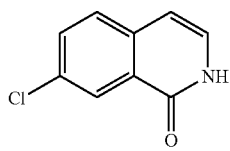

Data: ¹H NMR (400 MHz, CD₃SOCD₃) δ ppm 6.58 (d, J=7.1 Hz, 1H), 7.20 (dd, J=7.1, 5.9 Hz, 1H), 7.72 (m, 2H), 8.10 (m, 1H).

Step 2:

Modifications: 3.5 g 7-chloro-2H-isoquinolin-1-one used, 2.8 g product obtained (72% yield).

Product:

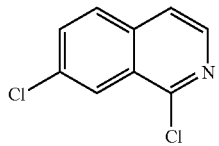

Data: ¹H NMR (500 MHz, CDCl₃) δ ppm 7.59 (d, J=5.5 Hz, 1H), 7.69 (dd, J=8.9, 2.1 Hz, 1H), 7.80 (d, J=8.6 Hz, 1H), 8.29 (d, J=5.5 Hz, 1H), 8.34 (s, 1H); MS: (M+H)⁺ 198.

Step 3:

Modifications: 208 mg 1,7-dichloro-isoquinoline used, 350 mg product obtained (89% yield).

Product:

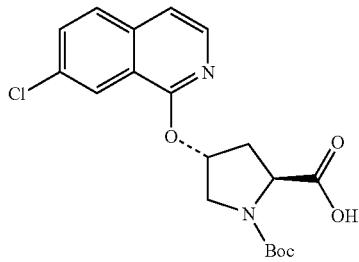

Data: MS: (M+Na)⁺ 415.

The following intermediates were prepared as described herein and can be incorporated into compounds of Formula I

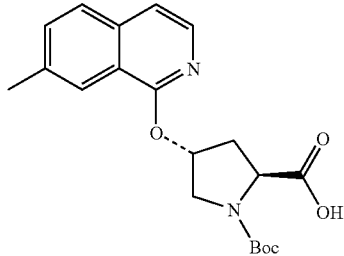

Step 1:

Modifications: 25 g 4-methylcinnamic acid used, 15.3 g product obtained (62% yield).

Product:

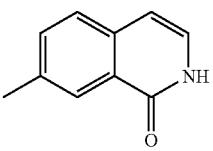

Data: ¹H NMR (400 MHz, CD₃OD) δ ppm 2.50 (s, 3H), 6.54 (d, J=7.1 Hz, 1H), 7.13 (d, J=7.1 Hz, 1H), 7.49 (m, 2H), 8.22 (s, 1H), 11.49 (s, 1H); MS: (M+H)⁺ 160.

Step 2:

Modifications: 15.3 g 7-methyl-2H-isoquinolin-1-one used, 5.15 g product obtained (30% yield).

Product:

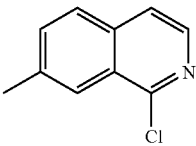

Data: ¹H NMR (400 MHz, CDCl₃) δ ppm 2.58 (s, 3H), 7.56 (m, 2H), 7.73 (d, J=8.3 Hz, 1H), 8.09 (s, 1H), 8.20 (d, J=5.6 Hz, 1H); MS: (M+H)⁺ 178.

Step 3:

Modifications: 205 mg 1-chloro-7-methyl-isoquinoline used, 350 mg product obtained (89% yield).

Product:

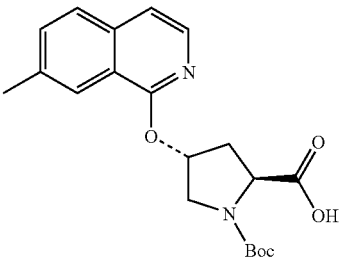

Data: MS: (M+H)⁺ 373.

The following intermediates were prepared as described herein and can be incorporated into compounds of Formula I

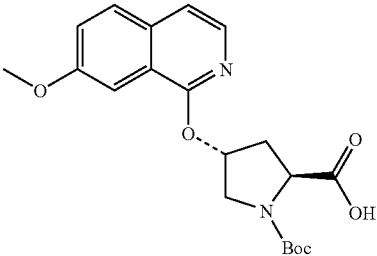

Step 1:

Modifications: 33 g using 4-methoxycinnamic acid used, 7 g product obtained (33% yield).

Product:

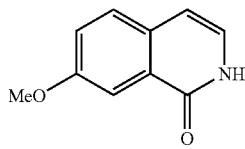

Data: ¹H NMR (500 MHz, CD₃COCD₃) δ ppm 3.90 (s, 3H), 6.49 (d, J=7.0 Hz, 1H), 7.10 (d, J=7.3 Hz, 1H), 7.28 (dd, J=8.6, 2.8 Hz, 1H), 7.57 (d, J=8.9 Hz, 1H), 7.71 (d, J=2.8 Hz, 1H).

Step 2:

Modifications: 4 g 7-methoxy-2H-isoquinolin-1-one used, 3 g product obtained (68% yield).

Product:

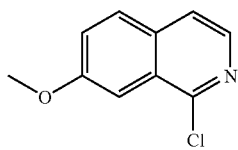

Data: ¹H NMR (400 MHz, CDCl₃) δ ppm 3.98 (s, 3H), 7.38 (dd, J=8.9, 2.6 Hz, 1H), 7.52 (m, 2H), 7.73 (d, J=8.8 Hz, 1H), 8.16 (d, J=5.4 Hz, 1H).

Step 3:

Modifications: 533 mg 1-chloro-7-methoxy-isoquinoline used, 1115 mg product obtained (100% yield).

Product:

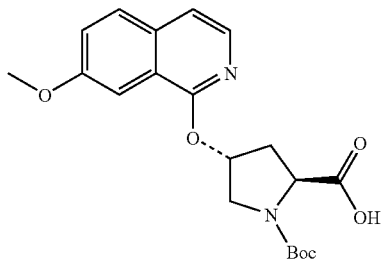

The following intermediates were prepared as described herein and can be incorporated into compounds of Formula I

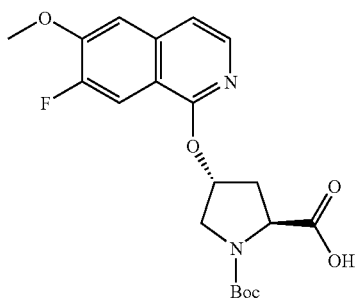

Step 1:

Modifications: 19.6 g 4-fluoro-3-methoxycinnamic acid used, 9.5 g product obtained (48% yield).

Product:

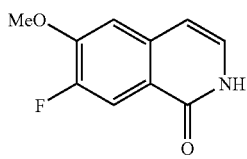

Data: ¹H NMR (400 MHz, CD₃COCD₃) δ ppm 4.00 (s, 1H), 6.49 (d, J=7.34 Hz, 1H), 7.19 (d, J=7.09 Hz, 1H), 7.29 (d, J=8.07 Hz, 1H), 7.86 (d, J=11.74 Hz, 1H).

Step 2:

Modifications: 9 g 7-fluoro-6-methoxy-2H-isoquinolin-1-one used, 7 g product obtained (70% yield).

Product:

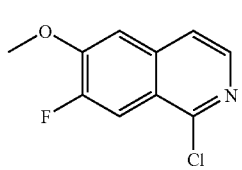

Data: ¹H NMR (400 MHz, CDCl₃) δ ppm 4.04 (s, 3H), 7.17 (d, J=8.07 Hz, 1H), 7.48 (d, J=5.62 Hz, 1H), 7.94 (d, J=11.49 Hz, 1H), 8.20 (d, J=5.62 Hz, 1H).

Step 3:

Modifications: 222 mg 1-chloro-7-fluoro-6-methoxy-isoquinoline used, 406 mg products obtained.

Products:

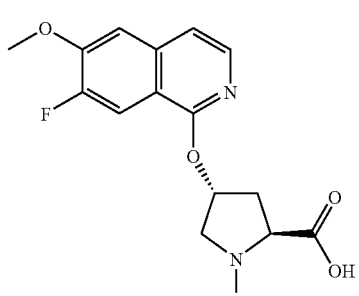

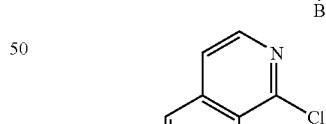

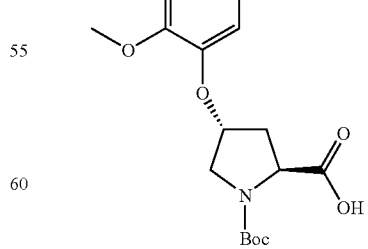

The following intermediates were prepared as described herein and can be incorporated into compounds of Formula I

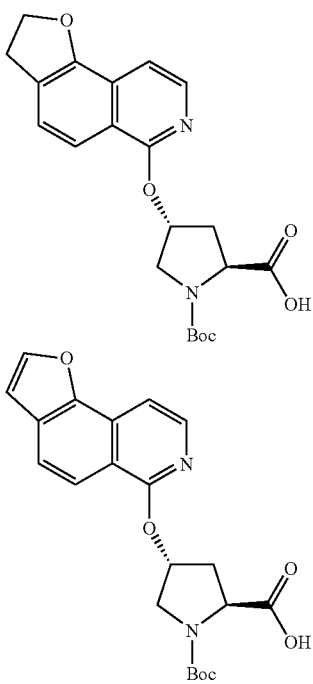

Step 1:
Modifications: 3.8 g 3-(2,3-dihydro-benzofuran-7-yl)-acrylic acid used, 2 g product obtained (53% yield).

Product:

Data: $^1$H NMR (400 MHz, CD$_3$OD) δ ppm 3.37 (t, J=9.05 Hz, 1H), 4.73 (t, J=9.05 Hz, 2H), 6.67 (d, J=7.09 Hz, 1H), 7.10 (d, J=7.09 Hz, 1H), 7.37 (d, J=8.07 Hz, 1H), 7.81 (d, J=8.07 Hz, 1H); MS: (M+H)$^+$ 188.

Step 2:
Modifications: 1.87 g 2,3-dihydro-7H-furo[2,3-f]isoquinolin-6-one used, 1.84 g product obtained (90% yield).

Product:

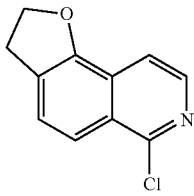

Data: $^1$H NMR (400 Hz, CDCl$_3$) δ ppm 3.43 (t, J=9.05 Hz, 2H), 4.82 (t, J=9.05 Hz, 2H), 7.52 (d, J=8.56 Hz, 1H), 7.66 (d, J=5.62 Hz, 1H), 7.84 (d, J=8.31 Hz, 1H), 8.19 (d, J=5.62 Hz, 1H); MS (M+H)$^+$ 206.

Step 3:
Modifications: 206 mg 6-chloro-2,3-dihydro-furo[2,3-f]isoquinoline used, 300 mg products mixture obtained.

Products:

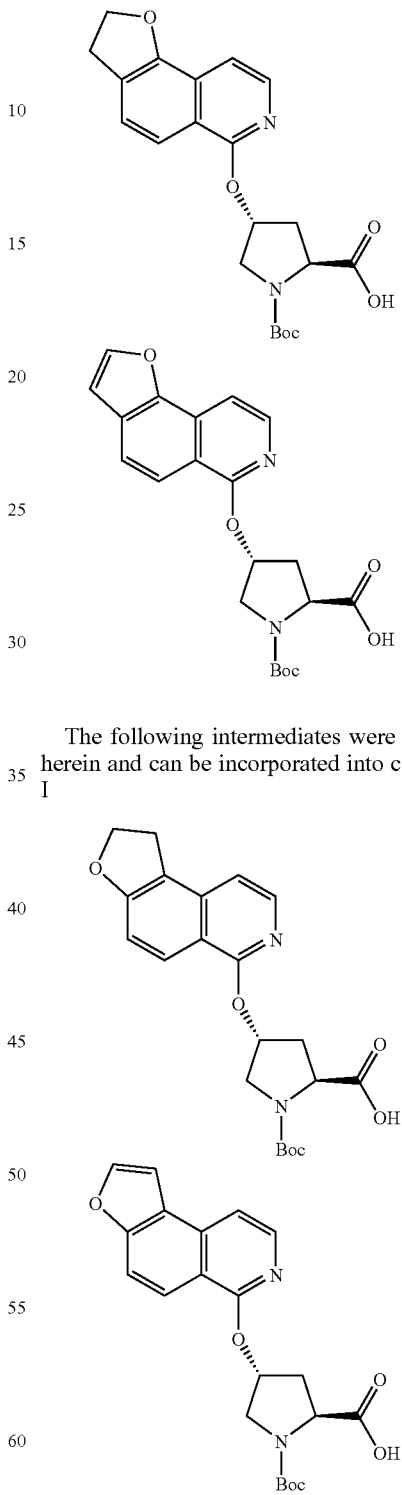

The following intermediates were prepared as described herein and can be incorporated into compounds of Formula I

Step 1:
Modifications: 1.14 g 3-(2,3-dihydro-benzofuran-4-yl)-acrylic acid used, 600 mg product obtained (52% yield).

Product:

Data: ¹H NMR (400 MHz, CD₃OD) δ ppm 3.35 (t, J=8.93 Hz, 2H), 4.74 (t, J=8.93 Hz, 2H), 6.49 (d, J=7.09 Hz, 1H), 6.95 (d, J=8.56 Hz, 1H), 7.25 (d, J=7.09 Hz, 1H), 8.13 (d, J=8.80 Hz, 1H); MS (M+H)⁺ 188.

Step 2:
Modifications: 560 mg 1,7-dihydro-2H-furo[3,2-f]isoquinolin-6-one used, 380 mg product obtained (48% yield).

Product:

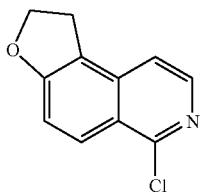

Data: ¹H NMR (400 Hz, CDCl₃) δ ppm 3.47 (t, J=9.05 Hz, 2H), 4.84 (t, J=9.05 Hz, 2H), 7.24 (d, J=8.56 Hz, 1H), 7.33 (d, J=5.87 Hz, 1H), 8.20 (m, 2H); MS (M+H)⁺ 206.

Step 3:
Modifications: 105 mg 6-chloro-1,2-dihydro-furo[3,2-f]isoquinoline used, 390 mg products mixture obtained.

Products:

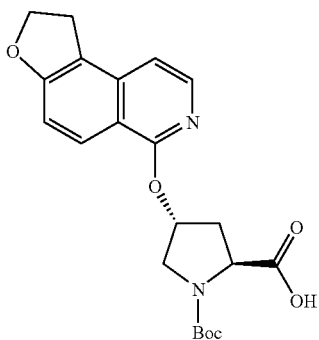

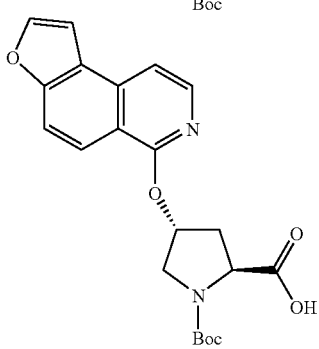

The following intermediates were prepared as described herein and can be incorporated into compounds of Formula I

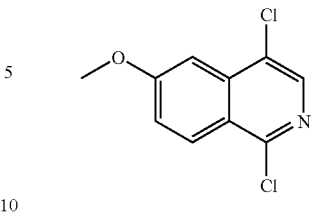

Step 1:
Modifications: A mixture of 6-methoxy-2H-isoquinolin-1-one (700 mg) and NCS (532 mg) in MeCN (10 mL) was refluxed for 3 h. Filtration gave 600 mg (72%) of the desired product as a solid.

Product:

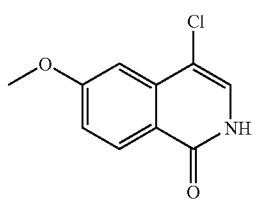

Data: ¹H NMR (400 MHz, CD₃OD) δ ppm 3.96 (s, 1H), 7.19 (dd, J=8.80, 2.45 Hz, 1H), 7.28 (d, J=2.45 Hz, 1H), 7.34 (s, 1H), 8.25 (d, J=9.05 Hz, 1H); MS: (M+H)⁺ 210.

Step 2:
Modifications: 500 mg 4-chloro-6-methoxy-2H-isoquinolin-1-one used, 400 mg product obtained.

Product:

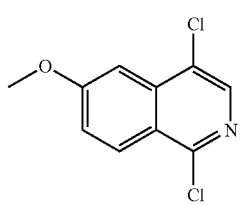

Data: ¹H NMR (400 Hz, CDCl₃) δ ppm 4.01 (s, 3H), 7.35 (d, J=2.45 Hz, 1H), 7.41 (d, J=2.45 Hz, 1H), 8.24 (d, J=9.29 Hz, 1H), 8.27 (s, 1H); MS: (M+H)⁺ 229.

Method B

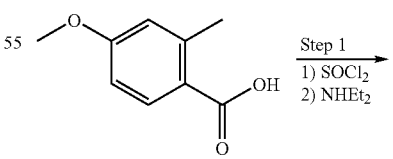

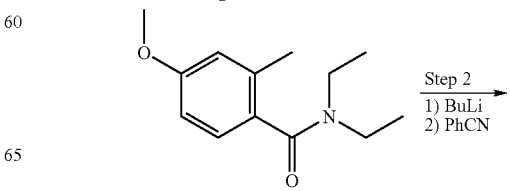

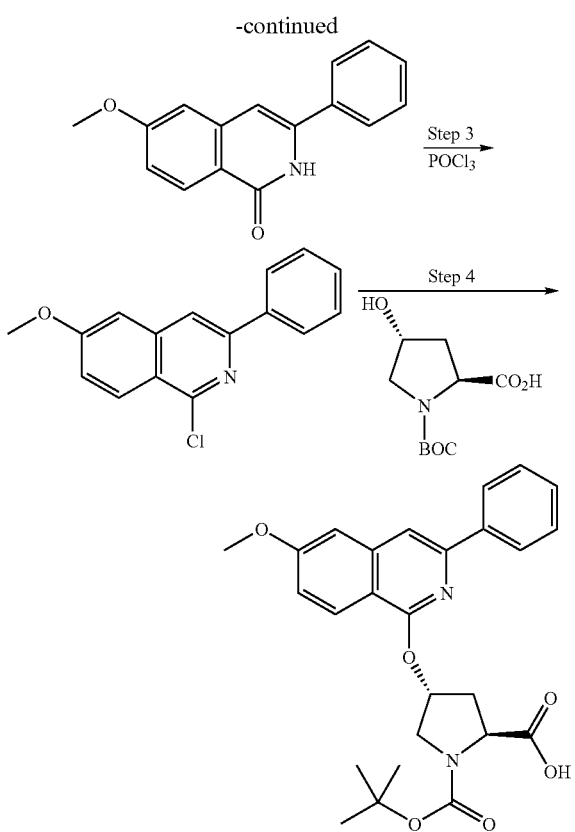

Step 1:

A mixture of 4-methoxy-2-methyl-benzoic acid (5.00 g, 30.1 mmol) and thionyl chloride (20.0 g, 0.17 mol) was heated to reflux for 30 min. Removed the volatile in vacuo. After pumping overnight, the viscous oily acid chloride was used as crude for the next reaction without any purification.

To a solution of 4-methoxy-2-methyl-benzoyl chloride in CH₂Cl₂ (60 mL) at 0° C. was added diethylamine dropwise. The formed mixture was allowed to warm up to the ambient temperature for 2 h with stirring. Removed the volatiles in vacuo. The residue was triturated with EtOAc (100 mL) and filtered. The filtrate was washed with 1M HCl, 1M NaOH and brine, dried over MgSO₄. Evaporation of the solvent yielded 6.51 g (98%) of the desired product as a viscous oil.

LC-MS (retention time: 1.20 min, method B), MS m/z 222 (M⁺+H).

Step 2:

To a solution of N,N-diethyl-4-methoxy-2-methyl-benzamide (221 mg, 1.0 mmol) in THF (2 mL) at −78° C. was added n-BuLi (0.84 mL of 2.5 M in hexane, 2.10 mmol) dropwise. The formed orange solution was kept at this temperature for additional 30 min before dropwise addition of benzonitrile (103 mg, 1.0 mmol). The final solution was allowed to warm up to the ambient temperature over night with stirring. Quenched with iced 5% citric acid. Filtered, washed with water, dried. Trituration with 2:1 hexane-EtOAc (5 mL) yielded 205 mg (82%) of the desired product as a white solid.

¹H NMR (d₆-DMSO) δ 3.89 (s, 3H), 6.84 (s, 1H), 7.05–7.07 (m, 1H), 7.18 (d, J=2.5 Hz, 1H), 7.44–7.51 (m, 3H), 7.78 (d, J=7.0 Hz, 1H), 8.11 (d, J=9.0 Hz, 1H); LC-MS (retention time: 1.20 min, method B), MS m/z 252 (M⁺+H).

Step 3:

This product, 1-chloro-6-methoxy-3-phenyl-isoquinoline, was prepared by the same method as described above except using 6-methoxy-3-phenyl-2H-isoquinolin-1-one instead.

¹H NMR (CDCl₃) δ 3.97 (s, 3H), 7.12 (d, J=2.5 Hz, 1H), 7.23–7.26 (m, 1H), 7.40–7.42 (m, 1H), 7.46–7.50 (m, 2H), 7.89 (s, 1H), 8.08 (d, J=7.0 Hz, 2H), 8.21 (d, J=9.0 Hz, 1H); LC-MS (retention time: 1.90 min, method B), MS m/z 270, 271 (M⁺+H).

The following intermediates were prepared as described herein and can be incorporated into compounds of Formula I

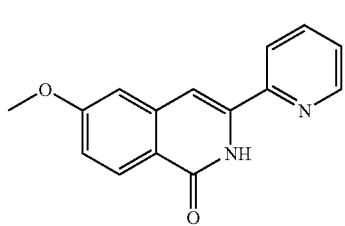

To a solution of N,N-Diethyl-4-methoxy-2-methyl-benzamide (332 mg, 1.5 mmol) in THF (15 mL) at −78° C., t-BuLi (1.7 M solution in pentane, 1.3 mL, 2.25 mmol) was added. The resulting red solution was stirred at −78° C. for 10 min, then 2-cyanopyridine (156 mg, 1.5 mmol) was added. The reaction mixture was then warmed to rt and stirred for overnight. The reaction was quenched with saturated NH₄Cl solution and extracted with ethyl acetate twice. The combined organic layers were dried (MgSO₄) and concentrated. The crude product was purified by Prep. HPLC to give yellowish solid as TFA salt. (85 mg, 15% yield)

¹H NMR (400 MHz, CD₃OD) δ 3.91 (m, 3H), 7.09 (dd, J=9.05, 2.45 Hz, 1H), 7.17 (d, J=2.45 Hz, 1H), 7.37 (s, 1H), 7.42 (m, 1H), 7.92 (m, 1H), 8.08 (d, J=8.07 Hz, 1H), 8.18 (d, J=9.05 Hz, 1H), 8.65 (d, J=4.89 Hz, 1H).

LC-MS (retention time: 2.14 min.), MS m/z 253 (MH⁺).

Step 2 (Scheme 3, Step 1):

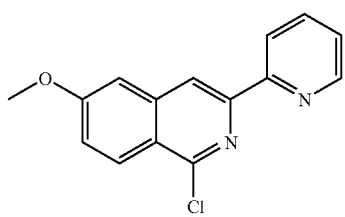

6-Methoxy-3-pyridin-2-yl-2H-isoquinolin-1-one TFA salt (85 mg, 0.232 mmol) was heated under reflux with POCl₃ (3.0 mL) for 2 days. Then POCl₃ was distilled off and the residue was quenched with ice. It was then neutralized with 10 N NaOH solution and the brown solid was collected as pure product. (62 mg, 99% yield)

LC-MS (retention time: 2.063 min.), MS m/z 271 (MH⁺).

The following intermediates were prepared as described herein and can be incorporated into compounds of Formula I

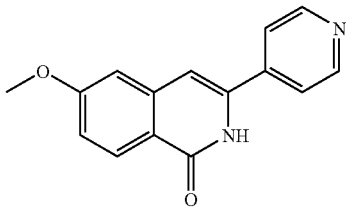

To a solution of N,N-Diethyl-4-methoxy-2-methyl-benzamide (332 mg, 1.5 mmol) in THF (15 mL) at −78° C., t-BuLi (1.7 M solution in pentane, 1.3 mL, 2.25 mmol) was added. The resulting red solution was stirred at −78° C. for 10 min, then 4-cyanopyridine (164 mg, 1.575 mmol) was added. The reaction mixture was then warmed to rt and stirred for overnight. The reaction was quenched with saturated NH$_4$Cl solution and the yellow precipitate was collected as pure product. (145 mg, 38% yield)

$^1$H NMR(CD$_3$OD, 400 MHz) δ 3.91 (s, 3H), 7.18 (dd, J=8.8 Hz, 2.8 Hz, 1H), 7.26 (m, 2H), 8.06 (d, J=6.0 Hz, 2H), 8.16 (d, J=8.8 Hz, 1H), 8.84 (d, J=6.0 Hz, 2H).

LC-MS (retention time: 1.300 min.), MS m/z 253 (MH$^+$).

Step 2 (Scheme 3, Step 1):

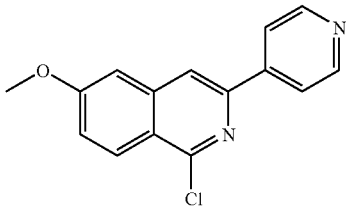

6-Methoxy-3-pyridin-4-yl-2H-isoquinolin-1-one (134 mg, 0.531 mmol) was heated under reflux with POCl$_3$ (6.0 mL) for 5 days. Then POCl$_3$ was distilled off and the residue was quenched with ice. It was then neutralized with saturated NaHCO$_3$ solution and the brown solid was collected as pure product. (125 mg, 87% yield)

$^1$H NMR (DMSO-d$_6$, 400 MHz) δ 3.99 (s, 3H), 7.53 (dd, J=9.04 Hz, 2.44 Hz, 1H), 7.59 (d, J=2.69 Hz, 1H), 8.26 (d, J=9.05 Hz, 1H), 8.30 (d, J=5.38 Hz, 2H), 8.73 (s, 1H), 8.85 (d, J=6.36 Hz, 2H).

LC-MS (retention time: 2.027 min.), MS m/z 271 (MH$^+$).

The following intermediates were prepared as described herein and can be incorporated into compounds of Formula I

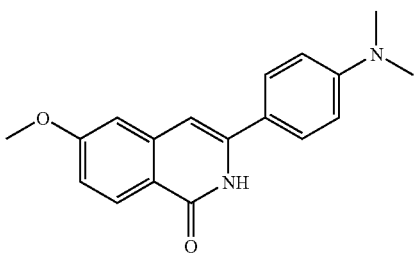

To a solution of N,N-Diethyl-4-methoxy-2-methyl-benzamide (332 mg, 1.5 mmol) in THF (15 mL) at −78° C., t-BuLi (1.7 M solution in pentane, 1.3 mL, 2.25 mmol) was added. The resulting red solution was stirred at −78° C. for 10 min, then 4-dimethylamino benzonitrile (219 mg, 1.5 mmol) was added. The reaction mixture was then warmed to rt and stirred for overnight. The reaction was quenched with saturated NH$_4$Cl solution and the yellow precipitate was collected and triturated with ether to give an off-white solid as pure product. (247 mg, 56% yield)

$^1$H NMR (DMSO-d$^6$, 400 MHz) δ 2.97 (s, 6H), 3.87 (s, 3H), 6.72 (s, 1H), 6.78 (d, J=8.80 Hz, 2H), 6.97 (dd, J=8.80, 2.45 Hz, 1H), 7.10 (d, J=2.45 Hz, 1H), 7.65 (d, J=8.80 Hz, 2H), 8.05 (d, J=8.80 Hz, 1H), 11.11 (s, 1H).

LC-MS (retention time: 2.023 min.), MS m/z 295 (MH$^+$).

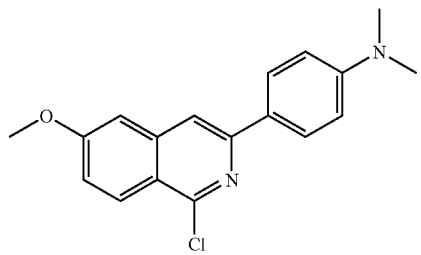

3-(4-Dimethylamino-phenyl)-6-methoxy-2H-isoquinolin-1-one (245 mg, 0.83 mmol) was heated under reflux with POCl$_3$ (10.0 mL) for 2 days. Then POCl$_3$ was distilled off and the residue was quenched with ice. It was then neutralized with 10 N NaOH solution and extracted with ethyl acetate twice. The organic layers were combined and dried (MgSO4). Evaporation of solvent gave an orange solid as product (215 mg, 83% yield)

$^1$H NMR (400 MHz, CD$_3$OD) δ 3.01 (s, 6H), 3.96 (s, 3H), 6.88 (d, J=9.05 Hz, 2H), 7.20 (dd, J=9.17, 2.57 Hz, 1H), 7.28 (d, J=2.45 Hz, 1H), 7.94 (s, 1H), 7.96 (d, J=9.05 Hz, 2H), 8.13 (d, J=9.29 Hz, 1H).

LC-MS (retention time: 2.543 min.), MS m/z 313 (MH$^+$).

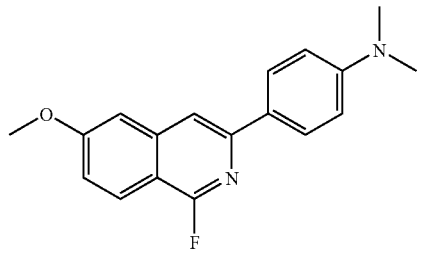

A mixture of [4-(1-Chloro-6-methoxy-isoquinolin-3-yl)-phenyl]-dimethyl-amine (110 mg, 0.35 mmol) and tetrabutyl phosphonium hydrogen difluoride (0.5 g) was heated at 140° C. in Smith microwave reactor for 20 min. Then it was added water and extracted with ethyl acetate. The organic layer was separated, washed with water and dried (MgSO$_4$). Evaporation of solvent gave a brownish solid as product. (85 mg, 82% yield)

LC-MS (retention time: 2.320 min.), MS m/z 297 (MH$^+$).

Method C

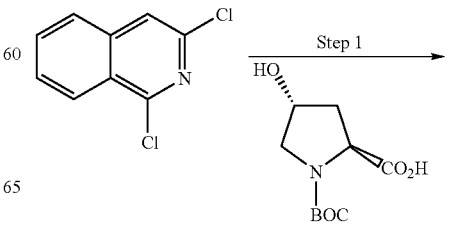

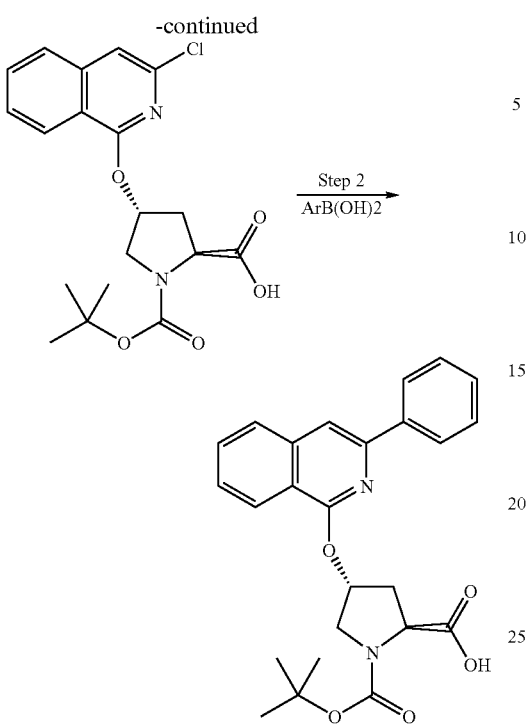

-continued

Step 2
ArB(OH)2 →

Step 1:

To a solution of N-BOC-3-(R)-hydroxy-L-proline (6.22 g, 26.9 mmol) in DMF (250 mL) at 0° C. was added NaH (60%, 3.23 g, 80.8 mmol) by several portions. The formed suspension was stirred at this temperature for 30 min. 1,3-dichloroisoquinoline (5.33 g, 26.9 mmol) was added as solid in one portion and the final mixture was stirred at the ambient temperature for 12 h. Quenched with iced 5% citric acid (aq), extracted with EtOAC (300 mL). The aqueous phase was extracted with EtOAC again. The combined organic layers were washed with 5% citric acid (aq) and brine respectively, dried over MgSO$_4$, filtered. The filtrate was evaporated in vacuo to dryness to yield 10.53 g (99.8%) of 4-(6-methoxy-isoquinolin-1-yloxy)-pyrrolidine-1,2-dicarboxylic acid 1-tert-butyl ester as an off-white foam. This material was used in the next step reaction as crude without further purification.

$^1$H NMR (CD$_3$OD) δ 1.43, 1.44 (rotamers, 9H), 2.39–2.44 (m, 1H), 2.68–2.72 (m, 1H), 3.80–3.90 (m, 2H), 4.44–4.52 (m, 1H), 5.77 (b, 1H), 7.39 (s, 1H), 7.58 (t, J=7.3 Hz, 1H), 7.71–7.78 (m, 2H), 8.16 (d, J=7.5 Hz, 1H);

LC-MS (retention time: 1.80 min, method B), MS m/z 392 (M$^+$+H).

Step 2:

A mixture of of 4-(6-methoxy-isoquinolin-1-yloxy)-pyrrolidine-1,2-dicarboxylic acid 1-tert-butyl ester (39 mg, 0.10 mmol), phenylboronic acid (14.6 mg, 0.12 mmol), sodium tert-butoxide (38 mg, 0.40 mmol) and ((t-Bu)$_2$POH)$_2$PdCl$_2$ (POPd) (5 mg, 0.01 mmol) in THF (2 mL) was heated to reflux for 4 h. After cooling down, the formed mixture was quenched with 5% citric acid (aq) and extracted with EtOAc (20 mL). The organic layer was washed with brine, dried over MgSO$_4$, filtered, evaporated. The residue was purified by prep-HPLC to yield 36 mg (83%) of the desired product as an off-white foam.

$^1$H NMR (CD$_3$OD) δ 1.43, 1.45 (rotamers, 9H), 2.51–2.56 (m, 1H), 2.74–2.82 (m, 1H), 3.88–3.92 (m, 1H), 3.98–4.01 (m, 1H), 4.50–4.57 (m, 1H), 5.95 (b, 1H), 7.36–7.39 (m, 1H), 7.45–7.48 (m, 2H), 7.55 (t, J=7.3 Hz, 1H), 7.70 (t, J=7.5 Hz, 1H), 7.84–7.89 (m, 2H), 8.14–8.17 (m, 3H), 9.05 (b, 1H);

LC-MS (retention time: 1.97 min, method B), MS m/z 435 (M$^+$+H).

The following intermediates were prepared as described herein and can be incorporated into compounds of Formula I

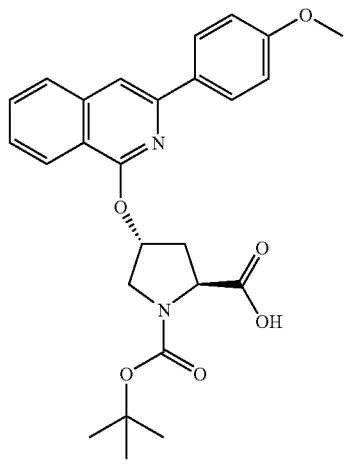

Prepared using 4-methoxyphenylboronic acid $^1$H NMR (CD$_3$OD) δ 1.40, 1.45 (rotamers, 9H), 2.50–2.55 (m, 1H), 2.73–2.81 (m, 1H), 3.81–3.89 (m, 4H), 3.98–4.01 (m, 1H), 4.50–4.57 (m, 1H), 5.93 (b, 1H), 7.02 (d, J=9.0 Hz, 2H), 7.50 (t, J=7.3 Hz, 1H), 7.67 (t, J=7.5 Hz, 1H), 7.73 (s, 1H), 7.83 (d, J=8.5 Hz, 1H), 8.09 (d, J=8.5 Hz, 2H), 8.15 (d, J=8.0 Hz, 1H);

LC-MS (retention time: 2.00 min, method B), MS m/z 465 (M$^+$+H).

The following intermediate was prepared as described above:

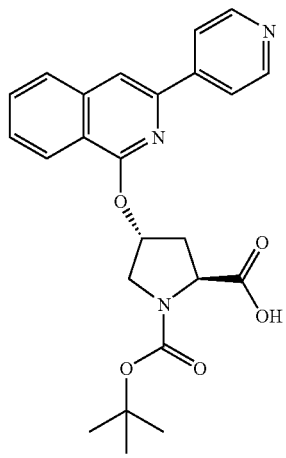

Prepared using 4-pyridylboronic acid $^1$H NMR (CD$_3$OD) δ 1.43, 1.46 (rotamers, 9H), 2.53–2.56 (m, 1H), 2.80–2.89 (m, 1H), 3.90–3.93 (m, 1H), 4.00–4.05 (m, 1H), 4.50–4.57 (m, 1H), 6.00, 6.05(rotamers, 1H), 7.80 (t, J=7.3 Hz, 1H), 7.87 (t, J=7.5 Hz, 1H), 8.08 (d, J=8.5 Hz, 1H), 8.32 (d, J=8.0 Hz, 1H), 8.49 (s, 1H), 8.84 (d, J=6.0 Hz, 2H), 8.84 (d, J=6.5 Hz, 2H);

LC-MS (retention time: 1.39 min, method B), MS m/z 436 (M⁺+H).

The following intermediates were prepared as described herein and can be incorporated into compounds of Formula I

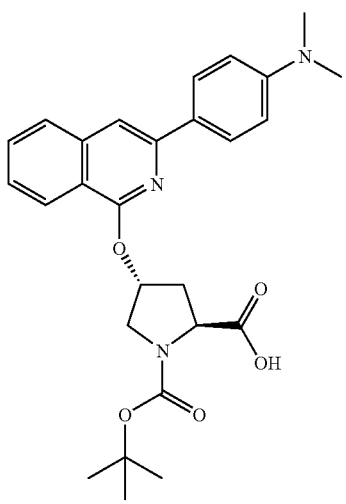

Prepared using 4-N,N-dimethylamino-phenylboronic acid

LC-MS (retention time: 1.64 min, method B), MS m/z 478 (M⁺+H).

Method D

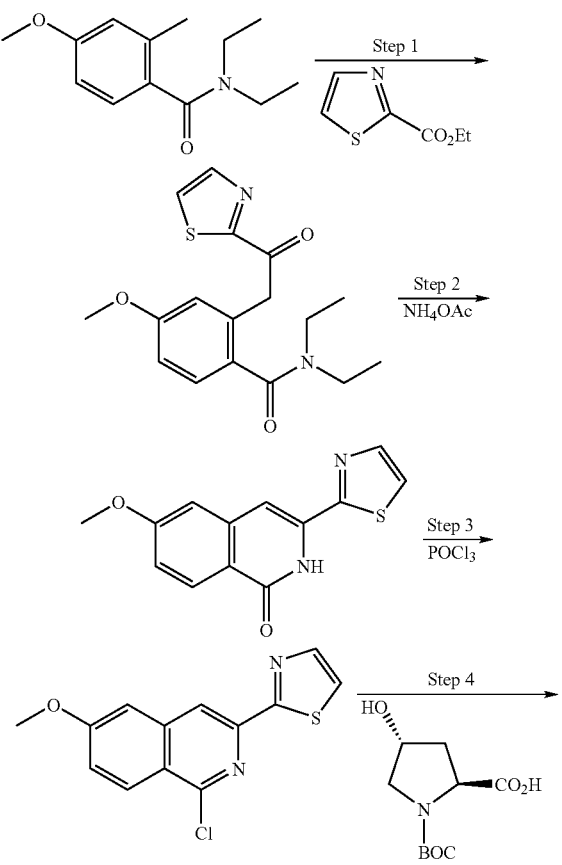

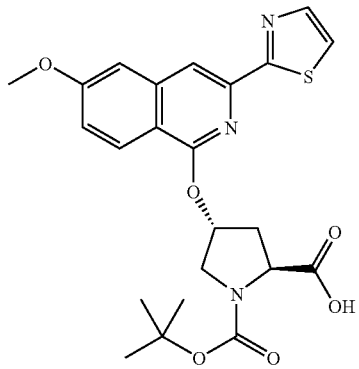

Step 1:

To a solution of N,N-diethyl-4-methoxy-2-methyl-benzamide (633 mg, 2.9 mmol) in THF (15 mL) at −78° C. was added n-BuLi (2.3 mL of 2.5 M in hexane, 5.74 mmol) dropwise. The formed red solution was kept at this temperature for additional 30 min before being cannulated to a solution of thiazole-2-carboxylic acid ethyl ester (A. Medici et al, Tetrahedron Lett. 1983, p2901) (450 mg, 2.9 mmol) in THF (5 mL) at −78° C. The final dark green solution was kept to this temperature for 2 h with stirring. Quenched with sat. NH₄Cl (aq) and extracted with EtOAc (50 mL). The organic layer was washed with sat. NH₄Cl (aq) and brine, dried, purified by flash column chromatography, eluting with 2:1 EtOAc:hexane to provide 405 mg (45%) of the desired product as an off-white viscous oil.

$^1$H NMR (CDCl₃) δ 1.08 (t, J=7.0 Hz, 6H), 3.22 (b, 2H), 3.44 (b, 2H), 3.79 (s, 3H), 4.59 (s, 2H), 6.79–6.81 (m, 1H), 6.86 (d, J=2.5 Hz, 1H), 7.16 (d, J=8.5 Hz, 1H), 7.66 (d, J=3.0 Hz, 1H), 8.00 (d, J=3.0 Hz, 1H);

LC-MS (retention time: 1.30 min, method B), MS m/z 333 (M⁺+H).

Step 2:

A mixture of N,N-diethyl-4-methoxy-2-(2-oxo-2-thiazol-2-yl-ethyl)-benzamide (405 mg, 1.22 mmol) and NH₄OAc (3.0 g, 38.9 mmol) was heated to 140° C. in a sealed tube for 1 h. The melted solution was poured into iced water, filtered, washed the cake thoroughly with water. The dried brownish solid (240 mg, 76%) was used as crude for the next reaction without further purification.

LC-MS (retention time: 1.24 min, method B), MS m/z 259 (M⁺+H).

Step 3:

This product, 1-chloro-6-methoxy-3-thiazol-2-yl-isoquinoline, was prepared as described above except using 6-methoxy-3-thiazol-2-yl-2H-isoquinolin-1-one instead.

$^1$H NMR (CDCl₃) δ 3.97 (s, 3H), 7.16 (d, J=4.0 Hz, 1H), 7.27–7.31 (m, 1H), 7.46 (d, J=5.0 Hz, 1H), 7.93 (d, J=5.5 Hz, 1H), 8.22 (d, J=15.5 Hz, 1H), 8.39 (s, 1H);

LC-MS (retention time: 1.66 min, method B), MS m/z 277 (M⁺+H).

Step 4:

This product was prepared by the same method as described above except using 1-chloro-6-methoxy-3-thiazol-2-yl-isoquinoline instead.

$^1$H NMR (CD₃OD) δ 0.97–1.09 (m, 12H), 1.24–1.29 (m, 10H), 1.44–1.46 (m, 1H), 1.87–1.90 (m, 1H), 2.20–2.26 (m, 1H), 2.30–2.36 (m, 1H), 2.65–2.71 (m, 1H), 2.93–2.96 (m,

1H), 3.96 (s, 3H), 4.12–4.27 (m, 2H), 4.38–4.52 (m, 2H), 5.12 (d, J=10.5 Hz, 1H), 5.29 (d, J=17.5 Hz, 1H), 5.69–5.74 (m, 1H), 5.99 (b, 1H), 7.14 (d, J=9.0 Hz, 1H), 7.33 (s, 1H), 7.66 (d, J=3.5 Hz, 1H), 7.93 (d, J=3.0 Hz, 1H), 8.05 (s, 1H), 8.11 (d, J=9.0 Hz, 1H), 9.14 (b, 1H);

LC-MS (retention time: 1.89 min, method B), MS m/z 797 (M⁺+H).

The following intermediates were prepared as described herein and can be incorporated into compounds of Formula I

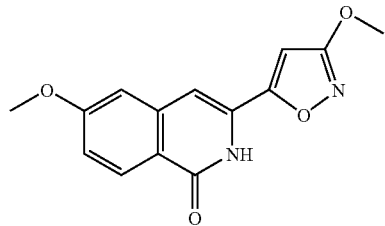

6-methoxy-3-(3-methoxy-isoxazol-5-yl)-2H-isoquinolin-1-one was prepared using N,N-diethyl-4-methoxy-2-[2-(3-methoxy-isoxazol-5-yl)-2-oxo-ethyl]-benzamide.

¹H NMR (DMSO-d₆) δ 3.89 (s, 3H), 3.97 (s, 3H), 7.01 (s, 1H), 7.14–7.16 (m, 2H), 7.43 (s, 1H), 8.13 (d, J=8.5 Hz, 1H);

LC-MS (retention time: 1.31 min, method B), MS m/z 273 (M⁺+H).

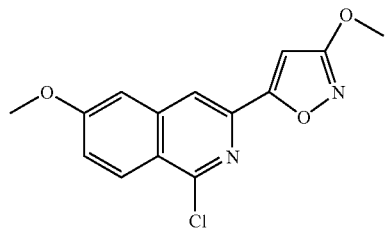

1-chloro-6-methoxy-3-(3-methoxy-isoxazol-5-yl)-isoquinoline was prepared using 6-methoxy-3-(3-methoxy-isoxazol-5-yl)-2H-isoquinolin-1-one ¹H NMR (CDCl₃) δ 3.97 (s, 3H), 4.04 (s, 3H), 6.60 (s, 1H), 7.17 (d, J=2.5 Hz, 1H), 7.31–7.33 (m, 1H), 8.02 (s, 1H), 8.23 (d, J=9.0 Hz, 1H);

LC-MS (retention time: 1.73 min, method B), MS m/z 291, 293 (M⁺+H)

The following intermediates were prepared as described herein and can be incorporated into compounds of Formula I

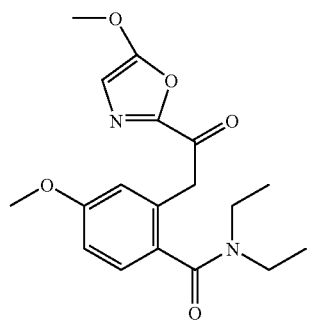

N,N-diethyl-4-methoxy-2-[2-(5-methoxy-oxazol-2-yl)-2-oxo-ethyl]-benzamide, was prepared using 5-methoxy-oxazole-2-carboxylic acid ethyl ester LC-MS (retention time: 1.24 min, method B), MS m/z 347 (M⁺+H).

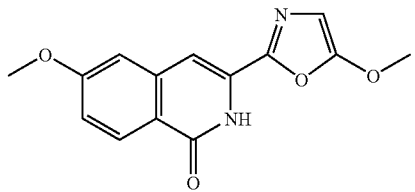

6-methoxy-3-(5-methoxy-oxazol-2-yl)-2H-isoquinolin-1-one, was prepared using N,N-diethyl-4-methoxy-2-[2-(5-methoxy-oxazol-2-yl)-2-oxo-ethyl]-benzamide.

¹H NMR (DMSO-d₆) δ 3.94 (s, 3H), 4.01 (s, 3H), 6.34 (s, 1H), 6.99 (d, J=2.0 Hz, 1H), 7.12–7.14 (m, 1H), 7.25 (s, 1H), 8.32 (d, J=9.0 Hz, 1H);

LC-MS (retention time: 1.22 min, method B), MS m/z 274 (M⁺+H).

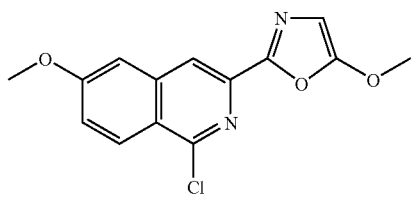

1-chloro-6-methoxy-3-(5-methoxy-oxazol-2-yl)-isoquinoline, was prepared using 6-methoxy-3-(5-methoxy-oxazole-2-yl)-2H-isoquinolin-1-one.

¹H NMR (CDCl₃) δ 3.96 (s, 3H), 4.00 (s, 3H), 6.34 (s, 1H), 7.12 (d, J=2.5 Hz, 1H), 7.28–7.31 (m, 1H), 8.13 (s, 1H), 8.23 (d, J=9.0 Hz, 1H);

LC-MS (retention time: 1.58 min, method B), MS m/z 291, 293 (M⁺+H).

The following intermediates were prepared as described herein and can be incorporated into compounds of Formula I

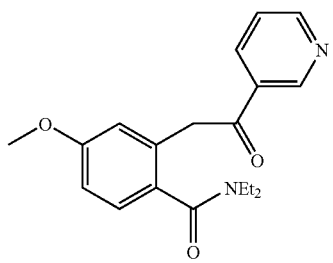

To a solution of N,N-Diethyl-4-methoxy-2-methyl-benzamide (332 mg, 1.5 mmol) in THF (15 mL) at −78° C., t-BuLi (1.7 M solution in pentane, 2.12 mL, 3.6 mmol) was added. The resulting red solution was stirred at −78° C. for 10 min, then methyl nicotinate (206 mg, 1.5 mmol) was added. The reaction mixture was stirred at −78° C. for 2 h. Then the reaction was quenched with saturated NH₄Cl solution and extracted with ethyl acetate twice. The combined organic layers were dried (MgSO₄) and concentrated. The crude product was purified by Prep. HPLC to give yellowish thick oil as TFA salt. (124 mg, 19% yield)

LC-MS (retention time: 1.740 min.), MS m/z 349 (M+Na⁺).

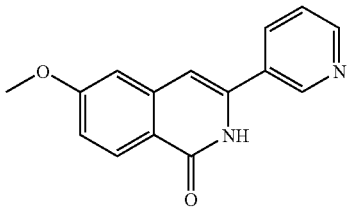

N,N-Diethyl-4-methoxy-2-(2-oxo-2-pyridin-3-yl-ethyl)-benzamide (120 mg, 0.272 mmol) was heated with ammonium acetate (1 g) for 3 hr. Then it was cooled down and added water. Extracted with ethyl acetate and the organic layer was separated. It was then dried (MgSO$_4$) and concentrated to give a brownish solid as product. (65 mg, 95% yield)

$^1$H NMR (400 MHz, DMSO-d$^6$) δ 3.89 (s, 3H), 6.93 (s, 1H), 7.10 (dd, J=8.80, 2.45 Hz, 1H), 7.19 (d, J=2.45 Hz, 1H), 7.52 (dd, J=7.46, 4.77 Hz, 1H), 8.15 (m, 2H), 8.64 (dd, J=4.89, 1.47 Hz, 1H), 8.96 (d, J=1.71 Hz, 1H), 11.51 (s, 1H).

LC-MS (retention time: 1.377 min.), MS m/z 253 (MH$^+$).

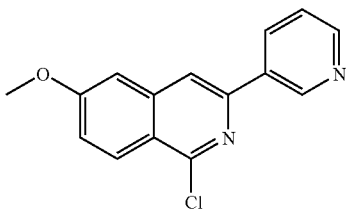

6-Methoxy-3-pyridin-3-yl-2H-isoquinolin-1-one (65 mg, 0.258 mmol) was heated under reflux with POCl$_3$ (2.5 mL) for 7 days. Then POCl$_3$ was distilled off and the residue was quenched with ice. It was then neutralized with 10 N NaOH solution and extracted with ethyl acetate twice. The combined organic layers were dried (MgSO$_4$) and concentrated to give yellow solid as product. (27 mg, 39% yield)

LC-MS (retention time: 2.090 min.), MS m/z 271 (MH$^+$).

The following intermediates were prepared as described herein and can be incorporated into compounds of Formula I

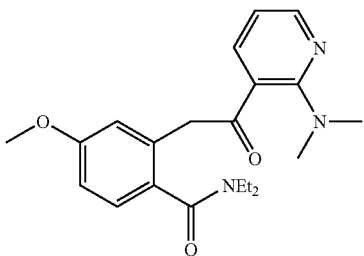

To a solution of N,N-Diethyl-4-methoxy-2-methyl-benzamide (332 mg, 1.5 mmol) in THF (15 mL) at −78° C., t-BuLi (1.7 M solution in pentane, 2.2 mL, 3.75 mmol) was added. The resulting red solution was stirred at −78° C. for 10 min, then N,N-dimethylanthranilic acid methyl ester (269 mg, 1.5 mmol) was added. The reaction mixture was stirred at −78° C. for 2 h. Then the reaction was quenched with saturated NH$_4$Cl solution and extracted with ethyl acetate twice. The combined organic layers were dried (MgSO$_4$) and concentrated. The crude product was purified by Prep. HPLC to give yellowish thick oil as product. (256 mg, 46% yield)

$^1$H NMR (400 MHz, CD$_3$OD) δ 0.99–1.13 (m, 6H), 3.23–3.31 (m, 8H), 3.39 (m, 2H), 3.82 (s, 3H), 4.35 (s, 2H), 6.91 (dd, J=8.44, 2.57 Hz, 1H), 6.99 (d, J=2.45 Hz, 1H), 7.22 (d, J=8.56 Hz, 1H), 7.69 (t, J=7.70 Hz, 1H), 7.84 (m, 1H), 7.96 (d, J=8.31 Hz, 1H), 8.18 (d, J=7.83 Hz, 1H).

LC-MS (retention time: 1.557 min.), MS m/z 369(MH$^+$).

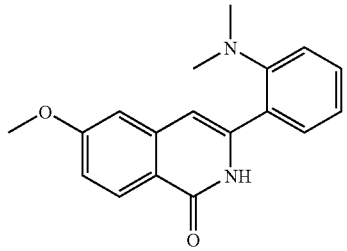

2-[2-(2-Dimethylamino-phenyl)-2-oxo-ethyl]-N,N-diethyl-4-methoxy-benzamide (250 mg, 0.678 mmol) was heated with ammonium acetate (1.5 g) for 2 hr. Then it was cooled down and added water. Extracted with ethyl acetate and the organic layer was separated. It was then dried (MgSO$_4$) and concentrated to give a yellowish solid as product. (125 mg, 63% yield)

$^1$H NMR (400 MHz, CD$_3$OD) δ 2.95 (s, 6H), 3.92 (s, 3H), 6.92 (s, 1H), 7.12 (dd, J=8.80, 2.45 Hz, 1H), 7.16 (d, J=2.45 Hz, 1H), 7.35 (m, 1H), 7.55 (m, 2H), 7.63 (d, J=7.83 Hz, 1H), 8.20 (d, J=9.05 Hz, 1H).

LC-MS (retention time: 2.097 min.), MS m/z 295 (MH$^+$).

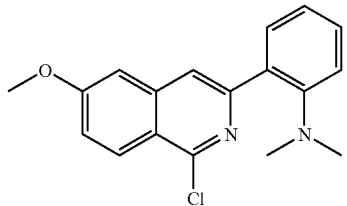

3-(2-Dimethylamino-phenyl)-6-methoxy-2H-isoquinolin-1-one (125 mg, 0.425 mmol) was heated under reflux with POCl$_3$ (4.0 mL) for one day. Then POCl$_3$ was distilled off and the residue was quenched with ice. It was then neutralized with 10 N NaOH solution and extracted with ethyl acetate twice. The organic layers were combined and dried (MgSO$_4$). Evaporation of solvent gave a brownish solid as product (82 mg, 62% yield)

LC-MS (retention time: 2.040 min.), MS m/z 313 (MH$^+$).

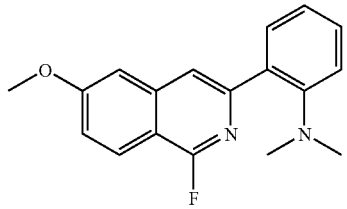

A mixture of [2-(1-Chloro-6-methoxy-isoquinolin-3-yl)-phenyl]-dimethyl-amine (82 mg, 0.262 mmol) and tetrabutyl phosphonium hydrogen difluoride (1.0 g) was heated at 140° C. in Smith microwave reactor for 20 min. Then it was added water and extracted with ethyl acetate. The organic layer was separated, washed with water and dried (MgSO$_4$). Evaporation of solvent gave the crude product which was purified by Prep. HPLC to afford a yellowish oil as product. (85 mg)

$^1$H NMR (400 MHz, CD$_3$OD) δ 3.41 (s, 6H), 4.00 (s, 3H), 7.42 (dd, J=9.05, 2.45 Hz, 1H), 7.53 (s, 1H), 7.71 (m, 2H), 7.99 (m, 1H), 8.16 (m, 2H), 8.31 (s, 1H).

LC-MS (retention time: 1.873 min.), MS m/z 297 (MH$^+$).

The following intermediates were prepared as described herein and can be incorporated into compounds of Formula I

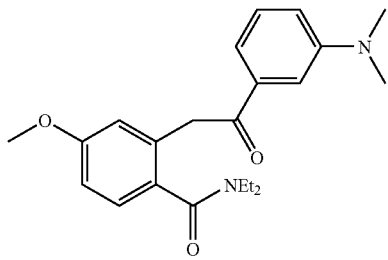

To a solution of N,N-Diethyl-4-methoxy-2-methyl-benzamide (332 mg, 1.5 mmol) in THF (15 mL) at −78° C., t-BuLi (1.7 M solution in pentane, 2.2 mL, 3.75 mmol) was added. The resulting red solution was stirred at −78° C. for 10 min, then (3-dimethylamino)benzoic acid methyl ester (269 mg, 1.5 mmol) was added. The reaction mixture was stirred at −78° C. for 2 h. Then the reaction was quenched with saturated NH$_4$Cl solution and extracted with ethyl acetate twice. The combined organic layers were dried (MgSO$_4$) and concentrated. The crude product was purified by Prep. HPLC to give yellowish thick oil as TFA salt. (245 mg, 33% yield)

1H NMR (400 MHz, CD$_3$OD) δ 1.01 (t, J=6.85 Hz, 3H), 1.09 (m, 3H), 3.11 (s, 6H), 3.21 (m, 2H), 3.40 (m, 2H), 3.79 (s, 3H), 4.39 (s, 2H), 6.84–6.91 (m, 2H), 7.19 (d, J=8.32 Hz, 1H), 7.35 (m, 1H), 7.49 (t, J=8.07 Hz, 1H), 7.66–7.71 (m, 2H).

LC-MS (retention time: 1.930 min.), MS m/z 369(MH$^+$).

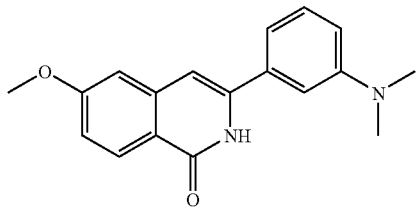

2-[2-(3-Dimethylamino-phenyl)-2-oxo-ethyl]-N,N-diethyl-4-methoxy-benzamide (240 mg, 0.497 mmol) was heated with ammonium acetate (2.0 g) for 2.5 hr. Then it was cooled down and added water. A brownish solid was collected as pure product. (95 mg, 65% yield)

1H NMR (400 MHz, CD$_3$OD) δ 2.98 (s, 6H), 3.88 (s, 3H), 6.74–6.87 (m, 2H), 7.01–7.07 (m, 3H), 7.18 (d, J=2.44 Hz, 1H), 7.28 (t, J=7.82 Hz, 1H), 8.10 (d, J=8.80 Hz, 1H).

LC-MS (retention time: 1.773 min.), MS m/z 295 (MH$^+$).

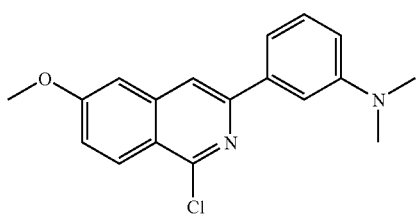

3-(3-Dimethylamino-phenyl)-6-methoxy-2H-isoquinolin-1-one (92 mg, 0.312 mmol) was heated under reflux with POCl$_3$ (3.0 mL) for 2 days. Then POCl$_3$ was distilled off and the residue was quenched with ice. It was then neutralized with saturated NaHCO$_3$ solution and extracted with ethyl acetate twice. The organic layers were combined and dried (MgSO$_4$). Evaporation of solvent gave a brownish thick oil as product. (72 mg, 74% yield)

LC-MS (retention time: 2.297 min.), MS m/z 313 (MH$^+$).

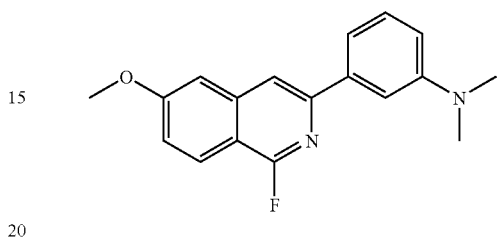

A mixture of [3-(1-Chloro-6-methoxy-isoquinolin-3-yl)-phenyl]-dimethylamine (72 mg, 0.23 mmol) and tetrabutyl phosphonium hydrogen difluoride (0.5 g) was heated at 140° C. in Smith microwave reactor for 20 min. Then it was added water and extracted with ethyl acetate. The organic layer was separated, washed with water and dried (MgSO$_4$). Evaporation of solvent gave a brownish oil as product. (58 mg, 85% yield)

LC-MS (retention time: 2.193 min.), MS m/z 297 (MH$^+$).

The following intermediates were prepared as described herein and can be incorporated into compounds of Formula I

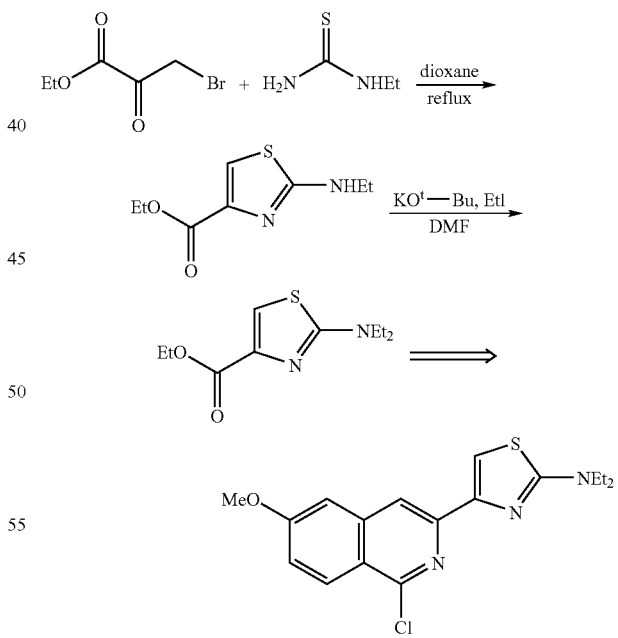

Condensation of ethyl bromopyruvate with ethyl thiourea in refluxing dioxane afforded the monoalkylamino thiazole as HBr salt in quantitative yield. Alkylation of 2-ethylamino-thiazole-4-carboxylic acid ethyl ester with EtI in DMF provided 2-diethylamino-thiazole-4-carboxylic acid ethyl ester. LC/MS m/z 229 (MH)$^+$ Method E

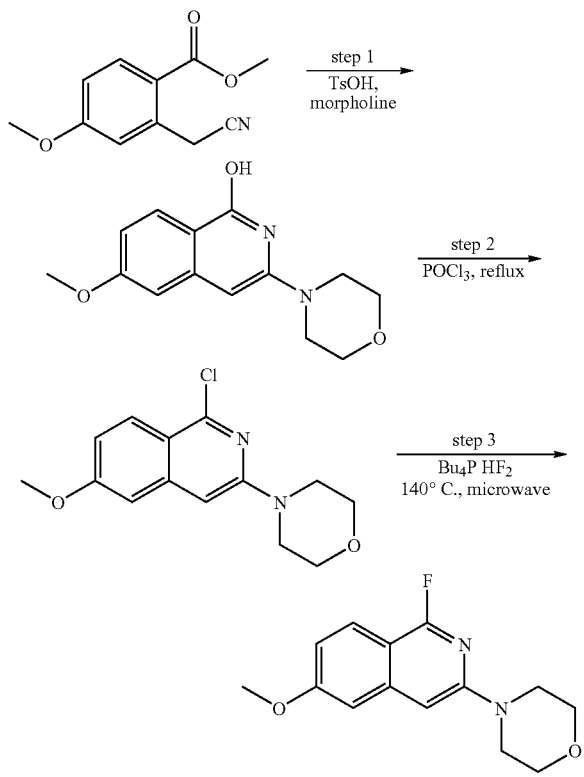

Step 1:
A suspension of 2-cyanomethyl-4-methoxy-benzoic acid methyl ester (1.9 g and TsOH. H$_2$O (0.15 g, mmol) in morpholine 5 mL) was refluxed for 4 h and removed the solvent in vavuo. The residue was recrystalyzed from EtOAc/hexanes with drops of MeOH to provide the product (0.43 g, 17%): LC-MS retention time: 1.07 method H), MS m/z 266 (M$^+$+1).

Step 2:
A mixture of 6-methoxy-3-morpholin-4-yl-isoquinolin-1-ol (0.298 g, 1.15 mmol) in POCl$_3$ (20 mL) was refluxed for 2 h, removed the solvent in vacuo and cold water was added. The pH was adjustde to >11 by addition of 1.0 N NaOH. The aqueous layer was extracted with EtOAc. The extract was dried (MgSO$_4$), removed the solvent in vacuo to provide the produt (0.299 g, 94%): LC-MS retention time: 1.68 method H), MS m/z 279 (M$^+$+1).

Step 3:
A mixture of 1-Chloro-6-methoxy-3-morpholin-4-yl-isoquinoline (0.050 g, 0.18 mmol) and tetrabutyl phosphorium hydrgen difloride (0.8 g, 2.8 mmol) [Synlett 1992, (4), 345–6] was heated at 140° C. in microwave for 10 min. the reaction mixture was diluted with EtOAc and filtered through an ISCO 25 g precolumn with a layer of silicon gel on the top, removed the solvent to provide the product (0.037 mg, 77%): $^1$H NMR (CHLOROFORM-D) δ ppm 3.48 (m, 4H), 3.84 (m, 4H), 3.89 (s, 3H), 6.46 (d, J=1.22 Hz, 1H), 6.85 (s, 1H), 6.90 (dd, J=9.16, 2.44 Hz, 1H), 7.82 (d, J=8.85 Hz, 1H). LC-MS retention time: 1.56 method H), MS m/z 263 (M$^+$+1).

Method F 6-fluoro and 6-alkyl isoquinolines used in the preparation of compounds of Formula 1 were prepared via a Pomeranz-Fritsch synthesis (Typical procedure: Preparation of optically active 8,8-disubstituted 1,1-biisoquinoline, K. Hirao, R. Tsuchiya, Y. Yano, H. Tsue, *Heterocycles* 42(1) 1996, 415–422) as outlined below. The products were converted into the 1-chloro derivatives via N-oxide intermediates.

General Synthetic Scheme

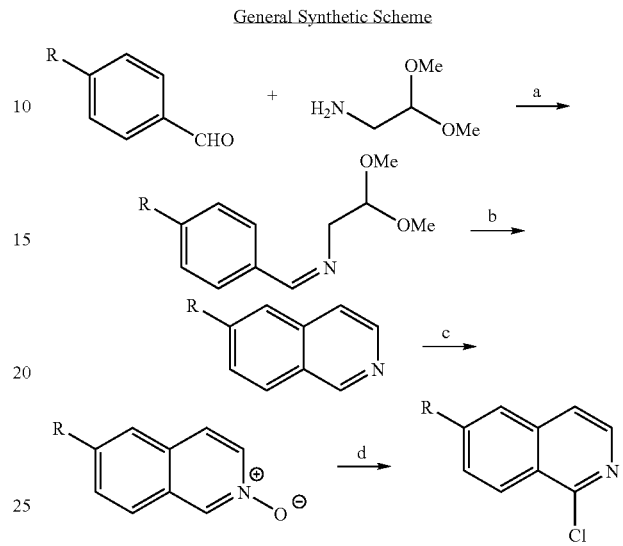

Reagents and reaction conditions: (a) reflux in benzene, azeotropic removal of water; (b) first step: ethyl chloroformate, trimethyl phosphite in THF, second step: titanium tetrachloride in chloroform; (c) MCPBA in CH$_2$Cl$_2$; (d) POCl$_3$ in benzene

| R | Isoquinoline, Yield | 1-Chloride, combined yield |
| --- | --- | --- |
| F | 20 | 43 |
| Et | 76 | 65 |
| i-Pr | 14 | 18 |
| t-Bu | 47 | 55 |

Preparation of 6-isopropoxyl and 6-tert-butoxyl isoquinoline intermediates:

Some 6-alkoxy-1-chloro isoquinolines were prepared by a direct, ipso displacement of the 6-fluoro-1-chloroisoquinoline with the corresponding alkoxide metal ions such as potassium tert-butoxide (53%) and sodium isopropoxide (54%).

General Synthetic Scheme

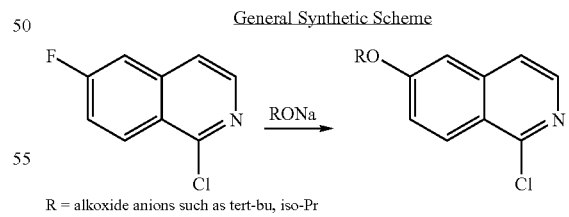

R = alkoxide anions such as tert-bu, iso-Pr

The 6-fluoro-1-chloroisoquinoline was subjected to an aromatic nucleophilic displacement with sodium isopropoxide and potassium tert-butoxide in DMF to give the corresponding 6-isopropoxyl (54%): $^1$H NMR (400 MHz, CHLOROFORM-d) δ ppm 1.43 (d, J=6.11 Hz, 6H) 4.76 (m, J=6.11 Hz, 1H) 7.08 (d, J=2.45 Hz, 1H) 7.29 (dd, J=9.29, 2.45 Hz, 1H) 7.50 (d, J=5.62 Hz, 1H) 8.18 (d, J=5.87 Hz, 1H) 8.24 (d, J=9.29 Hz, 1H) and 6-tert-butoxy]-1-chloro isoquinolines (55%): ¹H NMR (400 MHz, CHLOROFORM-d) δ ppm 1.48 (s, 9H) 7.31 (m, 2H) 7.47 (d, J=5.62 Hz, 1H) 8.18 (d, J=5.62 Hz, 1H) 8.21 (d, J=9.78 Hz, 1H) as the major product respectively. These 6-alkoxyl-1-chloro isoquinolines were incorporated into compounds of Formula I as described herein.

Method G

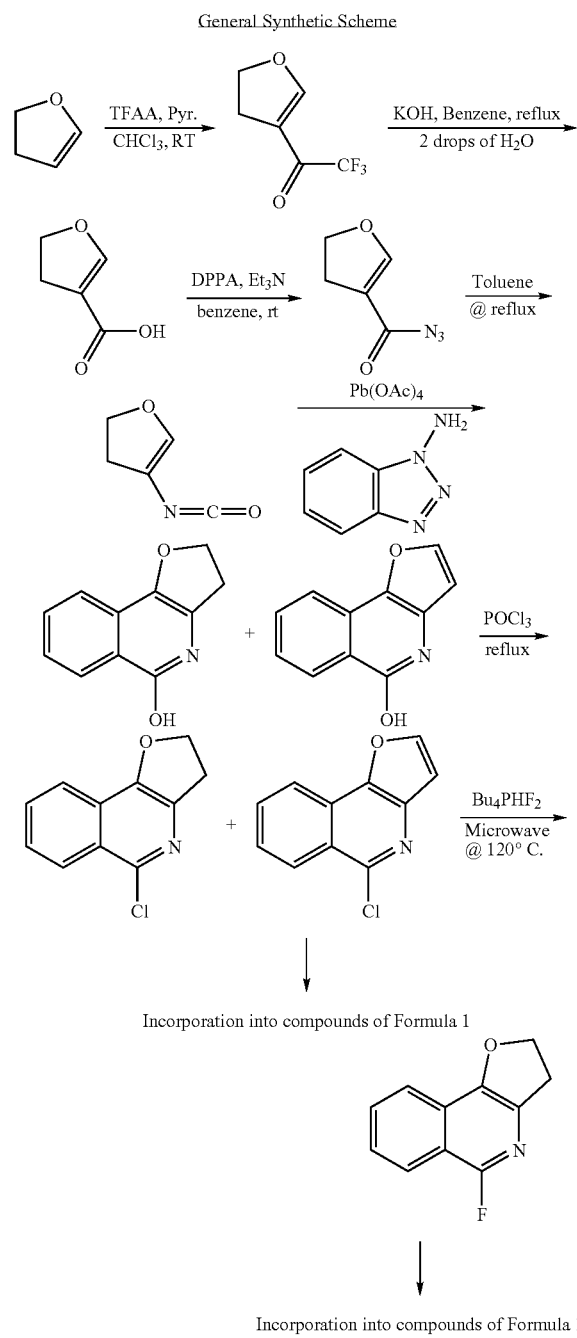

Incorporation into compounds of Formula 1

This synthesis made use of the technologies described, in part, in the following references:
(1) Hojo, Masaru; Masuda, Ryoichi; Sakaguchi, Syuhei; Takagawa, Makoto, *Synthesis* (1986), (12), 1016–17
(2) Rigby, James H.; Holsworth, Daniel D.; James, Kelly. Vinyl Isocyanates In Synthesis. [4+2] Cycloaddition Reactions With Benzyne Addends. *Journal Of Organic Chemistry* (1989), 54(17), 4019–20

(3) Uchibori, Y.; Umeno, M.; Yoshiokai, H.; *Heterocycles*, 1992, 34 (8), 1507–1510

Step 1d: Preparation of racemic (1R,2S)/(1S,2R)-1-amino-2-vinylcyclopropane carboxylic acid ethyl ester hydrochloride (Method A and Method B) and chiral resolution of this racemate for the preparation of N-(1R,2S)-1-amino-2-vinyl-cyclopropane carboxylic acid ethyl ester hydrochloride (Method C)

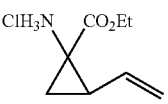

The named compound was made (Step d) racemic by each of the following methods A and B. This racemate could also be resolved to afford chiral Boc-(1R,2S)-1-amino-2-vinyl-cyclopropyl carboxylic acid ester which was deprotected under acid conditions to afford (1R,2S)-1-amino-2-vinylcyclopropane carboxylic acid ester hydrochloride (Method C).

Method A

A.1 Preparation of N-Benzyl Imine of Glycine Ethyl Ester

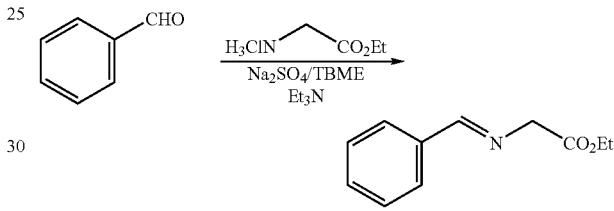

Glycine ethyl ester hydrochloride (303.8 g, 2.16 mole) was suspended in tert-butylmethyl ether (1.6 L). Benzaldehyde (231 g, 2.16 mole) and anhydrous sodium sulfate (154.6 g, 1.09 mole) were added and the mixture cooled to 0° C. using an ice-water bath. Triethylamine (455 mL, 3.26 mole) was added dropwise over 30 min and the mixture stirred for 48 h at rt. The reaction was then quenched by addition of ice-cold water (1 L) and the organic layer was separated. The aqueous phase was extracted with tert-butyl-methyl ether (0.5 L) and the combined organic phases washed with a mixture of saturated aqueous NaHCO₃ (1 L) and brine (1 L). The solution was dried over MgSO₄, concentrated in vacuo to afford 392.4 g of the N-benzyl imine product as a thick yellow oil that was used directly in the next step. ¹H NMR (CDCl₃, 300 MHz) δ 1.32 (t, J=7.1 Hz, 3H), 4.24 (q, J=7.1 Hz, 2H), 4.41 (d, J=1.1 Hz, 2H), 7.39–7.47 (m, 3H), 7.78–7.81 (m, 2H), 8.31 (s, 1H).

A.2 Preparation of racemic N-Boc-(1R,2S)/(1S,2R)-1-amino-2-vinylcyclopropane carboxylic acid ethyl ester

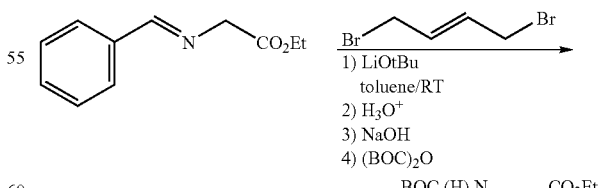

To a suspension of lithium tert-butoxide (84.06 g, 1.05 mol) in dry toluene (1.2 L), was added dropwise a mixture of the N-benzyl imine of glycine ethyl ester (100.4 g, 0.526 mol) and trans-1,4-dibromo-2-butene (107.0 g, 0.500 mol) in dry toluene (0.6 L) over 60 min. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 h. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10 N NaOH, the organic layer separated, and the aqueous phase extracted with TBME (2×500 mL). The combined organic extracts were dried (MgSO$_4$) and concentrated to a volume of 1 L. To this solution of free amine, was added BOC$_2$O or di-tert-butyldicarbonate (131.0 g, 0.6 mol) and the mixture stirred 4 days at rt. Additional di-tert-butyldicarbonate (50 g, 0.23 mol) was added to the reaction, the mixture refluxed for 3 h, and was then allowed cool to room temperature overnight. The reaction mixture was dried over MgSO$_4$ and concentrated in vacuo to afford 80 g of crude material. This residue was purified by flash chromatography (2.5 Kg of SiO$_2$, eluted with 1% to 2% MeOH/CH$_2$Cl$_2$) to afford 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR (CDCl$_3$, 300 MHz) δ 1.26 (t, J=7.1 Hz, 3H), 1.46 (s, 9H), 1.43–1.49 (m, 1H), 1.76–1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M−1)

A.3 Preparation of Racemic (1R,2S)/(1S,2R)1-amino-2-vinylcyclopropane carboxylic acid ethyl ester hydrochloride

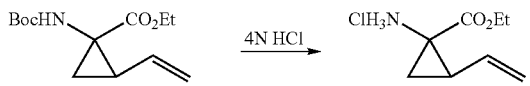

N-Boc-(1R,2S)/(1S,2R)-1-amino-2-vinylcyclopropane carboxylic acid ethyl ester (9.39 g, 36.8 mmol) was dissolved in 4 N HCl/dioxane (90 ml, 360 mmol) and was stirred for 2 h at rt. The reaction mixture was concentrated to supply (1R,2S)/(1S,2R)-1-amino-2-vinylcyclopropane carboxylic acid ethyl ester hydrochloride in quanitative yield (7 g, 100%). $^1$H NMR (methanol-d$_4$) δ 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26–4.34 (m, 2H), 5.24 (dd, 10.3, 1.3 Hz, 1H) 5.40 (d, J=17.2, 1H), 5.69–5.81 (m, 1H).

B.1 Preparation of Racemic N-Boc-1-amino-2-vinylcyclopropane carboxylic acid ethyl ester hydrochloride Method B

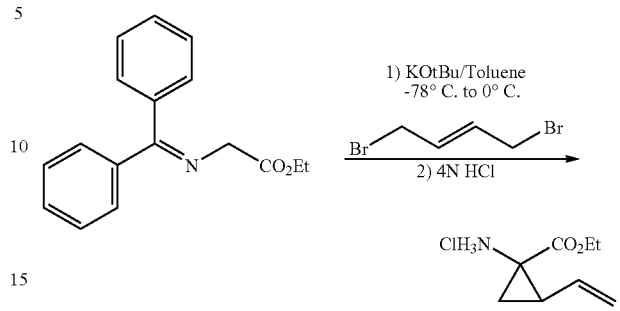

To a solution of potassium tert-butoxide (11.55 g, 102.9 mmol) in THF (450 mL) at −78° C. was added the commercially available N,N-dibenzyl imine of glycine ethyl ester (25.0 g, 93.53 mmol) in THF (112 mL). The reaction mixture was warmed to 0° C., stirred for 40 min, and was then cooled back to −78° C. To this solution was added trans-1,4-dibromo-2-butene (20.0 g, 93.50 mmol), the mixture stirred for 1 h at 0° C. and was cooled back to −78° C. Potassium tert-butoxide (11.55 g, 102.9 mmol) was added, the mixture immediately warmed to 0° C., and was stirred one more hour before concentrating in vacuo. The crude product was taken up in Et$_2$O (530 mL), 1N aq. HCl solution (106 mL, 106 mmol) added and the resulting biphasic mixture stirred for 3.5 h at rt. The layers were separated and the aqueous layer was washed with Et$_2$O (2×) and basified with a saturated aq. NaHCO$_3$ solution. The desired amine was extracted with Et$_2$O (3×) and the combined organic extract was washed with brine, dried (MgSO$_4$), and concentrated in vacuo to obtain the free amine. This material was treated with a 4N HCl solution in dioxane (100 mL, 400 mmol) and concentrated to afford (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Method C

C.1 Resolution of N-Boc-(1R,2S)/(1S,2R)-1-amino-2-vinylcyclopropane carboxylic acid ethyl ester

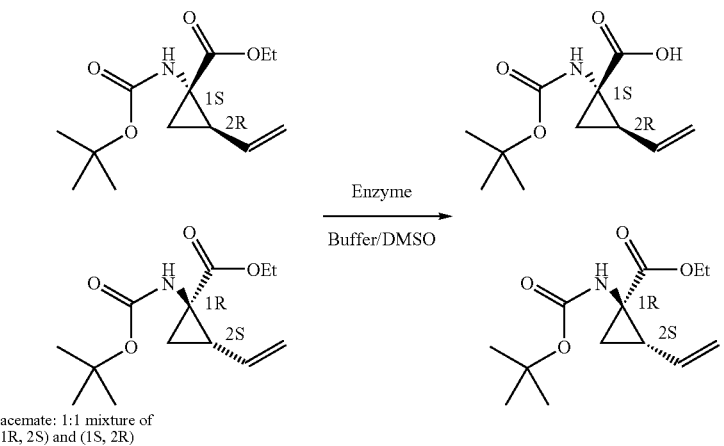

racemate: 1:1 mixture of (1R, 2S) and (1S, 2R)

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Alcalase 2.4 L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 min. The reaction temperature was then maintained at 40° C. for 24.5 h during which time the pH of the mixture was adjusted to 8.0 at the 1.5 h and 19.5 h time points using 50% NaOH in water. After 24.5 h, the enantio-excess of the ester was determined to be 97.2%, and the reaction was cooled to room temperature (26° C.) and stirred overnight (16 h) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% NaHCO$_3$ (3×100 mL), water (3×100 mL), and evaporated in vacuo to give the enantiomerically pure N-Boc-(1R,2S)/-1-amino-2-vinylcyclopropane carboxylic acid ethyl ester as light yellow solid (42.55 g; purity: 97% @ 210 nm, containing no acid; 100% enantiomeric excess ("ee").

The aqueous layer from the extraction process was then acidified to pH 2 with 50% H$_2$SO$_4$ and extracted with MTBE (2×2 L). The MTBE extract was washed with water (3×100 mL) and evaporated to give the acid as light yellow solid (42.74 g; purity: 99% @ 210 nm, containing no ester).

Resolution B

To 0.5 mL 100 mM Heps.Na buffer (pH 8.5) in a well of a 24 well plate (capacity: 10 ml/well), 0.1 mL of Savinase 16.0L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 h, enantio-excess of the ester was determined to be 44.3% as following: 0.1 mL of the reaction mixture was removed and mixed well with 1 mL ethanol; after centrifugation, 10 microliter ("µl") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 µl of the supernatant was analyzed with the chiral HPLC and enantio-excess of the ester was determined to be 100%.

Resolution C

To 0.5 ml 100 mM Heps.Na buffer (pH 8.5) in a well of a 24 well plate (capacity: 10 mL/well), 0.1 ml of Esperase 8.0L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after cenrifugation, 10 µl of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 µl of the supernatant was analyzed with the chiral HPLC and enantio-excess of the ester was determined to be 100%.

Samples analysis was carried out in the following manner:

1) Sample preparation: About 0.5 ml of the reaction mixture was mixed well with 10 volume of EtOH. After centrifugation, 10 µl of the supernatant was injected onto HPLC column.

2) Conversion Determination:
   Column: YMC ODS A, 4.6×50 mm, S-5 µm
   Solvent: A, 1 mM HCl in water; B, MeCN
   Gradient: 30% B for 1 min; 30% to 45% B over 0.5 min; 45% B for 1.5 min; 45% to 30% B over 0.5 min.
   Flow rate: 2 ml/min
   UV Detection: 210 nm
   Retention time: acid, 1.2 min; ester, 2.8 min.

3) Enantio-excess Determination for the Ester:
   Column: CHIRACEL OD-RH, 4.6×150 mm, S-5 µm
   Mobile phase: MeCN/50 mM HClO$_4$ in water (67/33)
   Flow rate: 0.75 ml/min.
   UV Detection: 210 nm.
   Retention Time:
   (1S,2R)-1-amino-2-vinylcyclopropane carboxylic acid 5.2 min;
   Racemate (1R,2S)/(1S,2R)-1-amino-2-vinylcyclopropane carboxylic acid ethyl ester 18.5 min and 20.0 min;
   (1R,2S)-1-amino-2-vinylcyclopropane carboxylic acid ethyl ester 18.5 min.

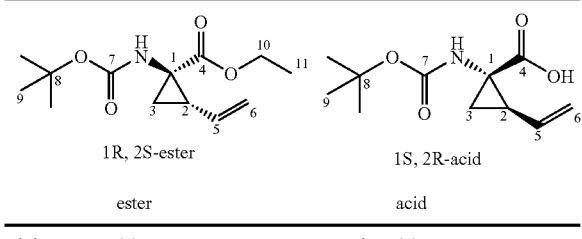

| | 1R, 2S-ester ester | | 1S, 2R-acid acid | |
|---|---|---|---|---|
| High Resolution-Mass Spec | (+) ESI, C13H22NO4, [M + H]$^+$, cal. 256.1549, found 256.1542 | | (−) ESI, C11H16NO4, [M − H]$^-$, cal. 226.1079, found 226.1089 | |

NMR observed chemical shift
Solvent: CDCl$_3$ (proton δ 7.24 PPM, C-13 δ 77.0 ppm)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J = 9.0 Hz) | 34.1 | 2.17 (q, J = Hz) | 35.0 |
| 3a | 1.76 (br) | 23.2 | 1.79 (br) | 23.4 |
| 3b | 1.46 (br) | | 1.51, (br) | |
| 4 | — | 170.8 | — | 175.8 |
| 5 | 5.74 (ddd, J = 9.0, 10.0, 17.0 Hz) | 133.7 | 5.75 (m) | 133.4 |
| 6a | 5.25 (d, J = 17.0 Hz) | 117.6 | 5.28 (d, J = 17.0 Hz) | 118.1 |
| 6b | 5.08 (dd, J = 10.0, 1.5 Hz) | | 5.12 (d, J = 10.5 Hz) | |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J = 7.5 Hz) | 14.2 | — | — |

Resolution D

5 L of 0.3 M sodium phosphate buffer (pH 8) was maintained at 38° C. in a 20 Liter jacked reactor, stirred at 130 rpm. Four liters of Alcalase 2.4L (Novozymes North America Inc.) and 1 liter of DI water were added to the reactor. When temperature of the mixture closed to 38° C., pH was adjusted to 7.8 with 10 N NaOH. A solution of the racemic N-Boc-(1R,2S)/(1S,2R)-1-amino-2-vinylcyclopropane carboxylic acid ethyl ester (500 grams) in 5 liters DMSO was added to the reactor over a period of 1 hour via an addition funel. The reaction temperature was then adjusted to 48° C. After 21 hours, enantio-excess of the ester reached 99.3%. Heating was stopped at 24 hour and the reaction was slowly cooled down to room temperature (about 25° C.) and stirred overnight. pH of the reaction mixture was adjusted to 8.5 with 10 N NaOH and the mixture was extracted with MTBE (2×4 L). The combined MTBE extract was washed with 5% NaHCO$_3$ (3×400 ml) and water (3×400 ml), and evaporated to give enantiomerically pure N-Boc-(1R,2S)/-1-amino-2-vinylcyclopropane carboxylic acid ethyl ester as light yellow crystal (259 g; purity: 96.9% @ 210 nm, containing no acid; 100% ee).

reaction was cooled down to 25° C. pH of the reaction mixture was adjusted to 8.5 with 10 N NaOH and the mixture was extracted with MTBE (2×5 L). The combined MTBE extract was washed with 5% NaHCO$_3$ (3×500 ml) and water (3×200 ml), and evaporated to give 110 gram of yellow oil. The oil was set at room temperature under house vacuum and gave enantiomerically pure N-Boc-(1R,2S)/-1-amino-2-vinylcyclopropane carboxylic acid ethyl ester as colorless long rod crystal (101 g; purity: 97.9% @ 210 nm, containing no acid; 100% ee).

The crystal structure enantiomerically pure N-Boc-(1R,2S)/-1-amino-2-vinylcyclopropane carboxylic acid ethyl ester has been characterized by single crystal analysis (X-ray NB#: 52795-093, refcode: 634592N1). The absolute configuration is not established for lack of a known chiral center or heavier atom(s). A chain structure along the crystallographic α-axis is formed via intermolecular hydrogen bonding between the amide group and the carbonyl oxygen atom (N . . . O 3.159 Å).

Structure of N-Boc-(1R,2S)-1-amino-2-vinylcyclopropane carboxylic acid ethyl ester:

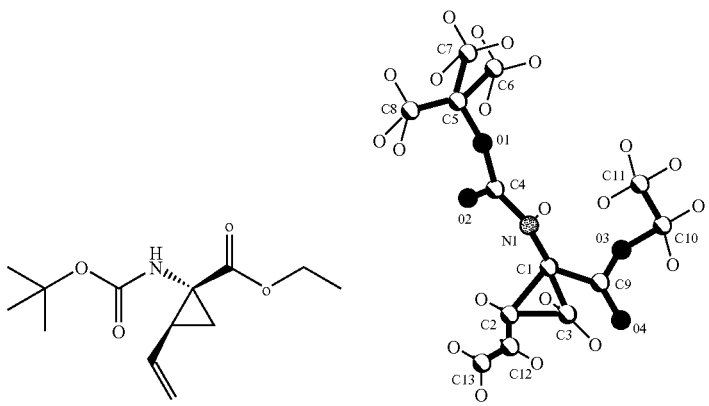

| Crystal Data: | Experimental: |
|---|---|
| Chemical formula: C$_{13}$H$_{21}$N$_1$O$_4$ | Crystallization |
| Crystal system: Orthorhombic | Crystal source: MTBE |
| Space Group: P2$_1$2$_1$2$_1$ | Crystal description: Colorless rod |
| a = 5.2902(1) Å    α = 90° | Crystal size (mm): 0.12 × 0.26 × 0.30 |
| b = 13.8946(2) Å    β = 90° | Data Collection |
| c = 19.9768(3) Å    γ = 90° | Temperature (K): 293 |
| V = 1468.40(4) Å$^3$ | θ$_{max}$ (°): 65.2 (Cu Kα) |
| Z = 4    d$_x$ = 1.155 g cm$^{-3}$ | No. of reflections measured: 7518 |
| No. of reflections for lattice parameters: 6817 | No. of independent reflections: 2390 (R$_{int}$ = 0.0776) |
| θ range for lattice parameters (°): 2.2–65.2 | No. of observed reflections (1 ≧ 2σ): 2284 |
| Absorption coefficient (mm$^{-1}$): 0.700 | Absorption correction (T$_{min}$–T$_{max}$): 0.688–1.000 |

Resolution E

10 L of 0.1 M sodium phosphate buffer (pH 8) was maintained at 40° C. in a 20 Liter jacked reactor, stirred at 360 rpm. 1.5 liters of Alcalase 2.4L (Novozymes North America Inc.) was added to the reactor. When temperature of the mixture closed to 38° C., pH was adjusted to 8.0 with 10 N NaOH. A solution of the racemic N-Boc-(1R,2S)/(1S, 2R)-1-amino-2-vinylcyclopropane carboxylic acid ethyl ester (200 grams) in 2 liters DMSO was added to the reactor over a period of 1 hour via an addition funel. The reaction temperature was then adjusted to 40° C. After 3 hours, pH was adjusted to 8.0 with 10 N NaOH. After 21 hours, the Resolution F 5 L of 0.2 M sodium borate buffer (pH 9) was maintained at 45° C. in a 20 liter jacked reactor, stirred at 400 rpm. Three liter of DI water and four liters of Savinase 16L, type EX (Novozymes North America Inc.) were added to the reactor. When temperature of the mixture closed to 45° C., pH was adjusted to 8.5 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 40 min, via an addition funel. The reaction temperature was then adjusted to 48° C. After 2 hours, pH was adjusted to pH 9.0 with 10 N NaOH. At 18 hour, enantio-excess of the ester reached 72%, pH was adjusted to 9.0 with 10 N NaOH. At 24 hour, temperature was lowered to 35° C. At 42 hour, temperature was raised to 48° C. and pH was adjusted to 9.0 with 10 N NaOH. Heating was stopped at 48 hour and the reaction was slowly cooled down to room temperature (about 25° C.) and stirred overnight. At 66 hour, pH of the reaction mixture was 8.6. The mixture was extracted with MTBE (2×4 L). The combined MTBE extract was washed with 5% NaHCO$_3$ (6×300 ml) and water (3×300 ml), and evaporated to give give enantiomerically pure N-Boc-(1R, 2S)/-1-amino-2-vinylcyclopropane carboxylic acid ethyl ester as light yellow crystal (101A g; purity: 95.9% @ 210 nm, containing no acid; 98.6% ee).

C.2 Preparation of chiral (1R,2S)-1-amino-2-vinylcyclopropane carboxylic acid ethyl ester hydrochloride

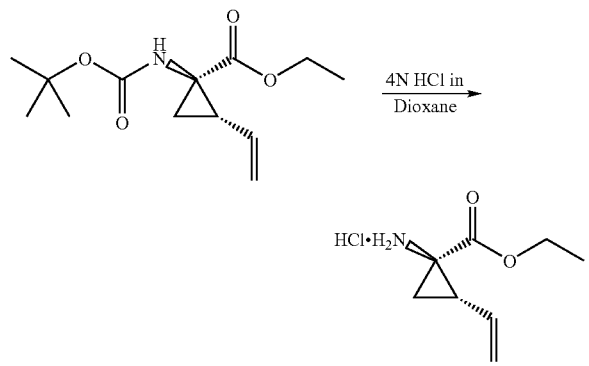

N-BOC-(1R,2S)-1-amino-2-vinylcyclopropanecarboxylic acid ethyl ester (8.5 g, 33.3 mmol) was stirred under an N$_2$ atmosphere with 200 mL of 4N HCl/dioxane (Aldrich) at rt for 3 h. The solvent was removed under reduced pressure keeping the temperature below 40 C. This gave 6.57 g (~100%) of (1R,2S)-1-amino-2-vinylcyclopropanecarboxylic acid ethyl ester hydrochloride as a light tan solid. $^1$H NMR (300 MHz, CD$_3$OD) δ 1.31 (t, J=7.0 Hz, 3H), 1.69–1.82 (m, 2H), 2.38 (q, J=8.8 Hz, 1H), 4.29 (q, J=7.0 Hz, 2H), 5.22 (d, J=10.3 Hz, 1H), 5.40 (d, J=17.2 Hz, 1H), 5.69–5.81 (m, 1H). LC-MS (Method A, retention time: 0.58 min), MS m/z 156 (M$^+$+1).

Example 2

Preparation of Compound 1, 14-tert-Butoxycarbonylamino-18-(isoquinolin-1-yloxy)-2,15-dioxo-3,16-diaza-tricyclo[14.3.0.0$^{4,6}$]nonadec-7-ene-4-carboxylic acid Example 2, Compound 1

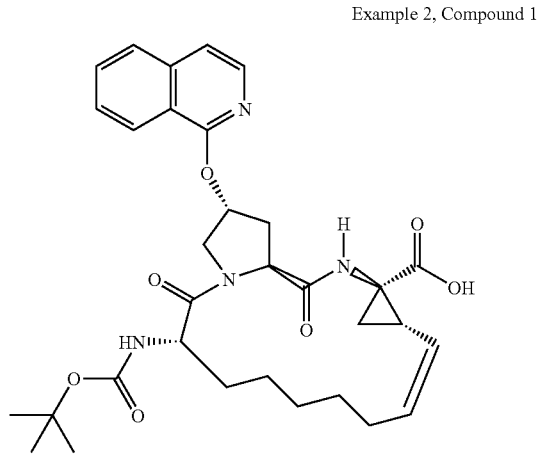

Step 2A, Preparation of 2-(1-Ethoxycarbonyl-2-vinyl-cyclopropylcarbamoyl)-4-(isoquinolin-1-yloxy)-pyrrolidine-1-carboxylic acid tert-butyl ester

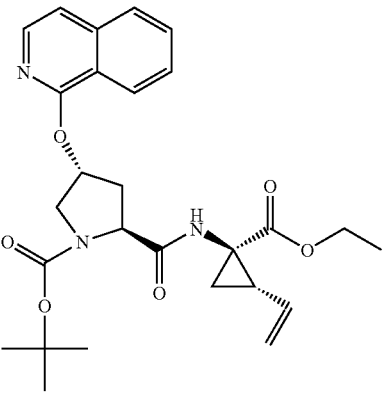

A stirred slurry of 4-(isoquinolin-1-yloxy)-pyrrolidine-1,2-dicarboxylic acid 1-tert-butyl ester (5.69 g, 15.9 mmol) in 200 mL of methylene chloride was treated sequentially with diisopropylethylamine (13.8 mL, 79.0 mmol), HBTU (7.10 g, 18.7 mmol), HOBT.H$_2$O (2.86 g, 18.7 mmol), and 1R,2S-1-amino-2-vinylcyclopropane carboxylic acid ethyl ester hydrochloride (3.19 g, 16.7 mmol). The gold homogeneous solution was stirred at rt under N$_2$ for 18 h, and then concentrated in vacuo to give 10 g of a brown oil. This was partitioned between ethyl acetate and sat. aq. NaHCO$_3$. The organic phase was washed with brine, dried (MgSO$_4$), and concentrated in vacuo. Flash chromatography (2–5% MeOH in methylene chloride) gave 5.5 g (70%) of 2-(1-ethoxycarbonyl-2-vinyl-cyclopropylcarbamoyl)-4-(isoquinolin-1-yloxy)-pyrrolidine-1-carboxylic acid tert-butyl ester: LC-MS (Method A, retention time: 3.42 min), MS m/z 496 (M$^+$+1).

Step 2B, Preparation of 1-{[4-(Isoquinolin-1-yloxy)-pyrrolidine-2-carbonyl]-amino}-2-vinyl-cyclopropanecarboxylic acid ethyl ester, bis hydrochloride

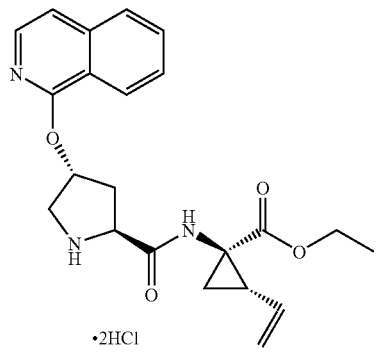

A stirred slurry of 2-(1-ethoxycarbonyl-2-vinyl-cyclopropylcarbamoyl)-4-(isoquinolin-1-yloxy)-pyrrolidine-1-carboxylic acid tert-butyl ester (5.40 g, 10.9 mmol) was treated with 2N HCl/ether (Aldrich)(250 mL) for 24 h. The reaction mixture was concentrated in vacuo to give 5.3 g (~100%) of 1-{[4-(isoquinolin-1-yloxy)-pyrrolidine-2-carbonyl]-amino}-2-vinyl-cyclopropanecarboxylic acid ethyl ester, bis hydrochloride as a white solid: LC-MS (Method A, retention time: 2.40 min), MS m/z 396 (M$^+$+1).

Step 2C, Preparation of 1-{[1-(2-tert-Butoxycarbonylamino-non-8-enoyl)-4-(isoquinolin-1-yloxy)-pyrrolidine-2-carbonyl]-amino}-2-vinyl-cyclopronanecarboxylic acid ethyl ester

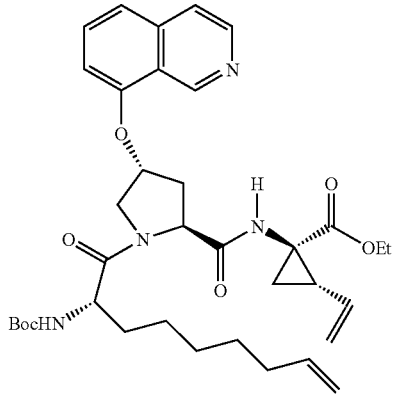

2(S)-tert-butoxycarbonylamino-8-nonenoic acid (purchased from RSP Amino Acids)(1.0 g, 3.68 mmol) dissolved in 100 mL of DMF was treated sequentially with 1-{[4-(isoquinolin-1-yloxy)-pyrrolidine-2-carbonyl]-amino}-2-vinyl-cyclopropanecarboxylic acid ethyl ester, bis hydrochloride (1.46 g, 3.68 mmol), N-methyl morpholine (1.4 mL, 12.9 mmol), and HATU (PE biosystems) (1.68 g, 4.42 mmol). The reaction mixture was stirred at rt under $N_2$ for 24 h, and then concentrated in vacuo. The residue was partitioned between ethyl acetate and pH 4 buffer (biphthalate). The organic phase was washed with sat. aq. $NaHCO_3$, dried ($MgSO_4$), and concentrated in vacuo to give 2.2 g of the crude product. Flash chromatography (20–50% ethyl acetate/hexane) gave 1.9 g (79%) of 1-{[1-(2-tert-butoxycarbonylamino-non-8-enoyl)-4-(isoquinolin-1-yloxy)-pyrrolidine-2-carbonyl]-amino}-2-vinyl-cyclopropanecarboxylic acid ethyl ester as a glassy colorless solid:

LC-MS (Method A, retention time: 3.72 min), MS m/z 649 ($M^+$+1).

Step 2D, Preparation of 14-tert-Butoxycarbonylamino-18-(isoquinolin-1-yloxy)-2,15-dioxo-3,16-diaza-tricyclo[14.3.0.0$^{4,6}$]nonadec-7-ene-4-carboxylic acid ethyl ester

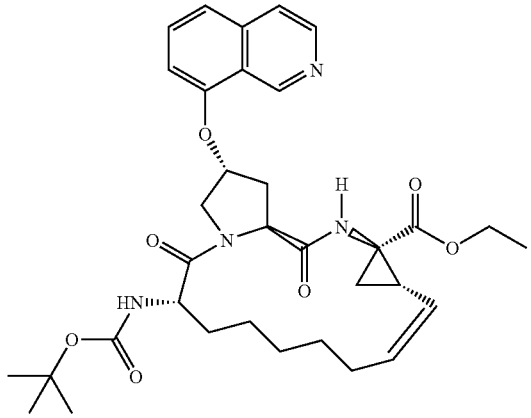

A solution of 1-{[1-(2-tert-butoxycarbonylamino-non-8-enoyl)-4-(isoquinolin-1-yloxy)-pyrrolidine-2-carbonyl]-amino}-2-vinyl-cyclopropanecarboxylic acid ethyl ester (1.72 g, 2.65 mmol) and tricyclohexylphosphine[1,3-bis(2,4,6-trimethylphenyl)-4,5-dihydroimidazol-2-ylidene][benzylidene]ruthenium (IV) dichloride (Strem) (225 mg, 0.265 mmol) in 650 mL of methylene chloride was refluxed under $N_2$. The light orange homogeneous solution was refluxed for 24 h to give a dark orange solution. The reaction mixture was cooled to rt and concentrated in vacuo to give 1.7 g of an orange oil. Flash chromatography (20–40% ethyl acetate/hexane) gave 1.4 g (85%) of 14-tert-butoxycarbonylamino-18-(isoquinolin-1-yloxy)-2,15-dioxo-3,16-diaza-tricyclo[14.3.0.0$^{4,6}$]-nonadec-7-ene-4-carboxylic acid ethyl ester as a white solid: $^1$H NMR (300 MHz, $CD_3Cl_3$) δ 1.29 (t, J=7.3 Hz, 3H), 1.34 (s, 9H), 1.35–1.71 (m, 9H), 1.86–1.97 (m, 2H), 2.08–2.27 (m, 2H), 2.38–2.47 (m, 1H), 2.96–3.04 (m, 1H), 4.02–4.23 (m, 4H), 4.55 (m, 1H), 4.91 (dd, J=8.4 Hz, 4.0 Hz, 1H), 5.25 (t, J=9.5 Hz, 1H), 5.32 (d, J=8.8 Hz, 1H), 5.50 (m, 1H), 5.81 (m, 1H), 6.96 (s, 1H), 7.23 (m, 1H), 7.51 (t, J=7.3 Hz, 1H), 7.65 (t, J=8.4 Hz, 1H), 7.73 (d, J=8.4 Hz, 1H), 7.93 (d, J=5.9 Hz, 1H), 8.17 (d, J=8.4 Hz, 1H). LC-MS (Method A, retention time: 3.52 min), MS m/z 621 ($M^+$+1).

Step 2E, Preparation of Compound 1, 14-tert-Butoxycarbonylamino-18-(isoquinolin-1-yloxy)-2,15-dioxo-3,16-diaza-tricyclo[14.3.0.0$^{4,6}$]nonadec-7-ene-4-carboxylic acid Compound 1

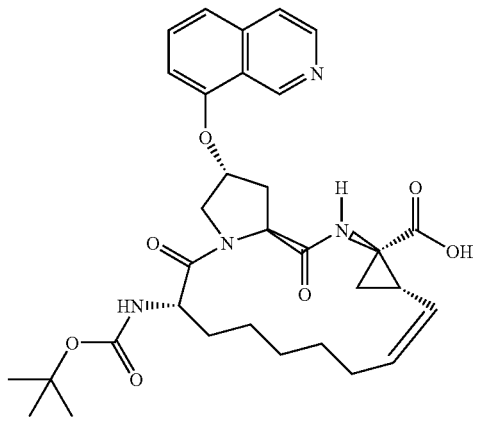

14-tert-butoxycarbonylamino-18-(isoquinolin-1-yloxy)-2,15-dioxo-3,16-diaza-tricyclo[14.3.0.0$^{4,6}$]-nonadec-7-ene-4-carboxylic acid ethyl ester (1.10 g, 1.77 mmol) was dissolved in the mixed solvent system; THF (18 mL), methanol (8 mL), and water (2 mL). Powdered lithium hydroxide hydrate (744 mg, 17.7 mmol) was added. The light yellow slurry was stirred at rt under N2 for 24 h, and then concentrated in vacuo. The residue was partitioned between ether and water. The ether phase was discarded, and the aqueous phase was treated with 4N HCl until the pH was 4. This acidic solution was extracted with ether four times. The combined ether extracts were dried ($MgSO_4$) and concentrated in vacuo to give 0.95 g (90%) of 14-tert-butoxycarbonylamino-18-(isoquinolin-1-yloxy)-2,15-dioxo-3,16-diaza-tricyclo[14.3.0.0$^{4,6}$]-nonadec-7-ene-4-carboxylic acid as a white solid: $^1$H NMR (300 MHz, $CD_3Cl_3$) δ 1.30 (s, 9H), 1.34–1.46 (m, 4H), 1.52–1.68 (m, 2H), 1.84 (m, 2H), 2.08–2.58 (m, 6H), 2.78–2.87 (m, 1H), 4.07 (m, 1H), 4.32 (d, J=11.3 Hz, 1H), 4.41 (m, 1H), 4.79 (t, J=7.3 Hz, 1H), 5.14 (t, J=9.5 Hz, 1H), 5.23 (d, J=7.3 Hz, 1H), 5.60 (q, J=8.8 Hz, 1H), 5.86 (s, 1H), 7.08 (s, 1H), 7.22 (d, J=6.2 Hz, 1H), 7.48 (t, J=7.7 Hz, 1H), 7.64 (t, J=8.0 Hz, 1H), 7.72 (d, J=8.1 Hz, 1H), 7.94 (d, J=5.9 Hz, 1H), 8.17 (s, J=8.4 Hz, 1H). LC-MS (Method A, retention time: 3.32 min), MS m/z 593 ($M^+$+1)

Example 3a

Preparation of Cyclopropylsulfonamide

Method A:

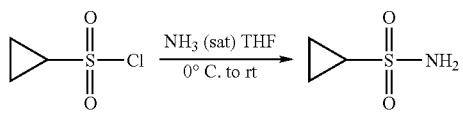

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF, the solution warmed to rt overnite and stirred one additional day. The mixture was concentrated until 1–2 mL of solvent remained, applied on to 30 g plug of $SiO_2$ (eluted with 30% to 60% EtOAc/Hexanes) to afford 3.45 g (100%) of cyclopropyl sulfonamide as a white solid. $^1$H NMR (Methanol-$d_4$) δ 0.94–1.07 (m, 4H), 2.52–2.60 (m, 1H); $^{13}$C NMR (methanol-$d_4$) δ 5.92, 33.01.

Method B:

Step 1: Preparation of N-tert-Butyl-(3-chloro)propylsulfonamide

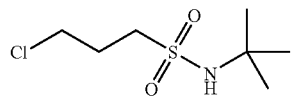

tert-Butylamine (3.0 mol, 315.3 mL) was dissolved in THF (2.5 L). The solution was cooled to −20° C. 3-Chloropropanesulfonyl chloride (1.5 mol, 182.4 mL) was added slowly. The reaction mixture was allowed to warm to rt and stirred for 24 h. The mixture was filtered, and the filtrate was concentrated in vacuo. The residue was dissolved in $CH_2Cl_2$ (2.0 L). The resulting solution was washed with 1 N HCl (1.0 L), water (1.0 L), brine (1.0 L) and dried over $Na_2SO_4$. It was filtered and concentrated in vacuo to give a slightly yellow solid, which was crystallized from hexane to afford the product as a white solid (316.0 g, 99%).

$^1$H NMR ($CDCl_3$) δ 1.38 (s, 9H), 2.30–2.27 (m, 2H), 3.22 (t, J=7.35 Hz, 2H), 3.68 (t, J=6.2 Hz, 2H), 4.35 (b, 1H).

Step 2: Preparation of Cyclopropanesulfonic acid tert-butylamide

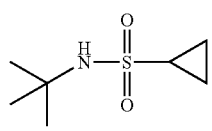

To a solution of N-tert-butyl-(3-chloro)propylsulfonamide (2.14 g, 10.0 mmol) in THF (100 mL) was added n-BuLi (2.5 M in hexane, 8.0 mL, 20.0 mmol) at −78° C. The reation mixture was allowed to warm up to room temperature over period of 1 h. The volatiles were removed in vacuo. The residue was partitioned between EtOAC and water (200 mL, 200 mL). The separated organic phase was washed with brine, dried over $Na_2SO_4$, filtered and concentrated in vacuo. The residue was recrystallized from hexane to yield the desired product as a white solid (1.0 g, 56%).

$^1$H NMR ($CDCl_3$) δ 0.98–1.00 (m, 2H), 1.18–1.19 (m, 2H), 1.39 (s, 9H), 2.48–2.51 (m, 1H), 4.19 (b, 1H).

Step 3: Preparation of Cyclopropylsulfonamide

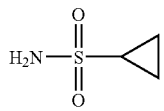

A solution of cyclopropanesulfonic acid tert-butylamide (110.0 g, 0.62 mol) in TFA (500 mL) was stirred at room temperature for 16 h. The volatile was removed in vacuo. The residue was recrystallized from EtOAC/hexane (60 mL/240 mL) to yield the desired product as a white solid (68.5 g, 91%).

$^1$H NMR (DMSO-$d_6$) δ 0.84–0.88 (m, 2H), 0.95–0.98 (m, 2H), 2.41–2.58 (m, 1H), 6.56 (b, 2H).

Example 3b

Preparation of C1-substituted Cyclopropylsulfonamides

Preparation of N-tert-butyl-(1-methyl)cyclopropyl-sulfonamide.

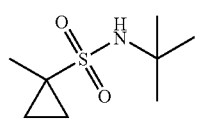

Step 1a Preparation of N-tert-butyl-(3-chloro)propylsulfonamide.

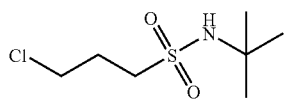

As shown above.

Step 1b. Preparation of N-tert-Butyl-(1-methyl)cyclopropyl-sulfonamide.

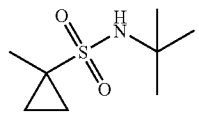

A solution of N-tert-butyl-(3-chloro)propylsulfonamide (4.3 g, 20 mmol) was dissolved in dry THF (100 mL) and cooled to −78° C. To this solution was added n-BuLi (17.6 mL, 44 mmol, 2.5 M in hexane) slowly. The dry ice bath was removed and the reaction mixture was allowed to warm to rt over a period of 1.5 h. This mixture was then cooled to −78° C., and a solution of n-BuLi (20 mmol, 8 mL, 2.5 M in hexane) was added. The reaction mixture was warmed to rt, recooled to −78° C. over a period of 2 h and a neat solution of methyl iodide (5.68 g, 40 mmol) added. The reaction mixture was allowed to warm to rt overnight, quenched with saturated $NH_4Cl$ (100 mL) at rt. It was extracted with EtOAc (100 mL). The organic phase was washed with brine (100 mL), dried ($MgSO_4$), and concentrated in vacuo to give a yellow oil which was crystallized from hexane to afford the product as a slightly yellow solid (3.1 g, 81%): ¹H NMR (CDCl₃) δ 0.79 (m, 2H), 1.36 (s, 9H), 1.52 (m, 2H), 1.62 (s, 3H), 4.10 (bs, 1H).

Step 1c: Preparation of 1-methylcyclopropylsulfonamide

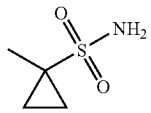

A solution of N-tert-butyl-(1-methyl)cyclopropylsulfonamide (1.91 g, 10 mmol) was dissolved in TFA (30 mL), and the reaction mixture stirred at rt for 16 h. The solvent was removed in vacuo to give a yellow oil which was crystallized from EtOAc/hexane (1:4, 40 mL) to yield Example 3, 1-methylcyclopropylsulfonamide, as a white solid (1.25 g, 96%): ¹H NMR (CDCl₃) δ 0.84 (m, 2H), 1.41 (m, 2H), 1.58 (s, 3H), 4.65 (bs, 2H). Anal. Calcd. For C₄H₉NO₂S: C, 35.54; H, 6.71; N, 10.36. Found: C, 35.67; H, 6.80; N, 10.40.

Preparation of 1-Benzylcyclopropylsulfonamide

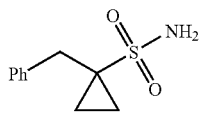

Steps 1b: Preparation of N-tert-Butyl-(1-benzyl)cyclopropyl-sulfonamide.

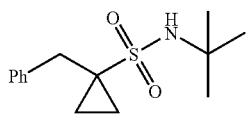

This compound was obtained in 60% yield using the procedure described for the synthesis of N-tert-butyl-(1-methyl)cyclopropylsulfonamide except 1.05 equivalents of benzyl bromide were used, followed by trituration with 10% EtOAc in hexane: ¹H NMR (CDCl₃) δ 0.92 (m, 2H), 1.36 (m, 2H), 1.43 (s, 9H), 3.25 (s, 2H), 4.62 (bs, 1H), 7.29–7.36 (m, 5H).

Steps 1c: Preparation of 1-Benzylcyclo-propylsulfonamide

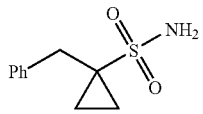

This compound 1-benzylcyclopropylsulfonamide, was obtained in 66% yield from N-tert-butyl(1-benzyl)cyclopropylsulfonamide using the procedure described for the synthesis of 1-methylcyclopropylsulfonamide, followed by recrystallization from the minimum amount of 10% EtOAc in hexane: ¹H NMR (CDCl₃) δ 0.90 (m, 2H), 1.42 (m, 2H), 3.25 (s, 2H), 4.05 (s, 2H), 7.29 (m, 3H), 7.34 (m, 2H); ¹³C NMR (CDCl₃) δ 11.1, 36.8, 41.9, 127.4, 128.8, 129.9, 136.5.

Preparation of 1-Propylcyclopropylsulfonamide

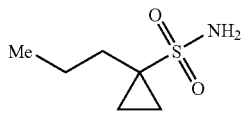

Steps 1b: Preparation of N-tert-Butyl-(1-benzyl)cyclopropyl-sulfonamide.

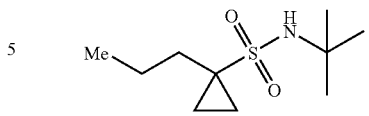

This compound was prepared using the process desribed for the preparation of 1-methylcyclopropylsulfonamide except propyl halide was utilized in place of methyl iodide in the second step of this process.

Preparation of N-tert-Butyl-(1-allyl)cyclopropylsulfonamide.

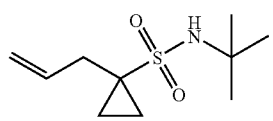

This compound, N-tert-Butyl-(1-allyl)cyclopropylsulfonamide, was obtained in 97% yield according to the procedure described in the synthesis of N-tert-Butyl-(1-methyl)cyclopropylsul-fonamide except 1.25 equivalents of allyl bromide were used as electrophile. The compound was taken directly into the next reaction without purification: ¹H NMR (CDCl₃) δ 0.83 (m, 2H), 1.34 (s, 9H), 1.37 (m, 2H), 2.64 (d, J=7.3 Hz, 2H), 4.25 (bs, 1H), 5.07–5.10 (m, 2H), 6.70–6.85 (m, 1H).

Preparation of 1-allylcyclopropylsulfonamide.

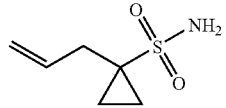

This compound, 1-allylcyclopropylsulfonamide, was obtained in 40% yield from N-tert-butyl-(1-allyl)cyclopropylsulfonamide according to the procedure described in the synthesis of 1-Methylcyclopropylsulfonamide. The compound was purified by column chromotography over SiO₂ using 2% MeOH in CH₂Cl₂ as the eluent: ¹H NMR (CDCl₃) δ 0.88 (m, 2H), 1.37 (m, 2H), 2.66 (d, J=7.0 Hz, 2H), 4.80 (s, 2H), 5.16 (m, 2H), 5.82 (m, 1H); ¹³C NMR (CDCl₃) δ 11.2, 35.6, 40.7, 119.0, 133.6.

Preparation of N-tert-Butyl-[1-(1-hydroxy)cyclohexyl]-cyclopropylsulfonamide.

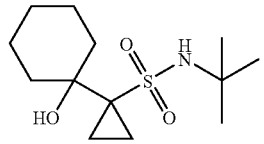

This compound was obtained in 84% yield using to the procedure described for the synthesis of N-tert-Butyl-(1-methyl)cyclopropylsul-fonamide except 1.30 equivalents of cyclohexanone were used, followed by recrystallization from the minimum amount of 20% EtOAc in hexane: ¹H NMR (CDCl₃) δ 1.05 (m, 4H), 1.26 (m, 2H), 1.37 (s, 9H), 1.57–1.59 (m, 6H), 1.97 (m, 2H), 2.87 (bs, 1H), 4.55 (bs, 1H).

Preparation of 1-(1-cyclohexenyl)cyclopropyl-sulfonamide.

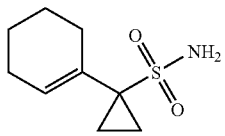

This compound, 1-(1-cyclohexenyl)-cyclopropylsulfonamide was obtained in 85% yield from N-tert-butyl-[1-(1-hydroxy)cyclohexyl]-cyclopropylsulfonamide using the procedure described for the synthesis of 1-methylcyclopropylsulfonamide, followed by recrystallization from the minimum amount of EtOAc and hexane: $^1$H NMR (DMSO-$d_6$) δ 0.82 (m, 2H), 1.28 (m, 2H), 1.51 (m, 2H), 1.55 (m, 2H), 2.01 (s, 2H), 2.16 (s, 2H), 5.89 (s, 1H), 6.46 (s, 2H); $^{13}$C NMR (DMSO-$d_6$) δ 11.6, 21.5, 22.3, 25.0, 27.2, 46.9, 131.6, 132.2; LR-MS (ESI): 200 ($M^+$-1).

Preparation of N-tert-Butyl-(1-benzoyl)cyclopropyl-sulfonamide.

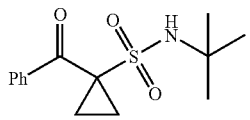

This compound was obtained in 66% yield using the procedure described for the synthesis of N-tert-Butyl-(1-methyl)cyclopropylsulfonamide except 1.2 equivalents of methyl benzoate was used as the electrophile. The compound was purified by column chromatography over $SiO_2$ using 30% to 100% $CH_2Cl_2$ in hexane: $^1$H NMR (CDCl$_3$) δ 1.31 (s, 9H), 1.52 (m, 2H), 1.81 (m, 2H), 4.16 (bs, 1H), 7.46 (m, 2H), 7.57 (m, 1H), 8.05 (d, J=8.5 Hz, 2H).

Preparation of 1-benzoylcyclo-propylsulfonamide.

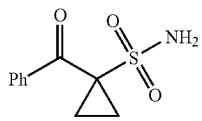

This compound 1-benzoylcyclopropyl-sulfonamide, was obtained in 87% yield from N-tert-butyl(1-benzoyl)cyclopropylsul-fonamide using the procedure described for the synthesis of 1-Methylcyclopropylsulfonamide, followed by recrystallization from the minimum amount of EtOAc in hexane: $^1$H NMR (DMSO-$d_6$) δ 1.39 (m, 2H), 1.61 (m, 2H), 7.22 (s, 2H), 7.53 (t, J=7.6 Hz, 2H), 7.65 (t, J=7.6 Hz, 1H), 8.06 (d, J=8.2 Hz, 2H); $^{13}$C NMR (DMSO-$d_6$) δ 12.3, 48.4, 128.1, 130.0, 133.4, 135.3, 192.0.

Preparation of N-tert-Butyl-(1-phenylaminocarboxy)-cyclopropylsulfonamide

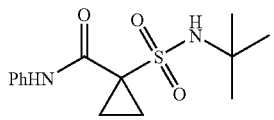

This compound was obtained in 42% yield using the procedure described for the synthesis of N-tert-Butyl-(1-methyl)cyclopropylsulfonamide using 1 equivalent of phenylisocyanate, followed by recrystallization from the minimum amount of EtOAc in hexane $^1$H NMR (CDCl$_3$) δ 1.38 (s, 9H), 1.67–1.71 (m, 4H), 4.30 (bs, 1H), 7.10 (t, J=7.5 Hz, 1H), 7.34 (t, J=7.5 Hz, 2H), 7.53 (t, J=7.5 Hz, 2H).

Example 4

Preparation of Cycloalkylsulfonamides from Cyloalkylbromides

Preparation of Cyclobutylsulfonamide from Cylobutylbromide

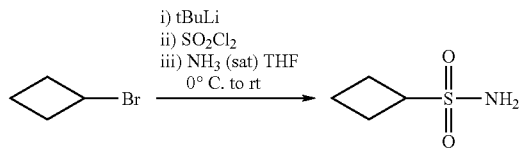

To a solution of 5.0 g (37.0 mmol) of cyclobutyl bromide in 30 mL of anhydrous diethyl ether (Et$_2$O) cooled to −78° C. was added 44 mL (74.8 mmol) of 1.7M tert-butyl lithium in pentanes and the solution slowly warmed to −35° C. over 1.5 h. This mixture was cannulated slowly into a solution of 5.0 g (37.0 mmol) of freshly distilled sulfuryl chloride in 100 mL of hexanes cooled to −40° C., warmed to 0° C. over 1 h and carefully concentrated in vacuo. This mixture was redissolved in Et$_2$O, washed once with some ice-cold water, dried (MgSO$_4$) and concentrated carefully. This mixture was redissolved in 20 mL of THF, added dropwise to 500 mL of saturated NH$_3$ in THF and was allowed to stir overnite. The mixture was concentrated in vacuo to a crude yellow solid and was recrystallized from the minimum amount of CH$_2$Cl$_2$ in hexanes with 1–2 drops of MeOH to afford 1.90 g (38%) of cyclobutylsulfonamide as a white solid. $^1$H NMR (CDCl$_3$) δ 1.95–2.06 (m, 2H), 2.30–2.54 (m, 4H), 3.86 (p, J=8 Hz, 1H), 4.75 (brs, 2H); $^{13}$C NMR (CDCl$_3$) δ 16.43, 23.93, 56.29. HRMS m/z (M–H)— calcd for $C_4H_8NSO_2$: 134.0276, found 134.0282.

Preparation of Cyclopentyl Sulfonamide

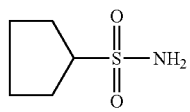

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to −78° C. The mixture was warmed to 0° C. over 1 h and was then carefully concentrated in vacuo. This mixture was redissolved in Et$_2$O (200 mL), washed once with some ice-cold water (200 mL), dried (MgSO$_4$) and concentrated carefully. This mixture was redissolved in 35 mL of THF, added dropwise to 500 mL of saturated NH$_3$ in THF and was allowed to stir overnite. The mixture was concentrated in vacuo to a crude yellow solid, the residue filtered through 50 g of silica gel using 70% EtOAc-hexanes as the eluent and the solution was then concentrated. The residue was recrystallized from the minimum amount of CH$_2$Cl$_2$ in hexanes with 1–2 drops of MeOH to afford 2.49 g (41%) of cyclopentylsulfonamide as a white solid. $^1$H NMR (CDCl$_3$) δ 1.58–1.72 (m, 2H), 1.74–1.88 (m, 2H), 1.94–2.14 (m, 4H), 3.48–3.59 (m, 1H), 4.80 (bs, 2H); $^{13}$C NMR (CDCl$_3$) δ 25.90, 28.33, 63.54; MS m/e 148 (M–H)$^-$.

Preparation of Cyclohexyl Sulfonamide

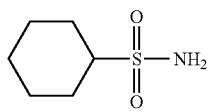

A solution of 18.5 mL (37.0 mmol) of 2M cyclohexyl-magnesium chloride (TCI Americas) in ether was added dropwise to a solution of 3.0 mL (37.0 mmol) freshly distilled sulfuryl chloride in 100 mL of hexanes cooled to −78° C. The mixture was warmed to 0° C. over 1 h and was then carefully concentrated in vacuo. This mixture was redissolved in Et$_2$O (200 mL), washed once with some ice-cold water (200 mL), dried (MgSO$_4$) and concentrated carefully This mixture was redissolved in 35 mL of THF, added dropwise to 500 mL of saturated NH$_3$ in THF and was allowed to stir overnite. The mixture was concentrated in vacuo to a crude yellow solid, the residue filtered through 50 g of silica gel using 70% EtOAc-hexanes as the eluent and was concentrated. The residue was recrystallized from the minimum amount of CH$_2$Cl$_2$ in hexanes with 1–2 drops of MeOH to afford 1.66 g (30%) of cyclohexylsulfonamide as a white solid: $^1$H NMR (CDCl$_3$) δ 1.11–1.37 (m, 3H), 1.43–1.56 (m, 2H), 1.67–1.76 (m, 1H), 1.86–1.96 (m, 2H), 2.18–2.28 (m, 2H), 2.91 (tt, J=12, 3.5 Hz, 1H), 4.70 (bs, 2H); $^{13}$CH NMR (CDCl$_3$) δ 25.04, 25.04, 26.56, 62.74; MS m/e 162 (M−1)$^−$.

Example 5

Preparation of Compound 2, [18-(Isoquinolin-1-yloxy)-4-methanesulfonylaminocarbonyl-2,15-di-oxo-3,16-diaza-tricyclo[14.3.0.0$^{4,6}$]nonadec-7-en-14-yl]-carbamic acid tert-butyl ester Compound 2

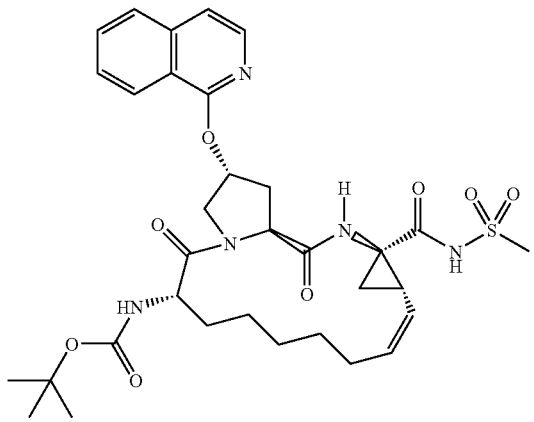

Prepared from 14-tert-butoxycarbonylamino-18-(iso-quinolin-1-yloxy)-2,15-dioxo-3,16-diaza-tricyclo[14.3.0.0$^{4,6}$]-nonadec-7-ene-4-carboxylic acid (50 mg, 0.075 mmol) and methane sulfonamide (9.3 mg, 0.098 mmol) as described in the general procedure above to give [18-(isoquinolin-1-yloxy)-4-methanesulfonylaminocarbonyl-2,15-dioxo-3,16-diaza-tricyclo[14.3.0.0$^{4,6}$]nonadec-7-en-14-yl]-carbamic acid tert-butyl ester as a white powder: $^1$H NMR (300 MHz, CD$_3$Cl$_3$) δ 1.18 (s, 9H), 1.25–1.96 (m, 11H), 2.26 (m, 1H), 2.54 (m, 1H), 2.71 (m, 2H), 3.18 (s, 3H), 4.08 (m, 1H), 4.26 (m, 1H), 4.64 (m, 2H), 5.00 (m, 2H), 5.73 (m, 1H), 6.01 (s, 1H), 6.73 (s, 1H), 7.28 (d, J=5.5 Hz, 1H), 7.50 (t, J=7.3 Hz, 1H), 7.65–7.76 (m, 2H), 7.98 (d, J=5.9 Hz, 1H), 8.19 (d, J=7.7 Hz, 1H), 10.28 (s, 1H). LC-MS (Method A, retention time: 3.57 min), MS m/z 670 (M$^+$+1).

Example 6

Preparation of Compound 3, [18-(Isoquinolin-1-yloxy)-2,15-dioxo-4-(propane-2-sulfonylaminocar-bonyl)-3,16-diaza-tricyclo-[14.3.0.0$^{4,6}$]nonadec-7-en-14-yl]-carbamic acid tert-butyl ester Compound 3

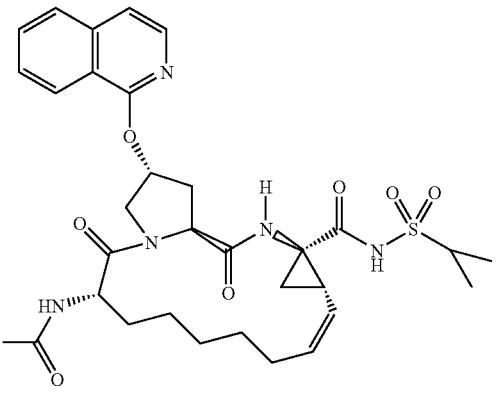

14-tert-butoxycarbonylamino-18-(isoquinolin-1-yloxy)-2,15-dioxo-3,16-diaza-tricyclo[14.3.0.0$^{4,6}$]-nonadec-7-ene-4-carboxylic acid (67 mg, 0.10 mmol) was dissolved in 5 mL of THF and treated with CDI (21 mg, 0.13 mmol). (Care was taken to avoid moisture by using oven dried glassware and maintaining a dry N2 atmosphere.) After refluxing the reaction mixture for one hour, it was cooled to rt and treated sequentially with isopropylsulfonamide (16 mg, 0.13 mmol) and DBU (20 mg, 0.13 mmol). After stirring for 24 h at rt, the THF was removed by rotary evaporation. The residue was partitioned between ethyl acetate and pH 4 buffer. The organic phase was dried (MgSO4) and concentrated in vacuo to give the crude product. Flash chromatography (1–5% MeOH/methylene chloride) gave 50 mg (71%) of the desired product. Further purification by preparative HPLC (YMC ODS-A, S5, 20×100 mm, gradient: 60% to 100% B) gave 30 mg (43%) of [18-(isoquinolin-1-yloxy)-2,15-dioxo-4-(propane-2-sulfonylaminocarbonyl)-3,16-diaza-tricyclo[14.3.0.0$^{4,6}$]nonadec-7-en-14-yl]-carbamic acid tert-butyl ester as a white powder: $^1$H NMR (300 MHz, CD$_3$Cl$_3$) δ 1.22 (S, 9H), 1.31 (d. J=6.6 Hz, 3H), 1.41 (d, J=6.9 Hz, 3H), 1.20–1.96 (m, 11H), 2.30 (q, J=8.4 Hz, 1H), 2.56 (m, 1H), 2.69 (m, 2H), 3.69 (m, 1H), 4.03 (m, 1H), 4.29 (m, 1H), 4.62 (m, 2H), 4.97–5.06 (m, 2H), 5.68 (q, J=9.5 Hz, 1H), 5.91 (s, 1H), 6.76 (s, 1H), 7.23 (m, 1H), 7.45 (t, J=7.7 Hz, 1H), 7.63 (t, J=8.1 Hz, 1H), 7.71 (d, J=8.1 Hz, 1H), 7.97 (d, J=5.9 Hz, 1H), 8.17 (d, J=8.1 Hz, 1H), 9.89 (s, 1H). LC-MS (Method A, retention time: 3.79 min), MS m/z 670 (M$^+$+1).

Example 7

Preparation of Compound 4, [4-Cyclopropanesulfonylaminocarbonyl-18-(isoquinolin-1-yloxy)-2,15-dioxo-3,16-diaza-tricyclo[14.3.0.0$^{4,6}$]nonadec-7-en-14-yl]-carbamic acid tert-butyl ester Compound 4

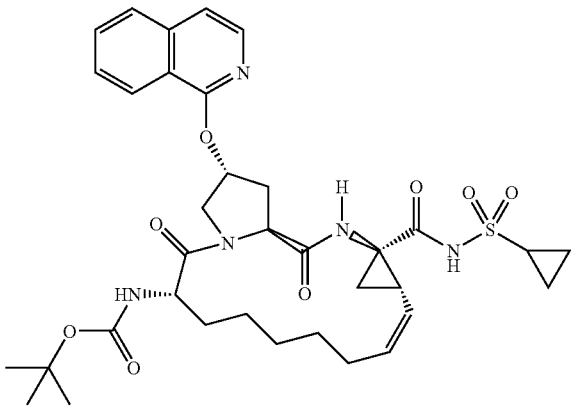

Prepared from 14-tert-butoxycarbonylamino-18-(isoquinolin-1-yloxy)-2,15-dioxo-3,16-diaza-tricyclo[14.3.0.0$^{4,6}$]-nonadec-7-ene-4-carboxylic acid etherate (100 mg, 0.15 mmol) and cyclopropylsulfonamide (24 mg, 0.20 mmol) as described in the general procedure above. Flash chromatography (2% methanol/methylene chloride) gave 55 mg (53%) of [4-cyclopropanesulfonylaminocarbonyl-18-(isoquinolin-1-yloxy)-2,15-dioxo-3,16-diaza-tricyclo-[14.3.0.0$^{4,6}$]-nonadec-7-en-14-yl]-carbamic acid tert-butyl ester as a white powder: $^1$H NMR (500 MHz, CD$_3$Cl$_3$) δ 0.89–0.95 (m, 1H), 1.03–1.16 (m, 3H), 1.22 (s, 9H), 1.18–1.48 (m, 8H), 1.78 (m, 1H), 1.87 (m, 1H), 1.94 (m, 1H), 2.29 (q, J=9.0 Hz, 1H), 2.56 (m, 1H), 2.67 (dd, J=7.9 Hz, 2.7 Hz, 2H), 2.90 (m, 1H), 4.04 (dd, J=11.3 Hz, 4.0 Hz, 1H), 4.29 (m, 1H), 4.61 (m, 2H), 4.97–5.03 (m, 2H), 5.70 (m, 1H), 5.94 (s, 1H), 6.67 (s, 1H), 7.25 (m, 1H), 7.47 (t, J=7.3 Hz, 1H), 7.64 (t, J=7.3 Hz, 1H), 7.72 (d, J=7.9 Hz, 1H), 7.97 (d, J=5.8 Hz, 1H), 8.17 (d, J=8.5 Hz, 1H), 10.20 (s, 1H). LC-MS (Method A, retention time: 3.67 min), MS m/z 696 (M$^+$+1).

Example 8

[4-(1-Benzyl-cyclopropanesulfonylaminocarbonyl)-18-(isoquinolin-1-yloxy)-2,15-dioxo-3,16-diaza-tricyclo[14.3.0.0$^{4,6}$]nonadec-7-en-14-yl]-carbamic acid tert-butyl ester Compound 5

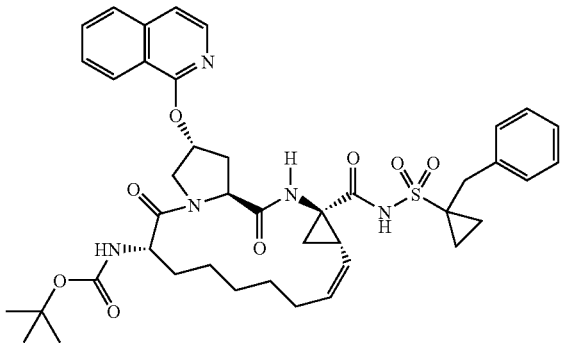

Prepared from 14-tert-butoxycarbonylamino-18-(isoquinolin-1-yloxy)-2,15-dioxo-3,16-diaza-tricyclo[14.3.0.0$^{4,6}$]-nonadec-7-ene-4-carboxylic acid (50 mg, 0.075 mmol) and 1-benzyl-cyclopropanesulfonic acid amide (21 mg, 0.098 mmol, prepared as described above) to give [4-(1-benzyl-cyclopropanesulfonylaminocarbonyl)-18-(isoquinolin-1-yloxy)-2,15-dioxo-3,16-diaza-tricyclo[14.3.0.0$^{4,6}$] nonadec-7-en-14-yl]-carbamic acid tert-butyl ester as a white powder: $^1$H NMR (500 MHz, CD$_3$Cl$_3$) δ 1.23 (s, 9H), 1.04–1.92 (m, 14H), 1.96 (m, 1H), 2.32 (dd, J=17.7 Hz, 9.5 Hz, 1H), 2.59 (m, 1H), 2.70 (m, 2H), 3.20 (d, J=13.4 Hz, 1H), 3.41 (d, J=13.7 Hz, 1H), 4.02 (m, 1H), 4.29 (m, 1H), 4.61 (m, 2H), 5.01 (d, J=7.6 Hz, 1H), 5.15 (m, 1H), 5.78 (m, 1H), 5.92 (s, 1H), 6.65 (s, 1H), 7.08 (d, J=8.2 Hz, 2H), 7.26 (m, 4H), 7.46 (t, J=7.3 Hz, 1H), 7.64 (t, J=7.3 Hz, 1H), 7.72 (d, J=8.2 Hz, 1H), 7.97 (d, J=5.8 Hz, 1H), 8.17 (d, J=8.9 Hz, 1H), 10.05 (s, 1H). LC-MS (Method A, retention time: 3.87 min), MS m/z 786 (M$^+$+1).

Example 9

Preparation of Compound 6, [18-(Isoquinolin-1-yloxy)-2,15-dioxo-4-(1-propyl-cyclopropanesulfonylaminocarbonyl)-3,16-diaza-tricyclo[14.3.0.0$^{4,6}$] nonadec-7-en-14-yl]-carbamic acid tert-butyl ester Compound 6

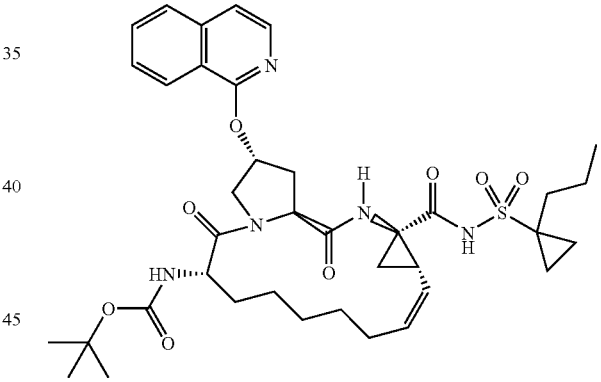

Prepared from 14-tert-butoxycarbonylamino-18-(isoquinolin-1-yloxy)-2,15-dioxo-3,16-diaza-tricyclo[14.3.0.0$^{4,6}$]-nonadec-7-ene-4-carboxylic acid (50 mg, 0.075 mmol) and 1-propyl-cyclopropanesulfonic acid amide (16 mg, 0.098 mmol, prepared as described above) to give [18-(isoquinolin-1-yloxy)-2,15-dioxo-4-(1-propyl-cyclopropanesulfonylaminocarbonyl)-3,16-diaza-tricyclo[14.3.0.0$^{4,6}$]nonadec-7-en-14-yl]-carbamic acid tert-butyl ester as a white powder: $^1$H NMR (300 MHz, CD$_3$Cl$_3$) δ 0.82–0.93 (m, 5H), 1.23 (s, 9H), 1.30–1.94 (m, 17H), 2.28 (m, 1H), 2.54(m, 1H), 2.68 (dd, J=8.1 Hz, 3.2 Hz, 2H), 4.05 (m, 1H), 4.30 (m, 1H), 4.63–4.66 (m, 2H), 4.96–5.09 (m, 2H), 5.70 (m, 1H), 5.92 (s, 1H), 6.69 (s, 1H), 7.23 (m, 1H), 7.46 (t, J=8.1 Hz, 1H), 7.63 (t, J=8.1 Hz, 1H), 7.72 (d, J=8.1 Hz, 1H), 7.97(d, J=5.9 Hz, 1H), 8.17 (d, J=8.4 Hz, 1H), 10.12 (s, 1H). LC-MS (Method A, retention time: 3.77 min), MS m/z 738 (M$^+$+1).

Example 10

Preparation of Compound 7, [18-(Isoquinolin-1-yloxy)-2,15-dioxo-4-(1-propyl-cyclopropanesulfonylaminocarbonyl)-3,16-diaza-tricyclo[14.3.0.0$^{4,6}$]nonadec-14-yl]-carbamic acid tert-butyl ester

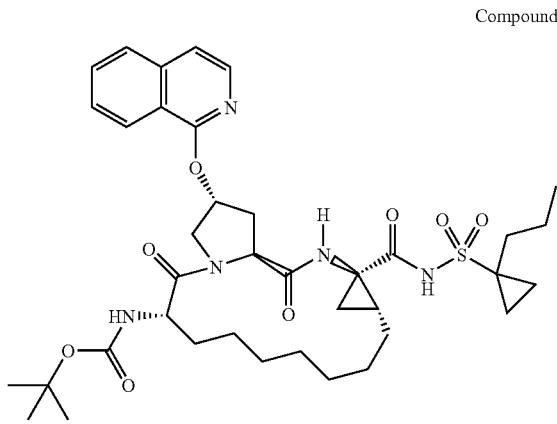

Compound 7

To a mixture of 73 mg (0.1 mmol) of [18-(Isoquinolin-1-yloxy)-2,15-dioxo-4-(1-propylcyclopropanesulfonylamino-carbonyl)-3,16-diaza-tricyclo[14.3.0.0$^{4,6}$]nonadec-7-en-14-yl]-carbamic acid tert-butyl ester in 3 mL of methanol was added 332 mg (2 mmol) of dipotassium azodicarboxylate. Glacial acetic acid (240 mg, 4 mmol) in 2 mL of methanol was added slowly by a syringe pump over 5 h. The mixture was stirred at rt. After 5 h, another 332 mg (2 mmol) of dipotassium azodicarboxylate and 240 mg (4 mmol) of glacial acetic acid was added over the course of 5 h and the stirring was continued overnight. This cycle was repeated twice. LC-MS showed about 40% starting material still remaining. The solvent was then removed on a rotary evaporator. Water was added to the residue and the mixture was extracted three times with ethyl acetate. It was then dried with magnesium sulfate, filtered and concentrated in vacuo. The resulting oil was dissolved in methanol and purified by preparative HPLC (YMC ODS-A, S5, 20×100 mm, gradient: 80% B to 85% B, 15 min, hold 2 min, flow rate 25 mL/min) to isolate the product as a white powder (25 mg, 34%).

$^1$H NMR (500 MHz, CD$_3$Cl$_3$) δ 0.91 (m, 5H), 1.30 (s, 9H), 1.20–1.80 (m, 21H), 1.86–1.93 (m, 2H), 2.57 (m, 1H), 2.67 (m, 1H), 4.10 (m, 1H), 4.36 (d, J=12.2 Hz, 1H), 4.44 (t, J=8.2 Hz, 1H), 4.61 (t, J=7.9 Hz, 1H), 5.16 (d, J=8.2 Hz, 1H), 5.92 (bs, 1H), 6.58 (bs, 1H), 7.25 (m, 1H), 7.49 (t, J=7.3 Hz, 1H), 7.65 (t, J=7.3 Hz, 1H), 7.73 (d, J=8.2 Hz, 1H), 7.97 (d, J=5.8 Hz, 1H), 8.15 (d, J=8.2 Hz, 1H), 10.09 (s, 1H). LC-MS (Method A, retention time: 3.83 min), MS m/z 740(M$^+$+1).

Example 11

Preparation of Compound 8, [18-(Isoquinolin-1-yloxy)-4-(1-methyl-cyclopropanesulfonylaminocarbonyl)-2,15-dioxo-3,16-diaza-tricyclo[14.3.0.0$^{4,6}$]nonadec-7-en-14-yl]-carbamic acid tert-butyl ester

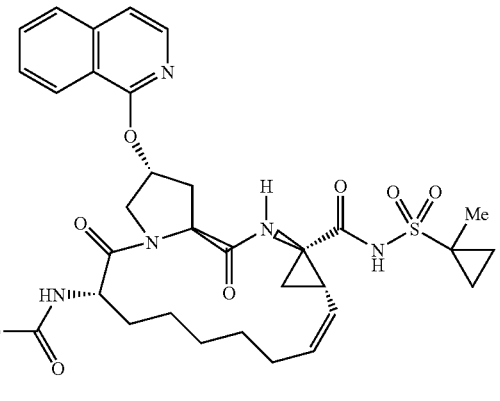

Compound 8

Prepared from 14-tert-butoxycarbonylamino-18-(isoquinolin-1-yloxy)-2,15-dioxo-3,16-diaza-tricyclo[14.3.0.0$^{4,6}$]-nonadec-7-ene-4-carboxylic acid etherate (105 mg, 0.177 mmol) and 1-methyl-cyclopropanesulfonic acid amide (31 mg, 0.23 mmol, prepared as described above). Flash chromatography (2% methanol/methylene chloride) gave 73 mg (58%) of [18-(isoquinolin-1-yloxy)-4-(1-methyl-cyclopropanesulfonylaminocarbonyl)-2,15-dioxo-3,16-diaza-tricyclo[14.3.0.0$^{4,6}$]nonadec-7-en-14-yl]-carbamic acid tert-butyl ester as a white powder: LC-MS (Method A, retention time: 3.50 min), MS m/z 710 (M$^+$+1).

Example 12

Preparation of Compound 9, [4-Cyclobutanesulfonylaminocarbonyl-18-(isoquinolin-1-yloxy)-2,15-dioxo-3,16-diaza-tricyclo[14.3.0.0$^{4,6}$]nonadec-7-en-14-yl]-carbamic acid tert-butyl ester

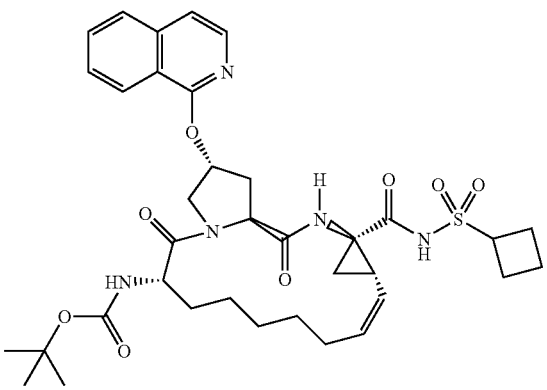

Compound 9

Prepared from 14-tert-butoxycarbonylamino-18-(isoquinolin-1-yloxy)-2,15-dioxo-3,16-diaza-tricyclo[14.3.0.

$0^{4,6}$]-nonadec-7-ene-4-carboxylic acid etherate (114 mg, 0.192 mmol) and cyclobutanesulfonic acid amide (34 mg, 0.25 mmol) as described in the general procedure above. Flash chromatography (2% methanol/methylene chloride) gave 73 mg (58%) of [18-(isoquinolin-1-yloxy)-4-(1-methyl-cyclopropanesulfonylaminocarbonyl)-2,15-dioxo-3,16-diaza-tricyclo[14.3.0.0$^{4,6}$]nonadec-7-en-14-yl]-carbamic acid tert-butyl ester as a white powder: LC-MS (Method A, retention time: 3.55 min), MS m/z 710 (M$^+$+1).

Example 13

Preparation of Compound 10, [4-Cyclopropane-sulfonylaminocarbonyl-18-(isoquinolin-1-yloxy)-2,15-dioxo-3,16-diaza-tricyclo[14.3.0.0$^{4,6}$]nonadec-14-yl]-carbamic acid tert-butyl ester Compound 10

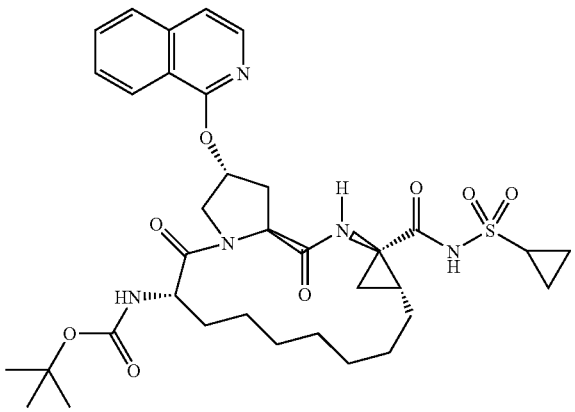

To a mixture of 140 mg (0.2 mmol) of [4-cyclopropane-sulfonylaminocarbonyl-18-(isoquinolin-1-yloxy)-2,15-dioxo-3,16-diaza-tricyclo[14.3.0.0$^{4,6}$]nonadec-7-en-14-yl]-carbamic acid tert-butyl ester in 3 mL of methanol was added 656 mg (4 mmol) of dipotassium azodicarboxylate. Glacial acetic acid (480 mg, 8 mmol) in 2 mL of methanol was added slowly by a syringe pump over 5 h. The mixture was stirred at rt. After 5 h, another 656 mg (4 mmol) of dipotassium azodicarboxylate and 480 mg (8 mmol) of glacial acetic acid was added over the course of 5 h and the stirring was continued overnight. This cycle was repeated twice. LC-MS showed about 40% starting material still was remaining. The solvent was then removed on a rotary evaporator. Water was added to the residue and the mixture was extracted three times with ethyl acetate. It was then dried with magnesium sulfate, filtered and concentrated in vacuo. The resulting oil was dissolved in methanol and purified by preparative HPLC (YMC XTERRA, S5, 30×50 mm, gradient: 72% B to 78% B, 15 min, hold 2 min, flow rate 40 ml/min) to isolate the product as a white powder (80 mg, 57%). LC-MS (Method A, retention time: 3.59 min), MS m/z 698 (M$^+$+1).

Example 14

Preparation of Compound 11, Cyclopropanesulfonic acid [14-amino-18-(isoquinolin-1-yloxy)-2,15-dioxo-3,16-diaza-tricyclo[14.3.0.0$^{4,6}$]nonadec-7-ene-4-carbonyl]-amide bis hydrochloride Compound 11

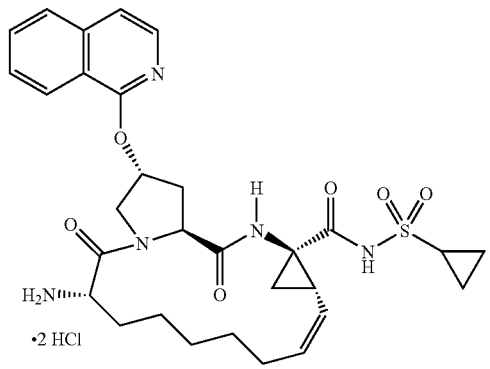

A stirred slurry of [4-cyclopropane-sulfonylaminocarbonyl-18-(isoquinolin-1-yloxy)-2,15-dioxo-3,16-diaza-tricyclo[14.3.0.0$^{4,6}$]nonadec-7-en-14-yl]-carbamic acid tert-butyl ester (1.20 g, 1.7 mmol) was treated with 4N HCl/dioxane (Aldrich)(10 mL) for 4 h. The reaction mixture was concentrated in vacuo to give 1.10 g (92%) of cyclopropanesulfonic acid [14-amino-18-(isoquinolin-1-yloxy)-2,15-dioxo-3,16-diaza-tricyclo[14.3.0.0$^{4,6}$]nonadec-7-ene-4-carbonyl]-amide bis hydrochloride as a white solid: LC-MS (Method B, retention time: 1.39 min), MS m/z 596 (M$^+$+1–2HCl).

Example 15

Preparation of Compound 12 [4-Cyclopropanesulfonylaminocarbonyl-18-(isoquinolin-1-yloxy)-2,15-dioxo-3,16-diaza-tricyclo[14.3.0.0$^{4,6}$]nonadec-7-en-14-yl]-carbamic acid methyl ester Compound 12

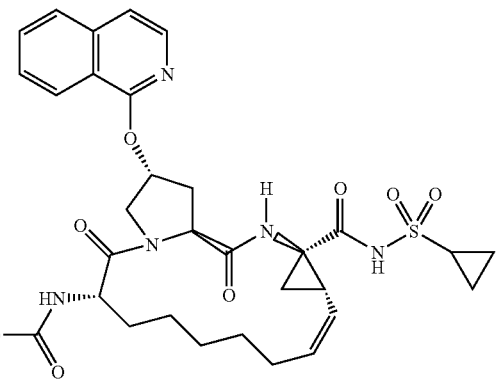

To a mixture of cyclopropanesulfonic acid [14-amino-18-(isoquinolin-1-yloxy)-2,15-dioxo-3,16-diaza-tricyclo [14.3.0.0$^{4,6}$]nonadec-7-ene-4-carbonyl]-amide bis hydrochloride (50 mg, 0.075 mmol) in 2 mL of DCM was added 44 μL (0.25 mmol) of DIPEA and 9 mg (0.10 mmol) of methyl chloroformate. The mixture was stirred at rt for 2 h. It was then diluted with EtOAc and washed with pH 4 buffer (2×) and brine (1×). The organic phase was dried (MgSO$_4$) and concentrated in vacuo to give the crude product. Flash chromatography (2% MeOH/DCM) gave 40 mg (82%) of the desired product as a white solid: LC-MS (Method A, retention time: 3.05 min), MS m/z 654 (M$^+$+1).

Example 16

Preparation of Compound 13, [4-Cyclopropane-sulfonylaminocarbonyl-18-(isoquinolin-1-yloxy)-2,15-dioxo-3,16-diaza-tricyclo[14.3.0.0$^{4,6}$]nonadec-7-en-14-yl]-carbamic acid 2,2-dimethyl-propyl ester Compound 13

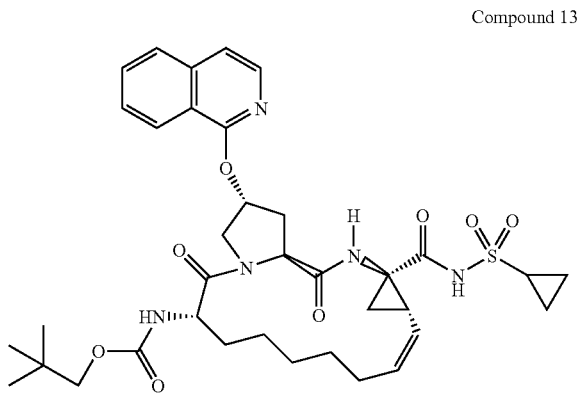

To a mixture of cyclopropanesulfonic acid [14-amino-18-(isoquinolin-1-yloxy)-2,15-dioxo-3,16-diaza-tricyclo[14.3.0.0$^{4,6}$]nonadec-7-ene-4-carbonyl]-amide bis hydrochloride (50 mg, 0.075 mmol) in 2 mL of DCM was added 44 µL (0.25 mmol) of DIPEA and 15 mg (0.1 mmol) of neopentyl chloroformate. The mixture was stirred at rt for 2 h. It was then diluted with EtOAc and washed with pH 4 buffer (2×) and brine (1×). The organic phase was dried (MgSO$_4$) and concentrated in vacuo to give the crude product. The resulting oil was dissolved in methanol and purified by preparative HPLC (YMC XTERRA, S5, 30×50 mm, gradient: 65% B to 100% B, 15 min, hold 2 min, flow rate 40 mL/min) to isolate the product as a white powder (42 mg, 79%): LC-MS (Method A, retention time: 3.58 min), MS m/z 710 (M$^+$+1).

General Procedure for Preparation of Chloroformates

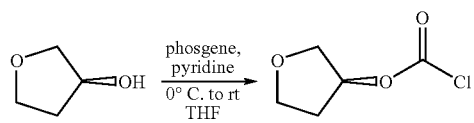

This procedure was used for the preparation of non-commercially available chloroformates. To a solution of 5.96 g (67.6 mmol) of commercially available reagents (S)-3-hydroxytetrahydrofuran and pyridine (5.8 mL; 72 mmol) in THF (150 mL) cooled to 0° C. was added a 1.93 M solution of phosgene in toluene (48 mL, 92.6 mmol over 10 min under argon. The resulting solution was allowed to warm to rt over 2 h, the resulting solid filtered, and the mother liquor carefully concentrated in vacuo at room temperature until theoretical mass was obtained. The resulting residue was dissolved in 100 mL of THF to prepare a 0.68M stock solution of 3(S)-oxo-tetrahydrofuran chloroformate that could be stored in the freezer until use. In analogous fashion, other commercially available alcohols could be converted to 0.68M stock solutions of the corresponding chloroformates.

Example 17

Preparation of Compound 14, [4-Cyclopropane-sulfonylaminocarbonyl-18-(isoquinolin-1-yloxy)-2,15-dioxo-3,16-diaza-tricyclo[14.3.0.0$^{4,6}$]nonadec-7-en-14-yl]-carbamic acid tetrahydro-pyran-4-yl ester Compound 14

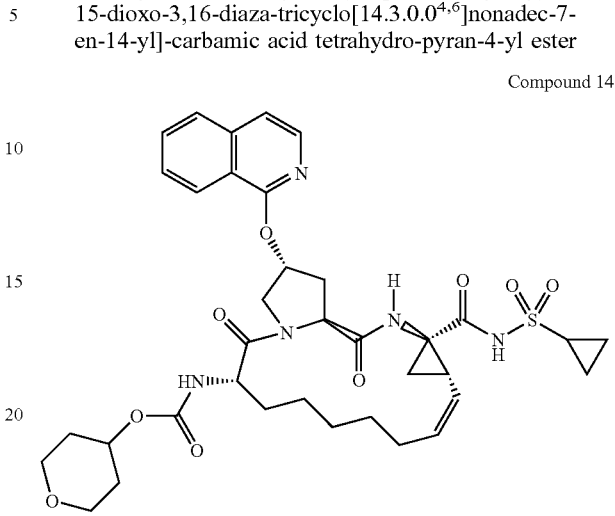

Prepared from cyclopropanesulfonic acid [14-amino-18-(isoquinolin-1-yloxy)-2,15-dioxo-3,16-diaza-tricyclo[14.3.0.0$^{4,6}$]nonadec-7-ene-4-carbonyl]-amide bis hydrochloride (50 mg, 0.075 mmol, 44 µL (0.25 mmol) of DIPEA and 0.17 mL (0.1 mmol) of tetrahydropyran chloroformate (prepared by treating tetrahydro-pyran-4-ol with phosgene) in DCM as described in the procedure above to give 28 mg (52%) of a white solid. Preparative HPLC condition: YMC XTERRA, S5, 19×100 mm, gradient: 50% B to 100% B, 10 min, hold 2 min, flow rate 25 mL/min. LC-MS (Method A, retention time: 3.13 min), MS m/z 724 (M$^+$+1).

Example 18

Preparation of Compound 15, [4-Cyclopropane-sulfonylaminocarbonyl-18-(isoquinolin-1-yloxy)-2,15-dioxo-3,16-diaza-tricyclo[14.3.0.0$^{4,6}$]nonadec-7-en-14-yl]-carbamic acid tetrahydro-furan-3-yl ester Compound 15

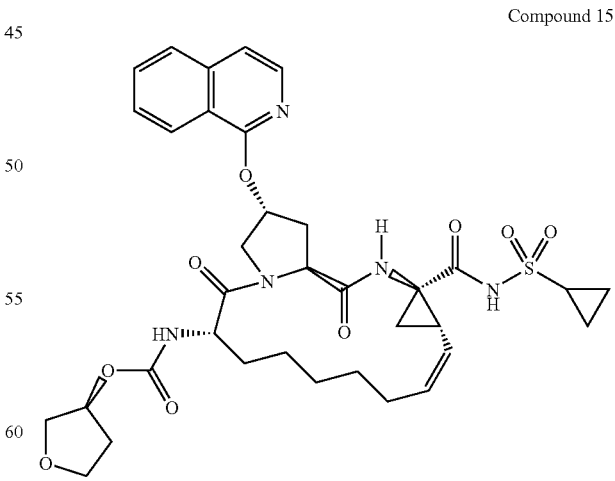

Prepared from cyclopropanesulfonic acid [14-amino-18-(isoquinolin-1-yloxy)-2,15-dioxo-3,16-diaza-tricyclo[14.3.0.0$^{4,6}$]nonadec-7-ene-4-carbonyl]-amide bis hydrochloride (50 mg, 0.075 mmol), 44 µL (0.25 mmol) of DIPEA and 0.10 mL (0.1 mmol) of tetrahydro-furan-3-yl chloroformate (prepared by treating tetrahydrofuran-3-ol with phosgene) in DCM as described in the procedure above to give 28 mg (52%) of a white solid. Preparative HPLC condition: YMC ODS-A, S5, 30×50 mm, gradient: 50% B to 85% B, 8 min, hold 2 min, flow rate 45 ml/min. LC-MS (Method A, retention time: 3.05 min), MS m/z 710 (M⁺+1).

Example 19

Preparation of Compound 16, [4-Cyclopropane-sulfonylaminocarbonyl-18-(isoquinolin-1-yloxy)-2,15-dioxo-3,16-diaza-tricyclo[14.3.0.0⁴,⁶]nonadec-7-en-14-yl]-carbamic acid isopropyl ester

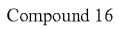

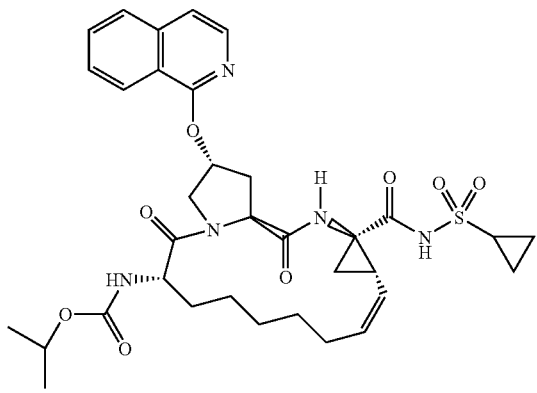

Prepared from cyclopropanesulfonic acid [14-amino-18-(isoquinolin-1-yloxy)-2,15-dioxo-3,16-diaza-tricyclo[14.3.0.0⁴,⁶]nonadec-7-ene-4-carbonyl)-amide bis hydrochloride (50 mg, 0.075 mmol), 44 mL (0.25 mmol) of DIPEA and 0.10 mL (0.1 mmol) of 1 M isopropyl chloroformate in toluene (Aldrich) as described in the procedure above to give 40 mg (78%) of a white solid. Preparative HPLC condition: YMC XTERRA, S5, 30×50 mm, gradient: 50% B to 100% B. 15 min. hold 2 min. flow rate 40 mL/min) NMR (300 MHz, CD₃OD) δ. LC-MS (Method A, retention time: 3.32 min), MS m/z 682 (M⁺+1).

Example 20

Preparation of (1S,4R,6S,14S,18R)-7-cis-14-tert-butoxycarbonylamino-18-hydroxy-2,15-dioxo-3,16-diazatricyclo[14.3.0.0⁴,⁶]nonadec-7-ene-4-carboxylic acid for use in the preparation of Compound 17 of Example 21

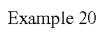

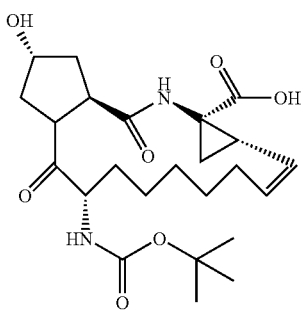

Step 20A: Preparation of 1-(2(S)-tert-Butoxycarbonylamino-non-8-enoyl)-4(R)-hydroxy-pyrrolidine-2(S)-carboxylic acid methyl ester

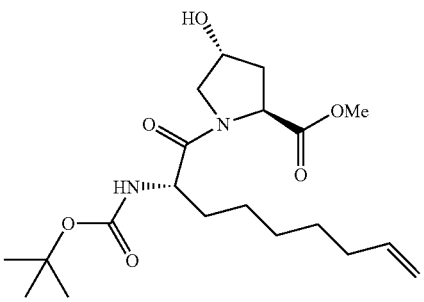

A solution of 2(S)-tert-butoxycarbonylamino-8-nonenoic acid (purchased from RSP Amino Acids)(3.5 g, 12.9 mmol) in 200 mL of DCM was treated sequentially with 4(R)-hydroxypyrrolidine-2(S)-carboxylic acid methyl ester hydrochloride (2.15 g, 11.8 mmol), N-methyl morpholine (4.25 mL, 38.6 mmol), and HATU (5.37 g, 14.1 mmol). The reaction mixture was stirred at rt under N₂ for 3 days, and then concentrated in vacuo. The residue was partitioned between ethyl acetate and pH 4 buffer (biphthalate). The organic phase was washed with sat. aq. NaHCO₃, dried (MgSO₄), and concentrated in vacuo to give the crude product. Flash chromatography (50% ethyl acetate/hexane to 100% ethyl acetate) gave 4.7 g (~100%) of 1-(2(S)-tert-Butoxycarbonylamino-non-8-enoyl)-4(R)-hydroxypyrrolidine-2(S)-carboxylic acid methyl ester as a colorless oil: ¹H NMR (500 MHz, CD₃OD) δ 1.33–1.50(m, 8H), 1.46 (s, 9H), 1.57 (m, 1H), 1.72 (m, 1H) 2.08 (m, 2H), 2.28 (m, 1H), 3.72 (s, 3H,) 3.75–3.87 (m, 2H), 4.36 (m, 1H), 4.51 (bs, 1H), 4.57 (t, J=8.2 Hz, 1H), 4.95 (d, J=10.4 Hz, 1H), 5.01 (m, 1H), 5.83 (m, 1H). LC-MS (Method A, retention time: 3.01 min), MS m/z 399 (M⁺+1).

Step 20B: Preparation of 1-{[1-(2(S)-tert-Butoxycarbonylamino-non-8-enoyl)-4(R)-hydroxy-pyrrolidine-2(S)carbonyl]-(1R)-amino}-2(S)-vinyl-cyclopropanecarboxylic acid ethyl ester

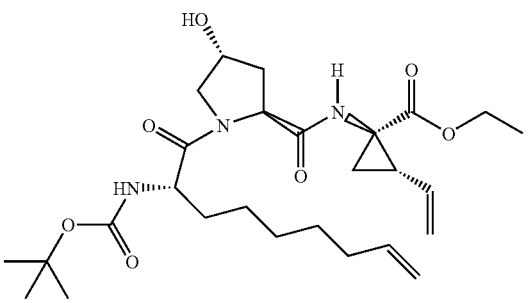

1-(2(S)-tert-Butoxycarbonylamino-non-8-enoyl)-4(R)-hydroxy-pyrrolidine-2(S)-carboxylic acid methyl ester (4.7 g, 11.8 mmol) was dissolved in THF (80 mL), methanol (20 mL), and water (40 mL). Powdered lithium hydroxide (5.6 g, 233 mmol) was added. The light yellow slurry was stirred at rt under N₂ for 16 h, and then concentrated in vacuo. The residue was partioned between ether and water. The ether phase was discarded, and the aqueous phase was treated with 1N HCl until the pH was 4. This acidic solution was extracted with EtOAc (3×). The combined EtOAc extracts were dried (MgSO₄) and concentrated in vacuo to give 4.36 g (96%) of 1-(2(S)-tert-butoxycarbonylamino-8-nonenoyl)-

4(R)-hydroxy-pyrrolidine-2(S)-carboxylic acid as a white solid. This acid was then dissolved in 150 mL of DMF and (1R,2S)-1-amino-2-vinylcyclopropane carboxylic acid ethyl ester hydrochloride (2.61 g, 13.6 mmol), N-methyl morpholine (2.5 mL, 22.6 mmol), and HATU (5.2 g, 13.7 mmol) was added. The reaction mixture was stirred at rt under $N_2$ for 16 h, and then concentrated in vacuo. The residue was partitioned between ethyl acetate and pH 4 buffer (biphthalate). The organic phase was washed with sat. aq. $NaHCO_3$, dried ($MgSO_4$), and concentrated in vacuo to give the crude product. Flash chromatography (60%–80% ethyl acetate/hexane) gave 6.0 g (98%) of 1-{[1-(2(S)-tert-Butoxycarbonylamino-non-8-enoyl)-4(R)-hydroxy-pyrrolidine-2(S)carbonyl]-(1R)-amino}-2(S)-vinyl-cyclopropanecarboxylic acid ethyl ester as a white solid: $^1H$ NMR (500 MHz, $CD_3OD$) δ 1.25 (t, J=7.2 Hz, 3H), 1.33–1.80 (m, 10H), 1.46 (s, 9H), 2.09 (m, 3H), 2.25 (m, 2H), 3.76 (m, 2H), 4.14 (m, 2H), 4.27 (dd, J=8.5, 5.2 Hz, 1H), 4.50 (m, 2H), 4.94 (d, J=10.1 Hz, 1H), 5.01 (dd, J=17.1, 1.8 Hz, 1H), 5.11 (dd, J=10.4, 1.8 Hz, 1H), 5.30 (d, J=15.6 Hz, 1H), 5.80 (m, 2H), 8.57 (s, 1H). LC-MS (Method A, retention time: 3.21 min), MS m/z 522 ($M^+$+1).

Step 20C: Preparation of (1S,4R,6S,14S,18R)-7-cis-14-tert-butoxycarbonylamino-18-hydroxy-2,15-dioxo-3,16-diazatricyclo[14.3.0.0$^{4,6}$]nonadec-7-ene-4-carboxylic acid ethyl ester

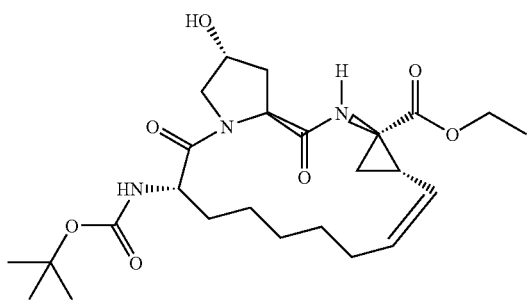

A solution of 1-{[1-(2(S)-tert-Butoxycarbonyl-amino-non-8-enoyl)-4(R)-hydroxy-pyrrolidine-2(S)carbonyl]-(1R)-amino}-2(S)-vinylcyclopropane-carboxylic acid ethyl ester (800 mg, 1.53 mmol) in 2 L of methylene chloride was flushed with $N_2$ for 0.5 h. Then tricyclohexylphosphine[1,3-bis(2,4,6-trimethyl-phenyl)-4,5-dihydroimidazol-2-ylidene][benzylidene]-ruthenium (IV) dichloride (Strem) (64 mg, 0.075 mmol) was added, and the mixture was flushed with $N_2$ for another 10 min. The light orange homogeneous solution was refluxed for 2 h to give a dark orange solution. The reaction mixture was cooled to rt and concentrated in vacuo to give an orange oil. Flash chromatography (ethyl acetate) gave 460 mg (61%) of (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid ethyl ester as a gray solid. $^1H$ NMR (500 MHz, $CDCl_3$) δ 1.19 (t, J=7.2 Hz, 3H), 1.42 (s, 9H), 1.22–1.8 (m, 8H), 1.87 (m, 2H), 2.03–2.22 (m, 4H), 2.63 (m, 1H), 3.65 (m, 1H), 4.09 (m, 3H), 4.45 (m, 1H), 4.56 (s, 1H), 4.82 (m, 1H), 5.23 (m, 1H), 5.51 (s, 1H), 7.16 (s, 1H). LC-MS (Method A, retention time: 2.97 min), MS m/z 494 ($M^+$+1).

Step 20D: (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid

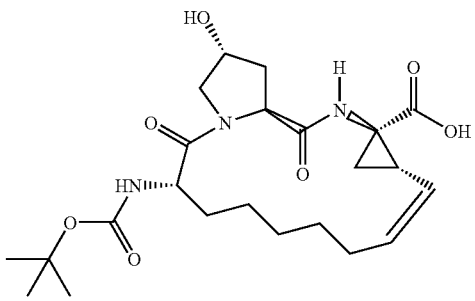

To a solution of (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid ethyl ester (493 mg, 1.0 mmol) in THF (4 mL), methanol (1 mL), and water (2 mL), was added powdered lithium hydroxide (480 mg, 20 mmol), and the light yellow slurry stirred at rt under $N_2$ for 16 h. The mixture was then concentrated in vacuo and the residue partioned between ether and water. The ether phase was discarded, and the aqueous phase was treated with 1 N HCl until pH 4. This acidic solution was extracted with EtOAc three times. The combined EtOAc extracts were dried ($MgSO_4$) and concentrated in vacuo to give 460 mg (98%) of Example 26, (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid as a gray solid. $^1H$ NMR (500 MHz, $CD_3OD$) δ ppm 1.26 (t, J=7.2 Hz, 3H), 1.35–1.52 (m, 15H), 1.57–1.68 (m, 3H), 1.79 (m, 1H), 2.04 (m, 1H), 2.16–2.41 (m, 3H), 3.80 (dd, J=10.7, 4.3 Hz, 1H), 3.88 (m, 1H), 4.38 (dd, J=8.9, 3.1 Hz, 1H), 4.55 (m, 2H), 5.39 (t, J=9.8 Hz, 1H), 5.58 (m, 1H). LC-MS (Method A, retention time: 2.64 min), MS m/z 466 ($M^+$+1).

Example 21

Preparation of Compound 17B, [4-Cyclopropane-sulfonylaminocarbonyl-18-(6-methoxy-isoquinolin-1-yloxy)-2,15-dioxo-3,16-diaza-tricyclo[14.3.0.0$^{4,6}$] nonadec-7-en-14-yl]-carbamic acid tert-butyl ester Compound 17B

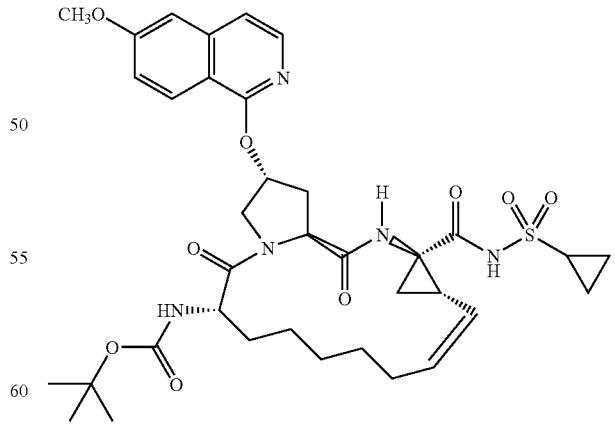

To a mixture of 4-tert-butoxycarbonylamino-18-hydroxy-2,15-dioxo-3,16-diaza-tricyclo[14.3.0.0$^{4,6}$]nonadec-7-ene-4-carboxylic acid (215 mg, 0.46 mmol) in DMSO (5 mL) was added t-BuOK (125 mg, 1.11 mmol) and 1-chloro-6-methoxy-isoquinoline (110 mg, 0.56 mmol). The reaction was stirred for 16 h at rt. The reaction mixture then was partitioned between ether (10 mL) and water (10 mL). The aqueous phase was acidified to pH 4 using 1 N HCl. The resulting solution was extracted with EtOAc (3×20 mL). The combined EtOAc extracts were dried (MgSO₄), filtered, and concentrated in vacuo to give a white solid. Flash chromatography (2% MeOH/CH₂Cl₂) gave 140 mg (49%) of the carboxylic acid derivative as a white solid. LC-MS (Method B, retention time: 1.80 min), MS m/z 543 (M⁺+1). The above solid (140 mg, 0.22 mmol) was treated with cyclopropylsulfonamide (35 mg, 0.28 mmol) as described in the general procedure above to give the crude product. Flash chromatography (2% MeOH/DCM) gave 90 mg of the desired product. Further purification by preparative HPLC (YMC Xterra, S5, 30×50 mm, 50% to 100% B, gradient 9 min, hold 1 min, flow rate 40 mL/min) gave 30 mg (19%) of the product as a white powder: LC-MS (Method B, retention time: 1.86 min), MS m/z 726 (M⁺+1).

Example 22

Preparation of 1-{[4-(6-Methoxy-isoquinolin-1-yloxy)-pyrrolidine-2-carbonyl]-amino}-2-vinyl-cyclopropanecarboxylic acid ethyl ester (as bis HCl salt) use in Example 24

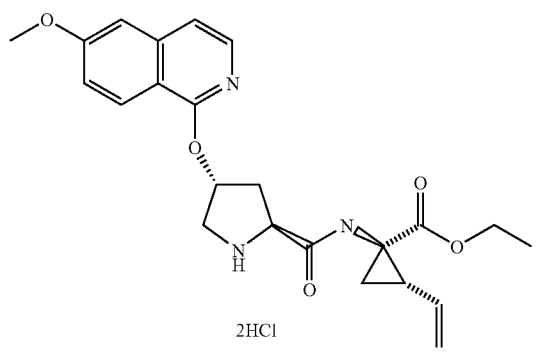

Example 22

2HCl

Prepared utilizing the same synthetic sequence employed for the preparation of the product of Step 2B of Example 3 except 6-Methoxy-1-chloroquinoline (described in Example 1, eg. Step 1a and Step 1b) was used in place of 1-chloroquinoline.

Example 23

Preparation of Example 23, 2(S)-tert-butoxycarbonylamino-3-pent-4-enylsulfanylpropionic acid for use in Example 24

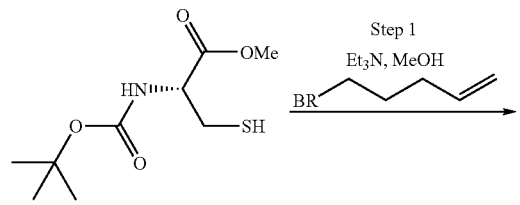

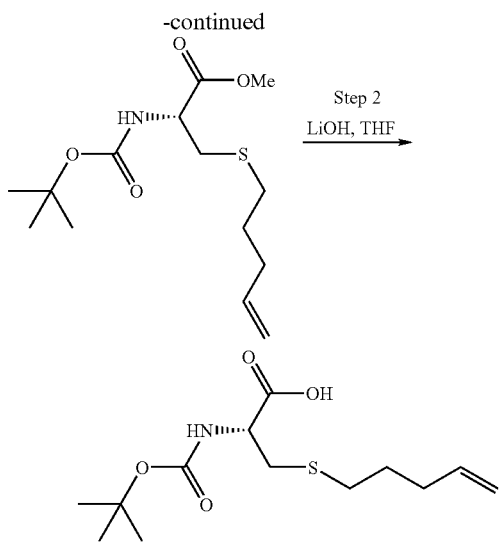

Example 23

Step 1: To a solution of N-Boc-cysteine methyl ester (3.36 g, 0.014 mol) in methanol (166 mL) at RT was added triethylamine (10.8 mL) and 1-bromopent-4-ene (3.19 g, 21 mmol, 1.5 equivalents) and the resulting solution was stirred at room temperature overnight. The mixture was then concentrated in vacuo and the resulting residual mixture was purified using flash chromatography (hexane, ethyl acetate gradient) to provide 1.76 g (41%) of the desired thioether. ¹H NMR (500 MHz, CDCl₃) δ 1.43 (s, 9H), 1.64 (m, 2H), 2.11 (m, 2H), 2.51 (m, 2H), 2.95 (m, 2H), 3.75 (s, 3H), 4.51 (m, 1H), 4.95–5.03 (m, 2H), 5.34 (m, 1H), 5.80 (1H, m). LC-MS (Method B, except gradient time was 3 min., and flow rate was 4 m/min, retention time: 2.29 min), MS m/z 304(M⁺+1).

Step 2: The thioether product of step 1 (9.51 g, 31.4 mmol) was added to a mixture of 1M LiOH in water (200 mL) and THF (200 mL) and the resulting mixture was stirred at room temperature overnight. The reaction mixture was then acidified using 1N hydrochloric acid and the resulting mixture was extracted several times with ethyl acetate. The extracts were combined, dried over magnesium sulfate, and concentrated in vacuo to provide the desired acid which was used as is in the next reaction.

Example 24

Preparation of Compound 18B, [4-Cyclopropane-sulfonylaminocarbonyl-18-(6-methoxy-isoquinolin-1-yloxy)-2,15-dioxo-12-thia-3,16-diaza-tricyclo[14.3.0.0⁴,⁶]nonadec-7-en-14-yl]-carbamic acid tert-butyl ester Compound 18B

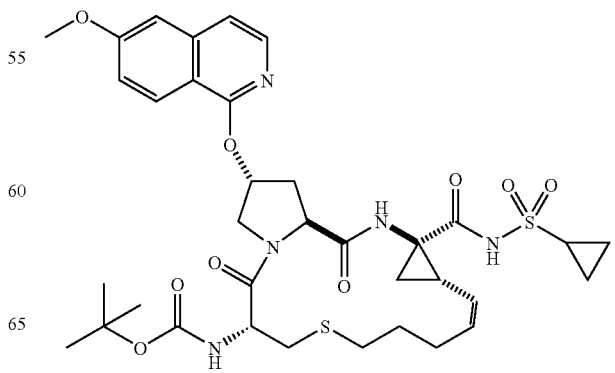

Step 24A, Preparation of 1-{[1-(2-tert-Butoxycarbonylamino-3-pent-4-enylsulfanyl-propionyl)-4-(6-methoxy-isoquinolin-1-yloxy)-pyrrolidine-2-carbonyl]-amino}-2-vinyl-cyclopropanecarboxylic acid ethyl ester

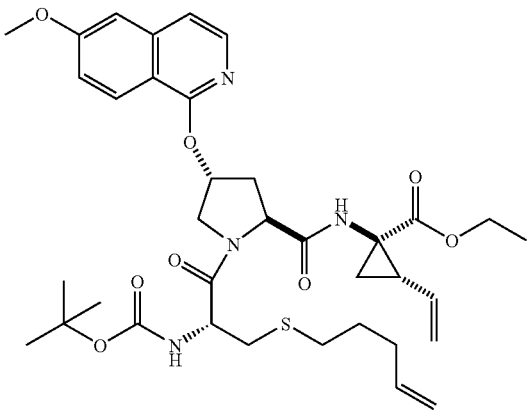

To a solution of the carboxylic acid of Example 23 (289 mg, 1.00 mmol, 1 eq) in DMF (9 mL) was added sequentially the dipeptide product of Example 22 (498 mg, 1.00 mmol, 1 eq), HATU (456 mg, 1.20 mmol, 1.2 eq), and N-methyl morpholine (385 µL, 3.50 mmol, 3.5 eq). The solution was allowed to stir at room temperature overnight, at which time LC/MS indicated the formation of product and disappearance of starting material 2. A pH 4 buffer solution was added, and the mixture extracted three times with ethyl acetate. The organic layers were washed with brine, dried over magnesium sulfate, and concentrated in vacuo. Chromatography was performed (Silica Gel, Ethyl acetate/Hexane gradient) to obtain pure tripeptide 3 in quantitative yield.

$^1$H NMR (400 MHz, CDCl$_3$) δ 8.03 (d, J=9.3 Hz, 1H), 7.89 (d, J=5.9 Hz, 1H), 7.56 (br s, 1H), 7.15–7.09 (m, 2H), 7.01 (d, J=2.5 Hz, 1H), 5.86–5.68 (m, 3H), 5.39–5.22 (m, 2H), 5.12–4.82 (m, 4H), 4.61 (app q, J=6.8 Hz, 1H), 4.24–4.04 (m, 3H), 3.91 (s, 3H), 3.02–2.90 (m, 1H), 2.84–2.69 (m, 2H), 2.66 (m, 3H), 2.24–2.08 (m, 2H), 1.88 (dd, J=5.5, 8.0 Hz, 1H), 1.68 (app quint, J=7.5 Hz, 2H), 1.56 (dd, J=5.4, 9.5 Hz, 1H), 1.42 (m, 1H), 1.31 (s, 9H), 1.27–1.20 (m, 4H). [m/z]+H 697, ERRA 3.0×50 mm S7 retention time=1.937 min, HPLC method 2 min gradient 0% B to 100% B, then 1 min at 100% B (3 min total run time)

Step 24B, Preparation of 14-tert-Butoxycarbonylamino-18-(6-methoxy-isoquinolin-1-yloxy)-2,15-dioxo-12-thia-3,16-diaza-tricyclo[14.3.0.0$^{4,6}$]nonadec-7-ene-4-carboxylic acid ethyl ester

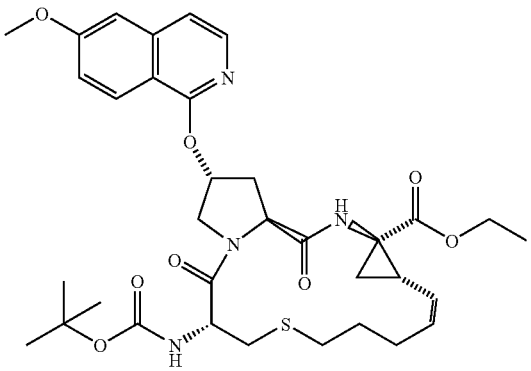

To a solution of tripeptide prodict of Step 24A (384.6 mg, 553 µmol, 1 eq) in dichloroethane (159 mL) was added tricyclohexylphosphine[1,3-bis(2,4,6-trimethylphenyl)-4,5-dihydroimidazol-2-ylidene[benzylidine]ruthenium(IV) dichloride (48.5 mg, 57 µmol, 0.10 eq) and refluxed for 16 h. The reaction was concentrated in vacuo. Chromatography was performed (Silica Gel, Ethyl acetate/Hexane gradient) to obtain pure macrocycle, in 73% yield.

$^1$H NMR (500 MHz, CDCl$_3$) δ 8.04 (d, J=9.2 Hz, 1H), 7.86 (d, J=5.8 Hz, 1H), 7.59 (br s, 1H), 7.16–7.09 (m, 2H), 7.00 (d, J=2.4 Hz, 1H), 5.78–5.71 (m, 1H), 5.64 (d, J=7.6 Hz, 1H), 5.58–5.50 (m, 1H), 5.36 (m, 1H), 5.03 (dd, J=4.2, 8.3 Hz, 1H), 4.81–4.75 (m, 1H), 4.27–4.14 (m, 2H), 3.98–3.93 (m, 1H), 3.91 (s, 3H), 3.13–3.02 (m, 2H), 3.00–2.94 (m, 1H), 2.69 (dt, J=3.9, 11.2 Hz, 1H), 2.52–2.42 (m, 2H), 2.36–2.26 (m, 2H), 2.16–2.08 (m, 1H), 1.96 (dd, J=5.5, 8.2 Hz, 1H), 1.86–1.76 (m, 1H), 1.68–1.58 (m, 2H), 1.37 (s, 9H), 1.29 (t, J=7.2 Hz, 1H), 1.27–1.21 (m, 1H).

[m/z]+H 669

XTERRA 3.0×50 mm S7 retention time=1.797, HPLC method 2 min gradient 0% B to 100% B, then 1 min at 100% B (3 min total run time)

Step 24C, Preparation of 18A, 14-tert-Butoxycarbonylamino-18-(6-methoxy-isoquinolin-1-yloxy)-2,15-dioxo-12-thia-3,16-diaza-tricyclo[14.3.0.0$^{4,6}$]nonadec-7-ene-4-carboxylic acid Compound 18A

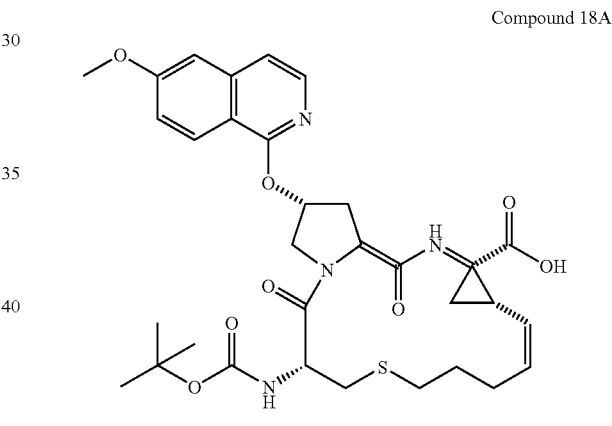

To a solution of the macrocycle ester product of Step 24B (271 mg, 406 µmol, 1 eq) in THF (4.1 mL) was added LiOH (97 mg, 4.04 mmol, 10 eq), water (0.45 mL), and MeOH (1.9 mL). The reaction was allowed to stir for 16 h, at which time LC/MS indicated the hydrolysis was complete. A 1 M solution of HCl in water was added, and the resulting mixture was extracted 3 times into ethyl acetate. The organic extracts were washed with brine, dried over magnesium sulfate, and concentrated in vacuo to provide pure carboxylic acid in quantitative yield.

$^1$H NMR (400 MHz, DMSO-d$_6$) δ 12.50 (br s, 1H), 8.59 (br s, 1H), 8.22 (d, J=7.8 Hz, 1H), 8.14–8.07 (m, 1H), 7.46 (br s, 2H), 7.33–7.25 (m, 2H), 5.95 (br s, 1H), 5.79–5.56 (m, 2H), 4.66–4.57 (m, 1H), 4.50–4.37 (m, 2H), 4.24–4.11 (m, 2H), 4.05(s, 3H), 3.60–3.40 (m, 2H), 3.09–2.97 (m, 1H), 2.91–2.81 (m, 1H), 2.65–2.58 (m, 1H), 2.56–2.44 (m, 2H), 2.44–2.33 (m, 1H), 1.84–1.73 (m, 1H), 1.72–1.57 (m, 2H), 1.34(s, 9H), 1.08–0.95 (m, 1H).

[m/z]+H 641

XTERRA 3.0×50 mm S7 retention time=1.673, HPLC method 2 min gradient 0% B to 100% B, then 1 min at 100% B (3 min total run time)

Step 24D, Preparation of Compound 18B, [4-Cyclopropane-sulfonylaminocarbonyl-18-(6-methoxy-isoquinolin-1-yloxy)-2,15-dioxo-12-thia-3,16-diaza-tricyclo[14.3.0.0$^{4,6}$]nonadec-7-en-14-yl]-carbamic acid tert-butyl ester Compound 18B

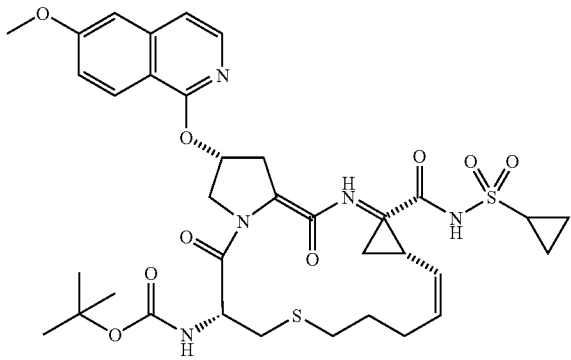

To a solution of the carboxylic acid product of Step 24C (236.3 mg, 369 μmol, 1 eq) in THF (5.2 mL) was added carbonyl diimidazole (143 mg, 738 μmol, 2 eq) and refluxed for 2.5 h. The solution was cooled to room temperature, at which time cyclopropyl sulfonamide (158 mg, 1.1 mmol, 3 eq) and DBU (127 μL, 849 μmol, 2.3 eq) were added. The reaction was allowed to stir at room temperature for 16 h. A 1M solution of HCl in water was added, and the product was extracted three times into methylene chloride. The organic layers were washed with brine, dried over magnesium sulfate, and concentrated in vacuo. Chromatography was performed (Silica Gel, Ethyl acetate/Hexane gradient) to obtain pure sulfonamide Compound 18, in 78% yield.

$^1$H NMR (400 MHz, CD$_3$OD) δ 8.10 (d, J=9.3 Hz, 1H), 7.89–7.83 (m, 2H), 7.21 (d, J=5.9 Hz, 1H), 7.13 (br s, 1H), 7.05 (d, J=9.1 Hz, 1H), 5.81 (br s, 1H), 5.68 (app q, J=8.9 Hz, 1H), 5.16 (app t, J=9.7 Hz, 1H), 4.59–4.52 (m, 2H), 4.40–4.32 (m, 1H), 4.12–4.04 (m, 1H), 3.89 (s, 3H), 2.98–2.78 (m, 3H), 2.73–2.41 (m, 6H), 2.02–1.98 (m, 1H), 1.75 (dd, J=5.5, 8.2 Hz, 1H), 1.71–1.53 (m, 3H), 1.32–1.20 (m, 1H), 1.16 (s, 9H), 1.14–0.95 (m, 2H).

[m/z]+H 744

XTERRA 3.0×50 mm, S7 retention time=1.700, HPLC method 2 min gradient 0% B to 100% B, then 1 min at 100% B (3 min total run time)

Example 25

Preparation of Compound 19 4-Cyclopropanesulfo-nylaminocarbonyl-18-(6-methoxy-isoquinolin-1-yloxy)-2,12,12,15-tetraoxo-12-thia-3,16-diaza-tricy-clo[14.3.0.0$^{4,6}$]nonadec-7-en-14-yl]-carbamic acid tert-butyl ester Compound 19

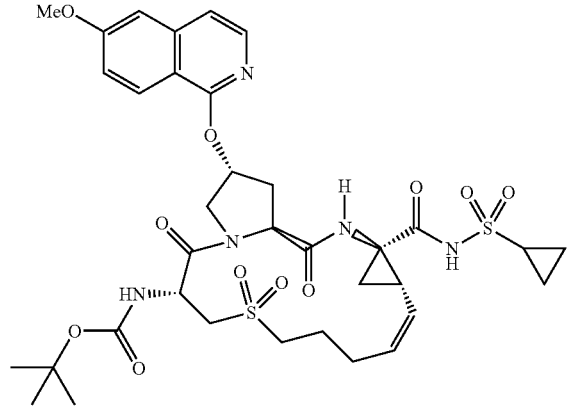

To a solution of Compound 18 (84.7 mg, 114 μmol) in MeOH (1.4 mL) and water (460 μL) at 0° C. was added oxone (210.6 mg, 343 μmol, 3.0 eq). The mixture was stirred for 20 min at 0° C., then allowed to stir for 3 h at ambient temperature. Water and methylene chloride were then added, and the layers separated. The aqueous layer was extracted twice more with methylene chloride. The combined organic layers were dried over magnesium sulfate and concentrated in vacuo. The product was purified by prep TLC (ethyl acetate) to afford the sulfone (37.2 mg, 42% yield).

$^1$H NMR (CD$_3$OD) δ 8.11 (d, J=9.5 Hz, 1H), 7.88 (d, J=6.1 Hz, 1H), 7.23 (d, J=5.8 Hz, 1H), 7.20–7.15 (m, 1H), 7.11 (dd, J=1.8, 8.9 Hz, 1H), 5.87–5.81 (m, 1H), 5.61–5.47 (m, 2H), 4.96–4.90 (m, 1H), 4.67 (t, J=7.8 Hz, 1H), 4.46–4.39 (m, 1H), 4.27–4.20 (m, 1H), 3.92 (s, 3H), 3.84–3.72 (m, 1H), 2.94–2.84 (m, 2H), 2.67–2.58 (m, 2H), 2.47–2.37 (m, 1H), 2.37–2.25 (m, 2H), 1.85–1.73 (m, 2H), 1.72–1.64 (m, 1H), 1.49–1.38 (m, 1H), 1.20 (s, 9H), 1.16–1.02 (m, 3H), 1.00–0.82 (m, 3H).

Example 26

Preparation of Compound 27 and Compound 28

Compound 27

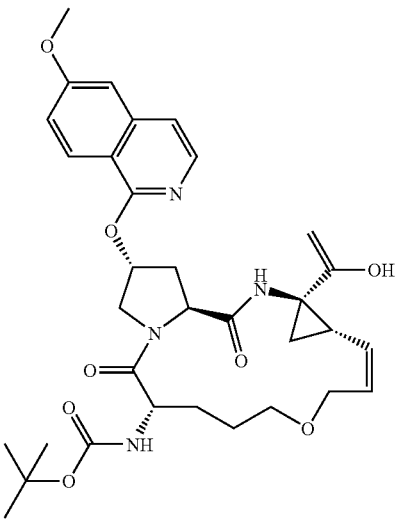

Compound 28

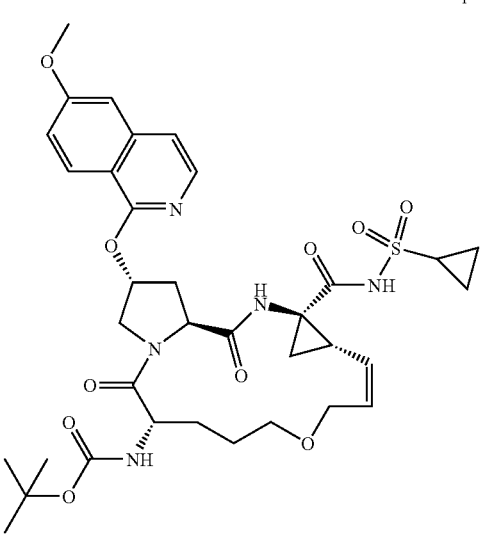

Step 26A: Preparation of Isopropyl pyrrolidin-5-one-2(S)-carboxylate

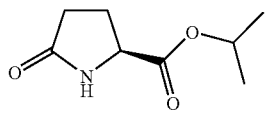

A solution of L-pyroglutamic acid (Aldrich, 25.0 g, 195 mmol) and para-toluenesulfonic acid mono hydrate (3.71 g, 19.5 mmol) was refluxed in isopropanol (40 mL) under nitrogen for 6 hours using a Dean-Stark trap variation (condensate returned through a Soxhlet extractor filled with 4 Å molecular sieves). After cooling to room temperature, the reaction was diluted with ether, washed with saturated aqueous sodium bicarbonate and then saturated aqueous NaCl, dried (MgSO$_4$) and evaporated to give a colorless syrup. It crystallized upon setting. Triturating the crystalline residue in hexane provided 31.9 g (96%) of isopropyl pyrrolidin-5-one-2(S)-carboxylate as white prisms: $^1$H NMR (300 MHz, Chloroform-D) δ 6.35 (br s, 1H), 5.04 (sept. 1H, J=6.2 Hz), 4.18 (dd, 1H, J=8.4, 5.3 Hz), 2.51–2.28 (m, 3H), 2.27–2.12 (m, 1H), 1.24 (d, 6H, J=6.2 Hz). LCMS m/z 172 (M+H)$^+$.

Step 26B: Preparation of Isopropyl 1-(tert-butoxycarbonyl)-pyrrolidin-5-one-2(S)-carboxylate

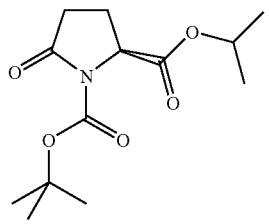

A solution of isopropyl pyrrolidin-5-one-2(S)-carboxylate (product of step 26A, 31.9 g, 188 mmol), di-tert-butyl dicarbonate (48.6 g, 225 mmol) and DMAP (2.30 g, 8.8 mmol) in acetonitrile (300 mL) was stirred at room temperature under N$_2$ for 30 minutes. The reaction was evaporated to about 100 mL, diluted with ether, washed with 1N HCl then saturated aqueous NaCl, dried (MgSO$_4$) and evaporated to give isopropyl 1-(tert-butoxycarbonyl)pyrrolidin-5-one-2(S)carboxylate as a light yellow oil, 50.1 g (99%): $^1$H NMR (300 MHz, Chloroform-D) δ 5.06 (sept. 1H, J=6.2 Hz), 4.53 (dd, 1H, J=9.5, 2.9 Hz), 2.66–2.40 (m, 2H), 2.36–2.22 (m, 1H), 2.03–1.93 (m, 1H), 1.47 (s, 9H), 1.26 (d, 3H, J=6.2 Hz), 1.24 (d, 3H, J=6.2 Hz). LCMS m/z 272 (M+H)$^+$.

Step 26C: Preparation of Isopropyl 2(S)-(tert-butoxycarbonylamino)-5-hydroxypentanoate

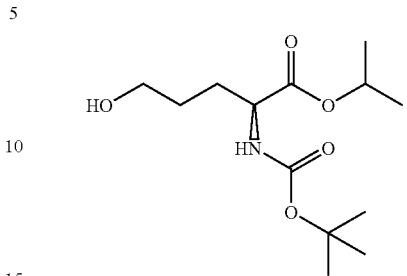

To a solution of isopropyl 1-(tert-butoxycarbonyl)pyrrolidin-5-one-2(S)-carboxylate (product of step 26B, 49.5 g, 183 mmol) in methanol (300 mL) was added sodium borohydride (10.0 g, 263 mmol) in ~1 g portions over 1.5 hours. The reaction was stirred under nitrogen for another 10 minutes. It was diluted with water, extracted with ether, combined organic fractions washed with saturated aqueous NaCl, dried (MgSO$_4$) and evaporated to give a light yellow oil. Flash chromatography (silica gel, 20–30% ethyl acetate/hexane) gave 31.8 g (64%) of isopropyl 2(S)-(tert-butoxycarbonylamino)-5-hydroxypentanoate as a colorless syrup: $^1$H NMR (300 MHz, Chloroform-D) δ 5.16 (br d, 1H, J=7.3 Hz), 5.03 (sept., 1H, J=6.2 Hz), 4.28 (br d, 1H, J=6.2 Hz), 3.67 (br dd, J=10.2, 5.5 Hz), 1.94–1.79 (m, 2H), 1.76–1.67 (m, 1H), 1.66–1.56 (m, 2H), 1.43 (s, 9H), 1.25 (d, 3H, J=6.2 Hz), 1.23 (d, 3H, J=6.2 Hz). LCMS m/z 276 (M+H)$^+$.

Step 26D: Preparation of Isopropyl-5-allyloxy-2(S)-(tert-butoxycarbonylamino)pentanoate

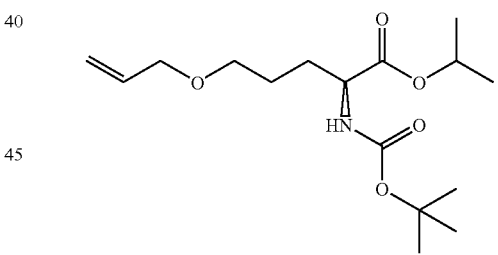

A degassed mixture of isopropyl 2(S)-(tert-butoxycarbonylamino)-5-hydroxypentanoate (product of step 26C, 17.6 g, 63.9 mmol), allyl methyl carbonate (24.0 ml, 213 mmol), Pd$_2$(dba)$_3$ (1.62 g, 1.78 mmol) and BINAP (4.42 g, 7.10 mmol) in THF (150 mL) was refluxed under nitrogen for 3 hours. After cooling to room temperature, the reaction was diluted with ether, filtered through celite and evaporated giving a dark brown syrup. Flash chromatography of the residue (silica gel, 30% ether/hexane) gave isopropyl 5-allyloxy-2(S)-(tert-butoxycarbonylamino)pentanoate as a viscous colorless oil, 16.3 g (81%): $^1$H NMR (300 MHz, Chloroform-D) δ 5.88 (ddt, 1H, 17.4, 10.4, 5.5), 5.28 (m, 1H), 5.22–5.11 (m, 1H), 5.02 (sept., 1H, J=6.2 Hz), 4.21 (br t, 1H, J=6.7 Hz), 3.94 (dt, 2H, J=5.9, 1.5 Hz), 3.42 (t, 2H, J=5.9 Hz), 1.90–1.82 (m, 1H), 1.75–1.57 (m, 3H), 1.42 (s, 9H), 1.21 (d, 3H, J=6.2 Hz), 1.19 (d, 3H, J=6.2 Hz). LCMS m/z 316 (M+H)$^+$.

Step 26E: Preparation of 5-Allyloxy-2(S)-(tert-butoxycarbonylamino)pentanoic acid

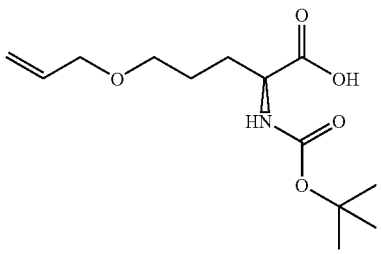

A mixture of isopropyl 5-allyloxy-2(S)-(tert-butoxycarbonylamino)pentanoate (product of step 26D, 16.1 g, 51.1 mmol) and lithium hydroxide hydrate (4.19 g, 102 mmol) in THF/water (100 mL/20 mL) was stirred at room temperature under nitrogen for 16 hours. The reaction was diluted with water, washed with ether, pH of aqueous fraction adjusted to ~4, extracted with ether, combined organic fractions washed with saturated NaCl, dried (MgSO$_4$) and evaporated giving 5-allyloxy-2(S)-(tert-butoxycarbonylamino)pentanoic acid as a light yellow syrup: $^1$H NMR (300 MHz, Chloroform-D) δ 5.89 (ddt, 1H, J=17.4, 10.4, 5.5), 5.25 (dd, 1H, J=17.4, 1.6 Hz), 5.17 (dd, 1H, J=10.4, 1.6 Hz), 4.30 (br d, 1H, J=6.2), 3.96 (dt, 2H, J=5.9, 1.5 Hz), 3.46 (t, 2H, J=5.9 Hz), 1.96–1.86 (m, 1H), 1.85–1.77 (m, 1H), 1.75–1.64 (m, 2H), 1.43 (s, 9H). LCMS m/z 274 (M+H)$^+$.

Step 26F Preparation of 1-{[1-(5-Allyloxy-2-tert-butoxycarbonylamino-pentanoyl)-4-(6-methoxy-isoquinolin-1-yloxy)-pyrrolidine-2-carbonyl]-amino}-2-vinyl-cyclopropanecarboxylic acid ethyl ester

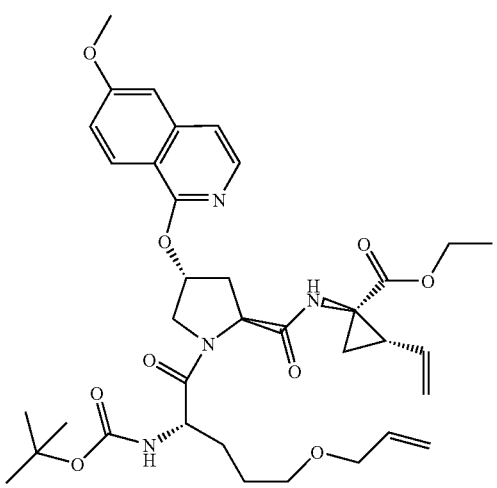

A solution of 1-{[4-(6-Methoxy-isoquinolin-1-yloxy)-pyrrolidine-2-carbonyl]-amino}-2-vinyl-cyclopropanecarboxylic acid ethyl ester dihydrochloride (Example 22)(3.60 g, 7.25 mmol) and 5-allyloxy-2-tert-butoxycarbonylamino-pentanoic acid (the product of step 26E, 1.98 g, 7.25 mmol) in 75 ml of DMF was treated with HATU (3.31 g, 8.7 mmol) and N-methylmorpholine (2.79 ml, 25.4 mmol). The reaction mixture was stirred at rt under N$_2$ for 4 h, and then quenched with pH 4 buffer (biphthalate). The resulting mixture was extracted with EtOAc. The organic phase was washed with sat. aq. NaCl, dried (MgSO$_4$), and concentrated in vacuo to give the crude product. Flash chromatography (silica gel, 10–60% ethyl acetate/hexane) gave 3.91 g (~79%) of 1-{[1-(5-Allyloxy-2-tert-butoxycarbonylamino-pentanoyl)-4-(6-methoxy-isoquinolin-1-yloxy)-pyrrolidine-2-carbonyl]-amino}-2-vinyl-cyclopropanecarboxylic acid ethyl ester as a yellow collapsed foam: $^1$H NMR (500 MHz, METHANOL-D4) δ 1.05–1.16 (m, 1H), 1.32 (s, 9H), 1.37–1.50 (m, 3H), 1.51–1.67 (m, 3H), 1.68–1.84 (m, 2H), 2.17–2.30 (m, 1H), 2.32–2.50 (m, 1H), 2.58–2.73 (m, 1H), 2.80 (s, 1H), 3.33–3.52 (m, 2H), 3.86–3.95 (m, 5H), 4.00–4.06 (m, 1H), 4.07–4.22 (m, 3H), 4.23–4.38 (m, 1H), 4.58–4.67 (m, 1H), 5.04–5.17 (m, 2H), 5.18–5.34 (m, 2H), 5.65–5.94 (m, 3H), 7.07–7.28 (m, 3H), 7.82–7.92 (m, 1H), 7.96–8.13 (m, 1H). LC-MS (Method B, retention time: 1.75 min), MS m/z 681 (M$^+$+1).

Step 26G: Preparation of 14-tert-Butoxycarbonylamino-18-(6-methoxy-isoquinolin-1-yloxy)-2,15-dioxo-10-oxa-3,16-diaza-tricyclo[14.3.0.0$^{4,6}$]nonadec-7-ene-4-carboxylic acid ethyl ester

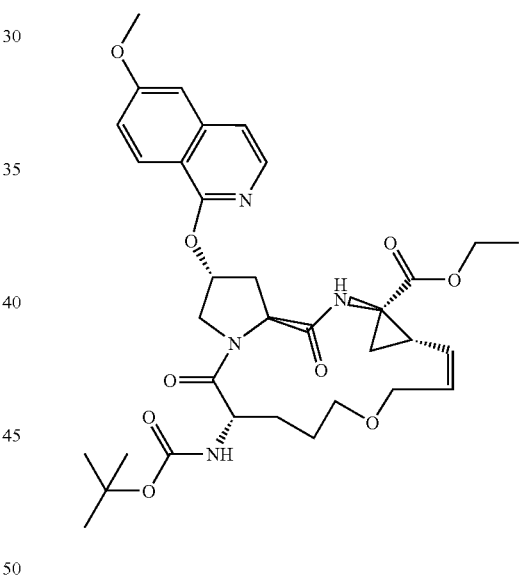

A solution of 1-{[1-(5-Allyloxy-2-tert-butoxycarbonylamino-pentanoyl)-4-(6-methoxy-isoquinolin-1-yloxy)-pyrrolidine-2-carbonyl]-amino}-2-vinyl-cyclopropanecarboxylic acid ethyl ester (the product of step 26F, 2.0 g, 2.94 mmol) in 800 ml of benzene was treated with Grubb's second generation catalyst (375 mg, 0.44 mmol). The reaction mixture was heated to 50° C., stirred under N$_2$ for 2 h, and then concentrated in vacuo. Flash chromatography (silica gel, 25–100% ethyl acetate/hexane) and treatment with activated carbon gave 677.6 mg (~35%) of 14-tert-butoxycarbonylamino-18-(6-methoxy-isoquinolin-1-yloxy)-2,15-dioxo-10-oxa-3,16-diaza-tricyclo[14.3.0.0$^{4,6}$]nonadec-7-ene-4-carboxylic acid ethyl ester as a brown collapsed foam: $^1$H NMR (500 MHz, METHANOL-D4) δ 1.06–1.30 (m, 12H), 1.51–2.03 (m, 6H), 2.41–2.70 (m, 3H), 3.39–3.50 (m, 1H), 3.51–3.61 (m, 1H), 3.77–3.87 (m, 1H), 3.92 (s, 3H), 4.02–4.18 (m, 3H), 4.24 (d, J=6.41 Hz, 1H), 4.36–4.48 (m, 1H), 4.55 (d, J=11.29 Hz, 1H), 4.65 (t, J=8.39 Hz, 1H), 5.55–5.72 (m, 2H), 5.85 (s, 1H), 7.08 (d, J=8.85 Hz, 1H), 7.17 (s, 1H), 7.24 (d, J=5.80 Hz, 1H), 7.89 (d, J=5.80 Hz, 1H), 8.16 (d, J=9.16 Hz, 1H). LC-MS (Method B, retention time: 1.58 min), MS m/z 653 (M$^+$+1).

Step 26H, Preparation of Compound 27, 14-tert-Butoxycarbonylamino-18-(6-methoxy-isoquinolin-1-yloxy)-2,15-dioxo-10-oxa-3,16-diaza-tricyclo[14.3.0.0$^{4,6}$]nonadec-7-ene-4-carboxylic acid Compound 27

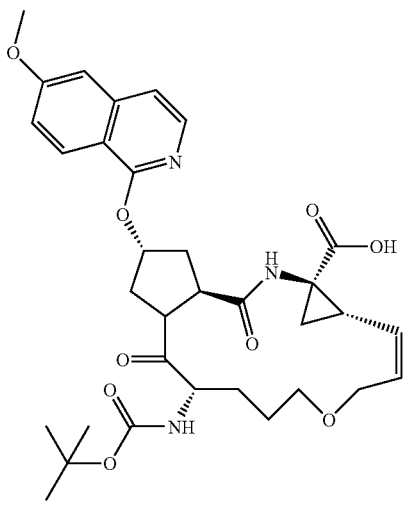

To a solution of 14-tert-butoxycarbonylamino-18-(6-methoxy-isoquinolin-1-yloxy)-2,15-dioxo-10-oxa-3,16-diaza-tricyclo[14.3.0.0$^{4,6}$]nonadec-7-ene-4-carboxylic acid ethyl ester (the product of step 26G, 667 mg, 1.02 mmol) in 25.7 ml of THF was added 2.9 ml of water, 11.4 ml of methanol, and powdered lithium hydroxide (489 mg, 20.4 mmol). The reaction mixture was stirred at rt for 6 h, and then concentrated in vacuo. The residue was partitioned between ethyl acetate and 20.4 ml of 1 N aq. HCl. To the resulting solution was added pH 4 buffer (biphthalate). The organic phase was washed with water, sat. aq. NaCl, dried (MgSO$_4$), and concentrated in vacuo to give the crude product. Flash chromatography (silica gel, 0–10% methanol/chloroform) gave 446 mg (~70%) of 14-tert-butoxycarbonylamino-18-(6-methoxy-isoquinolin-1-yloxy)-2,15-dioxo-10-oxa-3,16-diaza-tricyclo[14.3.0.0$^{4,6}$]nonadec-7-ene-4-carboxylic acid as a slightly pink collapsed foam: $^1$H NMR (500 MHz, METHANOL-D4) δ 0.99–1.16 (m, 1H), 1.22 (s, 9H), 1.50–2.04 (m, 6H), 2.40–2.73 (m, 3H), 3.41–3.50 (m, 1H), 3.51–3.62 (m, 1H), 3.73–3.86 (m, 1H), 3.90 (s, 3H), 4.03 (d, J=10.52 Hz, 1H), 4.21 (d, J=8.31 Hz, 1H), 4.42–4.72 (m, 3H), 5.65 (s, 2H), 5.82 (s, 1H), 7.06 (d, J=9.05 Hz, 1H), 7.15 (s, 1H), 7.22 (d, J=5.87 Hz, 1H), 7.87 (m, J=9.29 Hz, 2H), 8.14 (d, J=8.56 Hz, 1H). LC-MS (Method B, retention time: 1.46 min), MS m/z 625 (M$^+$+1).

Step 26I, Preparation of Compound 28, [4-Cyclopropanesulfonylaminocarbonyl-18-(6-methoxy-isoquinolin-1-yloxy)-2,15-dioxo-10-oxa-3,16-diaza-tricyclo[14.3.0.0$^{4,6}$]nonadec-7-en-14-yl]-carbamic acid tert-butyl ester Compound 28

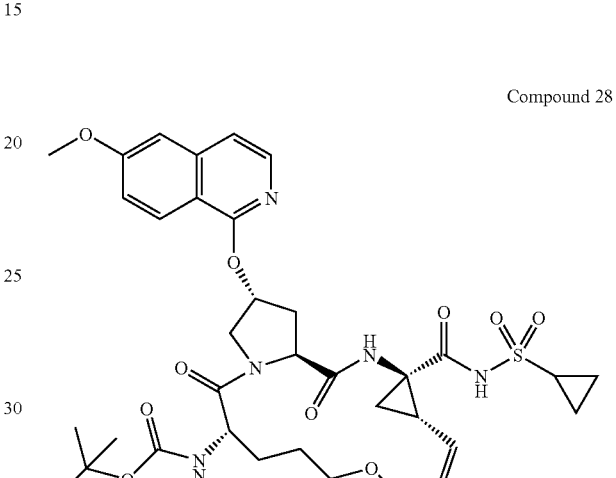

A solution of 14-tert-butoxycarbonylamino-18-(6-methoxy-isoquinolin-1-yloxy)-2,15-dioxo-10-oxa-3,16-diaza-tricyclo[14.3.0.0$^{4,6}$]nonadec-7-ene-4-carboxylic acid (the product of step 26H, 146.5 mg, 0.235 mmol) and carbonyldiimidazole (76 mg, 0.47 mmol) in 5 ml of THF was stirred at reflux under N$_2$ for 2 h, and then allowed to come to rt. To the reaction mixture was added cyclopropanesulfonic acid amide (86 mg, 0.71 mmol) and 1,8-diazabicyclo[5.4.0]undec-7-ene (81 μl, 0.54 mmol). The reaction mixture was stirred at rt under N$_2$ for 4 h, and then quenched with pH 4 buffer (biphthalate). The resulting mixture was extracted with EtOAc. The organic phase was washed with sat. aq. NaCl, dried (MgSO$_4$), and concentrated in vacuo to give the crude product. Flash chromatography (silica gel, 0–8% methanol/chloroform) gave 111.7 mg (~65%) of [4-Cyclopropanesulfonylaminocarbonyl-18-(6-methoxy-isoquinolin-1-yloxy)-2,15-dioxo-10-oxa-3,16-diaza-tricyclo[14.3.0.0$^{4,6}$]nonadec-7-en-14-yl]-carbamic acid tert-butyl ester (compound 27) as a white powder: $^1$H NMR (500 MHz, METHANOL-D4) δ 0.96–1.17 (m, 6H), 1.20 (s, 9H), 1.24–1.32 (m, 1H), 1.49–1.64 (m, 2H), 1.65–1.79 (m, 2H), 1.79–2.06 (m, 2H), 2.45–2.60 (m, 1H), 2.62–2.76 (m, 2H), 2.86–2.98 (m, 1H), 3.47–3.61 (m, 2H), 3.62–3.73 (m, 1H), 3.92 (s, 3H), 4.00 (d, J=10.38 Hz, 1H), 4.18 (d, J=10.99 Hz, 1H), 4.55–4.72 (m, 3H), 5.44 (t, J=9.92 Hz, 1H), 5.69–5.78 (m, 1H), 5.86 (s, 1H), 7.07 (d, J=7.02 Hz, 1H), 7.17 (s, 1H), 7.24 (d, J=5.80 Hz, 1H), 7.85–7.95 (m, 2H), 8.18 (d, J=8.85 Hz, 1H). LC-MS (Method B, retention time: 1.52 min), MS m/z 728 (M$^+$+1).

Preparation of Compound 61
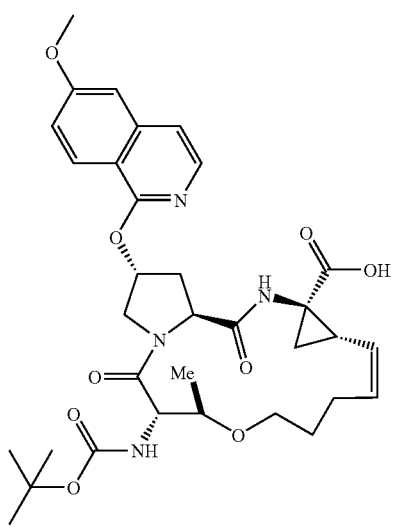
Compound 61
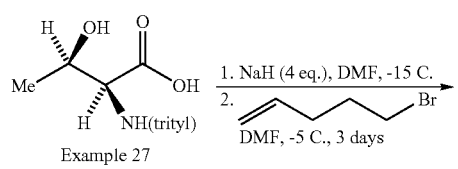
Example 27
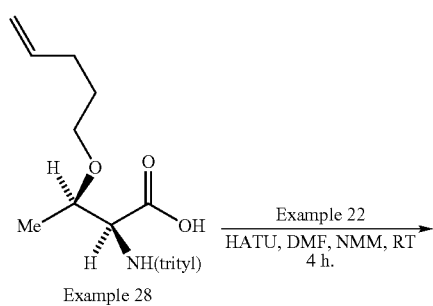
Example 28
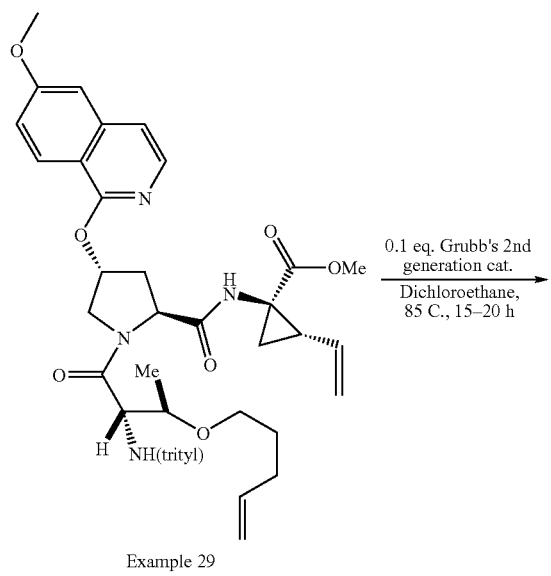
Example 29
-continued
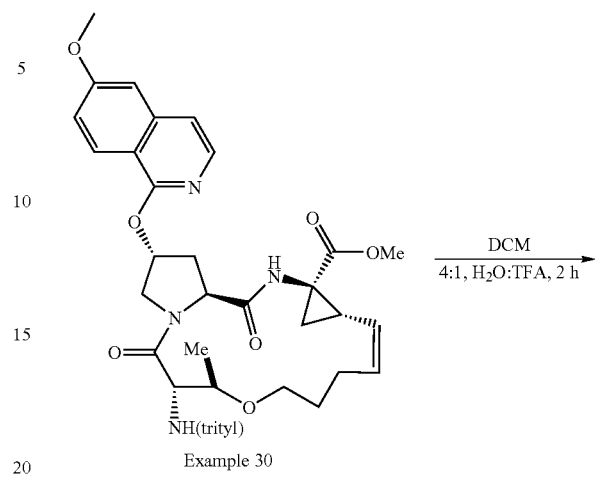
Example 30
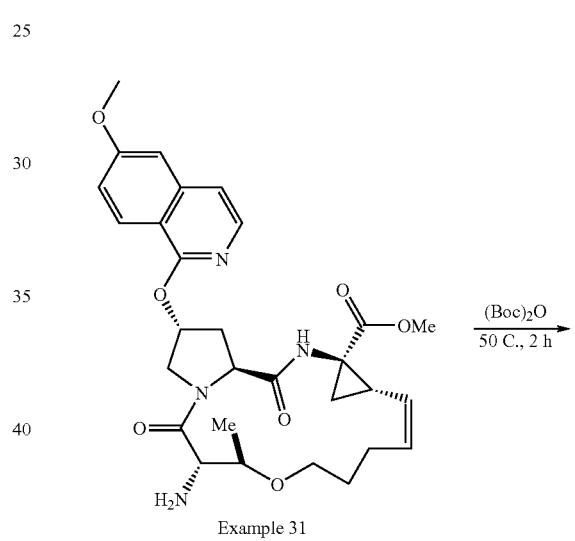
Example 31
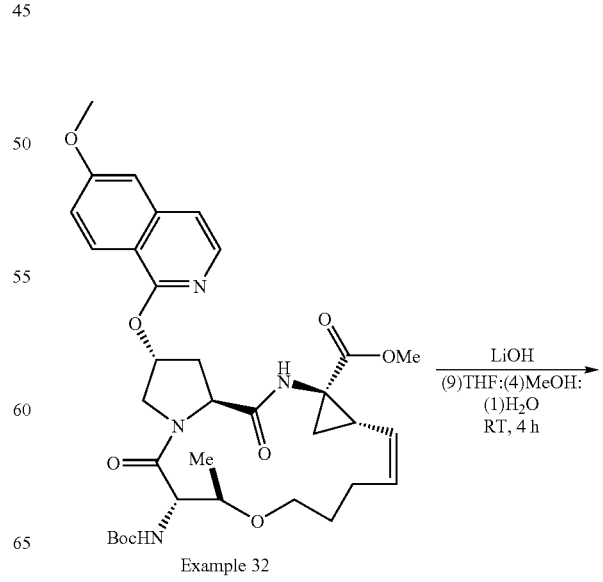
Example 32

149

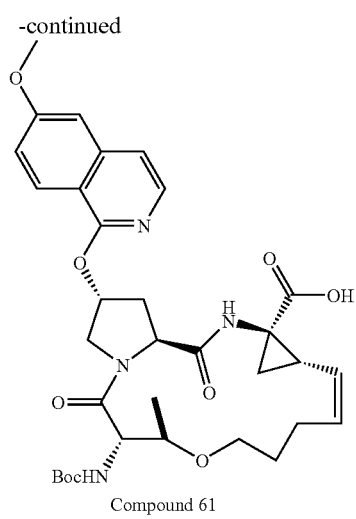

Compound 61

The preparation of Compound 61 was carried-out as shown in the above scheme and using procedures outlined below:

Preparation of Example 28:

Example 28 was prepared by adding a DMF solution of N-trityl protected threonine to a DMF solution of sodium hydride cooled to −15 C. The reaction mixture was stirred for 30 minutes at −15 C after which 5-bromo-1-pentene was added and the resulting mixture was warmed to −5 C. The reaction mixture was maintained at −5 C for 3 days after which time the reaction was quenched by the addition of 1N aqueous HCl and worked up using standard extraction procedures as described above. Example 28 was obtained in pure form by standard chromatography procedures.

Preparation of Example 29

Example 29 was prepared by coupling Example 28 with Example 22 as shown in the scheme using the general procedure described above for the preparation of structurally related Compounds and Examples.

Preparation of Example 30

Example 30 was prepared from Example 29 as shown in the scheme using procedures described above for the preparation of structurally related Compounds and Examples.

Preparation of Example 31

Example 31 was prepared from Example 30 as shown in the scheme. In the event 100 mg of Example 30 was dissolved in 2 ml of DCM and the resulting solution was treated with 82 microliters of a 4:1 solution of water and trifluoroacetic acid. The resulting mixture was stirred at room temperature for several hours after which the reaction mixture was concentrated and the resulting crude product mixture was purified by chromatography to provide Example 31.

Preparation of Compound 61

Compound 61 was prepared from Example 31 as shown in the scheme and using procedures described above for the preparation of related Compounds and Examples.

150

Preparation of Compound 62, Compound 66, and Compound 70

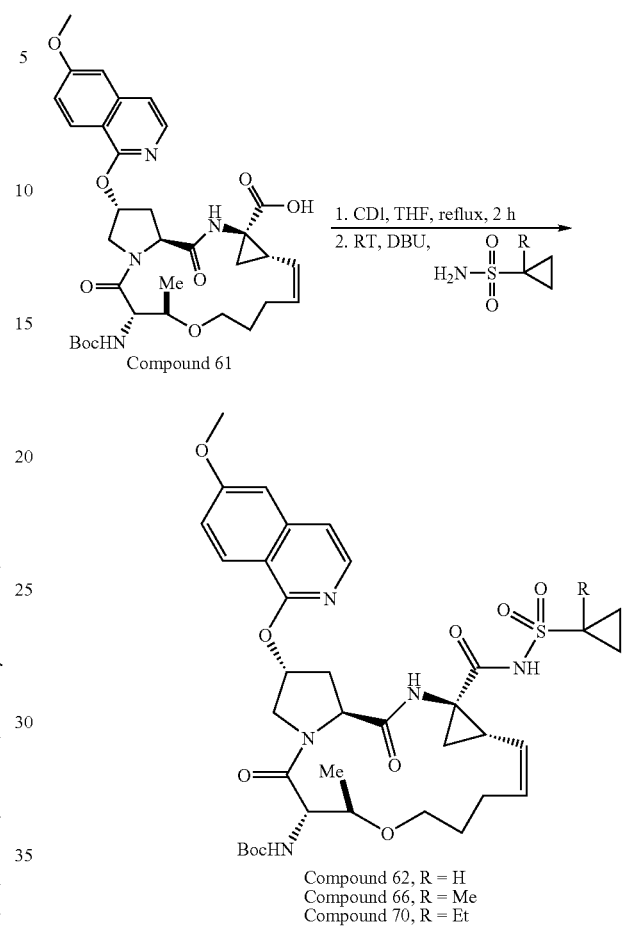

Compound 62, R = H
Compound 66, R = Me
Compound 70, R = Et

Compound 62 was prepared from Compound 61 as shown in the scheme, and by using the procedures decribed above for the preparation of related compounds and Examples.

Preparation of Compound 63, 64, 65, Compound 67, 68, 69, Compound 71, 72, 73

Preparation of Compound 63, Compound 67, Compound 71

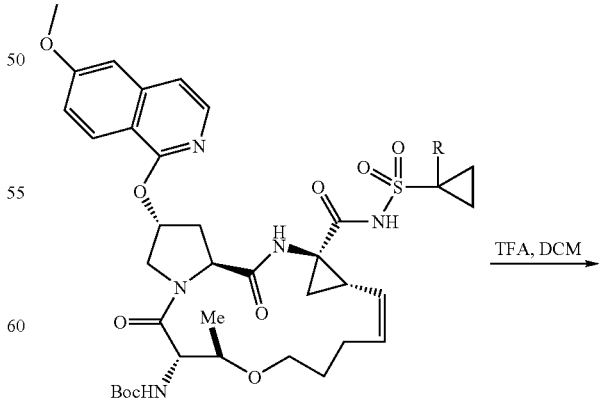

Compound 62, R = H
Compound 66, R = Me
Compound 70, R = Et

151
-continued
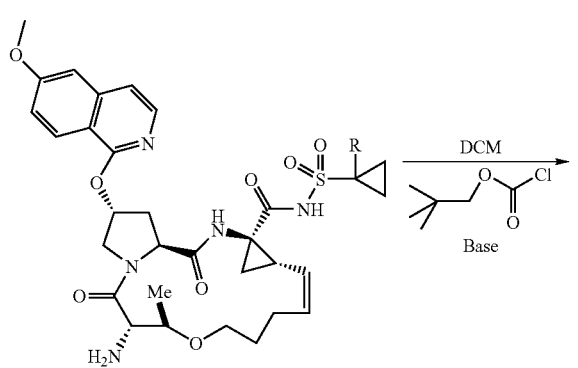
Example 33, R = H
Example 34, R = Me
Example 35, R = Et
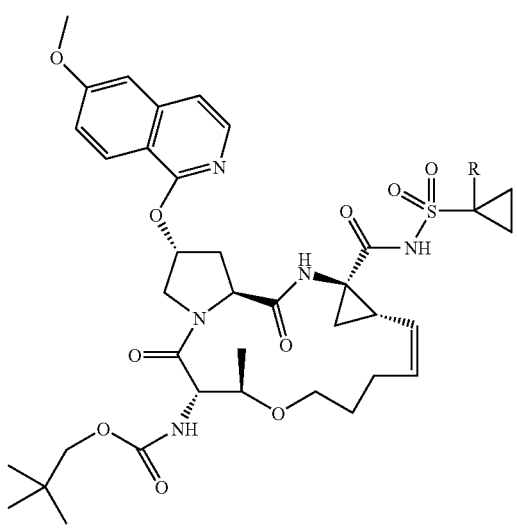
Compound 63, R = H
Compound 67, R = Me
Compound 71, R = Et
Preparation of Compound 64, Compound 68, Compound 72
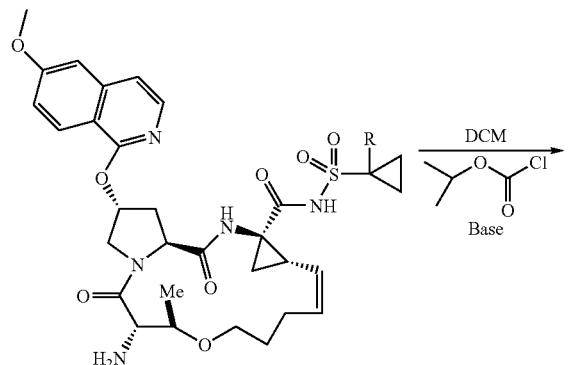
Example 33, R = H
Example 34, R = Me
Example 35, R = Et
152
-continued
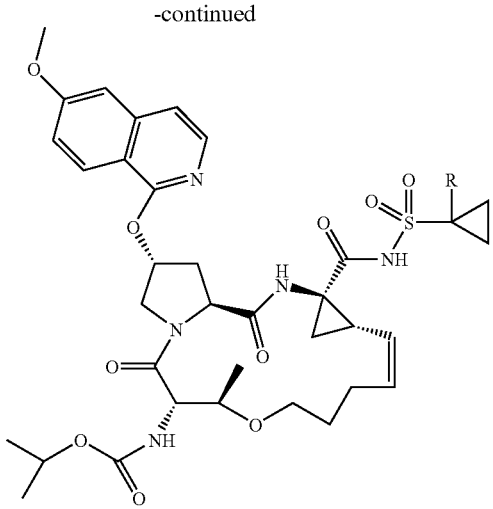
Compound 64, R = H
Compound 68, R = Me
Compound 72, R = Et
Preparation of Compound 65, Compound 69, Compound 73
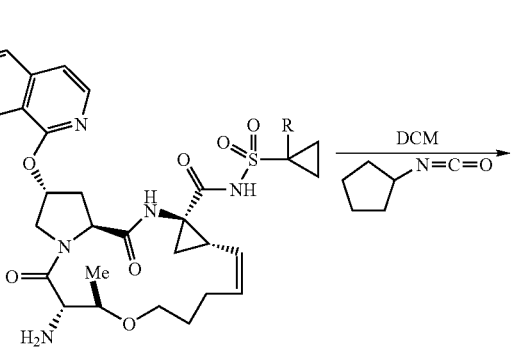
Example 33, R = H
Example 34, R = Me
Example 35, R = Et
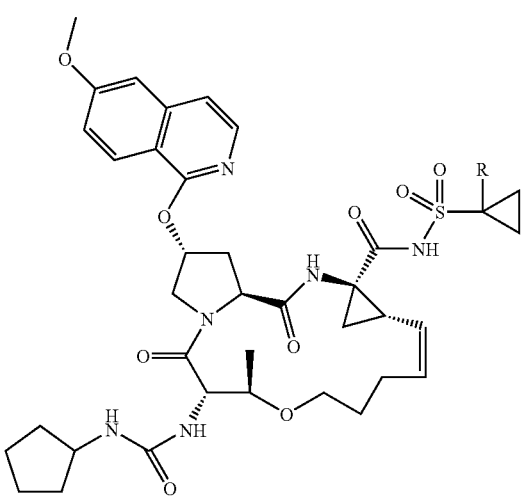
Compound 65, R = H
Compound 69, R = Me
Compound 73, R = Et Compounds 63, 64, 65, 67, 68, 69, 71, 72 and 73 were prepared as shown in the above synthetic scheme, and by using procedures described herein for the synthesis of related Examples and Compounds.

Example 36

Preparation of Compound 79 and Compound 80

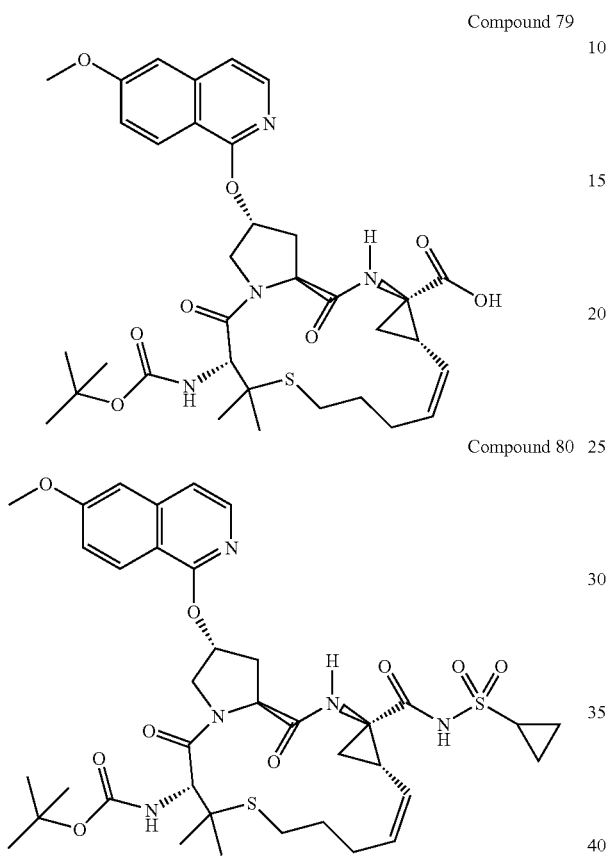

Compound 79

Compound 80

Step 36A: Preparation of N-t-Butoxycarbonyl-3-(4-pentenylthio)-L-valine, methyl ester

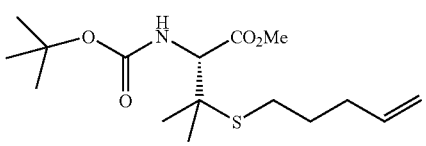

To a solution of 7.12 g (48 mmol, 1.0 eq) of L-penicillamine in 100 mL of 1,4-dioxane and 25 mL of water at room temperature was added 9.60 mL (96 mmol, 2.0 eq) of 10N aqueous sodium hydroxide solution, followed by the dropwise addition of 12.00 mL (101 mmol, 2.1 eq) of 5-bromo-1-pentene over several minutes. The resulting mixture was stirred at room temperature for 68 hours. At this point 12.50 g (57 mmol, 1.2 eq) of di-tert-butyl dicarbonate was added, and the mixture was stirred at room temperature for another 6 hours. The mixture was concentrated under vacuum, and the residue was dissolved in water. The aqueous mixture was washed with diethyl ether, adjusted to pH 3 employing 1N hydrochloric acid, and then extracted with ethyl acetate. The combined extracts were washed with brine, dried over anhydrous magnesium sulfate, filtered, and concentrated under vacuum.

The crude product (12.20 g) was dissolved in 120 mL of anhydrous dimethylsulfoxide. To this solution was added 10.50 g (76 mmol) of potassium carbonate and 4.70 mL (76 mmol) of iodomethane, and the resulting mixture was stirred at room temperature for 24 hours. The reaction mixture was diluted with water and extracted with ethyl acetate. The combined extracts were washed with water (2×) and brine, dried over anhydrous sodium sulfate, filtered, and concentrated under vacuum. Column chromatography on silica gel (elution: 2–10% ethyl acetate/hexane) provided 8.54 g of N-tert-butoxycarbonyl-3-(4-pentenylthio)-L-valine, methyl ester as a colorless oil. NMR (300 MHz, CDCl$_3$): δ 5.76 (d of d of t, 1H, J=17.2, 10.3, 6.6 Hz), 5.35 (br d, 1H, J=9.0 Hz), 5.05–4.94 (m, 2H), 4.27 (br d, 1H, J=9.0 Hz), 3.73 (s, 3H), 2.52 (m, 2H), 2.13 (quart., 2H, J=7.3 Hz), 1.61 (quint., 2H, J=7.3 Hz), 1.43 (s, 9H), 1.35 (s, 3H), 1.33 (s, 3H).

Step 36B: Preparation of N-tert-Butoxycarbonyl-3-(4-pentenylthio)-L-valine

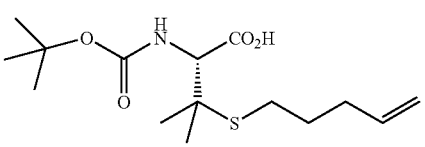

To a solution of 8.52 g (25.7 mmol) of N-tert-butoxycarbonyl-3-(4-pentenylthio)-L-valine, methyl ester in 200 mL of tetrahydrofuran at room temperature was added a solution of 1.10 g (26.2 mmol) of lithium hydroxide monohydrate in 50 mL of water. The resulting mixture was stirred at room temperature for 65 hours. To the reaction mixture then was added 28 mL of 1.00N hydrochloric acid. The mixture was diluted with diethyl ether, washed with water (3×) and brine, dried over anhydrous sodium sulfate, filtered, and concentrated under vacuum to afford 8.10 g of N-tert-butoxycarbonyl-3-(4-pentenylthio)-L-valine as a colorless oil. NMR (300 MHz, CDCl$_3$): δ 5.75 (d of d of t, 1H, J=17.2, 10.3, 6.6 Hz), 5.40 (br s, 1H), 5.05–4.94 (m, 2H), 4.28 (br s, 1H), 2.56 (m, 2H), 2.13 (quart., 2H, J=7.3 Hz), 1.63 (quint., 2H, J=7.3 Hz), 1.44 (s, 9H), 1.39 (s, 3H), 1.37 (s, 3H).

Step 36C: Preparation of (1S,4R,6S,14R,18R)-7-cis-14-tert-Butoxycarbonylamino-13,13-dimethyl-18-(6-methoxy-isoquinolin-1-yloxy)-2,15-dioxo-12-thia-3,16-diazatricyclo[14.3.0.0$^{4,6}$]nonadec-7-ene-4-carboxylic acid (Compound 79)

Compound 79

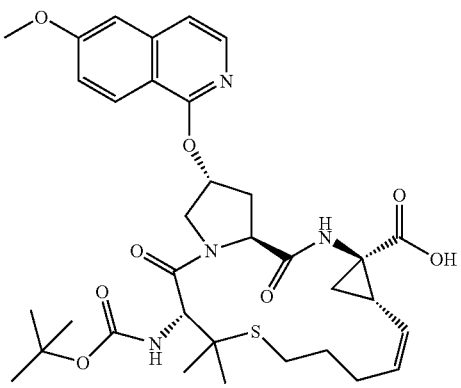

This compound was prepared from N-tert-butoxycarbonyl-3-(4-pentenylthio)-L-valine employing the procedures described in example 24. ESI-mass spectrum: m/e: 669 (M+H)⁺, 667 (M−H)⁻; high resolution mass spectrum: calc'd for $C_{34}H_{45}N_4O_8S$: 669.2958, found: 669.2975; NMR (500 MHz, $CD_3OD$) δ 8.06 (d, 1H, J=8.8 Hz), 7.90 (d, 1H, J=5.8 Hz), 7.24 (d, 1H, J=5.8 Hz), 7.16 (s, 1H), 7.09 (d, 1H, J=8.8 Hz), 6.69 (d, 1H, J=8.5 Hz), 5.80 (s, 1H), 5.72 (quart., 1H, J=8.5 Hz), 5.46 (t, 1H, J=8.5 Hz), 4.71 (t, 1H, J=8.5 Hz), 4.64 (d, 1H, J=9.1 Hz), 4.45 (d, 1H, J=11.6 Hz), 4.22 (m, 1H), 3.91 (s, 3H), 2.78 (m, 1H), 2.74–2.68 (m, 2H), 2.56 (m, 1H), 2.36–2.28 (m, 2H), 2.21 (m, 1H), 1.75 (m, 1H), 1.72–1.64 (m, 2H), 1.60 (m, 1H), 1.45 (s, 3H), 1.39 (s, 3H), 1.21 (s, 9H).

Step 36D: Preparation of (1S,4R,6S,14R,18R)-[7-cis-4-Cyclopropanesulfonylaminocarbonyl-13,13-dimethyl-18-(6-methoxyisoquinolin-1-yloxy)-2,15-dioxo-12-thia-3,16-diaza-tricyclo[14.3.0.0⁴,⁶]nonadec-7-en-14-yl]carbamic acid, tert-butyl ester (Compound 80)

Compound 80

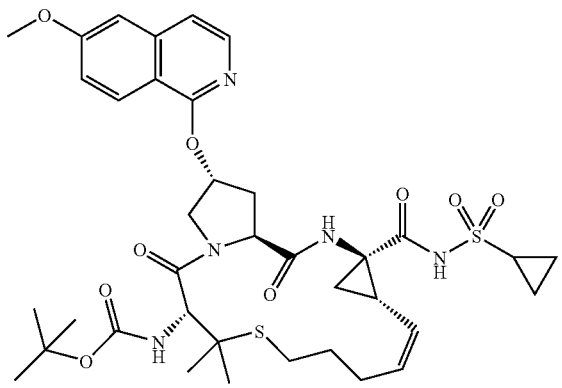

This compound was prepared from compound 79 employing the procedure described in example 24D. ESI-mass spectrum: m/e: 772 (M+H)⁺, 770 (M−H)⁻; high resolution mass spectrum: calc'd for $C_{37}H_{50}N_5O_9S_2$: 772.3050, found: 772.3060; NMR (500 MHz, $CD_3OD$) δ 8.06 (d, 1H, J=8.8 Hz), 7.90 (d, 1H, J=5.8 Hz), 7.24 (d, 1H, J=5.8 Hz), 7.17 (s 1H), 7.08 (d, 1H, J=8.8 Hz), 6.62 (d, 1H, J=8.5 Hz), 5.83 (s, 1H), 5.74 (quart., 1H, J=8.5 Hz), 5.26 (t, 1H, J=8.5 Hz), 4.67 (m, 1H), 4.46 (m, 2H), 4.19 (m, 1H), 3.92 (s, 3H), 2.93 (m, 1H), 2.74–2.67 (m, 3H), 2.58–2.48 (m, 3H), 2.11 (m, 1H), 1.82–1.75 (m, 2H), 1.61 (m, 1H), 1.54 (m, 1H), 1.45 (s, 3H), 1.37 (s, 3H), 1.27 (m, 1H), 1.18 (s, 9H), 1.09 (m, 1H), 1.07–0.99 (m, 2H).

Example 37

Preparation of Compound 84 and Compound 85

Compound 84

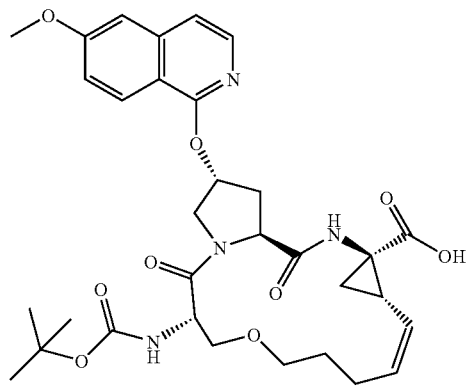

Compound 85

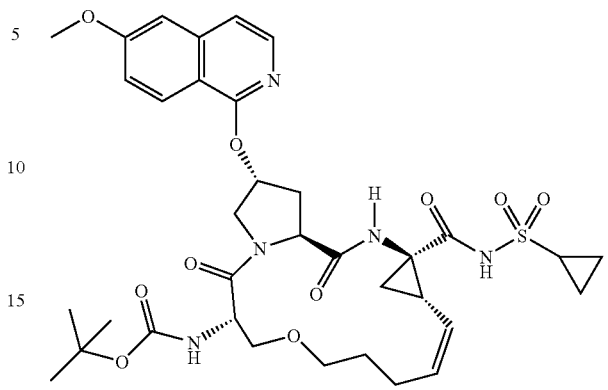

Step 37A: Preparation of N-tert-Butoxycarbonyl-O-(4-pentenyl)-L-serine, methyl ester

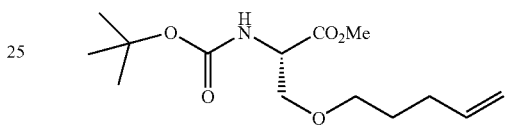

To a solution of 10.26 g (50 mmol, 1.0 eq) of N-tert-butoxycarbonyl-L-serine in 500 mL of anhydrous dimethylsulfoxide at room temperature was added 2.00 g (50 mmol, 1.0 eq) of 60% sodium hydride in mineral oil. This mixture was stirred at room temperature for 0.5 hour until the evolution of gas had ceased. To the resulting solution was added 6.00 mL (50 mmol, 1.0 eq) of 5-bromo-1-pentene followed immediately by another 2.00 g (50 mmol, 1.0 eq) of 60% sodium hydride in mineral oil. The reaction mixture then was stirred at room temperature for 16 hours. The mixture was diluted with 200 mL of water, adjusted to pH 3–4 by the addition of 50 mL of 1.00N hydrochloric acid, and extracted with ethyl acetate. The organic phase was washed with water (2×) and brine, dried over anhydrous sodium sulfate, filtered, and concentrated under vacuum. To remove the residual mineral oil the resulting material was dissolved in a dilute aqueous sodium hydroxide solution. This aqueous solution was washed with hexane and then adjusted to pH 4 employing hydrochloric acid, and extracted with ethyl acetate. The extract was washed with water (2×) and brine, dried over anhydrous sodium sulfate, filtered, and concentrated under vacuum.

The crude product (7.70 g) was dissolved in 100 mL of anhydrous dimethylsulfoxide. To this solution was added 7.80 g (56 mmol) of potassium carbonate and 3.50 mL (56 mmol) of iodomethane, and the resulting mixture was stirred at room temperature for 24 hours. The reaction mixture was diluted with water and extracted with ethyl acetate. The combined extracts were washed with water (2×) and brine, dried over anhydrous sodium sulfate, filtered, and concentrated under vacuum. Column chromatography on silica gel (elution: 2–10% ethyl acetate/hexane) provided 6.70 g of N-tert-butoxycarbonyl-O-(4-pentenyl)-L-serine, methyl ester as a colorless oil. NMR (300 MHz, $CDCl_3$): δ 5.78 (d of d of t, 1H, J=17.2, 10.2, 6.6 Hz), 5.34 (br d, 1H, J=8.0 Hz), 5.03–4.92 (m, 2H), 4.40 (m, 1H), 3.81 (d of d, 1H, J=9.5, 2.9

Hz), 3.74 (s, 3H), 3.61 (d of d, 1H, J=9.5, 3.5 Hz), 3.42 (m, 2H), 2.06 (quart., 2H, J=7.3 Hz), 1.61 (quint., 2H, J=7.3 Hz), 1.44 (s, 9H).

Step 37B: Preparation of N-tert-Butoxycarbonyl-O-(4-pentenyl)-L-serine

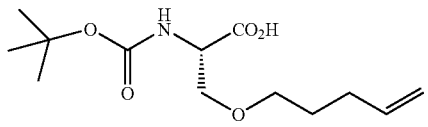

To a solution of 6.65 g (23 mmol) of N-tert-butoxycarbonyl-O-(4-pentenyl)-L-serine, methyl ester in 500 mL of tetrahydrofuran at room temperature was added a solution of 1.95 g (46 mmol) of lithium hydroxide monohydrate in 100 mL of water. The resulting mixture was stirred at room temperature for 40 hours. To the reaction mixture then was added 46 mL of 1.00N hydrochloric acid. The mixture was diluted with ethyl acetate, washed with water (3×) and brine, dried over anhydrous sodium sulfate, filtered, and concentrated under vacuum to afford 6.30 g of N-tert-butoxycarbonyl-O-(4-pentenyl)-L-serine as a colorless oil. NMR (300 MHz, CDCl$_3$): δ 5.77 (d of d of t, 1H, J=17.2, 10.2, 6.6 Hz), 5.37 (br d, 1H, J=8.0 Hz), 5.03–4.92 (m, 2H), 4.42 (m, 1H), 3.87 (d of d, 1H, J=9.5, 2.6 Hz), 3.63 (d of d, 1H, J=9.5, 4.0 Hz), 3.45 (t, 2H, J=6.6 Hz), 2.07 (quart., 2H, J=7.3 Hz), 1.64 (quint., 2H, J=7.3 Hz), 1.44 (s, 9H).

Step 37C: Preparation of (1S,4R,6S,14S,18R)-7-cis-14-tert-Butoxycarbonylamino-18-(6-methoxyisoquinolin-1-yloxy)-2,15-dioxo-12-oxa-3,16-diazatricyclo[14.3.0.0$^{4,6}$]-nonadec-7-ene-4-carboxylic acid (Compound 84)

Compound 84

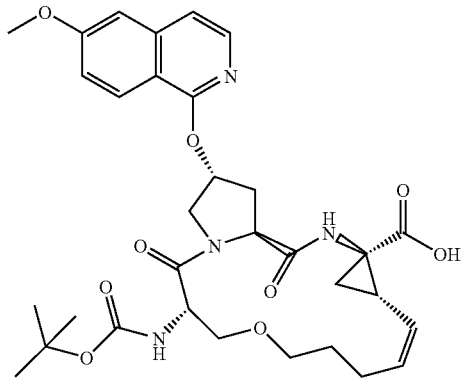

This compound was prepared from N-tert-butoxycarbonyl-3-(4-pentenylthio)-L-valine employing the procedures described in example 26. ESI-mass spectrum: m/e: 625 (M+H)$^+$, 623 (M−H)$^−$; high resolution mass spectrum: calc'd for $C_{32}H_{41}N_4O_9$: 625.2874, found: 625.2871; NMR (500 MHz, CD$_3$OD) δ 8.12 (d, 1H, J=9.0 Hz), 7.89 (d, 1H, J=5.8 Hz), 7.24 (d, 1H, J=5.8 Hz), 7.17 (s, 1H), 7.12 (d, 1H, J=9.0 Hz), 5.83 (s, 1H), 5.63 (quart., 1H, J=8.8 Hz), 5.45 (t, 1H, J=8.8 Hz), 4.74 (m, 1H), 4.60 (br s, 1H), 4.36 (d, 1H, J=11.0 Hz), 4.16 (d, 1H, J=8.0 Hz), 3.91 (s, 3H), 3.74 (m, 2H), 3.62 (m, 1H), 3.49 (m, 1H), 2.66 (m, 1H), 2.57 (m, 1H), 2.47–2.33 (m, 2H), 2.19 (m, 1H), 1.78 (m, 2H), 1.69 (m, 1H), 1.48 (m, 1H), 1.30 (s, 9H).

Step 37D: Preparation of (1S,4R,6S,14S,18R)-[7-cis-4-Cyclopropanesulfonylaminocarbonyl-18-(6-methoxy-isoquinolin-1-yloxy)-2,15-dioxo-12-oxa-3,16-diaza-tricyclo [14.3.0.0$^{4,6}$]nonadec-7-en-14-yl]-carbamic acid, tert-butyl ester (Compound 85)

Compound 85

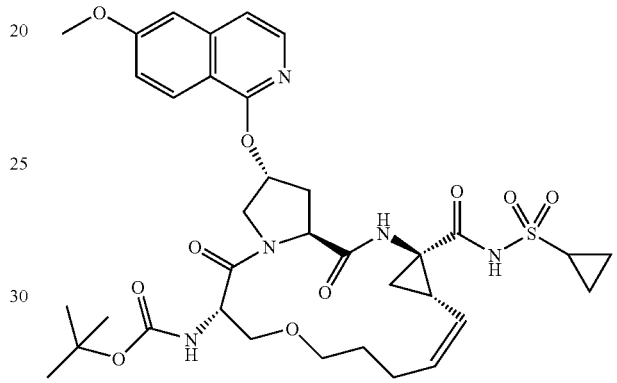

This compound was prepared from compound 84 employing the procedure described in example 261. ESI-mass spectrum: m/e: 728 (M+H)$^+$, 726 (M−H)$^−$; high resolution mass spectrum: calc'd for $C_{35}H_{46}N_5O_{10}S$: 728.2966, found: 728.2972; NMR (500 MHz, CD$_3$OD) δ 8.12 (m, 1H), 7.89 (d, 1H, J=5.8 Hz), 7.25 (d, 1H. J=5.8 Hz), 7.18 (s, 1H), 7.12 (d, 1H, J=8.0 Hz), 5.89 (s, 1H), 5.66 (quart., 1H. J=8.8 Hz), 5.19 (t, 1H. J=8.8 Hz), 4.71 (m, 1H), 4.52 (br s, 1H), 4.36 (d, 1H, J=10.0 Hz), 4.12 (m, 1H), 3.92 (s, 3H), 3.65 (m, 2H), 3.47 (m, 2H), 2.92 (m, 1H), 2.64 (m, 1H), 2.56 (m, 1H), 2.45 (m, 2H), 2.19 (m, 1H), 1.77 (m, 1H), 1.70–1.60 (m, 2H), 1.54 (m, 1H), 1.28 (s, 9H), 1.15–0.98 (m, 4H).

Example 38

Preparation of Compound 58

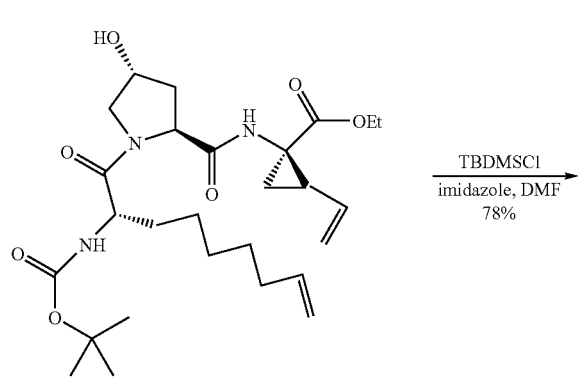

-continued
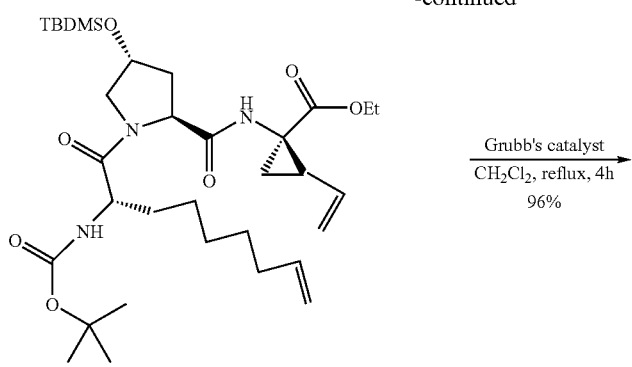
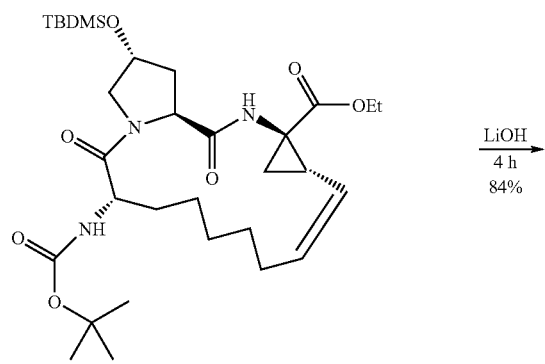
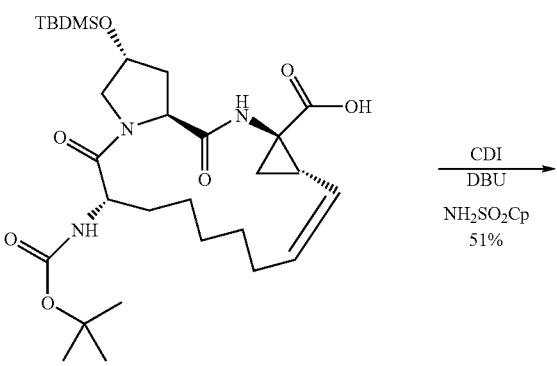
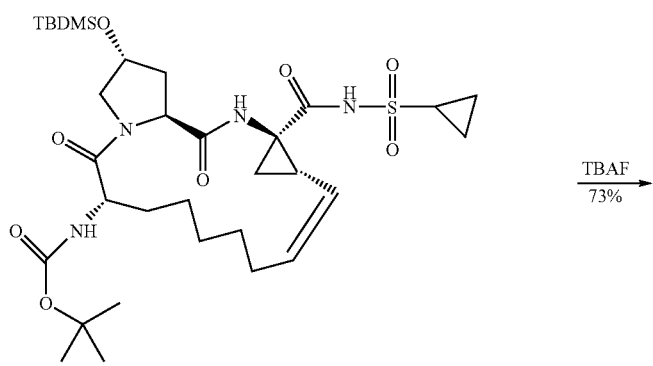

-continued

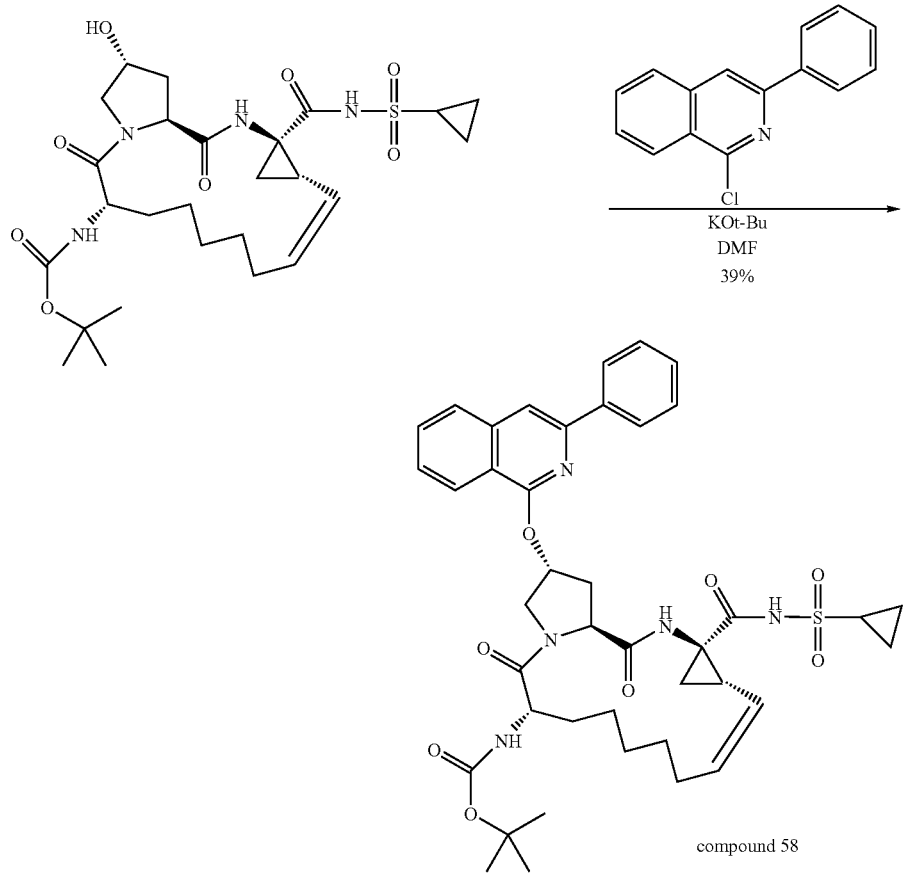

Step 38a: Preparation of 1-{[1-(2-tert-Butoxycarbonylamino-non-8-enoyl)-4-(tert-butyl-dimethyl-silanyloxy)-pyrrolidine-2-carbonyl]-amino}-2-vinylcycloproyanecarboxylic acid ethyl ester

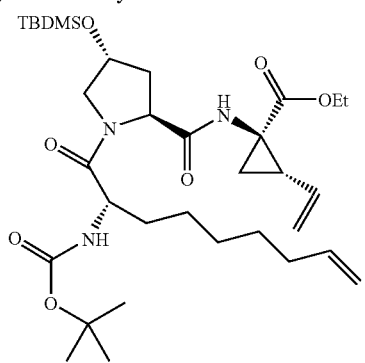

To a mixture of 1-{[1-(2(S)-tert-Butoxycarbonylamino-non-8-enoyl)-4(R)-hydroxypyrrolidine-2(S)carbonyl]-(1R)-amino}-2(S)-vinyl-cyclopropanecarboxylic acid ethyl ester (1.5 g, 2.87 mmoL) in 10 mL of DMF was added imidazole (0.25 g, 3.67 mmoL) and tert-butyl-dimethylsilyl chloride (516 mg, 3.44 mmoL). The mixture was stirred at rt for two days. The reaction mixture was then concentrated in vacuo, and the residue was dissolved in ethyl acetate. This solution was washed with water, dried over magnesium sulfate, and concentrated in vacuo to obtain a crude solid. Purification by flash chromatography (eluting with 20% ethyl acetate in hexane) gave 1.43 g (78%) of 1-{[1-(2-tert-butoxycarbonylamino-non-8-enoyl)-4-(tert-butyl-dimethyl-silanyloxy)-pyrrolidine-2-carbonyl]-amino}-2-vinylcyclopropanecarboxylic acid ethyl ester as a white solid.

$^1$H NMR (300 MHz, CD$_3$OD) δ 0.10 (s, 6H), 0.89 (s, 9H), 1.22 (m, 3H), 1.31–1.48 (m, 16H), 1.50–1.75 (m, 3H), 2.06 (m, 3H), 2.11–2.33 (m, 2H), 3.70 (m, 2H), 4.03–4.19 (m, 2H), 4.21 (m, 1H), 4.45 (t, J=7.87 Hz, 1H), 4.59 (m, 1H), 4.91 (d, J=9.15 Hz, 1H), 4.98 (d, J=17.20 Hz, 1H), 5.08 (dd, J=10.25, 1.83 Hz, 1H), 5.27 (dd, J=17.38, 1.65 Hz, 1H), 5.65–5.87 (m, 2H). LC-MS (Method A, retention time: 4.00 min), MS m/z 636 (M$^+$+1).

Step 38b: Preparation of 14-tert-Butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid, ethyl ester

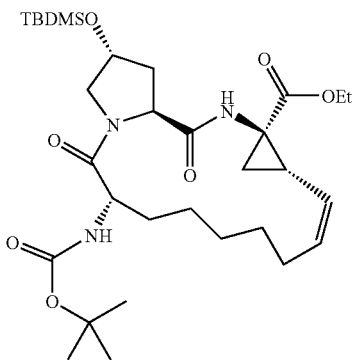

To a solution of 1-{[1-(2-tert-butoxycarbonylamino-non-8-enoyl)-4-(tert-butyl-dimethyl-silanyloxy)-pyrrolidine-2-carbonyl]-amino}-2-vinyl-cyclopropanecarboxylic acid ethyl ester (1.63 g, 2.56 mmoL) in 640 mL of methylene chloride was added 215 mg (0.26 mmoL) of tricyclohexylphosphine[1,3-bis(2,4,6-tri[benzylidene]ruthenium(IV) dichloride. The mixture was heated at reflux for 15 min. The residue was concentrated in vacuo, and then purified by flash chromatography eluting with 30% ethyl acetate/hexane. To further decolorize the sample, the crude product was chromatographed a second time eluting with 50% ether in hexane to give 1.5 g (96%) of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid ethyl ester as a white solid. $^1$H NMR (500 MHz, CD$_3$Cl) δ 0.06 (s, 3H), 0.07 (s, 3H), 0.86 (s, 9H), 1.18–1.24 (m, 6H), 1.34–1.64 (m, 14H), 1.86–1.96 (m, 3H), 2.02–2.09 (m, 1H), 2.11–2.17 (m, 1H), 2.19–2.28 (m, 1H), 2.57–2.63 (m, 1H), 3.50–3.54 (m, 1H), 3.71 (dd, J=10.22, 6.26 Hz, 1H), 4.06–4.17 (m, 2H), 4.52–4.58 (m, 2H), 4.75 (d, J=8.55 Hz, 1H), 5.21 (t, J=9.92 Hz, 1H), 5.35 (d, J=7.63 Hz, 1H), 5.45–5.50 (m, 1H), 6.94 (s, 1H). LC-MS (Method A, retention time: 3.88 min), MS m/z 608 (M$^+$+1).

Step 38c: Preparation of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid

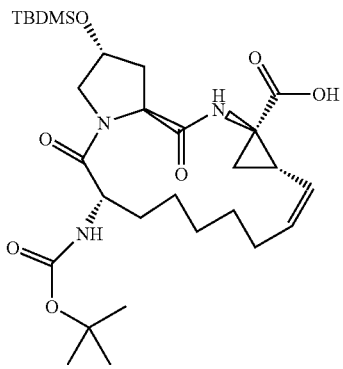

To a solution of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid ethyl ester (1.5 g, 2.47 mmoL) in a mixed solvent system of THF (4 mL), methanol (1 mL), and water (2 mL), was added powdered lithium hydroxide monohydrate (1.0 g, 50 mmoL). The light yellow slurry was stirred at rt under N$_2$ for 4 h. The mixture was then concentrated in vacuo, and the residue partioned between ether and water. The ether phase was discarded, and the aqueous phase was treated with 1 N HCl until reaching pH 4. This acidic solution was extracted with EtOAc (3×). The combined EtOAc extracts were dried (MgSO$_4$), and concentrated in vacuo to give 1.2 g (84%) of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid as an off-white solid. $^1$H NMR (300 MHz, CD$_3$OD) 0.12 (s, 6H), 0.89 (s, 9H), 1.23–1.64 (m, 17H), 1.70–1.87 (m, 1H), 1.90–2.49 (m, 6H), 3.70–3.80 (m, 1H), 3.83–3.90 (m, 1H), 4.28–4.36 (m, 1H), 4.47–4.55 (m, 1H), 4.65 (s, 1H), 5.30–5.39 (m, 1H), 5.53–5.62 (m, 1H). LC-MS (Method A, retention time: 3.69 min), MS m/z 580 (M$^+$+1).

Step 38d: Preparation of [18-(tert-butyl-dimethyl-silanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester

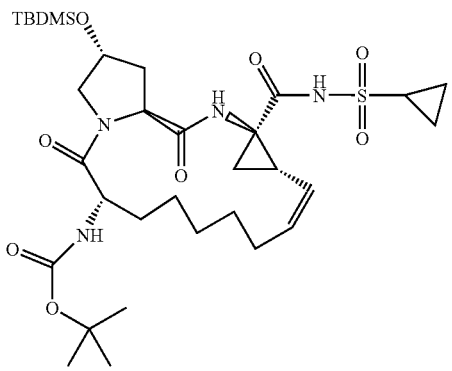

14-tert-Butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid (500 mg, 0.86 mmoL) was dissolved in 25 mL of THF and treated with CDI (180 mg, 1.12 mmoL). (Care was taken to avoid moisture by using oven dried glassware and maintaining a dry N2 atmosphere). After refluxing the reaction mixture for 2 h, it was cooled to rt and treated sequentially with cyclopropylsulfonamide (135 mg, 1.12 mmoL) and DBU (170 mg, 1.12 mmoL). The reaction mixture was stirred for 4 h at rt, and the THF was removed by rotary evaporation. The residue was partitioned between ethyl acetate and pH 4 buffer. The organic phase was dried (MgSO4) and concentrated in vacuo to give the crude product. It was then purified by flash chromatography (eluting with 33% ethyl acetate in hexane) to give 300 mg (51%) of [18-(tert-butyl-dimethyl-silanyloxy)-4-cyclopropanesulfonylaminocarbonyl-2,15-dioxo-3,16-diaza-tricyclo[14.3.0.046]nonadec-7-en-14-yl]-carbamic acid tert-butyl ester as a white solid. $^1$H NMR (300 MHz, CD$_3$OD) δ 1H 0.07 (s, 3H), 0.08 (s, 3H), 0.85 (s, 9H), 0.87–1.49 (m, 21H), 1.73–1.95 (m, 3H), 2.08–2.16 (m, 1H), 2.25–2.36 (m, 2H), 2.42–2.56 (m, 1H), 2.85–2.93 (m, 1H), 3.65–3.74(dd, J=10.61, 3.66 Hz, 1H), 3.89 (d, J=10.25 Hz, 1H), 4.34 (m, J=9.70, 9.70 Hz, 1H), 4.43 (t, J=7.87 Hz, 1H), 4.57 (s, 1H), 4.94–5.01 (m, 1H), 5.10 (d, J=8.78 Hz, 1H), 5.66–5.75 (m, 1H), 6.55 (s, 1H), 10.13 (s, 1H). LC-MS (Method A, retention time: 3.81 min), MS m/z 683 (M$^+$+1).

Step 38e: (4-Cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester

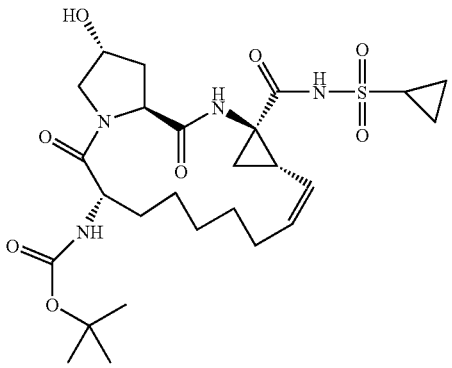

To a mixture of [18-(tert-butyl-dimethylsilanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester (330 mg, 0.48 mmoL) in 25 mL of THF was added tetrabutylammonium floride (150 mg, 0.54 mmoL). The reaction mixture was stirred at rt for 18 h, and then the THF was removed by rotary evaporation. The residue was partitioned between ethyl acetate and water. The organic phase was dried (MgSO$_4$) and concentrated in vacuo to give the crude product. It was then purified by triturating with hexane to yield 200 mg (73%) of (4-cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester as a white solid. $^1$H NMR (500 MHz, CD$_3$Cl) δ 1.87–1.64 (m, 21H), 1.70–1.98 (m, 3H), 2.15–2.56 (m, 5H), 2.85–2.94 (m, 1H), 3.71 (d, J=13.91 Hz, 1H), 4.10–4.26 (m, 2H), 4.51 (t, J=7.87 Hz, 1H), 4.62 (s, 1H), 4.98 (m, 1H), 5.06 (d, J=8.78 Hz, 1H), 5.64–5.71 (m, 1H), 6.72 (s, 1H), 10.24 (s, 1H). LC-MS (Method A, retention time: 2.85 min), MS m/z 569 (M$^+$+1).

Step 38f: Preparation of compound 58: [(Z)-(1S,4R,14S,18R)-4-cyclopropanesulfonylaminocarbonyl-2,15-dioxo-18-(3-phenyl-isoquinolin-1-yloxy)-3,16-diaza-tricyclo[14.3.0.0$^{4,6}$]nonadec-7-en-14-yl]-carbamic acid tert-butyl ester compound 58

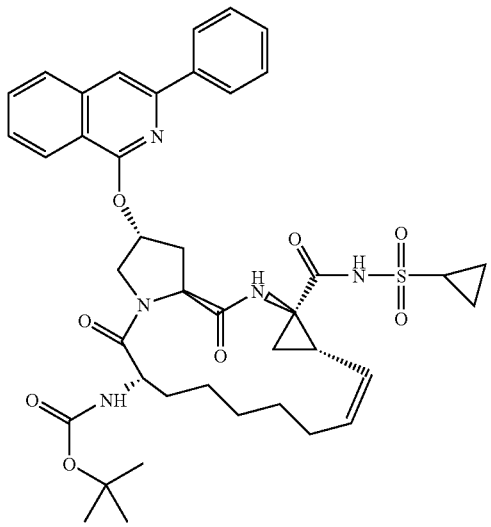

To a mixture of (4-cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester (20 mg, 0.035 mmoL) in 1 mL of DMF was added potassium t-butoxide (22 mg, 0.196 mmoL). The mixture was stirred at rt for 5 min, and then 1-chloro-3-phenylisoquinoline (15 mg, 0.062 mmoL) was added. The reaction mixture was stirred at rt for 15 h, and then concentrated in vacuo. This crude product was triturated with ether. The residue was dissolved in MeOH, and then purified by preparative HPLC.(YMC XTERRA, S5, 19×100 mm, gradient: 60% B to 100% B, 15 min, hold 2 min, flow rate 25 mL/min) to give 10 mg (39%) of compound 58, [(Z)-(1S,4R,14S,18R)-4-cyclopropanesulfonylaminocarbonyl-2,15-dioxo-18-(3-phenyl-isoquinolin-1-yloxy)-3,16-diaza-tricyclo[14.3.0.0$^{4,6}$]nonadec-7-en-14-yl]-carbamic acid tert-butyl ester, as a white solid. $^1$H NMR (500 MHz, CD$_3$Cl) δ 0.90–1.64 (m, 21H), 1.76–1.97 (m, 3H), 2.26–2.31 (m, 1H), 2.52–2.63 (br s, 1H), 2.69–2.81 (m, 2H), 2.88–2.93 (m, 1H), 4.11 (d, J=11.60 Hz, 1H), 4.33 (m, 1H), 4.61 (d, J=7.94 Hz, 2H), 4.99 (t, J=9.31 Hz, 1H), 5.05 (d, J=7.93 Hz, 1H), 5.69–5.74 (m, 1H), 6.08 (s, 1H), 6.60 (s, 1H), 7.38–7.47(m, 2H), 7.50 (t, J=7.63 Hz, 2H), 7.63 (t, J=7.32 Hz, 1H), 7.71 (s, 1H), 7.77 (d, J=8.24 Hz, 1H), 8.10 (d, J=7.32 Hz, 2H), 8.18 (d, J=7.93 Hz, 1H), 10.27 (s, 1H). LC-MS (Method A, retention time: 3.72 min), MS m/z 772 (M$^+$+1).

Example 39

Preparation of Compounds 144 and 145

Compound 144

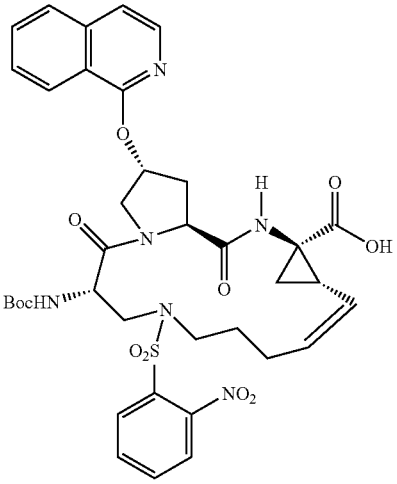

Compound 145

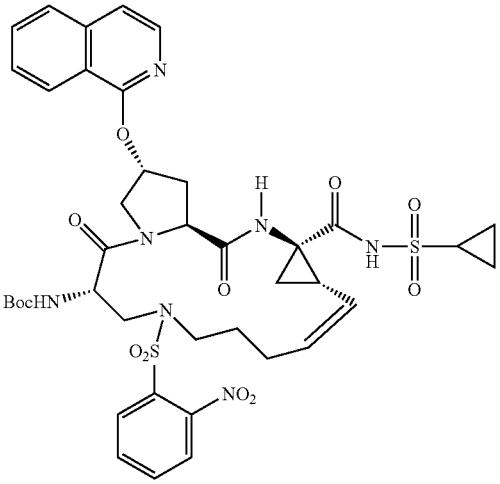

Step 39a: Preparation of (S)-2-(tert-butoxycarbonyl)-3-(2-nitro-N-(pent-4-enyl)phenylsulfonamido)propanoic acid v

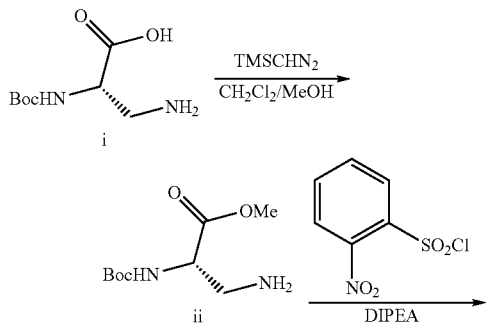

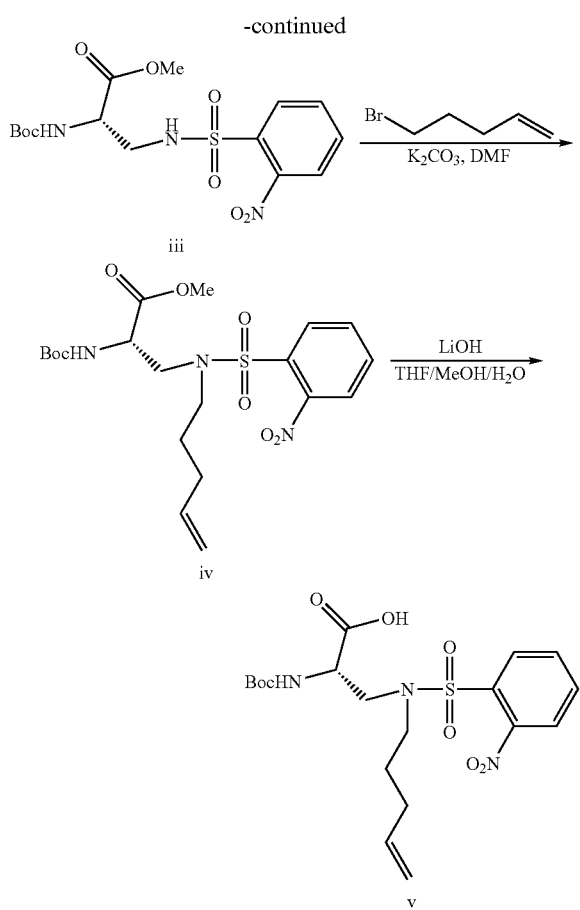

Preparation of (S)-methyl 3-amino-2-(tert-butoxycarbonyl) propanoate ii:

To a mixture of i (Boc-DAP-OH)(3.0 g 14.7 mmol) in 50 mL of methylene chloride was added 5 mL of methanol. To this solution was slowly added (trimethylsilyl)diazomethane (2 M in ether, 7.9 mL, 15.8 mmoL). The mixture was stirred at rt for 2 h until all of the solid dissolved and the solution turned light yellow. It was then concentrated to yield 3.2 g (99%) of (S)-methyl 3-amino-2-(tert-butoxycarbonyl)propanoate ii as a colorless oil. $^1$H NMR (CD$_3$OD, 300 MHz) δ 1.46 (s, 9H), 2.82–3.00 (m, 2H), 3.71 (s, 3H), 4.14 (brs, 1H).

Preparation of (S)-methyl 2-(tert-butoxycarbonyl)-3-(2-nitrophenylsulfonamido)propanoate iii:

To a mixture of (S)-methyl 3-amino-2-(tert-butoxycarbonyl)propanoate ii (1.6 g, 7.3 mmoL) in DCM (50 mL) was added DIPEA (1.64 mL, 9.4 mmoL) and 2-nitrobenzene sulfonyl chloride (1.62 g, 7.3 mmoL). The mixture was stirred at rt for 2 h. It was then concentrated, dissolved in ethyl acetate, which was then washed with sat. sodium bicarbonate, brine and dried over magnesium sulfate. It was then filtered, concentrated to yield 2.9 g (98%) of (S)-methyl 2-(tert-butoxycarbonyl)-3-(2-nitrophenylsulfonamido)propanoate iii as a yellow foam. $^1$H NMR (CD$_3$OD, 300 MHz) δ 1.41 (s, 9H), 3.36–3.51 (m, 2H), 3.71 (s, 3H), 4.22 (m, 1H), 7.80–7.90 (m, 3H), 8.07–8.10 (m, 1H).

Preparation of (S)-methyl 2-(tert-butoxycarbonyl)-3-(2-nitro-N-(pent-4-enyl)phenylsulfonamido)propanoate iv:

To a mixture of (S)-methyl 2-(tert-butoxycarbonyl)-3-(2-nitrophenylsulfonamido)-propanoate iii (150 mg, 0.37 mmol) in 3 mL of DMF was added potassium carbonate (102 mg, 0.74 mmoL). This mixture was stirred at rt for 20 min followed by the addition of 5-bromo-1-pentene (65 μL, 0.55 mmoL). The reaction mixture was stirred at rt for 2 days. It was then filtered, concentrated and purified by silica gel chromatography (eluting with 25% ethyl acetate in hexane) to give 75 mg (43%) of (S)-methyl 2-(tert-butoxycarbonyl)-3-(2-nitro-N-(pent-4-enyl)phenylsulfonamido) propanoate iv as a yellow solid. $^1$H NMR (CD$_3$OD, 300 MHz) δ 1.42 (s, 9H), 1.54–1.64 (m, 2H), 1.97 (q, J=7.20 Hz, 2H), 3.37 (m, 2H), 3.57–3.80 (m, 2H), 3.72 (s, 3H), 4.42 (dd, J=8.60, 5.31 Hz, 1H), 4.91–5.01 (m, 2H), 5.69–5.79 (m, 1H), 7.75–7.85 (m, 3H), 8.04 (m, 1H). LC-MS (Method D, retention time: 2.68 min), MS m/z 372 (M$^+$+1-Boc).

Preparation of (S)-2-(tert-butoxycarbonyl)-3-(2-nitro-N-(pent-4-enyl)phenylsulfonamido)propanoic acid v:

(S)-methyl 2-(tert-butoxycarbonyl)-3-(2-nitro-N-(pent-4-enyl)phenylsulfonamido)-propanoate iv (500 mg, 1.06 mmol) was dissolved in the mixed solvent system: THF (4 mL), methanol (1 mL), and water (2 mL). Powdered lithium hydroxide (250 mg, 10.4 mmol) was added. The light yellow slurry was stirred at rt for 15 h, and then concentrated in vacuo. The residue was partitioned between ether and water. The ether phase was discarded, and the aqueous phase was treated with 1 N HCl until the pH was 4. This acidic solution was extracted with ethyl acetate four times. The combined ethyl acetate extracts were dried (MgSO$_4$) and concentrated in vacuo to give 430 mg (89%) of (S)-2-(tert-butoxycarbonyl)-3-(2-nitro-N-(pent-4-enyl)phenylsulfonamido)propanoic acid v as a yellow oil. $^1$H NMR (CD$_3$OD, 300 MHz) δ 1.38 (s, 9H), 1.51–1.60 (m, 2H), 1.89–1.98 (m, 2H), 3.28–3.32 (m, 2H), 3.59–3.64 (dd, J=14.95, 9.46 Hz, 1H), 3.71–3.74 (m, 1H), 4.33 (dd, J=9.61, 4.43 Hz, 1H), 4.87–4.94 (m, 2H), 5.63–5.72 (m, 1H), 7.71–7.77 (m, 3H), 8.01 (dd, J=7.48, 1.37 Hz, 1H). LC-MS (Method D, retention time: 2.04 min), MS m/z 358 (M$^+$+1-Boc).

Step 39b: Preparation of (1R,2S)-ethyl 1-((3R,5S)-1-((S)-2-(tert-butoxycarbonyl)-3-(2-nitro-N-(pent-4-enyl)phenylsulfonamido)propanoyl)-3-(isoquinolin-1-yloxy)pyrrolidine-5-carboxamido)-2-vinylcyclopropanecarboxylate

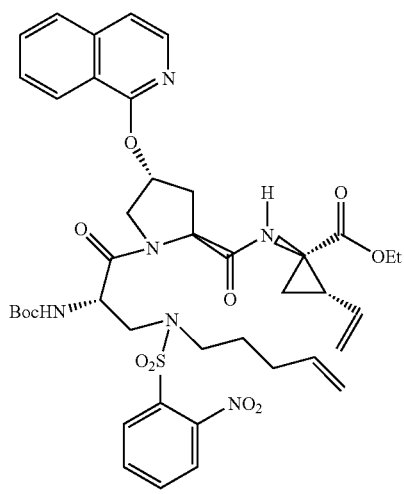

(S)-2-(tert-butoxycarbonyl)-3-(2-nitro-N-(pent-4-enyl) phenylsulfonamido)propanoic acid (1.10 g, 2.40 mmol) dissolved in 20 mL of DCM was treated sequentially with 1-{[4-(isoquinolin-1-yloxy)-pyrrolidine-2-carbonyl]-amino}-2-vinyl-cyclopropanecarboxylic acid ethyl ester, bis hydrochloride (1.27 g, 2.72 mmol), N-methyl morpholine (0.92 mL, 8.34 mmol), and HATU (PE biosystems)(1.28 g, 3.36 mmol). The reaction mixture was stirred at rt under N₂ for 15 h, and then concentrated in vacuo. The residue was partitioned between ethyl acetate and pH 4 buffer (biphthalate). The organic phase was washed with sat. aq. NaHCO₃, dried (MgSO₄), and concentrated in vacuo to give 2.0 g of the crude product. Flash chromatography (30% hexane/ethyl acetate) gave 1.4 g (70%) of (1R,2S)-ethyl 1-((3R,5S)-1-((S)-2-(tert-butoxycarbonyl)-3-(2-nitro-N-(pent-4-enyl)phenylsulfonamido)propanoyl)-3-(isoquinolin-1-yloxy)pyrrolidine-5-carboxamido)-2-vinylcyclopropanecarboxylate as a purple solid. ¹H NMR (CD₃OD, 500 MHz) δ 1.23–1.31 (m, 9H), 1.46–1.52 (m, 4H), 1.59 (br s, 1H), 1.66 (br s, 1H), 1.74 (dd, J=7.93, 5.19 Hz, 1H), 2.00 (br s, 2H), 2.29 (q, J=8.95 Hz, 1H), 2.47 (m, 1H), 2.72 (m, 1H), 3.38–3.51 (m, 2H), 3.68 (m, 2H), 4.09–4.26 (m, 3H), 4.37 (d, J=11.29 Hz, 1H), 4.64 (m, 1H), 4.72 (m, 1H), 4.95 (d, J=10.99 Hz, 1H), 4.99 (dd, J=18.92, 1.53 Hz, 1H), 5.12 (d, J=10.68 Hz, 1H), 5.32 (d, J=17.40 Hz, 1H), 5.73–5.86 (m, 2H), 5.92 (s, 1H), 7.36 (m, 1H), 7.58 (m, 1H), 7.73 (m, 1H), 7.80–7.88 (m, 4H), 7.99 (m, 1H), 8.11 (m, 1H), 8.24 (d, J=8.24 Hz, 1H). LC-MS (Method D, retention time: 3.15 min), MS m/z 835 (M⁺+1).

Step 39c:

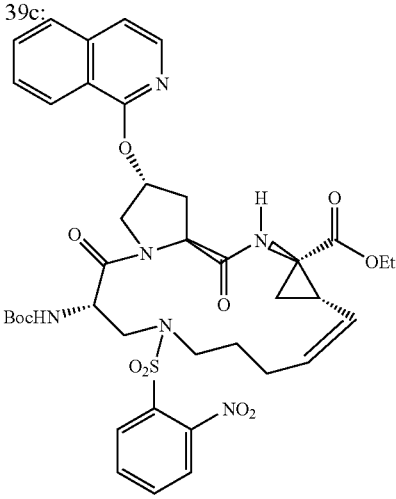

A solution of (1R,2S)-ethyl 1-((3R,5S)-1-((S)-2-(tert-butoxycarbonyl)-3-(2-nitro-N-(pent-4-enyl)phenylsulfonamido)propanoyl)-3-(isoquinolin-1-yloxy)pyrrolidine-5-carboxamido)-2-vinylcyclopropanecarboxylate (1.40 g, 1.67 mmol) and tricyclohexylphosphine[1,3-bis(2,4,6-trimethylphenyl)-4,5-dihydroimidazol-2-ylidene][benzylidene]ruthenium (IV) dichloride (Aldrich), (204 mg, 0.24 mmol) in 1500 mL of methylene chloride was refluxed under N₂. Shortly after reaching reflux temperature the reaction mixture was homogeneous and light orange in color. After refluxing for 2 h, the dark orange reaction mixture was cooled to rt and concentrated in vacuo to give 1.7 g of an orange oil. Flash chromatography (30% hexane/ethyl acetate) gave 1.1 g (82%) of the ester shown above as a purple solid. ¹H NMR (CD₃OD, 300 MHz) δ 1.11–1.31 (m, 12H), 1.51–1.80 (m, 4H), 1.97–2.15 (m, 2H), 2.34–2.50 (m, 2H), 2.62–2.69 (m, 1H), 3.17–3.33 (m, 2H), 3.44–3.60 (m, 2H), 4.01–4.05 (m, 1H), 4.12 (q, J=7.32 Hz, 2H), 4.37 (d, J=13.17 Hz, 1H), 4.58 (t, J=8.42 Hz, 1H), 4.71 (m, 1H), 5.61 (m, 2H), 5.88 (s, 1H), 6.91 (d, J=9.15 Hz, 1H), 7.30 (d, J=5.49 Hz, 1H), 7.52 (t, J=7.50 Hz, 1H), 7.66–7.73 (m, 1H), 7.76–7.80 (m, 4H), 7.95 (d, J=5.86 Hz, 1H), 8.11 (d, J=7.32 Hz, 1H), 8.17 (d, J=8.05 Hz, 1H), 8.84 (s, 1H). LC-MS (Method D, retention time: 2.91 min), MS m/z 807 (M⁺+1).

Step 39d: Preparation of Compound 144 compound 144

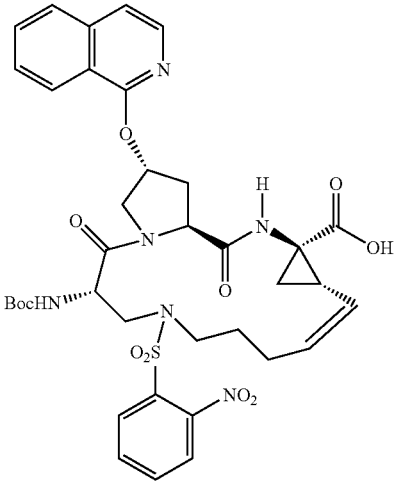

The ethyl ester prepared in step 39c (1.1 g, 1.3 mmol) was dissolved in the mixed solvent system: THF (16 mL), methanol (4 mL), and water (8 mL). Powdered lithium hydroxide hydrate (540 mg, 13.2 mmol) was added. The light yellow slurry was stirred at rt for 15 h, and then concentrated in vacuo. The residue was partitioned between ether and water. The ether phase was discarded, and the aqueous phase was treated with 1 N HCl until the pH was 4. This acidic solution was extracted with ethyl acetate four times. The combined ethyl acetate extracts were dried (MgSO₄) and concentrated in vacuo to give 878 mg (85%) of compound 144 as a purple solid. ¹H NMR (CD₃OD, 300 MHz) δ 1.11, 1.31 (s, 9H), 1.56–1.68 (m, 4H), 2.04–2.16 (m, 2H), 2.42–2.66 (m, 2H), 2.68–2.75 (m, 1H), 3.22–3.30 (m, 2H), 3.48–3.63 (m, 2H), 4.02–4.14 (m, 1H), 4.46 (d, J=12.44 Hz, 1H), 4.62 (t, J=8.42 Hz, 1H), 4.70–4.73 (m, 1H), 5.64 (m, 2H), 5.90 (s, 1H), 7.36 (d, J=5.86 Hz, 1H), 7.57 (t, J=7.68 Hz, 1H), 7.71–7.87 (m, 5H), 7.98 (d, J=5.86 Hz, 1H), 8.15 (m, 1H), 8.22 (d, J=8.05 Hz, 1H). LC-MS (Method D, retention time: 2.78 min), MS m/z 779 (M⁺+1).

Step 39e: Preparation of Compound 145 compound 145

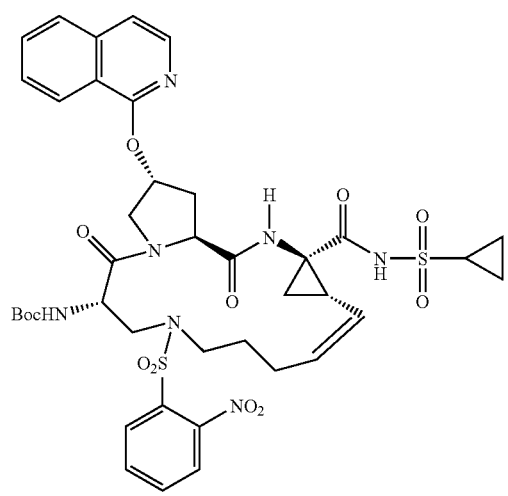

Compound 144 (0.878 g, 1.1 mmol) was dissolved in 15 mL of THF and treated with CDI (255 mg, 1.58 mmol). (Care was taken to avoid moisture by using oven dried glassware and maintaining a dry N₂ atmosphere.) After refluxing the reaction mixture for one hour, it was cooled to rt and treated sequentially with cyclopropylsulfonamide (194 mg, 1.6 mmol) and DBU (245 mg, 1.6 mmol). After stirring for 24 h at rt, the THF was removed by rotary evaporation. The residue was partitioned between ethyl acetate and pH 4 buffer. The organic phase was dried (MgSO₄) and concentrated in vacuo to give the crude product. Flash chromatography (3% MeOH/methylene chloride) gave 0.68 g (70%) of compound 145 as a white solid. $^1$H NMR (CD₃OD, 300 MHz) δ 1.07–1.37 (m, 13H), 1.11 (s, 9H), 1.60–1.78 (m, 4H), 1.97–2.02 (m, 1H), 2.28–2.35 (m, 1H), 2.44–2.51 (m, 1H), 2.75–2.68 (m, 1H), 2.75–2.80 (m, 1H), 2.94–3.00 (m, 1H), 3.20–3.25 (m, 1H), 3.28–3.47 (m, 2H), 3.57–3.62 (m, 1H), 4.05–4.08 (m, 1H), 4.51 (d, J=12.21 Hz, 1H), 4.65–4.68 (m, 1H), 4.84 (m, 1H), 5.15–5.23 (m, 1H), 5.70–5.75 (m, 1H), 5.94 (s, 1H), 7.35 (d, J=6.10 Hz, 1H), 7.57 (t, J=7.32 Hz, 1H), 7.74 (t, J=7.78 Hz, 1H), 7.78–7.89 (m, 4H), 8.00 (d, J=5.80 Hz, 1H), 8.20–8.25 (m, 2H). LC-MS (Method D, retention time: 2.89 min), MS m/z 882 (M⁺+1).

Example 40

Preparation of Compound 151

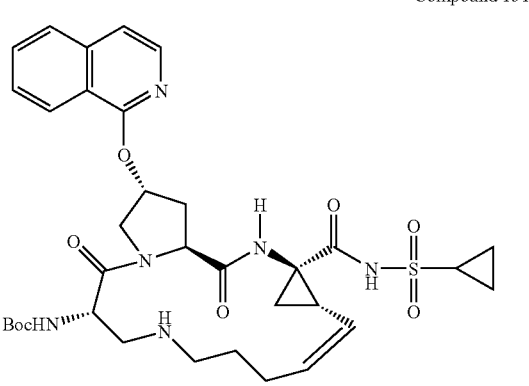

Compound 151

To a mixture of compound 145 (680 mg, 0.77 mmol) in acetonitrile (20 mL) was added potassium carbonate (319 mg, 2.31 mmol) and benzenethiol (186 mg, 1.69 mmol). The mixture was stirred at rt overnight and then concentrated in vacuo. The residue was diluted with water, and this aqueous solution was adjusted to pH 5 with 1 N HCl. A white solid precipitated formed in the solution. This heterogeneous mixture was extracted with ethyl acetate (3×). The combined extracts were dried (MgSO₄) and concentrated to yield a light yellow solid. This crude solid was then triturated with hexane several times to yield 510 mg (95%) of compound 151 as an off-white solid. $^1$H NMR (CD₃OD, 300 MHz) δ 1.06–1.88 (m, 13H), 1.23, 1.31 (s, 9H), 1.65 (dd, J=9.70, 5.67 Hz, 1H), 1.80 (dd, J=8.23, 5.67 Hz, 2H), 2.03 (brs, 1H), 2.18 (br s, 1H), 2.37–2.52 (m, 3H), 2.85–2.99 (m, 2H), 3.09–3.15 (m, 1H), 3.27 (m, 1H), 3.44 (m, 2H), 4.15–4.20 (m, 1H), 4.46 (m, 1H), 4.74–4.85 (m, 2H), 5.32 (t, J=10.25 Hz, 1H), 5.71 (m, 1H), 5.98(br s, 1H), 7.37 (d, J=5.86 Hz, 1H), 7.58 (t, J=8.23 Hz, 1H), 7.74 (t, J=7.68 Hz, 1H), 7.85 (d, J=8.05 Hz, 1H), 8.00 (d, J=5.86 Hz, 1H), 8.22 (d, J=8.05 Hz, 1H). LC-MS (Method D, retention time: 2.01 min), MS m/z 697 (M⁺+1).

Example 41

Preparation of Compound 146

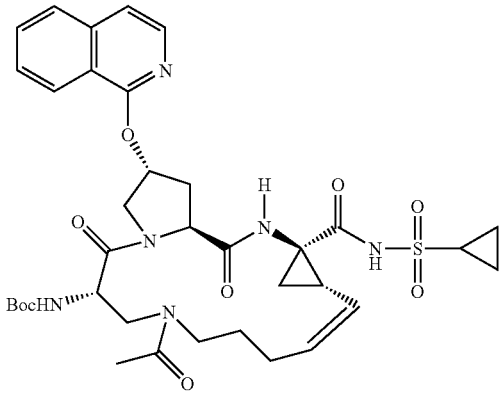

Compound 146

To a mixture of compound 151 (20 mg, 0.029 mmol) in 2 mL of DCM was added triethylamine (14 mg, 0.138 mmol) and acetic anhydride (8 mg, 0.078 mmol). This reaction mixture was stirred at rt for 2 h, and then concentrated in vacuo. The residue was dissolved in methanol and purified by preparative HPLC (YMC XTERRA, S5, 30×50 mm, gradient: 45% B to 85% B, 15 min, hold 2 min, flow rate 25 mL/min) to give 10 mg (47%) of compound 146 as a white solid. $^1$H NMR (CD₃OD, 300 MHz, 60° C.) δ 1.08–1.22 (m, 13H), 1.55–1.74 (m, 4H), 2.09–2.21(m, 2H), 2.13 (s, 3H), 2.33–2.48 (m, 2H), 2.66–2.75 (m, 1H), 2.90–2.99 (m, 1H), 3.12–3.25 (m, 2H), 3.45–3.60 (m, 2H), 3.75–3.84 (m, 1H), 4.98–4.05 (m, 1H), 4.70 (t, J=7.68 Hz, 1H), 4.89–4.97 (m, 1H), 5.26 (t, J=10.43 Hz, 1H), 5.2–5.75 (m, 1H), 5.92 (s, 1H), 7.29 (d, J=5.86 Hz, 1H), 7.50 (t, J=7.50 Hz, 1H), 7.64–7.69 (m, 1H), 7.77 (m, 1H), 7.95 (d, J=5.86 Hz, 1H), 8.18 (d, J=8.78 Hz, 1H). LC-MS (Method D, retention time: 2.64 min), MS m/z 739 (M⁺+1).

Example 42

Preparation of Compound 147

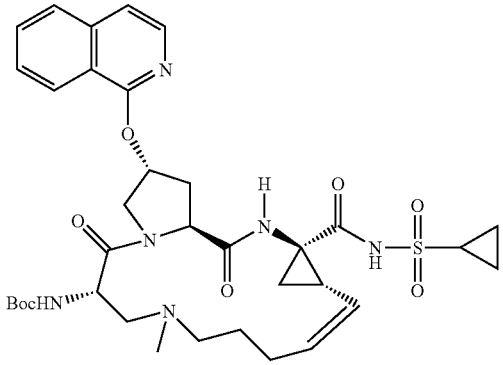

Compound 147

To a mixture of compound 151 (100 mg, 0.144 mmol) in 5 mL of DMF was added potassium carbonate (40 mg, 0.290 mmol) and methyl iodide (13 μL, 0.21 mmol). This reaction mixture was stirred at rt for 2 h. It was then concentrated in vacuo. The residue was dissolved in methanol and purified by preparative HPLC (YMC XTERRA, S5, 30×50 mm, gradient: 45% B to 70% B, 15 min, hold 2 min, flow rate 25 mL/min) to give 75 mg (73%) of compound 147 as a white solid. $^1$H NMR (CD$_3$OD, 300 MHz, 60° C.) δ 1.02–1.28 (m, 13H), 1.64 (dd, J=9.70, 5.67 Hz, 1H), 1.72–1.81(m, 2H), 1.91–2.10 (m, 1H), 2.13–2.30 (m, 1H), 2.36–2.50 (m, 2H), 2.54–2.68 (m, 1H), 2.76–2.99 (m, 2H), 3.05 (s, 3H), 3.11–3.46 (m, 4H), 3.79–3.96 (m, 1H), 4.17 (m, 1H), 4.76 (m, 2H), 5.31 (t, J=10.06 Hz, 1H), 5.71 (m, 1H), 5.99 (s, 1H), 7.33 (d, J=5.86 Hz, 1H), 7.55 (t, J=7.50 Hz, 1H), 7.70 (t, J=7.68 Hz, 1H), 7.81 (m, 1H), 7.96 (d, J=5.86 Hz, 1H), 8.17 (d, J=8.42 Hz, 1H). LC-MS (Method D, retention time: 1.98 min), MS m/z 711 (M$^+$+1).

Example 43

Preparation of Compound 148

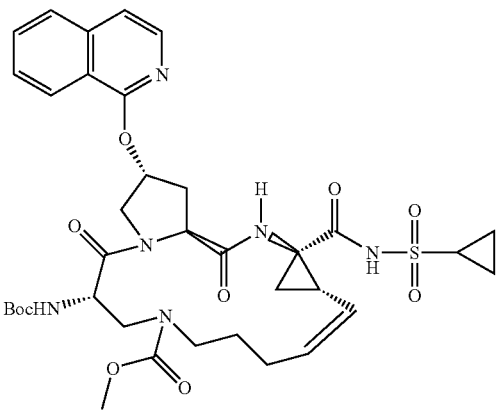

Compound 148

To a mixture of compound 151 (20 mg, 0.029 mmol) in 2 mL of DCM was added diisopropylamine (15 μL, 0.086 mmol) and methyl chloroformate (8 mg, 0.085 mmol). This reaction mixture was stirred at rt for 2 h, and then concentrated in vacuo. The residue was dissolved in methanol and purified by preparative HPLC (YMC XTERRA, S5, 30×50 mm, gradient: 50% B to 90% B, 15 min, hold 2 min, flow rate 25 mL/min) to give 15 mg (69%) of compound 148 as a white solid. $^1$H NMR (CD$_3$OD, 300 MHz) δ 1.09 (s, 9H), 1.07–1.45 (m, 13H), 1.56–1.61 (m, 1H), 1.70–1.76 (m, 3H), 2.95–2.10 (m, 1H), 2.13–2.26 (m, 1H), 2.33–2.55 (m, 2H), 2.71–2.78 (m, 1H), 2.93–3.02 (m, 1H), 3.33 (m, 2H), 3.48–3.57 (m, 2H), 3.75 (s, 3H), 4.04–4.12 (m, 1H), 4.64 (t, J=8.42 Hz, 1H), 4.90 (m, 2H), 5.19 (t, J=10.25 Hz, 1H), 5.69–5.77 (m, 1H), 5.93 (s, 1H), 7.34 (d, J=5.86 Hz, 1H), 7.55 (t, J=6.95 Hz, 1H), 7.72 (t, J=7.32 Hz, 1H), 7.83 (d, J=7.32 Hz, 1H), 7.98 (d, J=5.86 Hz, 1H), 8.20 (d, J=8.42 Hz, 1H), 9.21 (s, 1H). LC-MS (Method D, retention time: 2.75 min), MS m/z 755 (M$^+$+1).

Example 44

Preparation of Compound 150

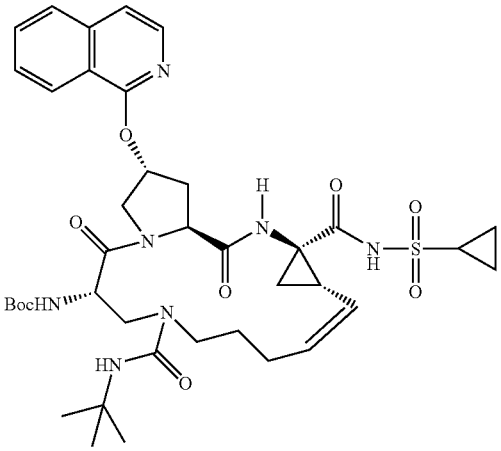

Compound 150

To a mixture of compound 151 (20 mg, 0.029 mmol) in 2 mL of DCM was added diisopropylamine (15 μL, 0.086 mmol) and tert-butyl isocyanate (8 μL, 0.058 mmol). The reaction mixture was stirred at rt for 2 h, and then concentrated in vacuo. The residue was dissolved in methanol and purified by preparative HPLC (YMC XTERRA, S5, 30×50 mm, gradient: 55% B to 90% B, 15 min, hold 2 min, flow rate 25 mL/min) to give 15 mg (65%) of compound 150 as a white solid (15 mg, 65%). $^1$H NMR (CD$_3$OD, 300 MHz) δ 1.06–1.34 (m, 13H), 1.21 (s, 9H), 1.40 (s, 9H), 1.58–1.75 (m, 3H), 1.97–2.09 (m, 1H), 2.11–2.23 (m, 1H), 2.37–2.50 (m, 2H), 2.69–2.82 (m, 1H), 2.94–3.04 (m, 1H), 3.22 (m, 1H), 0.36–3.46 (m, 2H), 4.12 (d, J=12.44 Hz, 1H), 4.39 (d, J=11.34 Hz, 1H), 4.50–4.57 (m, 1H), 4.69 (t, J=8.23 Hz, 1H), 5.20–5.27 (m, 1H), 5.69–5.78 (m, 1H), 5.90 (s, 1H), 7.34 (d, J=5.86 Hz, 1H), 7.57 (t, J=7.14 Hz, 1H), 7.73 (m, 1H), 7.83 (m, 1H), 7.98 (d, J=5.86 Hz, 1H), 8.24 (d, J=8.05 Hz, 1H). LC-MS (Method D, retention time: 3.04 min), MS m/z 796 (M$^+$+1).

Example 45

Preparation of Compound 153

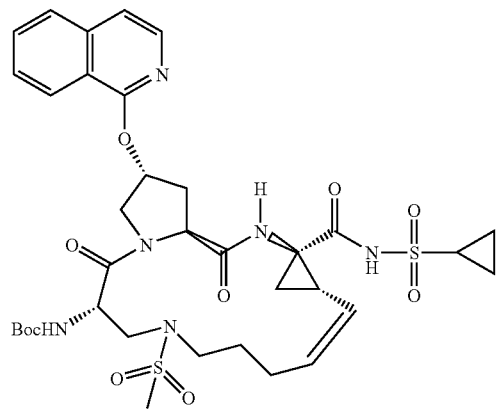

Compound 153

To a mixture of compound 151 (20 mg, 0.029 mmol) in 2 mL of DCM was added diisopropylamine (15 μL, 0.086 mmol) and methanesulfonyl chloride (5 μL 0.065 mmol). The reaction mixture was stirred at rt for 2 h, and then concentrated in vacuo. The residue was dissolved in methanol and purified by preparative HPLC (YMC XTERRA, S5, 30×50 mm, gradient: 50% B to 90% B, 15 min, hold 2 min, flow rate 25 mL/min) to give 17 mg (76%) of compound 153 as a white solid. $^1$H NMR (CD$_3$OD, 300 MHz) δ 1.02–1.49 (m, 13H), 1.59 (m, 1H), 1.72–1.86 (m, 3H), 1.96–2.09 (m, 1H), 2.37–2.50 (m, 2H), 2.63–2.80 (m, 2H), 2.91–3.08 (m, 5H), 2.97 (s, 3H), 3.22–3.45 (m, 3H), 4.19 (dd, J=11.89, 3.48 Hz, 1H), 4.52 (d, J=11.71 Hz, 1H), 4.62 (dd, J=9.88, 7.32 Hz, 1H), 4.83–4.96 (m, 1H), 5.17 (t, J=10.06 Hz, 1H), 5.75 (m, 1H), 5.94 (s, 1H), 7.33 (d, J=5.86 Hz, 1H), 7.57 (d, J=8.05 Hz, 1H), 7.72 (t, J=7.50 Hz, 1H), 7.82 (m, 1H), 7.99 (d, J=6.22 Hz, 1H), 8.20 (d, J=8.42 Hz, 1H). LC-MS (Method D, retention time: 2.59 min), MS m/z 775 (M$^+$+1).

Example 46

Preparation of Compound 141: [(Z)-(1S,4R,13S, 17R)-4-cyclopropanesulfonylaminocarbonyl-17-(6-methoxy-isoquinolin-1-yloxy)-2,14-dioxo-10-oxa-3, 15-diaza-tricyclo[13.3.0.0$^{4,6}$]octadec-7-en-13-yl]-carbamic acid tert-butyl ester

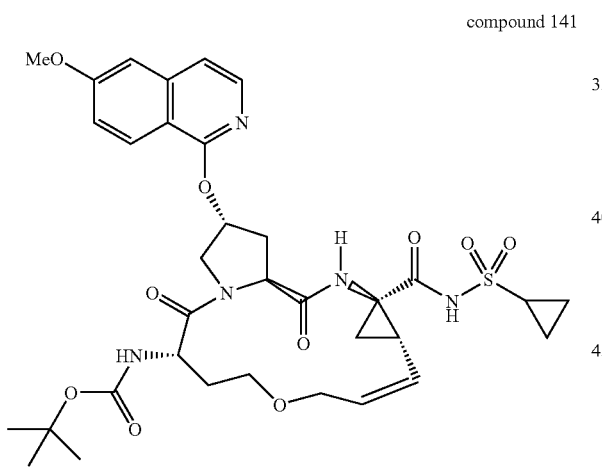

compound 141

Step 46a: Preparation of (S)-4-allyloxy-2-(tert-butoxycarbonylamino)butyric acid

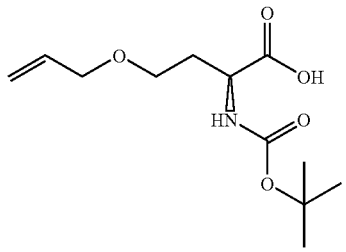

To a mixture of sodium hydride (913 mg, 22.8 mmoL) in DMF at 0° C. was added N-t-Boc-L-homoserine (2 g, 9.13 mmoL). This reaction mixture was stirred at 0° C. for 15 min, and then allyl bromide (1.38 g, 11.4 mmoL) was added. The mixture was warmed up to rt, and stirred for 2 h. It was then concentrated in vacuo. The residue was diluted with water, and sequentially washed with hexane and ether. The organic layers were discarded, and the aqueous layer was carefully adjusted to pH 3 with 1 N HCl. This acidic aqueous solution was extracted with ethyl acetate. The organic phase was dried (MgSO$_4$), and concentrated in vacuo to yield 2.2 g (93%) of (S)-4-allyloxy-2-(tert-butoxycarbonylamino)butyric acid as a colorless oil. $^1$H NMR (300 MHz, CD$_3$OD) δ 1.42 (s, 9H), 1.80–1.90 (m, 1H), 2.04–2.16 (m, 1H), 3.50–3.54 (m, 2H), 3.97 (d, J=0.39 Hz, 2H), 4.23 (dd, J=8.78, 4.39 Hz, 1H), 5.15 (d, J=10.25 Hz, 1H), 5.26 (dd, J=17.38, 1.65 Hz, 1H), 5.84–5.97 (m, 1H). This starting material was employed in the synthesis of (1R,2S)-ethyl 1-((3R,5S)-1-((S)-4-(allyloxy)-2-(tert-butoxycarbonyl)butanoyl)-3-(6-methoxyisoquinolin-1-yloxy)pyrrolidine-5-carboxamido)-2-vinylcyclopropane-carboxylate as described in example 2.

Step 46b: Preparation of (Z)-(1S,4R,13S,17R)-13-tert-butoxycarbonylamino-17-(6-methoxy-isoquinolin-1-yloxy)-2, 14-dioxo-10-oxa-3,15-diaza-tricyclo[13.3.0.0$^{4,6}$]octadec-7-ene-4-carboxylic acid ethyl ester

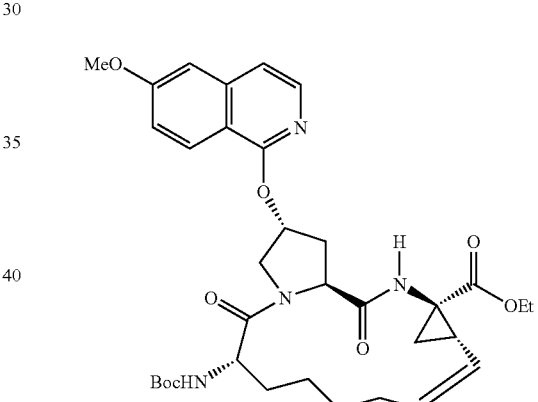

A solution of (1R,2S)-ethyl 1-((3R,5S)-1-((S)-4-(allyloxy)-2-(tert-butoxycarbonyl)butanoyl)-3-(6-methoxyisoquinolin-1-yloxy)pyrrolidine-5-carboxamido)-2-vinylcyclopropanecarboxylate (220 mg, 0.33 mmol) in 84 mL of methylene chloride was added tricyclohexylphosphine[1,3-bis(2,4,6-trimethyl-phenyl)-4,5-dihydroimidazol-2-ylidene][benzylidene]-ruthenium (IV) dichloride (27 mg, 0.032 mmoL). The light orange homogeneous solution was refluxed for 3 h to give a dark orange solution. At this time another portion of the ruthenium catalyst (13 mg, 0.016 mmoL) was added, and refluxing was continued for another 2 h. The reaction mixture was cooled to rt, and concentrated in vacuo to give an orange oil. Flash chromatography (ethyl acetate then 10% MeOH in ethyl acetate) gave 174 mg (80%) of (Z)-(1S,4R,13S,17R)-13-tert-butoxycarbonylamino-17-(6-methoxy-isoquinolin-1-yloxy)-2,14-dioxo-10-oxa-3,15-diaza-tricyclo[13.3.0.0$^{4,6}$]octadec-7-ene-4-carboxylic acid ethyl ester as a white solid. LC-MS (Method A, retention time: 3.74 min), MS m/z 639(M$^+$+1).

Step 46c: Preparation of Compounds 140 and 141:

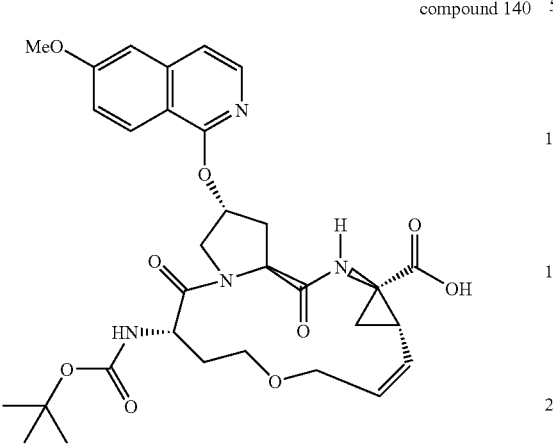

compound 140

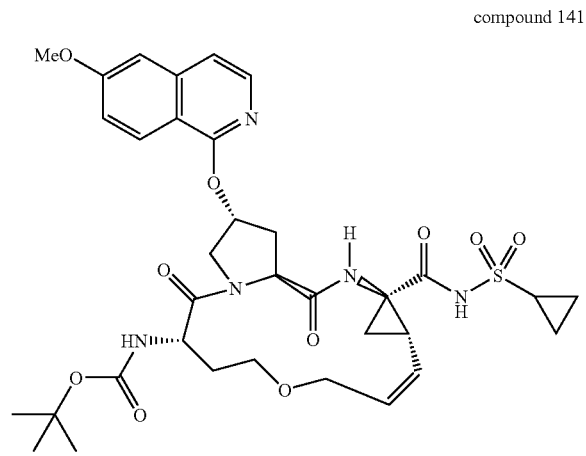

compound 141

(Z)-(1S,4R,13S,17R)-13-tert-butoxycarbonylamino-17-(6-methoxy-isoquinolin-1-yloxy)-2,14-dioxo-10-oxa-3,15-diaza-tricyclo[13.3.0.0$^{4,6}$]octadec-7-ene-4-carboxylic acid ethyl ester was hydrolyzed according to Example 2 (step 2E) to give compound 140. Compound 140 was converted to compound 141, [(Z)-(1S,4R,13S,17R)-4-cyclopropane-sulfonylaminocarbonyl-17-(6-methoxy-isoquinolin-1-yloxy)-2,14-dioxo-10-oxa-3,15-diaza-tricyclo[13.3.0.0$^{4,6}$]octadec-7-en-13-yl]-carbamic acid tert-butyl ester, according to Example 7. LC-MS (Method A, retention time: 3.51 min), MS m/z 714(M$^+$+1).

Example 47

General Procedure for Preparing P4-carbamates from Tertiary Alcohols

Preparation of compound 56: [(Z)-(1S,4R,14S,18R)-4-cyclopropanesulfonylaminocarbonyl-18-(isoquinolin-1-yloxy)-2,15-dioxo-3,16-diaza-tricyclo[14.3.0.0$^{4,6}$]nonadec-7-en-14-yl]-carbamic acid 1-methyl-cyclobutyl ester

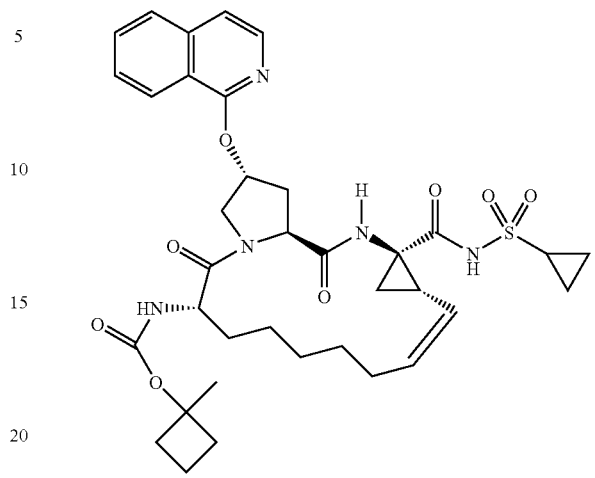

compound 56

Step 47a: Preparation of 1-methylcyclobutanol:

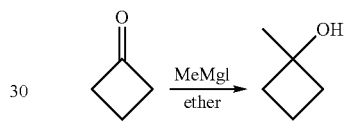

To a solution of 6 mL of methylmagnesium iodide (3M in ether) at −10° C. was added cyclobutanone (1 g, 14.3 mmol) dropwise. The mixture was stirred for 2.5 h (−10° C. to rt). Dilute HCl was added to the reaction mixture until all of the precipitate was dissolved. The homogeneous reaction mixture was extracted with ether (2×). The combined ether extracts were dried (MgSO$_4$), filtered, and concentrated in vacuo to give 0.9 g (73%) of 1-methylcyclobutanol as a yellow oil.

Step 47b. Preparation of [(Z)-(1S,4R,14S,18R)-4-cyclopropanesulfonylaminocarbonyl-18-(isoquinolin-1-yloxy)-2,15-dioxo-3,16-diaza-tricyclo[14.3.0.0$^{4,6}$]nonadec-7-en-14-yl]-carbamic acid 1-methyl-cyclobutyl ester To a slurry of KH (400 mg, 35% in oil, 3.5 mmol) was added 5 mL of hexane. It was stirred for 5 min, and then the hexane was removed. This process was repeated three times. THF (5 mL) was added to this prewashed KH, and then 1-methylcyclobutanol (200 mg, 2.3 mmol) was added at 0° C. The mixture was stirred (0° C. to rt) for 1 h, and then carbonic acid dipyridin-2-yl ester (753 mg, 3.5 mmol) was added. The mixture was stirred at rt for 4 h, and the reaction was diluted with sat. aq. NH$_4$Cl. The mixture was then extracted with EtOAc, and the solvent was removed in vacuo to obtain 200 mg of the crude carbonic acid 1-methyl-cyclobutyl ester pyridin-2-yl ester as an orange solid. It was used directly in the next step without further purification.

To a suspension of 50 mg (0.073 mmol) of compound 11 [1-(2-Amino-3,3-dimethyl-butyryl)-4-(6-methoxy-isoquinolin-1-yloxy)-pyrrolidine-2-carboxylic acid (1-cyclopropanesulfonylaminocarbonyl-2-vinyl-cyclopropyl)-amide bis hydrochloride salt] in CH$_2$Cl$_2$ was added diisopropylethylamine (29 mg, 0.22 mmoL) and 70 mg (0.33 mmol) of the reagent above (carbonic acid 1-methyl-cyclobutyl ester pyridin-2-yl ester). This reaction mixture was stirred at rt overnight, and then concentrated in vacuo. The residue was purified by preparative HPLC to give 32 mg (62%) of compound 56 as a white solid. Preparative HPLC condition: YMC XTERRA, S5, 19×100 mm, gradient: 50% B to 90% B, 15 min, hold 2 min, flow rate 25 mL/min. LC-MS (Method A, retention time: 3.47 min), MS m/z 708 (M$^+$+1).

Compound 59 was prepared by the general method used for compound 56 (example 47): 1-methylcyclopropanol was converted to the reagent carbonic acid 1-methyl-cyclopropyl ester pyridin-2-yl ester was prepared according to the method above (example 47). 1-Methyl-1-cyclopropanol was prepared by a slight modification of the procedure described by Kulinkovich, O. G.; Sviridov, S. V.; and Vasilevski, D. A. *Synthesis*, 1991, 234: To a stirred solution of methyl acetate (1.85 g, 25 mmol) and Ti(OPr-i)$_4$ (744 μL, 2.5 mmol) in diethyl ether (80 mL) is added ethylmagnesium bromide (3M solution in diethyl ether) (18 mL, 53 mmol) in diethyl ether (60 mL) slowly over a period of 1 h while maintaining the reaction temperature at 18–20° C. Once the addition is complete, stirring is continued for 10 min. The mixture is poured into cooled (5° C.) 10% aq. H$_2$SO$_4$ (250 mL) and the product is extracted with diethyl ether (3×50 mL). The combined ether extracts are washed with water (50 mL), dried (MgSO$_4$), and carefully concentrated by rotory evaporation (~20 torr, rt) to give 1.7 g of 1-methyl-1-cyclopropanol (purity~80%). $^1$H NMR (300 MHz, CDCl$_3$) δ 0.42–0.45 (m, 2H), 0.73–0.77 (m, 2H), 1.44 (s, 3H), 1.64 (br s, 1H).

The following compounds were also prepared using the general procedure above: compound 50 was prepared from 1-methylcyclopentanol; compounds 39 and 51 were prepared from 1,1,1-trifluoro-2-methylpropan-2-ol, compound 55 was prepared from 1,1-difluoro-2-methylpropan-2-ol (1,1-difluoro-2-methylpropan-2-ol was prepared according to the procedure described by Dickey, J. B. and Towne, E. B. U.S. Pat. No. 2,700,686), compounds 40 and 52 were prepared from 1-chloro-2-methylpropan-2-ol, compound 124 was prepared from 1,1,1-trichloro-2-methylpropan-2-ol, compound 123 was prepared from 3-hydroxy-3-methylbutan-2-one, and compound 139 was prepared from S-tert-butyl O-4-nitrophenyl carbonothioate (shown below)(This reagent was prepared as discribed by E. M. Gordon, J. C. Barrish, G. S. Bisacchi, C-Q. Sun, J. A. Tino, G. D. Vite, and R. Zahler in US005559256A.).

Example 48

Preparation of Compound 126

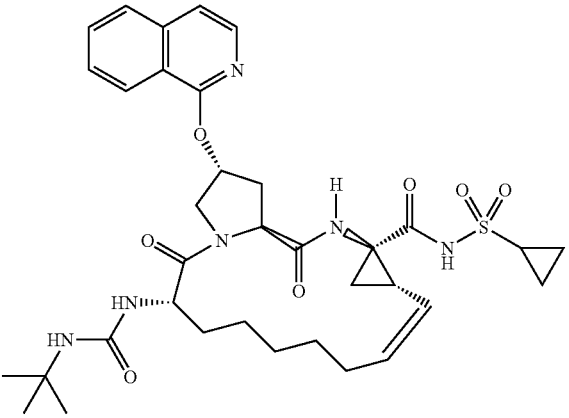

Compound 126

To a mixture of compound 11 {cyclopropanesulfonic acid [14-amino-18-(isoquinolin-1-yloxy)-2,15-dioxo-3,16-diaza-tricyclo[14.3.0.0$^{4,6}$]nonadec-7-ene-4-carbonyl]-amide bis hydrochloride} (20 mg, 0.029 mmol) in 2 mL of DCM was added 18 μL (0.10 mmol) of DIPEA and 4 mg (0.04 mmol) of t-butyl isocyanate. The mixture was stirred at rt overnight. It was then diluted with EtOAc and washed with pH 4 buffer (2×) and brine (1×). The organic phase was dried (MgSO$_4$) and concentrated in vacuo to give the crude product. The resulting oil was dissolved in methanol and purified by preparative HPLC (YMC XTERRA, S5, 19×100 mm, gradient: 50% B to 100% B, 15 min, hold 2 min, flow rate 25 mL/min) to isolate compound 126 as a white powder (17 mg, 82%): LC-MS (Method D, retention time: 3.24 min), MS m/z 695 (M$^+$+1). $^1$H NMR (300 MHz, CDCl$_3$) δ 0.86–0.96 (m, 2H), 1.12 (s, 9H), 1.01–1.49 (m, 18H), 1.52–1.66 (m, 1H), 1.70–1.78 (m, 1H), 1.83–1.95(m, 2H), 2.14–2.25 (m, 1H), 2.49 (brs, 1H), 2.71 (m, 2H), 2.86–2.92 (m, 1H), 4.07 (dd, J=1.71, 4.03 Hz, 1H), 4.40–4.44 (m, 1H), 4.62–4.69 (m, 2H), 4.94–5.00 (m, 1H), 5.65–5.74 (m, 1H), 5.97 (br s, 1H), 7.03 (s, 1H), 7.32 (d, J=6.22 Hz, 1H), 7.50–7.52 (m, 1H), 7.68–7.78 (m, 2H), 8.00 (d, J=5.86 Hz, 1H), 8.22 (d, J=7.68 Hz, 1H), 10.15 (s, 1H).

Example 49

Preparation of Compound 58

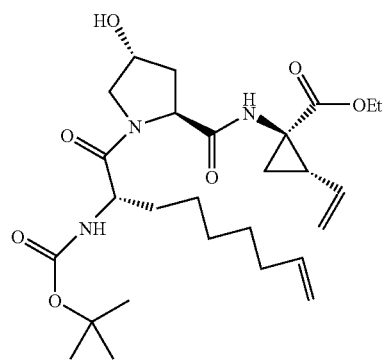

TBDMSCl
imidazole, DMF
78%

-continued
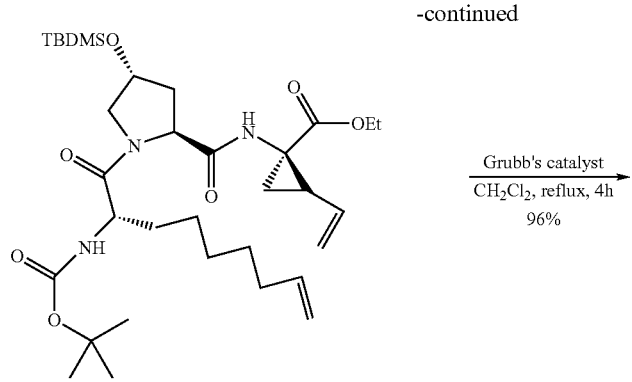
Grubb's catalyst
CH₂Cl₂, reflux, 4h
96%
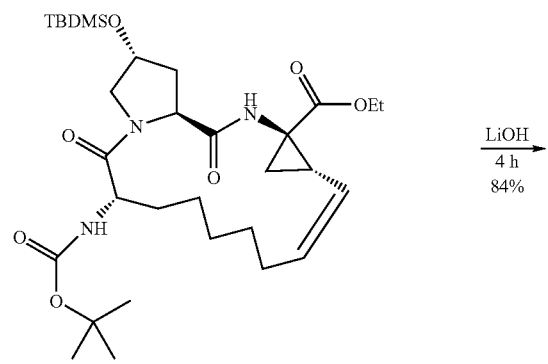
LiOH
4 h
84%
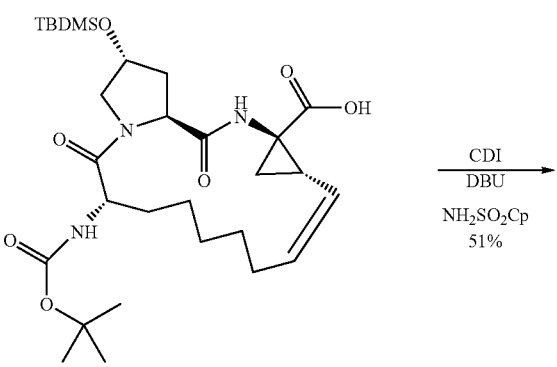
CDI
DBU
NH₂SO₂Cp
51%
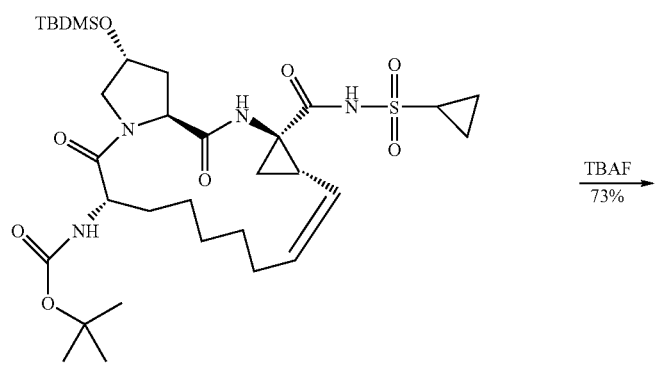
TBAF
73%

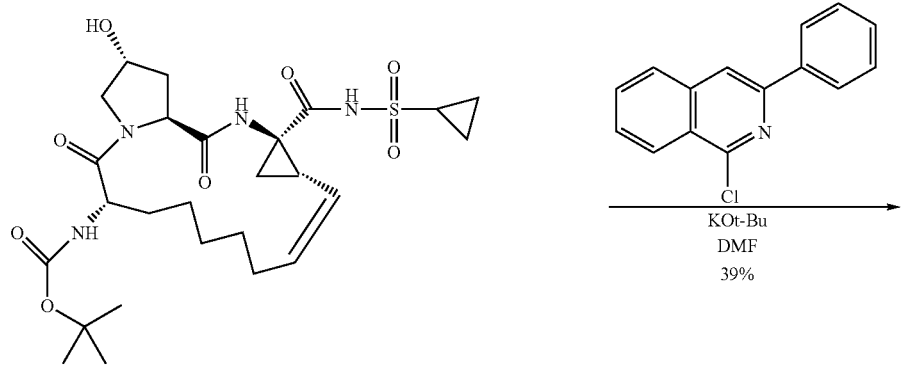

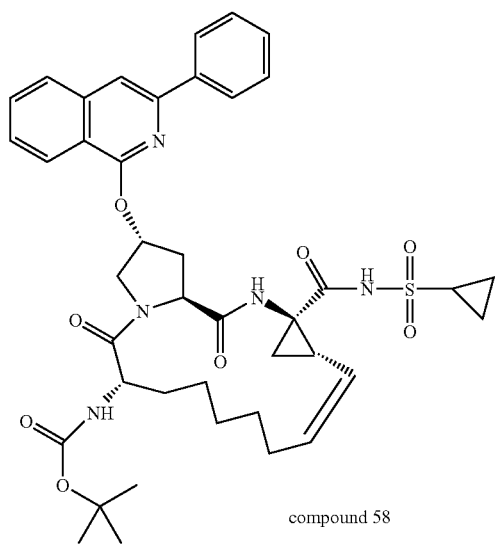

compound 58

Step 49a: Preparation of 1-{[1-(2-tert-Butoxycarbonylamino-non-8-enoyl)-4-(tert-butyl-dimethylsilanyloxy)-pyrrolidine-2-carbonyl]-amino}-2-vinylcyclopropanecarboxylic acid ethyl ester

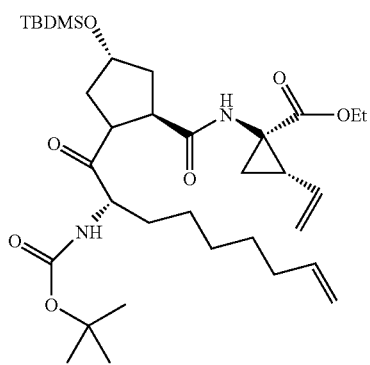

To a mixture of 1-{[1-(2(S)-tert-Butoxycarbonylamino-non-8-enoyl)-4(R)-hydroxy-pyrrolidine-2(S)carbonyl]-(1R)-amino}-2(S)-vinyl-cyclopropanecarboxylic acid ethyl ester (1.5 g, 2.87 mmoL)in 10 mL of DMF was added imidazole (0.25 g, 3.67 mmoL) and tert-butyl-dimethylsilyl chloride (516 mg, 3.44 mmoL). The mixture was stirred at rt for two days. The reaction mixture was then concentrated in vacuo, and the residue was dissolved in ethyl acetate. This solution was washed with water, dried over magnesium sulfate, and concentrated in vacuo to obtain a crude solid. Purification by flash chromatography (eluting with 20% ethyl acetate in hexane) gave 1.43 g (78%) of 1-{[1-(2-tert-butoxycarbonylamino-non-8-enoyl)-4-(tert-butyldimethylsilanyloxy)pyrrolidine-2-carbonyl]-amino}-2-vinylcyclopropanecarboxylic acid ethyl ester as a white solid.

$^1$H NMR (300 MHz, CD$_3$OD) δ 0.10 (s, 6H), 0.89 (s, 9H), 1.22 (m, 3H), 1.31–1.48 (m, 16H), 1.50–1.75 (m, 3H), 2.06 (m, 3H), 2.11–2.33 (m, 2H), 3.70 (m, 2H), 4.03–4.19 (m, 2H), 4.21 (m, 1H), 4.45 (t, J=7.87 Hz, 1H), 4.59 (m, 1H), 4.91 (d, J=9.15 Hz, 1H), 4.98 (d, J=17.20 Hz, 1H), 5.08 (dd, J=10.25, 1.83 Hz, 1H), 5.27 (dd, J=17.38, 1.65 Hz, 1H), 5.65–5.87 (m, 2H). LC-MS (Method A, retention time: 4.00 min), MS m/z 636 (M$^+$+1).

Step 49b: Preparation of 14-tert-butoxycarbonylamino-18-(tert-butyldimethylsilanyloxy)-2,15-dioxo-3,16-diaza-tricyclo[14.3.0.0$^{4,6}$]nonadec-7-ene-4-carboxylic acid ethyl ester

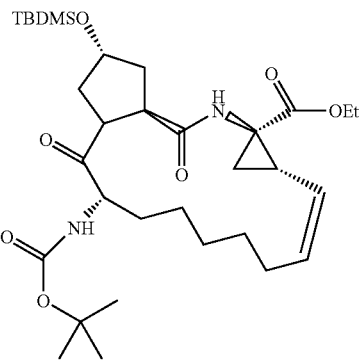

To a solution of 1-{[1-(2-tert-butoxycarbonylamino-non-8-enoyl)-4-(tert-butyl-dimethyl-silanyloxy)-pyrrolidine-2-carbonyl]-amino}-2-vinyl-cyclopropanecarboxylic acid ethyl ester (1.63 g, 2.56 mmoL) in 640 mL of methylene chloride was added 215 mg (0.26 mmoL) of tricyclohexylphosphine[1,3-bis(2,4,6-tri[benzylidene]ruthenium(IV) dichloride. The mixture was heated at reflux for 15 min. The residue was concentrated in vacuo, and then purified by flash chromatography eluting with 30% ethyl acetate/hexane. To further decolorize the sample, the crude product was chromatographed a second time eluting with 50% ether in hexane to give 1.5 g (96%) of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid ethyl ester as a white solid. $^1$H NMR (500 MHz, CD$_3$Cl) δ 0.06 (s, 3H), 0.07 (s, 3H), 0.86 (s, 9H), 1.18–1.24 (m, 6H), 1.34–1.64 (m, 14H), 1.86–1.96 (m, 3H), 2.02–2.09 (m, 1H), 2.11–2.17 (m, 1H), 2.19–2.28 (m, 1H), 2.57–2.63 (m, 1H), 3.50–3.54 (m, 1H), 3.71 (dd, J=10.22, 6.26 Hz, 1H), 4.06–4.17 (m, 2H), 4.52–4.58 (m, 2H), 4.75 (d, J=8.55 Hz, 1H), 5.21 (t, J=9.92 Hz, 1H), 5.35 (d, J=7.63 Hz, 1H), 5.45–5.50 (m, 1H), 6.94 (s, 1H). LC-MS (Method A, retention time: 3.88 min), MS m/z 608 (M$^+$+1).

Step 49c: Preparation of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid

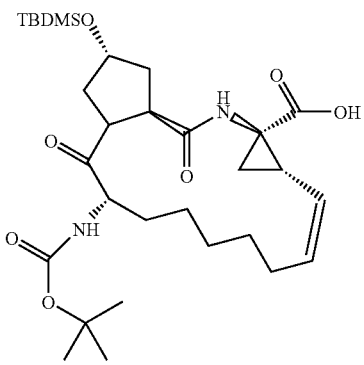

To a solution of 14-tert-butoxycarbonylamino-18-(tert-butyldimethylsilanyloxy)-2,15-dioxo-3,16-diaza-tricyclo [14.3.0.0$^{4,6}$]nonadec-7-ene-4-carboxylic acid ethyl ester (1.5 g, 2.47 mmoL) in a mixed solvent system of THF (4 mL), methanol (1 mL), and water (2 mL), was added powdered lithium hydroxide monohydrate (1.0 g, 50 mmoL). The light yellow slurry was stirred at rt under N$_2$ for 4 h. The mixture was then concentrated in vacuo, and the residue partioned between ether and water. The ether phase was discarded, and the aqueous phase was treated with 1 N HCl until reaching pH 4. This acidic solution was extracted with EtOAc (3×). The combined EtOAc extracts were dried (MgSO$_4$), and concentrated in vacuo to give 1.2 g (84%) of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid as an off-white solid. $^1$H NMR (300 MHz, CD$_3$OD) 0.12 (s, 6H), 0.89 (s, 9H), 1.23–1.64 (m, 17H), 1.70–1.87 (m, 1H), 1.90–2.49 (m, 6H), 3.70–3.80 (m, 1H), 3.83–3.90 (m, 1H), 4.28–4.36 (m, 1H), 4.47–4.55 (m, 1H), 4.65 (s, 1H), 5.30–5.39 (m, 1H), 5.53–5.62 (m, 1H). LC-MS (Method A, retention time: 3.69 min), MS m/z 580 (M$^+$+1).

Step 49d: Preparation of [18-(tert-butyl-dimethyl-silanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester

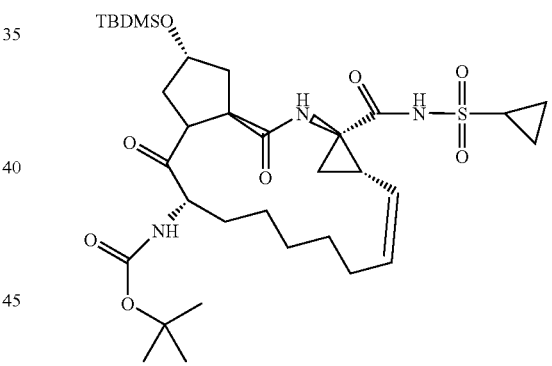

14-tert-Butoxycarbonylamino-18-(tert-butyldimethylsilanyloxy)-2,15-dioxo-3,16-diaza-tricyclo[14.3.0.0$^{4,6}$]nonadec-7-ene-4-carboxylic acid (500 mg, 0.86 mmoL) was dissolved in 25 mL of THF and treated with CDI (180 mg, 1.12 mmoL). (Care was taken to avoid moisture by using oven dried glassware and maintaining a dry N2 atmosphere). After refluxing the reaction mixture for 2 h, it was cooled to rt and treated sequentially with cyclopropylsulfonamide (135 mg, 1.12 mmoL) and DBU (170 mg, 1.12 mmoL). The reaction mixture was stirred for 4 h at rt, and the THF was removed by rotary evaporation. The residue was partitioned between ethyl acetate and pH 4 buffer. The organic phase was dried (MgSO4) and concentrated in vacuo to give the crude product. It was then purified by flash chromatography (eluting with 33% ethyl acetate in hexane) to give 300 mg (51%) of [18-(tert-butyl-dimethyl-silanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester as a white solid. $^1$H NMR (300 MHz, CD$_3$OD) δ 1H 0.07 (s, 3H), 0.08 (s, 3H), 0.85 (s, 9H), 0.87–1.49 (m, 21H), 1.73–1.95 (m, 3H), 2.08–2.16 (m, 1H), 2.25–2.36 (m, 2H), 2.42–2.56 (m, 1H), 2.85–2.93 (m, 1H), 3.65–3.74(dd, J=10.61, 3.66 Hz, 1H), 3.89 (d, J=10.25 Hz, 1H), 4.34 (m, J=9.70, 9.70 Hz, 1H), 4.43 (t, J=7.87 Hz, 1H), 4.57 (s, 1H), 4.94–5.01 (m, 1H), 5.10 (d, J=8.78 Hz, 1H), 5.66–5.75 (m, 1H), 6.55 (s, 1H), 10.13 (s, 1H). LC-MS (Method A, retention time: 3.81 min), MS m/z 683 (M$^+$+1).

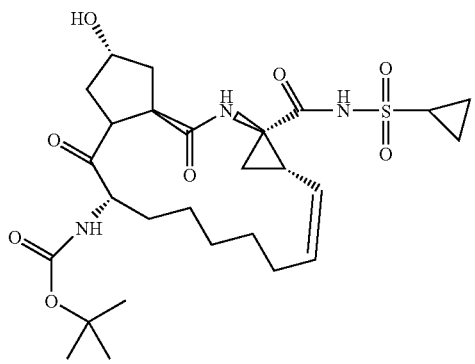

To a mixture of [18-(tert-butyl-dimethylsilanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester (330 mg, 0.48 mmoL) in 25 mL of THF was added tetrabutylammonium fluoride (150 mg, 0.54 mmoL). The reaction mixture was stirred at rt for 18 h, and then the THF was removed by rotary evaporation. The residue was partitioned between ethyl acetate and water. The organic phase was dried (MgSO$_4$) and concentrated in vacuo to give the crude product. It was then purified by triturating with hexane to yield 200 mg (73%) of (4-cyclopropanesulfonylaminocarbonyl-18-hydroxy-2,15-dioxo-3,16-diazatricyclo[14.3.0.0$^{4,6}$]nonadec-7-en-14-yl)-carbamic acid tert-butyl ester as a white solid. $^1$H NMR (500 MHz, CD$_3$Cl) δ 1.87–1.64 (m, 21H), 1.70–1.98 (m, 3H), 2.15–2.56 (m, 5H), 2.85–2.94 (m, 1H), 3.71 (d, J=13.91 Hz, 1H), 4.10–4.26 (m, 2H), 4.51 (t, J=7.87 Hz, 1H), 4.62 (s, 1H), 4.98 (m, 1H), 5.06 (d, J=8.78 Hz, 1H), 5.64–5.71 (m, 1H), 6.72 (s, 1H), 10.24 (s, 1H). LC-MS (Method A, retention time: 2.85 min), MS m/z 569 (M$^+$+1).

Step 49f: Preparation of compound 58: [(Z)-(1S,4R,14S, 18R)-4-cyclopropanesulfonylaminocarbonyl-2,15-dioxo-18-(3-phenyl-isoquinolin-1-yloxy)-3,16-diaza-tricyclo[14.3.0.0$^{4,6}$]nonadec-7-en-14-yl]-carbamic acid tert-butyl ester

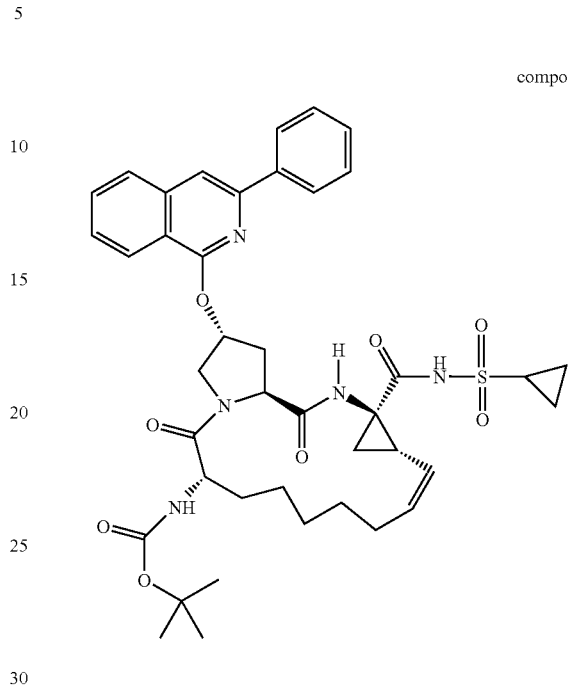

compound 58

To a mixture of (4-cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester (20 mg, 0.035 mmoL) in 1 mL of DMF was added potassium t-butoxide (22 mg, 0.196 mmoL). The mixture was stirred at rt for 5 min, and then 1-chloro-3-phenylisoquinoline (15 mg, 0.062 mmol) was added. The reaction mixture was stirred at rt for 15 h, and then concentrated in vacuo. This crude product was triturated with ether. The residue was dissolved in MeOH, and then purified by preparative HPLC.(YMC XTERRA, S5, 19×100 mm, gradient: 60% B to 100% B, 15 min, hold 2 min, flow rate 25 mL/min) to give 10 mg (39%) of compound 58, [(Z)-(1S,4R,14S,18R)-4-cyclopropane-sulfonylaminocarbonyl-2,15-dioxo-18-(3-phenyl-isoquinolin-1-yloxy)-3,16-diaza-tricyclo[14.3.0.0$^{4,6}$]nonadec-7-en-14-yl]-carbamic acid tert-butyl ester, as a white solid. $^1$H NMR (500 MHz, CD$_3$Cl) δ 0.90–1.64 (m, 21H), 1.76–1.97 (m, 3H), 2.26–2.31 (m, 1H), 2.52–2.63 (br s, 1H), 2.69–2.81 (m, 2H), 2.88–2.93 (m, 1H), 4.11 (d, J=11.60 Hz, 1H), 4.33 (m, 1H), 4.61 (d, J=7.94 Hz, 2H), 4.99 (t, J=9.31 Hz, 1H), 5.05 (d, J=7.93 Hz, 1H), 5.69–5.74 (m, 1H), 6.08 (s, 1H), 6.60 (s, 1H), 7.38–7.47(m, 2H), 7.50 (t, J=7.63 Hz, 2H), 7.63 (t, J=7.32 Hz, 1H), 7.71 (s, 1H), 7.77 (d, J=8.24 Hz, 1H), 8.10 (d, J=7.32 Hz, 2H), 8.18 (d, J=7.93 Hz, 1H), 10.27 (s, 1H). LC-MS (Method A, retention time: 3.72 min), MS m/z 772 (M$^+$+1).

The compounds of tables 2 and 3 were prepared employing the procedures ed in the above examples:

TABLE 2

| Cmpd | R₁ | R₃ | R₇ | R₈ | R₉ | Q | Mass Spec. + (M + H) |
|---|---|---|---|---|---|---|---|
| 1 | H | H | NHBoc | H | H | (CH₂)₅CH=CH– | 593 |
| 17A | H | OMe | NHBoc | H | H | (CH₂)₅CH=CH– | 623 |
| 18A | H | OMe | NHBoc | H | H | S(CH₂)₃CH=CH– | 641 |
| 27 | H | OMe | NHBoc | H | H | (CH₂)₂OCH₂CH=CH– | 625 |
| 61 | H | OMe | NHBoc | Me | H | O(CH₂)₃CH=CH– | 639 |
| 79 | H | OMe | NHBoc | Me | Me | S(CH₂)₃CH=CH– | 669 |
| 84 | H | OMe | NHBoc | H | H | O(CH₂)₄CH=CH– | 625 |
| 140 | H | OMe | NHBoc | H | H | CH₂OCH₂CH=CH– | 611 |
| 143 | H | OMe | NHBoc | H | H | (CH₂)₄CH=CH– branched | 609 |

TABLE 2-continued

| Cmpd | R₁ | R₃ | R₇ | R₈ | R₉ | Q | Mass Spec. + (M + H) |
|---|---|---|---|---|---|---|---|
| 144 | H | H | NHBoc | H | H | 2-NO₂-C₆H₄-SO₂-N(−)-CH₂CH₂CH₂CH=CH− | 779 |

TABLE 3

| Cmpd | R₂₃ | R₁ | R₃, R₄ | R₈ | R₉ | R₇ | Q | Mass Spec. + (M + H) |
|---|---|---|---|---|---|---|---|---|
| 2 | t-Bu (Me) | H | H, H | H | H | NHBoc | alkenyl chain | 670 |
| 3 | CH(Me)₂ | H | H, H | H | H | NHBoc | alkenyl chain | 698 |
| 4 | cyclopropyl | H | H, H | H | H | NHBoc | alkenyl chain | 696 |
| 5 | 1-benzyl-cyclopropyl | H | H, H | H | H | NHBoc | alkenyl chain | 786 |
| 6 | 1-ethyl-cyclopropyl | H | H, H | H | H | NHBoc | alkenyl chain | 738 |

TABLE 3-continued

| Cmpd | R23 | R1 | R3, R4 | R8 | R9 | R7 | Q | Mass Spec. + (M + H) |
|---|---|---|---|---|---|---|---|---|
| 7 | ethyl-cyclopropyl | H | H, H | H | H | NHBoc | octenyl | 740 |
| 8 | methyl-cyclopropyl | H | H, H | H | H | NHBoc | octenyl | 710 |
| 9 | cyclobutyl | H | H, H | H | H | NHBoc | octenyl | 710 |
| 10 | cyclopropyl | Cl | H, H | H | H | NHBoc | octenyl | 698 |
| 11 | cyclopropyl | H | H, H | H | H | NH3+Cl− | octenyl | 596 |
| 12 | cyclopropyl | H | H, H | H | H | NHC(O)OMe | octenyl | 654 |
| 13 | cyclopropyl | H | H, H | H | H | NHC(O)O-neopentyl | octenyl | 710 |
| 14 | cyclopropyl | H | H, H | H | H | NHC(O)O-tetrahydropyranyl | octenyl | 724 |
| 15 | cyclopropyl | H | H, H | H | H | NHC(O)O-tetrahydrofuranyl | octenyl | 710 |

TABLE 3-continued

| Cmpd | R23 | R1 | R3, R4 | R8 | R9 | R7 | Q | Mass Spec. + (M + H) |
|---|---|---|---|---|---|---|---|---|
| 16 | cyclopropyl | H | H, H | H | H | NHC(O)O-iPr | alkenyl chain | 682 |
| 17B | cyclopropyl | H | H, H | H | H | NHC(O)O-tBu | S-alkenyl | 726 |
| 18B | cyclopropyl | H | H, H | H | H | NHC(O)O-tBu | S-alkenyl | 744 |
| 19 | cyclopropyl | H | 6-OMe, H | H | H | NHC(O)O-tBu | SO2-alkenyl | 776 |
| 20 | cyclopropyl | H | H, H | H | H | NHC(O)O-cyclopentyl | alkenyl chain | 708 |
| 21 | cyclopropyl | H | H, H | H | H | NH-(3-methoxy-squarate) | alkenyl chain | 706 |
| 22 | cyclopropyl | H | H, H | H | H | NHC(O)CH2-cyclopropyl | alkenyl chain | 678 |
| 23 | cyclopropyl | H | H, H | H | H | NHC(O)NH-propyl | alkenyl chain | 681 |

TABLE 3-continued

| Cmpd | R₂₃ | R₁ | R₃, R₄ | R₈ | R₉ | R₇ | Q | Mass Spec. + (M + H) |
|---|---|---|---|---|---|---|---|---|
| 24 | cyclopropyl | H | H, H | H | H | NHC(O)CH₂OMe | (chain) | 668 |
| 25 | cyclopropyl | H | H, H | H | H | NHS(O)₂Me | (chain) | 674 |
| 26 | cyclopropyl | H | H, H | H | H | NHAc | (chain) | 638 |
| 28 | cyclopropyl | H | 6-OMe, H | H | H | NHBoc | (chain-O-chain) | 728 |
| 29 | Me-cyclopropyl | H | 6-OMe, H | H | H | NHBoc | (chain-O-chain) | 742 |
| 30 | Et-cyclopropyl | H | 6-OMe, H | H | H | NHBoc | (chain-O-chain) | 756 |
| 31 | cyclopropyl | H | 6-OMe, H | H | H | NHC(O)OiPr | (chain-O-chain) | 714 |
| 32 | cyclopropyl | H | 6-OMe, H | H | H | NHC(O)OCH₂C(CH₃)₃ | (chain-O-chain) | 742 |
| 33 | cyclopropyl | H | 6-OMe, H | H | H | NHC(O)NH-cyclopentyl | (chain-O-chain) | 739 |

TABLE 3-continued

| Cmpd | R23 | R1 | R3, R4 | R8 | R9 | R7 | Q | Mass Spec. + (M + H) |
|---|---|---|---|---|---|---|---|---|
| 34 | cyclopropyl-Me | H | 6-OMe, H | H | H | NHC(O)NH-tBu | CH2CH2-O-CH2-CH=CH- | 727 |
| 35 | cyclopropyl-Me | H | 6-OMe, H | H | H | NHC(O)O-iPr | CH2CH2-O-CH2-CH=CH- | 728 |
| 36 | cyclopropyl-Me | H | 6-OMe, H | H | H | NHC(O)NH-cyclopentyl | CH2CH2-O-CH2-CH=CH- | 753 |
| 37 | cyclopropyl-Et | H | 6-OMe, H | H | H | NHC(O)O-iPr | CH2CH2-O-CH2-CH=CH- | 742 |
| 38 | cyclopropyl-Et | H | 6-OMe, H | H | H | NHC(O)NH-cyclopentyl | CH2CH2-O-CH2-CH=CH- | 767 |
| 39 | cyclopropyl-Me | H | 6-OMe, H | H | H | NHC(O)O-C(CH3)2CF3 | CH2CH2-O-CH2-CH=CH- | 782 |
| 40 | cyclopropyl-Me | H | 6-OMe, H | H | H | NHC(O)O-C(CH3)2CH2Cl | CH2CH2-O-CH2-CH=CH- | 762, 764 |
| 41 | cyclopropyl-Me | H | 6-OMe, H | H | H | NHC(O)O-iPr | CH2CH2-S-CH2-CH=CH- | 744 |
| 42 | cyclopropyl-Me | H | 6-OMe, H | H | H | NHC(O)O-neopentyl | CH2CH2-S-CH2-CH=CH- | 772 |

TABLE 3-continued

| Cmpd | R23 | R1 | R3, R4 | R8 | R9 | R7 | Q | Mass Spec. + (M + H) |
|---|---|---|---|---|---|---|---|---|
| 43 | 1-methylcyclopropyl | H | 6-OMe, H | H | H | cyclopentylurea | S-butenyl | 769 |
| 44 | 1-ethylcyclopropyl | Et | 6-OMe, H | H | H | isopropyl carbamate | S-butenyl | 758 |
| 45 | 1-ethylcyclopropyl | Et | 6-OMe, H | H | H | neopentyl carbamate | S-butenyl | 786 |
| 46 | 1-ethylcyclopropyl | Et | 6-OMe, H | H | H | cyclopentylurea | S-butenyl | 783 |
| 47 | 1-ethylcyclopropyl | Et | 6-OMe, H | H | H | tBu carbamate | S(O)-butenyl | 788 |
| 48 | 1-ethylcyclopropyl | Et | 6-OMe, H | H | H | tBu carbamate | SO2-butenyl | 804 |
| 49 | 1-methylcyclopropyl | H | 6-OMe, H | H | H | tBu carbamate | SO2-butenyl | 790 |
| 50 | cyclopropyl | H | H, H | H | H | 1-methylcyclopentyl carbamate | hexenyl | 722 |

TABLE 3-continued

| Cmpd | R₂₃ | R₁ | R₃, R₄ | R₈ | R₉ | R₇ | Q | Mass Spec. + (M + H) |
|---|---|---|---|---|---|---|---|---|
| 51 | cyclopropyl | H | H, H | H | H | NHC(O)O-C(CH₃)₂CF₃ | octenyl | 750 |
| 52 | cyclopropyl | H | H, H | H | H | NHC(O)O-C(CH₃)₂CH₂Cl | octenyl | 730 |
| 53 | cyclopropyl | H | 6-OMe, H | H | H | NHC(O)O-tBu | octenyl | 740 |
| 54 | Et-cyclopropyl | H | 6-OMe, H | H | H | NHC(O)O-tBu | octenyl | 754 |
| 55 | cyclopropyl | H | 6-OMe, H | H | H | NHC(O)O-C(CH₃)₂CHF₂ | octenyl | 732 |
| 56 | cyclopropyl | H | H, H | H | H | NHC(O)O-(1-methylcyclobutyl) | octenyl | 708 |
| 57 | cyclopropyl | Cl | H, H | H | H | NHC(O)O-tBu | octenyl | 730 |
| 58 | cyclopropyl | Ph | H, H | H | H | NHC(O)O-tBu | octenyl | 722 |
| 59 | cyclopropyl | H | H, H | H | H | NHC(O)O-(1-methylcyclopropyl) | octenyl | 694 |

TABLE 3-continued

| Cmpd | R23 | R1 | R3, R4 | R8 | R9 | R7 | Q | Mass Spec. + (M + H) |
|------|-----|-----|--------|-----|-----|-----|---|----------------------|
| 60 | cyclopropyl | H | 6-OMe, H | H | H | NHC(O)-pyrrolidine | O-butenyl | 723 |
| 62 | cyclopropyl | H | 6-OMe, H | Me | H | NHBoc | O-butenyl | 742 |
| 63 | cyclopropyl | H | 6-OMe, H | Me | H | NHC(O)O-neopentyl | O-butenyl | 756 |
| 64 | cyclopropyl | H | 6-OMe, H | Me | H | NHC(O)O-iPr | O-butenyl | 728 |
| 65 | cyclopropyl | H | 6-OMe, H | Me | H | NHC(O)NH-cyclopentyl | O-butenyl | 753 |
| 66 | 1-Me-cyclopropyl | H | 6-OMe, H | Me | H | NHBoc | O-butenyl | 756 |
| 67 | 1-Me-cyclopropyl | H | 6-OMe, H | Me | H | NHC(O)O-neopentyl | O-butenyl | 770 |
| 68 | 1-Me-cyclopropyl | H | 6-OMe, H | Me | H | NHC(O)O-iPr | O-butenyl | 742 |
| 69 | 1-Me-cyclopropyl | H | 6-OMe, H | Me | H | NHC(O)NH-cyclopentyl | O-butenyl | 767 |

TABLE 3-continued

| Cmpd | R₂₃ | R₁ | R₃, R₄ | R₈ | R₉ | R₇ | Q | Mass Spec. + (M + H) |
|---|---|---|---|---|---|---|---|---|
| 70 | cyclopropyl-CH₂-Me | H | 6-OMe, H | Me | H | NHBoc | O-CH₂CH₂CH=CH- | 770 |
| 71 | cyclopropyl-CH₂-Me | H | 6-OMe, H | Me | H | NH-C(O)-O-neopentyl | O-CH₂CH₂CH=CH- | 784 |
| 72 | cyclopropyl-CH₂-Me | H | 6-OMe, H | Me | H | NH-C(O)-O-iPr | O-CH₂CH₂CH=CH- | 756 |
| 73 | cyclopropyl-CH₂-Me | H | 6-OMe, H | Me | H | NH-C(O)-NH-cyclopentyl | O-CH₂CH₂CH=CH- | 781 |
| 74 | cyclopropyl | H | 6-OMe, H | H | H | NH-C(O)-O-iPr | S-CH₂CH₂CH=CH- | 730 |
| 75 | cyclopropyl | H | 6-OMe, H | H | H | NH-C(O)-O-neopentyl | S-CH₂CH₂CH=CH- | 758 |
| 76 | cyclopropyl | H | 6-OMe, 7-Cl | H | H | NHBoc | S-CH₂CH₂CH=CH- | 778, 780 |
| 77 | cyclopropyl | H | 5-OMe, H | H | H | NHBoc | S-CH₂CH₂CH=CH- | 774 |
| 78 | cyclopropyl | H | 5-Cl, H | H | H | NHBoc | S-CH₂CH₂CH=CH- | 748, 750 |

TABLE 3-continued

| Cmpd | R₂₃ | R₁ | R₃, R₄ | R₈ | R₉ | R₇ | Q | Mass Spec. + (M + H) |
|---|---|---|---|---|---|---|---|---|
| 80 | cyclopropyl | H | 6-OMe, H | Me | Me | NHBoc (carbamate OtBu) | S-butenyl | 772 |
| 81 | cyclopropyl | H | 6-OMe, H | Me | Me | NHC(O)NH-tBu (urea) | S-butenyl | 771 |
| 82 | cyclopropyl | H | 6-OMe, H | Me | Me | NHC(O)NH-cyclopentyl | S-butenyl | 783 |
| 83 | cyclopropyl | H | 6-OMe, H | Me | Me | NH₃⁺Cl⁻ | S-butenyl | 672 |
| 85 | cyclopropyl | H | 6-OMe, H | H | H | NHBoc | O-butenyl | 728 |
| 86 | cyclopropyl | H | 6-OMe, H | H | H | NHC(O)NH-tBu | O-butenyl | 727 |
| 87 | cyclopropyl | H | 6-OMe, H | H | H | NHC(O)NH-cyclopentyl | O-butenyl | 739 |
| 88 | cyclopropyl | H | 6-OMe, H | H | H | NHC(O)O-neopentyl | O-butenyl | 742 |
| 89 | cyclopropyl | H | 6-OMe, H | H | H | NHC(O)O-iPr | O-butenyl | 714 |

TABLE 3-continued

| Cmpd | R23 | R1 | R3, R4 | R8 | R9 | R7 | Q | Mass Spec. + (M + H) |
|---|---|---|---|---|---|---|---|---|
| 90 | cyclopropyl | H | 6-OMe, H | H | H | NHC(O)O-cyclopentyl | O-butenyl | 740 |
| 91 | cyclopropyl | Ph | 6-OMe, H | H | H | NHC(O)O-tBu | O-butenyl | 804 |
| 92 | cyclopropyl | Ph | 6-OMe, H | H | H | NHC(O)NH-tBu | O-butenyl | 803 |
| 93 | cyclopropyl | Ph | 6-OMe, H | H | H | NHC(O)-pyrrolidinyl | O-butenyl | 801 |
| 94 | cyclopropyl | Ph | 6-OMe, H | H | H | NHC(O)O-cyclopentyl | O-butenyl | 816 |
| 95 | cyclopropyl | Ph | 6-OMe, H | H | H | NHC(O)O-neopentyl | O-butenyl | 818 |
| 96 | cyclopropyl | Ph | 6-OMe, H | H | H | NHC(O)O-iPr | O-butenyl | 790 |
| 97 | cyclopropyl | Ph | 6-OMe, H | H | H | NHC(O)O-tBu | O-propenyl | 804 |
| 98 | cyclopropyl | Ph | 6-OMe, H | H | H | NHC(O)O-iPr | O-propenyl | 790 |

TABLE 3-continued

| Cmpd | R23 | R1 | R3, R4 | R8 | R9 | R7 | Q | Mass Spec. + (M + H) |
|---|---|---|---|---|---|---|---|---|
| 99 | cyclopropyl | Ph | 6-OMe, H | H | H | cyclopentyl carbamate | CH2CH2-O-CH2-CH=CH- | 816 |
| 100 | cyclopropyl | Ph | 6-OMe, H | H | H | pyrrolidinyl urea | CH2CH2-O-CH2-CH=CH- | 801 |
| 101 | cyclopropyl | cyclopropyl | 6-OMe, H | H | H | cyclopentyl urea | CH2CH2-O-CH2-CH=CH- | 815 |
| 102 | cyclopropyl | Ph | 6-OMe, H | H | H | t-butyl urea | CH2CH2-O-CH2-CH=CH- | 803 |
| 103 | cyclopropyl | Ph | 6-OMe, H | H | H | neopentyl carbamate | CH2CH2-O-CH2-CH=CH- | 818 |
| 104 | cyclopropyl | Ph | 6-OMe, H | H | H | cyclopropyl thiourea | CH2CH2-O-CH2-CH=CH- | 803 |
| 105 | cyclopropyl | Ph | 6-OMe, H | H | H | 4-cyanophenyl urea | CH2CH2-O-CH2-CH=CH- | 848 |

TABLE 3-continued

| Cmpd | R23 | R1 | R3, R4 | R8 | R9 | R7 | Q | Mass Spec. + (M + H) |
|---|---|---|---|---|---|---|---|---|
| 106 | cyclopropyl | Ph | 6-OMe, H | H | H | NH-C(O)-imidazolidinone | OCH2CH=CH | 816 |
| 107 | cyclopropyl | 4-NMe2-Ph | 6-OMe, H | H | H | NH-C(O)-O-tBu | O-(CH2)3-CH= | 847 |
| 108 | cyclopropyl | 4-NMe2-Ph | 6-OMe, H | H | H | NH-C(O)-NH-tBu | O-(CH2)3-CH= | 846 |
| 109 | cyclopropyl | 4-NMe2-Ph | 6-OMe, H | H | H | NH-C(O)-O-iPr | O-(CH2)3-CH= | 833 |
| 110 | cyclopropyl | 4-NMe2-Ph | 6-OMe, H | H | H | NH-C(O)-O-cyclopentyl | O-(CH2)3-CH= | 859 |

TABLE 3-continued

| Cmpd | R23 | R1 | R3, R4 | R8 | R9 | R7 | Q | Mass Spec. + (M + H) |
|------|-----|-----|--------|-----|-----|-----|---|------------------------|
| 111 | cyclopropyl | 4-NMe2-phenyl | 6-OMe, H | H | H | NHC(O)-pyrrolidinyl | OCH2CH2CH=CH- | 844 |
| 112 | cyclopropyl | 4-NMe2-phenyl | 6-OMe, H | H | H | NHBoc | OCH2CH2CH=CH- | 847 |
| 113 | cyclopropyl | 4-NHM-phenyl | 6-OMe, H | H | H | NHBoc | OCH2CH2CH=CH- | 833 |
| 114 | cyclopropyl | 4-N(Me)CHO-phenyl | 6-OMe, H | H | H | NHBoc | OCH2CH2CH=CH- | 861 |
| 115 | 1-methylcyclopropyl | H | 6-OMe, H | H | H | NHBoc | SCH2CH2CH=CH- | 758 |

TABLE 3-continued

| Cmpd | R₂₃ | R₁ | R₃, R₄ | R₈ | R₉ | R₇ | Q | Mass Spec. + (M + H) |
|---|---|---|---|---|---|---|---|---|
| 116 | cyclopropyl-CH(Me) | H | H, H | H | H | NHC(O)O-tBu | S-CH₂CH₂CH=CH- | 724 |
| 117 | cyclopropyl | H | 6-OMe, H | H | H | NH₃⁺Cl⁻ | S-CH₂CH₂CH=CH- | 644 |
| 118 | cyclopropyl | H | H, H | H | H | NHC(O)SEt | CH₂CH₂CH₂CH=CH- | 684 |
| 119 | cyclopropyl | H | H, H | H | H | NHCHO | CH₂CH₂CH₂CH=CH- | 624 |
| 120 | cyclopropyl | H | H, H | H | H | NHC(O)CH(Me)₂ | CH₂CH₂CH₂CH=CH- | 664 |
| 121 | cyclopropyl-CH(Me) | H | 6-OMe, H | H | H | NHC(O)O-tBu | CH₂CH₂CH₂CH=CH- | 772 |
| 122 | cyclopropyl | H | H, H | H | H | NHC(O)OCH₂-(1-Me-cyclopropyl) | CH₂CH₂CH₂CH=CH- | 708 |
| 123 | cyclopropyl | H | H, H | H | H | NHC(O)OC(Me)₂C(O)- | CH₂CH₂CH₂CH=CH- | 724 |
| 124 | cyclopropyl | H | H, H | H | H | NHC(O)OC(Me)₂CCl₃ | CH₂CH₂CH₂CH=CH- | 798, 800 |

TABLE 3-continued

| Cmpd | R₂₃ | R₁ | R₃, R₄ | R₈ | R₉ | R₇ | Q | Mass Spec. + (M + H) |
|---|---|---|---|---|---|---|---|---|
| 125 | cyclopropyl | H | H, H | H | H | -NHC(O)O-C(Me)(Et) | alkenyl chain | 710 |
| 126 | cyclopropyl | H | H, H | H | H | -NHC(O)NH-tBu | alkenyl chain | 695 |
| 127 | cyclopropyl | H | H, H | H | H | -NHC(O)NH-cyclopentyl | alkenyl chain | 707 |
| 128 | cyclopropyl | H | H, H | H | H | -NHC(O)NH-iPr | alkenyl chain | 681 |
| 129 | cyclopropyl | H | H, H | H | H | -NHC(O)NH-C(Me)₂-tBu | alkenyl chain | 751 |
| 130 | cyclopropyl | H | 5-Cl, H | H | H | -NHC(O)O-tBu | alkenyl chain | 730 |
| 131 | cyclopropyl | H | 6-OMe, 7-Cl | H | H | -NHC(O)O-iPr | alkenyl chain | 760 |
| 132 | cyclopropyl | H | 5-F, 6-OMe | H | H | -NHC(O)O-tBu | alkenyl chain | 744 |
| 133 | cyclopropyl | H | 5-OMe, H | H | H | -NHC(O)O-tBu | alkenyl chain | 726 |

TABLE 3-continued

| Cmpd | R23 | R1 | R3, R4 | R8 | R9 | R7 | Q | Mass Spec. + (M + H) |
|---|---|---|---|---|---|---|---|---|
| 134 | cyclopropyl | H | 5,6-dimethoxy | H | H | NHC(O)O-tBu | alkenyl chain | 756 |
| 135 | cyclopropyl | H | 6-OMe, H | H | H | NHC(O)NH-tBu | alkenyl chain | 725 |
| 136 | cyclopropyl | H | 6-OMe, H | H | H | NHC(O)NH-cyclopentyl | alkenyl chain | 737 |
| 137 | cyclopropyl | Ph | 6-OMe, H | H | H | NHC(O)O-tBu | alkenyl chain | 802 |
| 138 | cyclopropyl | Ph | H, H | H | H | NHC(O)O-tBu | alkenyl chain | 772 |
| 139 | cyclopropyl | H | H, H | H | H | NHC(O)S-tBu | alkenyl chain | 742 |
| 141 | cyclopropyl | H | 6-OMe, H | H | H | NHC(O)O-tBu | CH2-O-CH2-CH=CH- | 714 |

TABLE 3-continued

| Cmpd | R₂₃ | R₁ | R₃, R₄ | R₈ | R₉ | R₇ | Q | Mass Spec. + (M + H) |
|------|-----|----|--------|----|----|----|----|----------------------|
| 142 | cyclopropyl | 4-(NMe₂)phenyl | 6-OMe, H | H | H | NHBoc | CH₂CH₂CH=CH- (alkenyl) | 845 |
| 145 | cyclopropyl | H | H, H | H | H | NHBoc | N(2-nitrobenzenesulfonyl)-alkenyl | 882 |
| 146 | cyclopropyl | H | H, H | H | H | NHBoc | N(acetyl)-alkenyl | 739 |
| 147 | cyclopropyl | H | H, H | H | H | NHBoc | N(Me)-alkenyl | 711 |
| 148 | cyclopropyl | H | H, H | H | H | NHBoc | N(CO₂Me)-alkenyl | 755 |

TABLE 3-continued

| Cmpd | R23 | R1 | R3, R4 | R8 | R9 | R7 | Q | Mass Spec. + (M + H) |
|---|---|---|---|---|---|---|---|---|
| 149 | cyclopropyl | H | H, H | H | H | NHBoc | N(CH2CH=CHCH2CH3)-C(O)O-CH2C(CH3)3 | 811 |
| 150 | cyclopropyl | H | H, H | H | H | NHBoc | N(CH2CH=CHCH2CH3)-C(O)NH-tBu | 796 |
| 151 | cyclopropyl | H | H, H | H | H | NHBoc | NH-CH2CH2CH2CH=CHCH3 | 697 |
| 152 | cyclopropyl | H | H, H | H | H | NHBoc | N(CH2CH2CH2CH=CHCH3)-C(O)-cyclopropyl | 765 |
| 153 | cyclopropyl | H | H, H | H | H | NHBoc | N(CH2CH2CH2CH=CHCH3)-S(O)2-CH3 | 775 |

The compounds of tables 4 and 5 could be prepared employing the procedures described in the above examples:

TABLE 4

| Cmpd | R23 | R1 | R3, R4 | R8 | R9 | R7 | Q |
|---|---|---|---|---|---|---|---|
| 201 | cyclopropyl | pyrrolidinyl | 6-OMe, H | H | H | NHBoc | hexenyl |
| 202 | 1-Me-cyclopropyl | morpholinyl | 6-OMe, H | H | H | NHBoc | hexenyl |
| 203 | cyclopropyl | 4-(morpholin-4-yl)phenyl | 6-OMe, H | H | H | NHBoc | hexenyl |
| 204 | cyclopropyl | 4-(OCF3)phenyl | 6-OMe, H | H | H | NHBoc | hexenyl |
| 205 | 1-Et-cyclopropyl | H | H, H | H | H | NHBoc | O-butenyl |
| 206 | cyclopropyl | H | H, H | H | Me | NHBoc | O-butenyl |
| 207 | cyclopropyl | H | 6-OMe, H | H | Me | NHBoc | O-butenyl |

TABLE 4-continued

TABLE 4-continued

| Cmpd | R23 | R1 | R3, R4 | R8 | R9 | R7 | Q |
|---|---|---|---|---|---|---|---|
| 215 | cyclopropyl | morpholinyl (N-linked) | 6-OMe, H | H | H | NHC(O)O-iPr | CH2-O-CH2CH=CH- |
| 216 | cyclopropyl | 4-(morpholin-4-yl)phenyl | 6-OMe, H | H | H | NHC(O)O-tBu | CH2-O-CH2CH=CH- |
| 217 | cyclopropyl | 4-(OCF3)phenyl | 6-OMe, H | H | H | NHC(O)O-tBu | CH2-O-CH2CH=CH- |
| 218 | cyclopropyl | H | H, H | Me | H | NHC(O)-pyrrolidin-1-yl | CH2CH2-O-CH2CH=CH- |
| 219 | cyclopropyl | pyrrolidin-1-yl | 6-OMe, H | H | H | NHC(O)O-tBu | CH2CH2-O-CH2CH=CH- |
| 220 | cyclopropyl | morpholinyl (N-linked) | 6-OMe, H | H | H | NHC(O)O-tBu | CH2CH2-O-CH2CH=CH- |

TABLE 4-continued

| Cmpd | R23 | R1 | R3, R4 | R8 | R9 | R7 | Q |
|---|---|---|---|---|---|---|---|
| 221 | cyclopropyl | 4-(morpholin-4-yl)phenyl | 6-OMe, H | H | H | NHBoc | -CH2CH2-O-CH2-CH= |
| 222 | cyclopropyl | 4-(OCF3)phenyl | 6-OMe, H | H | H | NHBoc | -CH2CH2-O-CH2-CH= |
| 223 | 1-methylcyclopropyl | pyrrolidin-1-yl | 6-OMe, H | H | H | NHBoc | -N(Me)-CH2CH2CH2-CH= |
| 224 | cyclopropyl | morpholin-4-yl | 6-OMe, H | H | H | NHBoc | -N(Me)-CH2CH2CH2-CH= |
| 225 | cyclopropyl | 4-(morpholin-4-yl)phenyl | 6-OMe, H | H | H | NH-C(O)O-cyclopentyl | -N(Me)-CH2CH2CH2-CH= |

TABLE 4-continued

| Cmpd | R23 | R1 | R3, R4 | R8 | R9 | R7 | Q |
|---|---|---|---|---|---|---|---|
| 226 | cyclopropyl | 4-OCF3-phenyl | 6-OMe, H | H | H | NHBoc | N(Me)-CH2CH2CH=CH- |
| 227 | 1-ethylcyclopropyl | 4-morpholinophenyl | 6-OMe, H | H | H | NHBoc | NH-CH2CH2CH=CH- |
| 228 | cyclopropyl | 4-OCF3-phenyl | 6-OMe, H | H | H | NHBoc | NH-CH2CH2CH=CH- |
| 229 | cyclopropyl | H | H, H | H | H | NHBoc | N(Me)-CH2CH2CH=CH- |
| 230 | cyclopropyl | H | 6-OMe, H | H | H | NHBoc | N(Me)-CH2CH2CH=CH- |
| 231 | cyclopropyl | 1-pyrrolidinyl | 6-OMe, H | H | H | NH-C(O)-pyrrolidinyl | N(Me)-CH2CH2CH=CH- |

TABLE 4-continued

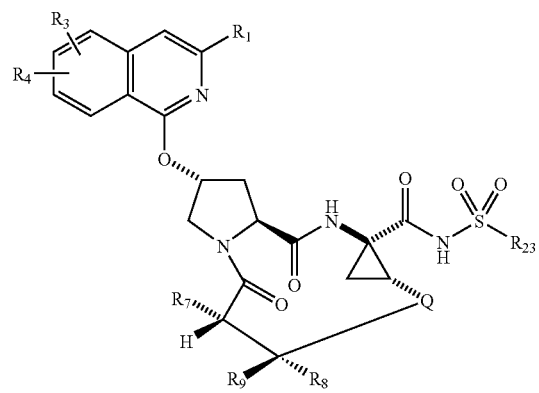

| Cmpd | R23 | R1 | R3, R4 | R8 | R9 | R7 | Q |
|---|---|---|---|---|---|---|---|
| 232 | cyclopropyl | morpholino-N | 6-OMe, H | H | H | NHBoc | CH2-N(Me)-CH2CH2CH=CH- |
| 233 | cyclopropyl | 4-(morpholino)phenyl | 6-OMe, H | H | H | NH-C(O)O-cyclopentyl | CH2-N(Me)-CH2CH2CH=CH- |
| 234 | cyclopropyl | 4-(OCF3)phenyl | 6-OMe, H | H | H | NHBoc | CH2-N(Me)-CH2CH2CH=CH- |
| 235 | cyclopropyl | H | H, H | H | H | NHBoc | S-CH2CH2CH2CH=CH- |
| 236 | cyclobutyl | pyrrolidino-N | 6-OMe, H | H | H | NHBoc | S-CH2CH2CH2CH=CH- |
| 237 | cyclopropyl | morpholino-N | 6-OMe, H | H | H | NHBoc | S-CH2CH2CH2CH=CH- |

TABLE 4-continued

| Cmpd | R23 | R1 | R3, R4 | R8 | R9 | R7 | Q |
|---|---|---|---|---|---|---|---|
| 238 | cyclopropyl | 4-(morpholin-4-yl)phenyl | 6-OMe, H | H | H | NHC(O)O-tBu | S-CH2CH2CH=CH- |
| 239 | cyclopropyl | 4-(OCF3)phenyl | 6-OMe, H | H | H | NHC(O)O-tBu | S-CH2CH2CH=CH- |
| 240 | cyclopropyl | H | 6-OMe, H | H | H | NHC(O)O-tBu | CH2-S-CH2CH2CH=CH- |
| 241 | cyclopropyl | pyrrolidin-1-yl | 6-OMe, H | H | H | NHC(O)O-tBu | CH2-S-CH2CH2CH=CH- |
| 242 | 1-Me-cyclopropyl | morpholin-4-yl | 6-OMe, H | H | H | NHC(O)O-tBu | CH2-S-CH2CH2CH=CH- |

TABLE 4-continued

| Cmpd | R23 | R1 | R3, R4 | R8 | R9 | R7 | Q |
|---|---|---|---|---|---|---|---|
| 243 | cyclopropyl | 4-morpholinophenyl | 6-OMe, H | H | H | NHC(O)O-cyclopentyl | CH2-S-CH2CH2-CH=CH- |
| 244 | cyclopropyl | 4-(OCF3)phenyl | 6-OMe, H | H | H | NHC(O)O-tBu | CH2-S-CH2CH2-CH=CH- |
| 245 | cyclopropyl | pyrrolidin-1-yl | 6-OMe, H | H | H | NHC(O)O-tBu | (CH2)4-CH=CH- |
| 246 | cyclopropyl | morpholin-4-yl | 6-OMe, H | H | H | NHC(O)O-tBu | (CH2)6 |
| 247 | cyclopropyl | 4-morpholinophenyl | 6-OMe, H | H | H | NHC(O)O-tBu | (CH2)6 |

TABLE 4-continued

| Cmpd | R23 | R1 | R3, R4 | R8 | R9 | R7 | Q |
|---|---|---|---|---|---|---|---|
| 248 | cyclopropyl | 4-(OCF3)phenyl | 6-OMe, H | H | H | NH-C(O)-pyrrolidine | -(CH2)6- |
| 249 | cyclopropyl | H | H, H | H | H | NH-C(O)O-tBu | -O-CH2CH2CH=CHCH2- |
| 250 | 1-Et-cyclopropyl | H | H, H | H | Me | NH-C(O)O-tBu | -O-(CH2)5- |
| 251 | cyclopropyl | H | 6-OMe, H | H | Me | NH-C(O)O-tBu | -O-(CH2)5- |
| 252 | cyclopropyl | pyrrolidin-1-yl | 6-OMe, H | H | Me | NH-C(O)O-cyclopentyl | -O-CH2CH2CH=CHCH2- |
| 253 | 1-Me-cyclopropyl | morpholin-4-yl | 6-OMe, H | H | Me | NH-C(O)O-tBu | -O-CH2CH2CH=CHCH2- |
| 254 | cyclopropyl | 4-(morpholin-4-yl)phenyl | 6-OMe, H | H | Me | NH-C(O)O-tBu | -O-(CH2)4- |

TABLE 4-continued
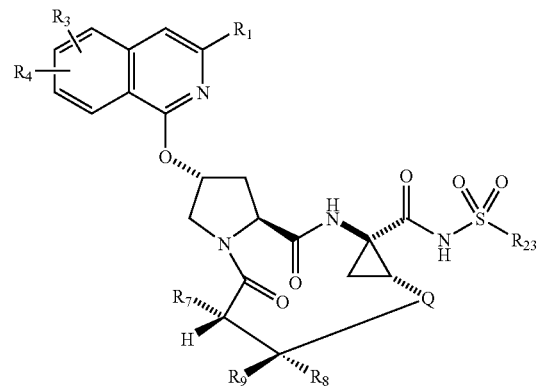
| Cmpd | R₂₃ | R₁ | R₃, R₄ | R₈ | R₉ | R₇ | Q |
|---|---|---|---|---|---|---|---|
| 255 | cyclopropyl | 4-(OCF₃)phenyl | 6-OMe, H | H | Me | NHBoc | O-(CH₂)₄- |
| 256 | cyclopropyl | H | H, H | H | Me | NHBoc | O-(CH₂)₄- |
| 257 | cyclopropyl | H | 6-OMe, H | H | Me | NHBoc | O-CH₂-CH=CH- |
| 258 | cyclopropyl | pyrrolidinyl | 6-OMe, H | H | Me | NH-C(O)-O-cyclopentyl | O-(CH₂)₄- |
| 259 | cyclopropyl | morpholinyl | 6-OMe, H | H | Me | NHBoc | O-(CH₂)₄- |
| 260 | cyclopropyl | 4-morpholinylphenyl | 6-OMe, H | H | Me | NHBoc | O-(CH₂)₄- |

TABLE 4-continued

| Cmpd | R23 | R1 | R3, R4 | R8 | R9 | R7 | Q |
|---|---|---|---|---|---|---|---|
| 261 | 1-ethylcyclopropyl | 4-(OCF3)phenyl | 6-OMe, H | H | Me | NHC(O)OiPr | OCH2CH2CH2 |
| 262 | cyclopropyl | H | H, H | H | Me | NHC(O)OtBu | CH2CH2OCH2CH2 |

| Cmpd | R23 | R1 | R3, R4 | R8 | R9 | R7 | Q |
|---|---|---|---|---|---|---|---|
| 263 | cyclopropyl | pyrrolidin-1-yl | 6-OMe, H | H | H | NHC(O)(pyrrolidin-1-yl) | CH2CH2OCH2CH2CH2 |
| 264 | cyclopropyl | morpholin-4-yl | 6-OMe, H | H | H | NHC(O)OtBu | CH2CH2OCH2CH2CH2 |
| 265 | cyclopropyl | 4-(morpholin-4-yl)phenyl | 6-OMe, H | H | H | NHC(O)OtBu | CH2CH2OCH2CH2CH2 |

-continued

| Cmpd | R₂₃ | R₁ | R₃, R₄ | R₈ | R₉ | R₇ | Q |
|---|---|---|---|---|---|---|---|
| 266 | cyclopropyl | 4-OCF₃-phenyl | 6-OMe, H | H | H | NHBoc | -CH₂CH₂-O-CH₂CH₂- |
| 267 | cyclopropyl | H | H, H | H | H | NHBoc | -CH₂-NH-(CH₂)₃- |
| 268 | cyclopropyl | H | 6-OMe, H | H | H | NHBoc | -CH₂-NH-(CH₂)₃- |
| 269 | cyclopropyl | pyrrolidin-1-yl | 6-OMe, H | H | H | NHBoc | -CH₂-NH-(CH₂)₃- |
| 270 | 1-Me-cyclopropyl | morpholin-4-yl | 6-OMe, H | H | H | NHBoc | -CH₂-NH-(CH₂)₃- |
| 271 | cyclopropyl | 4-(morpholin-4-yl)phenyl | 6-OMe, H | H | H | NHBoc | -CH₂-NH-(CH₂)₃- |
| 272 | cyclopropyl | 4-OCF₃-phenyl | 6-OMe, H | H | H | NHBoc | -CH₂-NH-(CH₂)₃- |
| 273 | cyclopropyl | H | H, H | H | H | NHBoc | |

-continued

| Cmpd | R₂₃ | R₁ | R₃, R₄ | R₈ | R₉ | R₇ | Q |
|---|---|---|---|---|---|---|---|
| 274 | cyclopropyl | H | 6-OMe, H | H | H | NH-C(O)-O-tBu | CH(CH₃)-N(CH₃)-pentyl |
| 275 | cyclobutyl | pyrrolidinyl | 6-OMe, H | H | H | NH-C(O)-O-tBu | CH(CH₃)-N(CH₃)-pentyl |
| 276 | cyclopropyl | morpholinyl | 6-OMe, H | H | H | NH-C(O)-O-tBu | CH(CH₃)-N(CH₃)-pentyl |
| 277 | cyclopropyl | 4-(morpholin-4-yl)phenyl | 6-OMe, H | H | H | NH-C(O)-O-cyclopentyl | CH(CH₃)-N(CH₃)-pentyl |
| 278 | cyclopropyl | 4-(OCF₃)phenyl | 6-OMe, H | H | H | NH-C(O)-O-tBu | CH(CH₃)-N(CH₃)-pentyl |
| 279 | 1-Et-cyclopropyl | H | H, H | H | H | NH-C(O)-O-tBu | CH(CH₃)-N(CH₃)-hexyl |
| 280 | cyclopropyl | H | 6-OMe, H | H | H | NH-C(O)-O-iPr | CH(CH₃)-N(CH₃)-hexyl |
| 281 | cyclopropyl | pyrrolidinyl | 6-OMe, H | H | H | NH-C(O)-O-tBu | CH(CH₃)-N(CH₃)-pentyl |

-continued

| Cmpd | R₂₃ | R₁ | R₃, R₄ | R₈ | R₉ | R₇ | Q |
|---|---|---|---|---|---|---|---|
| 282 | cyclopropyl | morpholine (N-linked) | 6-OMe, H | H | H | NHC(O)O-tBu | N(Me)-alkyl |
| 283 | cyclopropyl | 4-(morpholin-4-yl)phenyl | 6-OMe, H | H | H | NHC(O)O-tBu | N(Me)-alkyl |
| 284 | cyclopropyl | 4-(OCF₃)phenyl | 6-OMe, H | H | H | NHC(O)O-tBu | N(Me)-alkyl |
| 285 | 1-Me-cyclopropyl | H | H, H | H | H | NHC(O)O-tBu | S-alkyl |
| 286 | cyclopropyl | H | 6-OMe, H | H | H | NHC(O)O-tBu | S-alkyl |
| 287 | cyclopropyl | pyrrolidine (N-linked) | 6-OMe, H | H | H | NHC(O)O-cyclopentyl | S-alkyl |
| 288 | cyclopropyl | morpholine (N-linked) | 6-OMe, H | H | H | NHC(O)O-tBu | S-alkyl |

-continued

| Cmpd | R₂₃ | R₁ | R₃, R₄ | R₈ | R₉ | R₇ | Q |
|---|---|---|---|---|---|---|---|
| 289 | cyclopropyl | 4-(morpholin-4-yl)phenyl | 6-OMe, H | H | H | NHBoc | S-(CH₂)₅-CH₃ |
| 290 | cyclopropyl | 4-(OCF₃)phenyl | 6-OMe, H | H | H | NHBoc | S-(CH₂)₅-CH₃ |
| 291 | cyclopropyl | H | H, H | H | H | NHBoc | S-(CH₂)₅-CH₃ |
| 292 | cyclopropyl | H | 6-OMe, H | H | H | NHBoc | S-(CH₂)₅-CH₃ |
| 293 | cyclopropyl | pyrrolidin-1-yl | 6-OMe, H | H | H | NHBoc | CH₂-S-(CH₂)₃-CH₃ |
| 294 | cyclopropyl | morpholin-4-yl | 6-OMe, H | H | H | NHBoc | CH₂-S-(CH₂)₃-CH₃ |
| 295 | 1-Et-cyclopropyl | 4-(morpholin-4-yl)phenyl | 6-OMe, H | H | H | NHBoc | CH₂-S-(CH₂)₃-CH₃ |

-continued

| Cmpd | R23 | R1 | R3, R4 | R8 | R9 | R7 | Q |
|---|---|---|---|---|---|---|---|
| 296 | cyclopropyl | 4-OCF3-phenyl | 6-OMe, H | H | H | -NHC(O)-pyrrolidinyl | -CH2-S-CH2CH2-CH=CH- |
| 297 | cyclopropyl | H | 6-OMe, H | H | H | -NHC(O)O-tBu | -S-CH2CH2-CH=CH- |
| 298 | cyclopropyl | Ph | 6-OMe, H | H | H | -NHC(O)O-tBu | -S-CH2CH2-CH=CH- |
| 299 | 1-Me-cyclopropyl | pyrrolidinyl | 6-OMe, H | H | H | -NHC(O)O-tBu | -S-CH2CH2-CH=CH- |
| 300 | cyclopropyl | 4-OCF3-phenyl | 6-OMe, H | H | H | -NHC(O)O-tBu | -S-CH2CH2-CH=CH- |
| 301 | cyclopropyl | H | 6-OMe, H | Me | Me | -NHC(O)O-tBu | -S-CH2CH2-CH=CH- |
| 302 | cyclopropyl | Ph | 6-OMe, H | Me | Me | -NHC(O)-pyrrolidinyl | -S-CH2CH2-CH=CH- |
| 303 | cyclopropyl | pyrrolidinyl | 6-OMe, H | Me | Me | -NHC(O)O-tBu | -S-CH2CH2-CH=CH- |

-continued

| Cmpd | R23 | R1 | R3, R4 | R8 | R9 | R7 | Q |
|---|---|---|---|---|---|---|---|
| 304 | cyclopropyl | 4-OCF3-phenyl | 6-OMe, H | Me | Me | NHBoc | -S-CH2-CH2-CH=CH- |
| 305 | cyclopropyl | H | 6-OMe, H | H | H | NHBoc | -CH2-O-CH2-CH2-CH=CH- |
| 306 | cyclopropyl | Ph | 6-OMe, H | H | H | NH-C(O)-O-cyclopentyl | -CH2-O-CH2-CH2-CH=CH- |
| 307 | cyclopropyl | H | 6-OMe, H | H | H | NHBoc | -CH2-O-CH2-CH2-CH2-CH2- |
| 308 | cyclopropyl | H | 6-OMe, H | H | H | NHBoc | -O-CH2-CH2-CH2-CH=CH- |
| 309 | 1-Me-cyclopropyl | Ph | 6-OMe, H | H | H | NHBoc | -O-CH2-CH2-CH2-CH=CH- |
| 310 | cyclopropyl | H | 6-OMe, H | H | H | NHBoc | -CH2-O-CH2-CH2-CH2- |
| 311 | cyclopropyl | H | 6-OMe, H | H | H | NHBoc | -O-CH2-CH2-CH2-CH=CH- |
| 312 | cyclopropyl | Ph | 6-OMe, H | H | H | NHBoc | -O-CH2-CH2-CH2-CH=CH- |
| 313 | cyclopropyl | H | 6-OMe, H | H | H | NH-C(O)-pyrrolidinyl | -CH2-O-CH2-CH2-CH2- |

-continued

| Cmpd | R$_{23}$ | R$_1$ | R$_3$, R$_4$ | R$_8$ | R$_9$ | R$_7$ | Q |
|---|---|---|---|---|---|---|---|
| 314 | cyclopropyl | H | 6-OMe, H | H | H | NHC(O)O-tBu | -O-CH$_2$CH$_2$CH$_2$-CH=CH-CH$_2$- |
| 315 | cyclobutyl | Ph | 6-OMe, H | H | H | NHC(O)O-tBu | -O-CH$_2$CH$_2$CH$_2$-CH=CH-CH$_2$- |
| 316 | cyclopropyl | H | 6-OMe, H | H | H | NHC(O)O-tBu | -CH$_2$-O-CH$_2$CH$_2$CH$_2$CH$_2$- |
| 317 | cyclopropyl | H | 6-OMe, H | H | H | NHC(O)O-tBu | -NH-CH$_2$CH$_2$CH$_2$-CH=CH-CH$_2$- |
| 318 | cyclopropyl | Ph | 6-OMe, H | H | H | NHC(O)O-cyclopentyl | -NH-CH$_2$CH$_2$CH$_2$-CH=CH-CH$_2$- |
| 319 | cyclopropyl | H | 6-OMe, H | H | H | NHC(O)O-tBu | -NH-CH$_2$CH$_2$CH$_2$CH$_2$CH$_2$- |
| 320 | 1-Et-cyclopropyl | H | 6-OMe, H | H | H | NHC(O)O-tBu | -N(Me)-CH$_2$CH$_2$CH$_2$-CH=CH-CH$_2$- |
| 321 | cyclopropyl | Ph | 6-OMe, H | H | H | NHC(O)O-tBu | -N(Me)-CH$_2$CH$_2$CH$_2$-CH=CH-CH$_2$- |
| 322 | cyclopropyl | H | 6-OMe, H | H | H | NHC(O)O-tBu | -N(Me)-CH$_2$CH$_2$CH$_2$CH$_2$CH$_2$- |
| 323 | cyclopropyl | NMe$_2$ | 6-OMe, H | H | H | NHC(O)O-tBu | -CH$_2$CH$_2$CH$_2$-CH=CH-CH$_2$- |

-continued

| Cmpd | R23 | R1 | R3, R4 | R8 | R9 | R7 | Q |
|---|---|---|---|---|---|---|---|
| 324 | cyclopropyl | N(Me)Me | 6-OMe, H | H | H | NHC(O)O-cyclopentyl | O-CH2CH2CH2-CH=CH- |
| 325 | cyclopropyl | N(Me)Me | 6-OMe, H | H | H | NHC(O)O-tBu | O-CH2-CH=CH- |
| 326 | cyclopropyl | N(Me)Me | 6-OMe, H | H | H | NHC(O)-pyrrolidinyl | S-CH2CH2CH2-CH=CH- |
| 327 | cyclopropyl | N(Me)Me | 6-OMe, H | Me | Me | NHC(O)O-cyclopentyl | S-CH2CH2CH2-CH=CH- |
| 328 | cyclopropyl | N(Me)Me | 6-OMe, H | Me | H | NHC(O)O-tBu | O-CH2CH2CH2-CH=CH- |
| 329 | cyclopropyl | N(Me)Me | 6-OMe, H | H | H | NHC(O)-pyrrolidinyl | CH2-NH-CH2CH2-CH=CH- |
| 330 | cyclopropyl | N(Me)Me | 6-OMe, H | H | H | NHC(O)O-cyclopentyl | CH2-N(Me)-CH2CH2-CH=CH- |
| 331 | cyclopropyl | N(Me)Me | 6-OMe, H | H | H | NHC(O)O-cyclopentyl | -(CH2)6- |

TABLE 5

| Cmpd | R₁ | R₂ | R₃ |
|---|---|---|---|
| 401 | H | H | H |
| 402 | H | H | H |
| 403 | H | H | Me |
| 404 | H | H | —CF₃ |
| 405 | H | H | —CHF₂ |
| 406 | H | H | H |
| 407 | H | H | H |
| 408 | H | H | —OCH₃ |
| 409 | H | H | H |
| 410 | H | —OCH₃ | H |
| 411 | H | Me | H |
| 412 | Cl | —OCH₃ | H |
| 413 | H | H | H |
| 414 | H | H | H |
| 415 | H | H | H |
| 416 | H | H | H |
| 417 | H | H | F |
| 418 | H | H | —SCH₃ |
| 419 | H | H | H |
| 420 | H | H | ![thiophene ketone group] |
| 421 | H | H | H |
| 422 | H | H | ![morpholine group] |

TABLE 5-continued
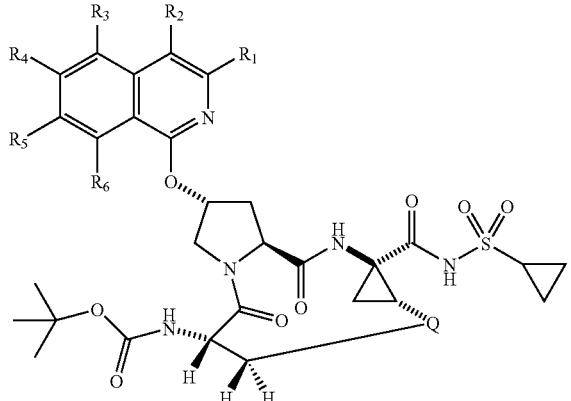
| | | | |
|---|---|---|---|
| 423 | 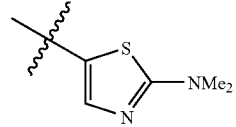 | H | H |
| 424 | 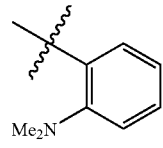 | H | H |
| 425 | 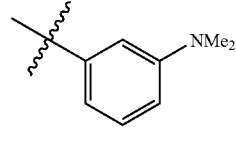 | H | H |
| 426 | 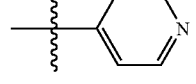 | H | H |
| 427 | 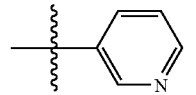 | H | H |
| 428 | 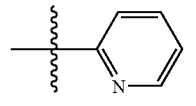 | H | H |
| 429 | 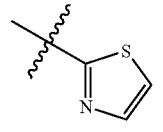 | H | H |
| 430 | 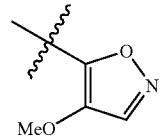 | H | H |
| 431 | 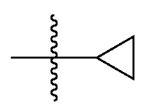 | H | H |

TABLE 5-continued
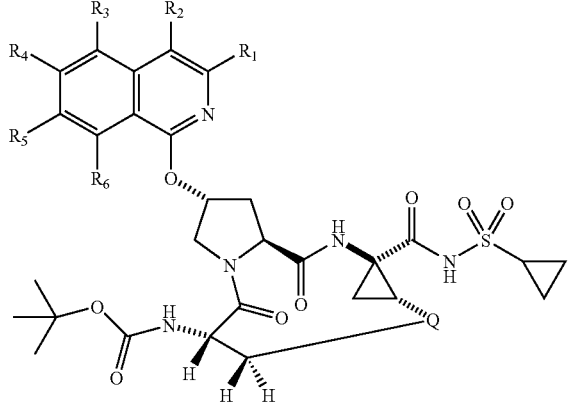
| # | | R1 | R2 |
|---|---|---|---|
| 432 | 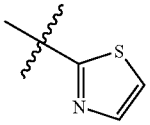 | —OCH₃ | H |
| 433 | 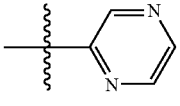 | —OCH₃ | H |
| 434 | 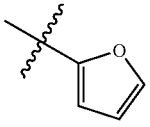 | —OCH₃ | H |
| 435 | 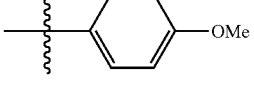 | H | H |
| 436 | 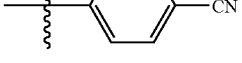 | H | H |
| 437 | 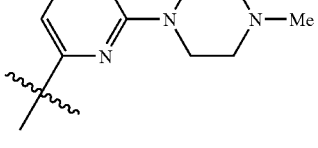 | H | H |
| 438 | 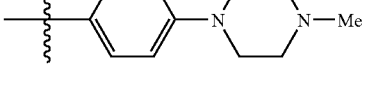 | H | —OCH₃ |
| 439 | 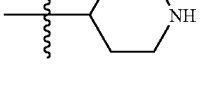 | H | —OCH₃ |
| 440 | 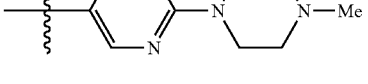 | H | H |

TABLE 5-continued
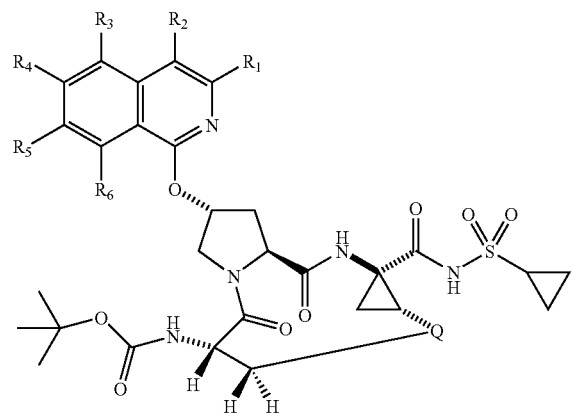
| 441 | H |  (C(=O)NMe₂) | H |
| 442 | 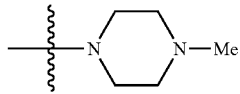 (N-piperazinyl-N-Me) | H | —OCH₃ |
| 443 |  (4-morpholino-3-fluorophenyl) | H | H |
| 444 | 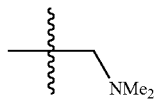 (CH₂CH₂NMe₂) | H | H |
| 445 | 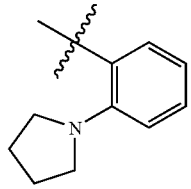 (2-pyrrolidinylphenyl) | —OH | H |
| 446 | 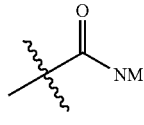 (C(=O)NMe₂) | —OH | H |
| 447 | 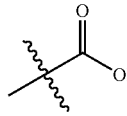 (C(=O)OH) | —OH | H |
| 448 | 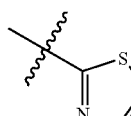 (thiazol-2-yl) | —OH | H |

TABLE 5-continued
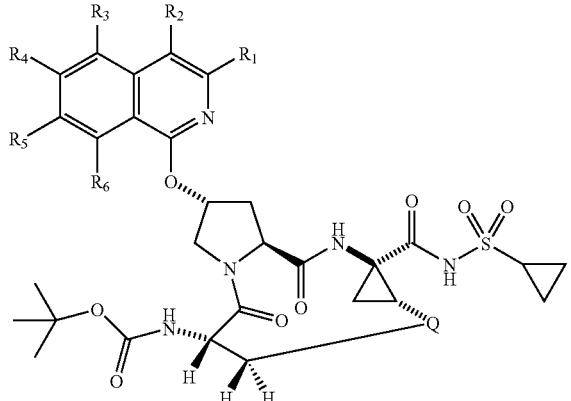
| | | | |
|---|---|---|---|
| 449 | 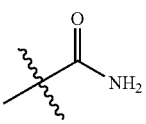 | H | H |
| 450 | 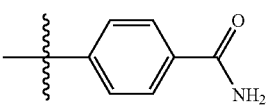 | H | H |
| 451 | 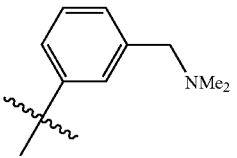 | H | H |
| 452 | 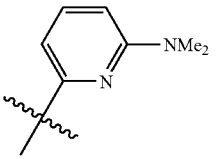 | H | H |
| 453 | 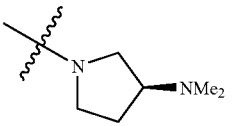 | H | H |
| 454 | 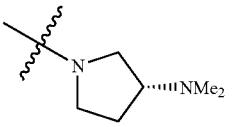 | H | H |
| 455 | 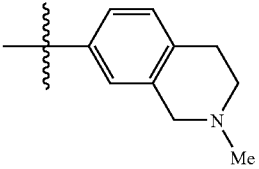 | H | —OCH$_3$ |
| 456 | 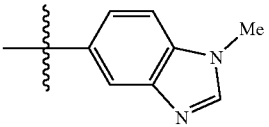 | H | H |

TABLE 5-continued
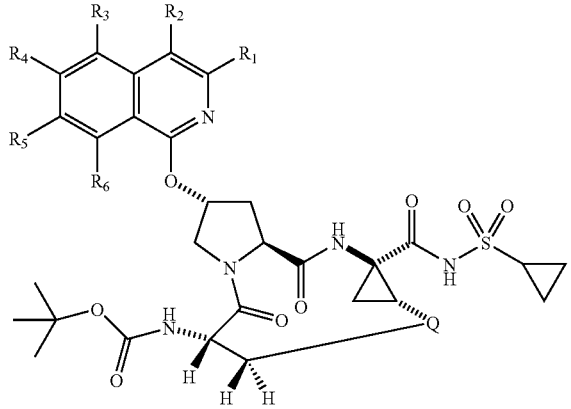
| Cmpd | R4 | R5 | R6 | Q |
|---|---|---|---|---|
| 401 | H | Me | H | 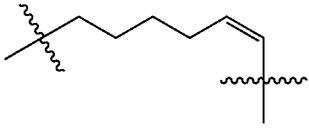 |
| 402 | H | H | Me | 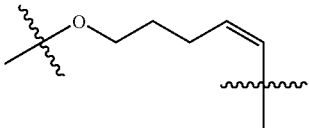 |
| 403 | H | H | H | 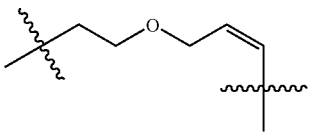 |
| 404 | H | H | H | 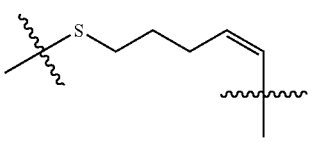 |
| 405 | H | H | H | 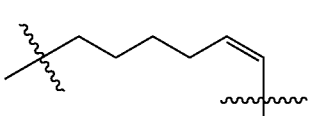 |
| 406 | —OCF$_3$ | H | H | 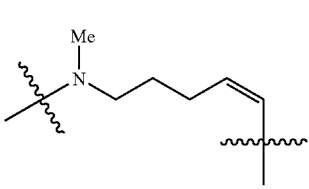 |
| 407 | —OH | H | H | 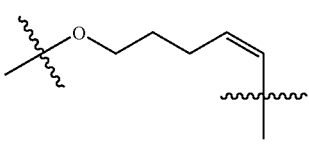 |

TABLE 5-continued
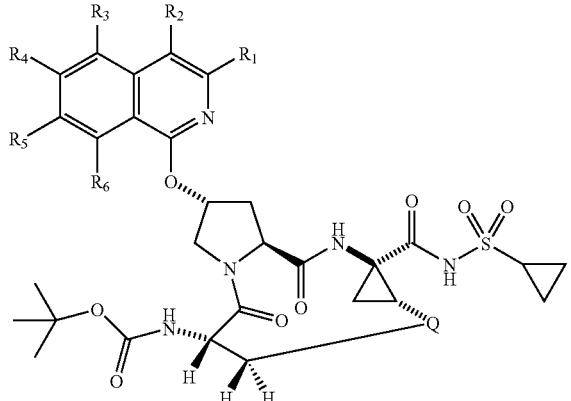

TABLE 5-continued
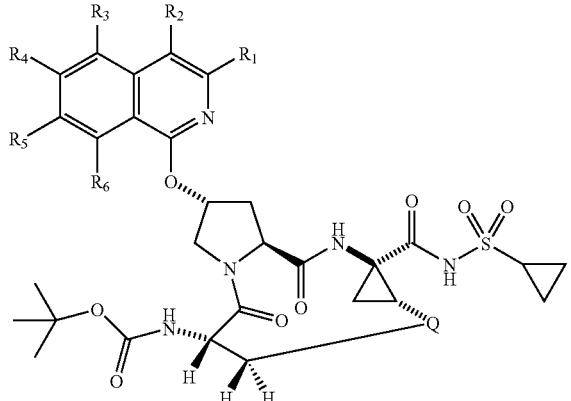
| 416 | —OCH₃ | F | H | (alkenyl chain) |
| 417 | —OCH₃ | H | H | (O-alkenyl chain) |
| 418 | —OCH₃ | H | H | (S-alkenyl chain) |
| 419 | (C(=O)NMe₂ group) | H | H | (alkenyl chain) |
| 420 | —OCH₃ | H | H | (CH₂CH₂OCH₂-alkenyl) |
| 421 | (pyrazolyl group) | H | H | (O-alkenyl chain) |
| 422 | H | H | H | (NH-alkenyl chain) |
| 423 | —OCH₃ | H | H | (O-alkenyl chain) |

TABLE 5-continued
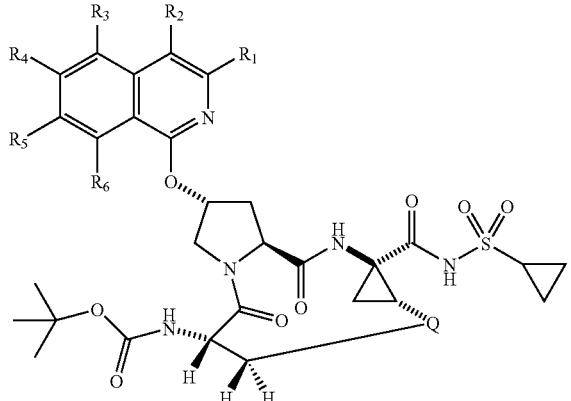
| | | | | |
|---|---|---|---|---|
| 424 | —OCH₃ | H | H | (S-CH₂CH₂CH₂-CH=CH-) |
| 425 | —OCH₃ | H | H | (CH₂CH₂CH₂CH₂CH₂-CH=CH-) |
| 426 | —OCH₃ | H | H | (N(Me)-CH₂CH₂CH₂-CH=CH-) |
| 427 | —OCH₃ | H | H | (O-CH₂CH₂CH₂-CH=CH-) |
| 428 | —OCH₃ | H | H | (O-CH₂CH₂CH₂-CH=CH-) |
| 429 | —OCH₃ | H | H | (CH₂CH₂CH₂CH₂CH₂-CH=CH-) |
| 430 | —OCH₃ | H | H | (CH₂CH₂-O-CH₂-CH=CH-) |
| 431 | —OCH₃ | H | H | (O-CH₂CH₂CH₂-CH=CH-) |

TABLE 5-continued
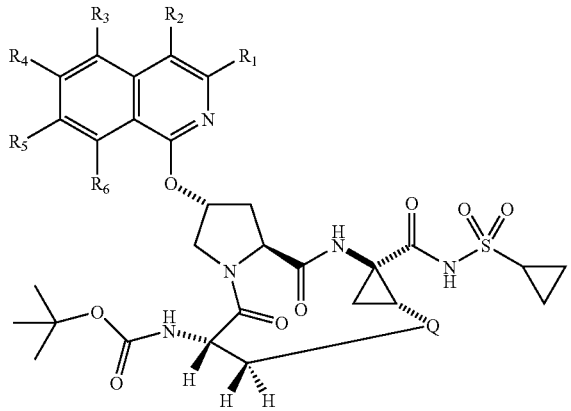
| | | | |
|---|---|---|---|
| 432 | H | H H | 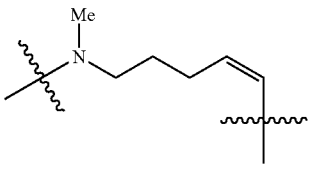 |
| 433 | H | H H | 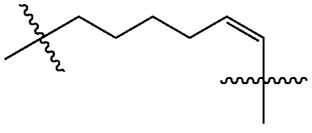 |
| 434 | H | H H | 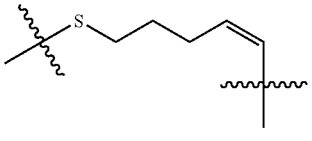 |
| 435 | H | H H | 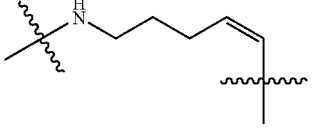 |
| 436 | H | H H | 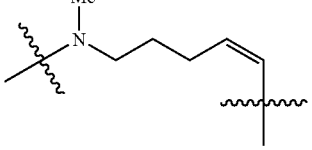 |
| 437 | —OCH$_3$ | H H | 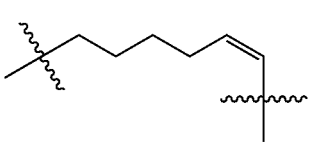 |
| 438 | H | H H | 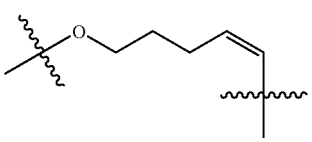 |

TABLE 5-continued
| | R3 | R2 | R1 | Q |
|---|---|---|---|---|
| 439 | H | H | H | 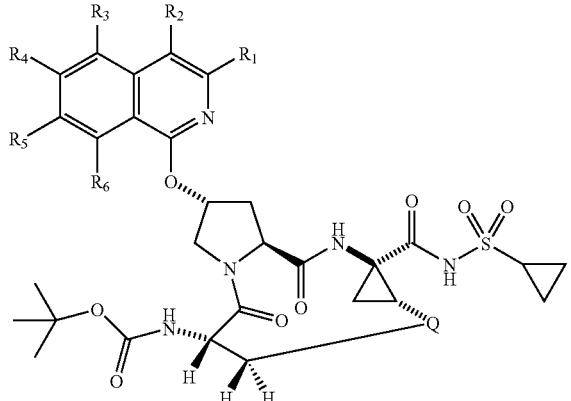 |
| 440 | —OCH₃ | H | H | 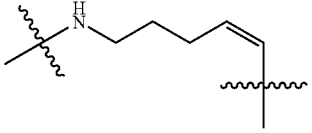 |
| 441 | H | H | H | 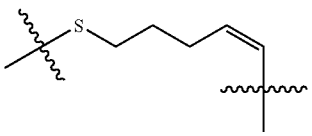 |
| 442 | H | H | H | 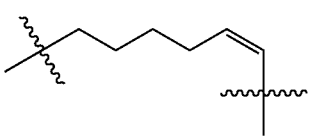 |
| 443 | —OCH₃ | H | H | 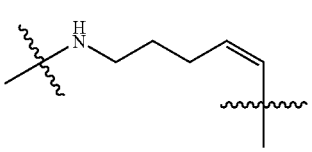 |
| 444 | —OCH₃ | H | H | 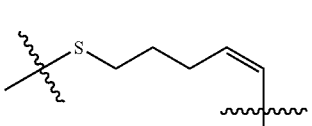 |
| 445 | H | H | H | 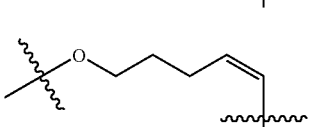 |
| 446 | H | H | H | 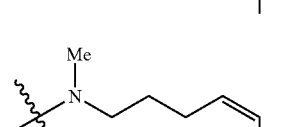 |

TABLE 5-continued
| 447 | H | H | H | 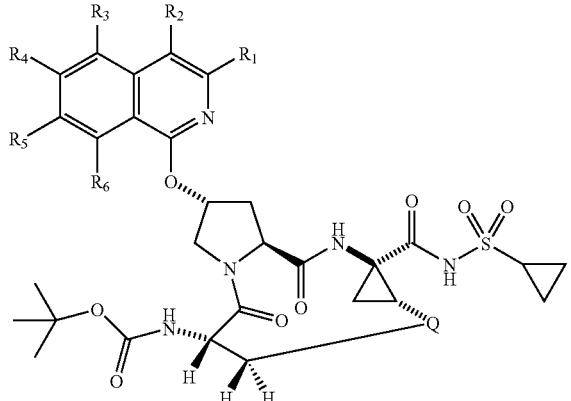 |
| 448 | H | H | H | 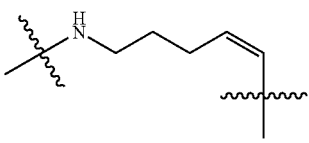 |
| 449 | H | H | H | 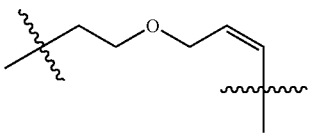 |
| 450 | —OCH$_3$ | H | H | 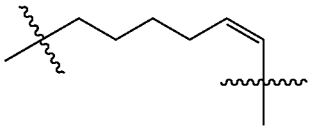 |
| 451 | —OCH$_3$ | H | H | 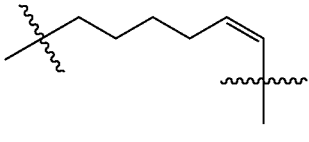 |
| 452 | —OCH$_3$ | H | H | 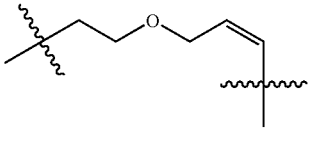 |
| 453 | —OCH$_3$ | H | H | 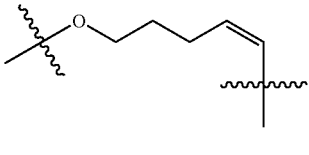 |
| 454 | —OCH$_3$ | H | H | 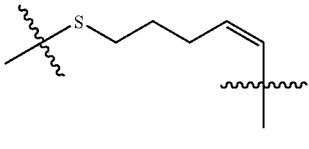 |

TABLE 5-continued

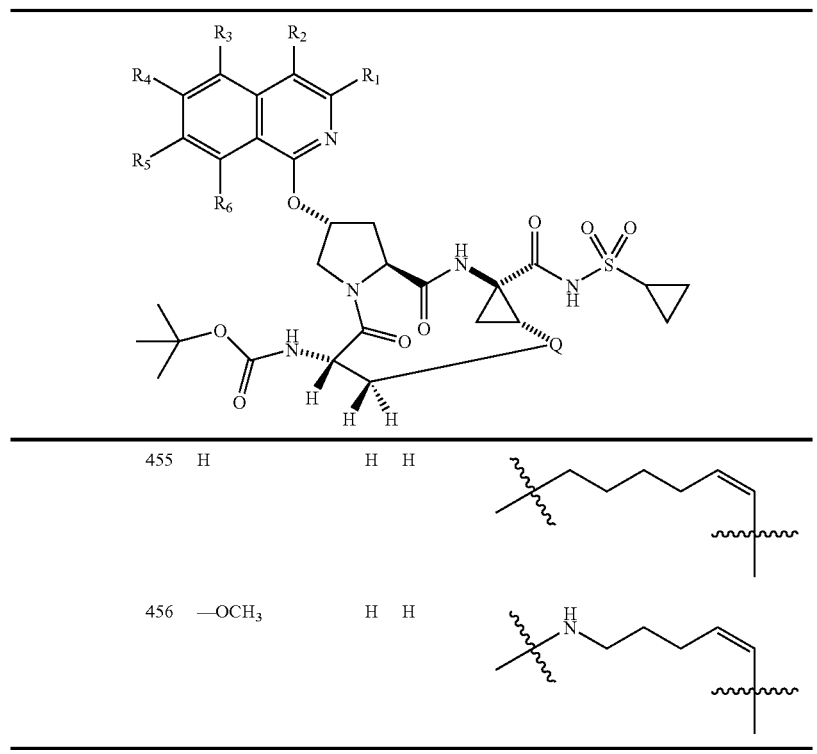

| 455 | H | H | H | (alkenyl chain) |
| 456 | —OCH₃ | H | H | (NH-alkenyl chain) |

Example 50

Biological Studies

Recombinant HCV NS3/4A Protease Complex FRET Peptide Assay

The purpose of this in vitro assay was to measure the inhibition of HCV NS3 protease complexes, derived from the BMS strain, $H_{77}C$ strain or J416S strain, as described below, by compounds of the present invention. This assay provides an indication of how effective compounds of the present invention would be in inhibiting HCV proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493–1503 (1993)). The amino acid sequence of the nonstructural region, NS2-5B, was shown to be >97% identical to HCV genotype 1a (H77C) and 87% identical to genotype 1b (J4L6S). The infectious clones, H77C (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94(16), 8738–8743 (1997); AF054247, see Yanagi, M., St Claire, M., Shapiro, M., Emerson, S. U., Purcell, R. H. and Bukh, J, Virology 244 (1), 161–172. (1998)).

The H77C and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):5620–32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol. 72(8):6758–69 (1998)) with modifications. Briefly, NS3/4A expression was induced with 0.5 mM Isopropyl β-D-1-thiogalactopyranoside (IPTG) for 22 hr at 20° C. A typical fermentation (10 L) yielded approximately 80 g of wet cell paste. The cells were resuspended in lysis buffer (10 mL/g) consisting of 25 mM N-(2-Hydroxyethyl)piperazine-N'-(2-Ethane Sulfonic acid) (HEPES), pH7.5, 20% glycerol, 500 mM Sodium Chloride (NaCl), 0.5% Triton-X100, 1 microgram/milliliter ("µg/mL") lysozyme, 5 mM Magnesium Chloride ($MgCl_2$), 1 ug/ml DnaseI, 5 mM β-Mercaptoethanol (βME), Protease inhibitor—Ethylenediamine Tetraacetic acid (EDTA) free (Roche), homogenized and incubated for 20 mins at 4° C. The homogenate was sonicated and clarified by ultra-centrifugation at 235000 g for 1 hr at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH8.0, 20% glycerol, 500 mM NaCl, 0.5% Triton-X100, 15 mM imidazole, 5 mM βME). The sample was loaded at a flow rate of 1 mL/min. The column was washed with 15 column volumes of buffer C (same as buffer B except with 0.2% Triton-X100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH7.5, 20% glycerol, 300 mM NaCl, 0.2% Triton-X100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77C and J4L6S strains, were judged to be greater than 90% by SDS-PAGE and mass spectrometry analyses.

The enzyme was stored at −80° C., thawed on ice and diluted prior to use in assay buffer. The substrate used for the NS3/4A protease assay was RET S1 (Resonance Energy Transfer Depsipeptide Substrate; AnaSpec, Inc. cat # 22991) (FRET peptide), described by Taliani et al. in Anal. Biochem. 240(2):60–67 (1996). The sequence of this peptide is loosely based on the NS4A/NS4B natural cleavage site except there is an ester linkage rather than an amide bond at the cleavage site. The peptide substrate was incubated with one of the three recombinant NS3/4A complexes, in the absence or presence of a compound of the present invention, and the formation of fluorescent reaction product was followed in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH7.5; 0.15M NaCl; 0.1% Triton; 15% Glycerol; 10 mM βME. Substrate: 2 µM final concentration (from a 2 mM stock solution in DMSO stored at −20° C.). HCV NS3/4A type 1a (1b), 2–3 nM final concentration (from a 5 µM stock solution in 25 mM HEPES, pH7.5, 20% glycerol, 300 mM NaCl, 0.2% Triton-X100, 110 mM βME). For compounds with potencies approaching the assay limit, the assay was made more sensitive by adding 50 µg/ml Bovine Serum Albumin (Sigma) to the assay buffer and reducing the end protease concentration to 300 pM.

The assay was performed in a 96-well polystyrene black plate from Falcon. Each well contained 25 microliter ("µl") NS3/4A protease complex in assay buffer, 50 µl of a compound of the present invention in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 minutes.

The percent inhibition was calculated with the following equation:

$$100-[(\delta F_{inh}/\delta F_{con}) \times 100]$$

where δF is the change in fluorescence over the linear range of the curve. A non-linear curve fit was applied to the inhibition-concentration data, and the 50% effective concentration ($IC_{50}$) was calculated by the use of Excel Xl-fit software using the equation, y=A+((B−A)/(1+((C/x)^D))).

All of the compounds tested were found to have IC50s of 1.2 µM or less. Further, compounds of the present invention, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the selectivity of the compounds of the present invention in inhibiting HCV NS3/4A protease as compared to other serine or cysteine proteases.

The specificities of compounds of the present invention were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using calorimetric p-nitroaniline (pNA) substrate specific for each enzyme was used as described previously (PCT Patent Application No. WO 00/09543) with some modifications to the serine protease assays. All enzymes were purchased from Sigma while the substrates were from Bachem.

Each assay included a 2 hr enzyme-inhibitor pre-incubation at room temperature followed by addition of substrate and hydrolysis to ~30% conversion as measured on a Spectramax Pro microplate reader. Compound concentrations varied from 100 to 0.4 micromolar ("µM") depending on their potency.

The final conditions for each assay were as follows:
50 millimolar ("mM") Tris(hydroxymethyl)aminomethane hydrochloride (Tris-HCl) pH8, 0.5M Sodium Sulfate ($Na_2SO_4$), 50 mM NaCl, 0.1 mM EDTA, 3% DMSO, 0.01% Tween-20 with:
133 µM succ-AAA-pNA and 20 nM HNE or 8 nM PPE; 100 µM succ-AAPF-pNA and 250 pM Chymotrypsin.
100 mM $NaHPO_4$ (Sodium Hydrogen Phosphate) pH 6, 0.1 mM EDTA, 3% DMSO, 1 mM TCEP (Tris(2-carboxyethyl)phosphine hydrochloride), 0.01% Tween-20, 30 µM Z-FR-pNA and 5 nM Cathepsin B (enzyme stock activated in buffer containing 20 mM TCEP before use).

The percentage of inhibition was calculated using the formula:

$$[1-((UV_{inh}-UV_{blank})/(UV_{ctl}-UV_{blank}))] \times 100$$

A non-linear curve fit was applied to the inhibition-concentration data, and the 50% effective concentration ($IC_{50}$) was calculated by the use of Excel Xl-fit software.

HCV Replion assays were utilized in the present invention, and were prepared, conducted and validated as follows:

Generation of HCV Replicon

An HCV replicon whole cell system was established as described by Lohmann V, Korner F, Koch J, Herian U, Theilmann L, Bartenschlager R., Science 285(5424): 110–3 (1999). This system enabled us to evaluate the effects of our HCV Protease compounds on HCV RNA replication. Briefly, using the HCV strain 1B sequence described in the Lohmann paper (Assession number: AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions. To generate cell lines, $4 \times 10^6$ Huh-7 cells (kindly provided by R. Bartenschlager and available from Health Science Research Resources Bank, Japan Health Sciences Foundation) were electroporated (GenePulser System, Bio-Rad) with 10 microgram("μg") of RNA transcript and plated into 100-mm dishes. After 24 h, selective media containing 1.0 milligrams/milliliter ("mg/ml") G418 was added and media was changed every 3 to 5 days. Approximately 4 weeks after electroporation, small colonies were visible which were isolated and expanded for further analysis. These cell lines were maintained at 37° C., 5% $CO_2$, 100% relative humidity in DMEM (Cat# 11965-084) Gibco-BRL, Rockville, Md., with 10% heat inactivated calf serum (Sigma), 10 ml of 100× penicillin/streptomycin (Cat# 15140-122) Gibco-BRL, Rockville, Md., Geneticin (Cat# 10131-027) Gibco-BRL, Rockville, Md. at 1 mg/ml. One of the cell lines (deposited as ATCC Accession No. PTA-4583 in the American Type Culture Collection) which had approximately 3,000 copies of HCV replicon RNA/cell was used for development of the assay (HCV 1b-377-neo replicon cells).

FRET Assay

Huh7 cells, constitutively expressing the HCV replicon, were grown in Dulbecco's Modified Eagle Media (DMEM) containing 10% Fetal calf serum (FCS) and 1 mg/ml G418 (Gibco-BRL). Cells were seeded the night before ($1.5 \times 10^4$ cells/well) in 96-well tissue-culture sterile plates. Compound and no compound controls were prepared in DMEM containing 4% FCS, 1:100 Penicillin/Streptomycin, 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnotstic Systems) for a $CC_{50}$ reading. The toxicity of compound ($CC_{50}$) was determined by adding $\frac{1}{10}^{th}$ volume of alamar Blue to the media incubating the cells. After 4 hr, the fluorescence signal from each well was read, with an excitation wavelength at 530 nm and an emission wavelength of 580 nm, using the Cytofluor Series 4000 (Perspective Biosystems). Plates were then rinsed thoroughly with Phosphate-Buffered Saline (PBS) (3 times 150 μl). The cells were lysed with 25 μl of a lysis assay reagent containing an HCV protease substrate (5× cell Luciferase cell culture lysis reagent (Promega #E153A) diluted to 1× with distilled water, NaCl added to 150 mM final, the FRET peptide diluted to 10 μM final from a 2 mM stock in 100% DMSO). The HCV protease substrate (FRET peptide; AnaSpec, Inc. cat #22991, described by Taliani et al. in Anal. Biochem. 240(2):60–67 (1996)) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The plate was then placed into the Cytofluor 4000 instrument which had been set to 340 nm excitation/490 nm emission, automatic mode for 21 cycles and the plate read in a kinetic mode at 25° C. Reactions were generally followed for approximately 15 minutes.

The percent inhibition for both efficacy and cytotoxicity were calculated with the following equation:

$$100-[(\delta F_{inh}/\delta F_{con}) \times 100]$$

where δF is the change in fluorescence over the linear range of the curve. A non-linear curve fit was applied to the inhibition-concentration data, and the 50% effective concentration ($EC_{50}$ and $CC_{50}$) was calculated by the use of Excel Xl-fit software using the equation, $y=A+((B-A)/(1+((C/x)^{\wedge}D)))$.

Luciferase Assay

As a secondary assay, $EC_{50}$ determinations from the replicon FRET assay were confirmed in a luciferase reporter assay. Utilization of a replicon luciferase reporter assay was first described by Krieger et al (Krieger N, Lohmann V, and Bartenschlager R, J. Virol. 75(10):4614–4624 (2001)). The replicon construct described for our FRET assay was modified by replacing the resistance gene neomycin with a cassette containing Renilla Luciferase gene fused to a sequence representing an NS3 cleavage site (NS4A/B site), followed by the Blasicidin resistance gene (restriction sites Asc1/Pme1 used for the subcloning). The adaptive mutation at position 1179 (serine to isoleucine) was also introduced (Blight K J, Kolykhalov, A A, Rice, C M, Science 290 (5498):1972–1974). A cell line containing the replicon was selected and maintained in 1.25 μg/ml Blasticidin. The luciferase reporter assay was set up by seeding the replicon cells the night before at a density of 7000 cells/well in 96-well plates. One day later, media was changed to fresh DMEM containing 4% FBS and compound dilutions were prepared and added to a final concentration of 0.5% DMSO (final media volume of 150 μl). Following an additional 4-day incubation in a 37° C./5% $CO_2$ incubator, cells were analyzed for Renilla luciferase activity using the Promega Dual-Glo Luciferase Assay System. Media (100 μl) was removed from each well. To the remaining 50 μl of media, 50 μl of Dual-Glo Luciferase Reagent was added, and plates rocked for 10 minutes to 2 hours at room temperature. Dual-Glo Stop & Glo Reagent (50 μl) was then added to each well, and plates were rocked again for an additional 10 minutes to 2 hours at room temperature. Plates were read on a Packard TopCount NXT using a luminescence program.

The percentage inhibition was calculated using the formula below:

$$\% \text{ control} = \frac{\text{average luciferase signal in experimental wells (+ compound)}}{\text{average luciferase signal in DMSO control wells(- compound)}}$$

The values were graphed and analyzed using XLFit to obtain the $EC_{50}$ value.

Representative compounds of the invention were assessed in the HCV NS3/4A protease recombinant enzyme assay, the HCV replicon cell-based assay and/or in several of the outlined specificity assays. For example, Compound 2 was found to have an $IC_{50}$ of 26 nM against the BMS strain NS3/4A protease in the enzyme assay. Similar potency values were obtained with the published H77C (IC$_{50}$ of 4.2 nM) and J4L6S (IC$_{50}$ of 1.9 nM) strains. The EC$_{50}$ value in the replicon assay was 146 nM.

In the specificity assays, the same compound was found to have the following activity: HNE>100 μM; PPE>100 μM; Chymotrypsin>100 μM; Cathepsin B>100 μM. These results indicate this family of compounds are highly specific for the NS3 protease and many of these members inhibit HCV replicon replication.

The compounds tested were found to have activities in the ranges as follow:

IC50 Activity Ranges (NS3/4A BMS Strain): A is <50 μM; B is <5 μM; C is <0.5 μM; D is <0.05 μM
EC50 Activity Range (for compounds tested): A is <50 μM; B is <5 μM; C is <0.5 μM; D is <0.05 μM Tables 6 & 7: Compound Activity Tables

TABLE 6

TABLE 6-continued
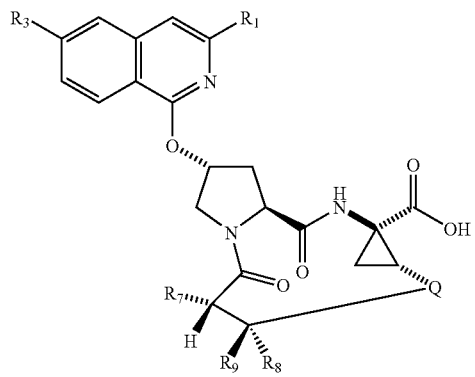
| Cmpd | R₁ | R₃ | R₇ | R₈ | R₉ | Q | IC50 (nM) | EC50 (nM) |
|------|----|----|----|----|----|----|-----------|-----------|
| 79 | H | OMe | NHBoc | Me | Me | S-CH₂CH₂CH=CH- linker | A | A |
| 84 | H | OMe | NHBoc | H | H | O-CH₂CH₂CH=CH- linker | C | B |
| 140 | H | OMe | NHBoc | H | H | CH₂-O-CH₂-CH=CH- linker | A | NT |
| 143 | H | OMe | NHBoc | H | H | CH₂CH₂CH₂CH=CH- linker | C | B |
| 144 | H | H | NHBoc | H | H | 2-NO₂-C₆H₄-SO₂-N(CH₂CH₂CH₂CH=CH-) linker | B | A |

TABLE 7
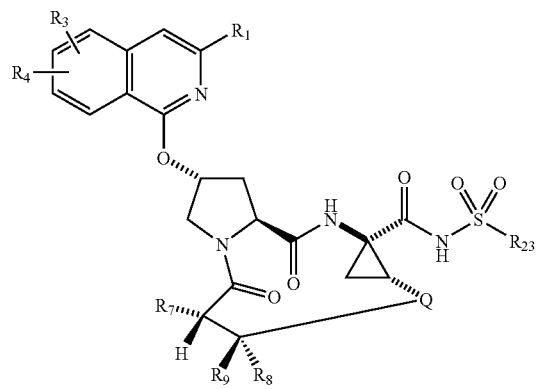
| Cmpd | R23 | R1 | R3, R4 | R8 | R9 | R7 |
|---|---|---|---|---|---|---|
| 2 | Me | H | H, H | H | H | NHBoc |
| 3 | CHMe2 | H | H, H | H | H | NHBoc |
| 4 | cyclopropyl | H | H, H | H | H | NHBoc |
| 5 | 1-benzylcyclopropyl | H | H, H | H | H | NHBoc |
| 6 | 1-ethylcyclopropyl | H | H, H | H | H | NHBoc |
| 7 | 1-ethylcyclopropyl | H | H, H | H | H | NHBoc |
| 8 | 1-methylcyclopropyl | H | H, H | H | H | NHBoc |
| 9 | cyclobutyl | H | H, H | H | H | NHBoc |
| 10 | cyclopropyl | H | H, H | H | H | NHBoc |

TABLE 7-continued

| | | | | | | |
|---|---|---|---|---|---|---|
| 11 | cyclopropyl | H | H, H | H | H | NH₃⁺Cl⁻ |
| 12 | cyclopropyl | H | H, H | H | H | NHC(O)OMe |
| 13 | cyclopropyl | H | H, H | H | H | NHC(O)O-neopentyl |
| 14 | cyclopropyl | H | H, H | H | H | NHC(O)O-tetrahydropyran-4-yl |
| 15 | cyclopropyl | H | H, H | H | H | NHC(O)O-tetrahydrofuran-3-yl |
| 16 | cyclopropyl | H | H, H | H | H | NHC(O)O-iPr |
| 17B | cyclopropyl | H | 6-OMe, H | H | H | NHC(O)OtBu |
| 18B | cyclopropyl | H | 6-OMe, H | H | H | NHC(O)OtBu |
| 19 | cyclopropyl | H | 6-OMe, H | H | H | NHC(O)OtBu |
| 20 | cyclopropyl | H | H, H | H | H | NHC(O)O-cyclopentyl |

TABLE 7-continued
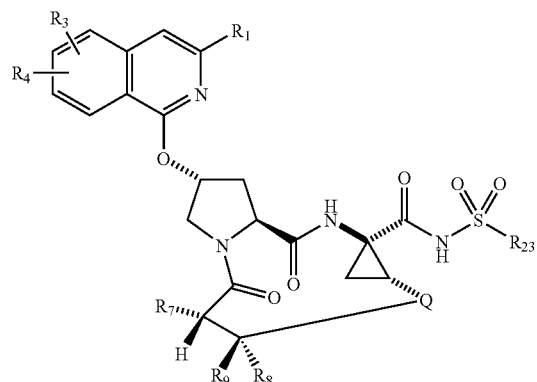
| | | | | | |
|---|---|---|---|---|---|
| 21 | cyclopropyl | H | H, H | H | H | 3-methoxy-4-oxo-cyclobutenyl-amino (MeO squaramide) |
| 22 | cyclopropyl | H | H, H | H | H | NHC(O)CH$_2$-cyclopropyl |
| 23 | cyclopropyl | H | H, H | H | H | NHC(O)NH-propyl |
| 24 | cyclopropyl | H | H, H | H | H | NHC(O)CH$_2$OMe |
| 25 | cyclopropyl | H | H, H | H | H | NHS(O)$_2$Me |
| 26 | cyclopropyl | H | H, H | H | H | NHC(O)Me |
| 28 | cyclopropyl | H | 6-OMe, H | H | H | NHC(O)O-tBu |
| 29 | cyclopropyl | H | 6-OMe, H | H | H | NHC(O)O-tBu |
| 30 | Et-cyclopropyl | H | 6-OMe, H | H | H | NHC(O)O-tBu |

TABLE 7-continued

| | | | | | |
|---|---|---|---|---|---|
| 31 | cyclopropyl | H | 6-OMe, H | H | H | NHC(O)O-iPr |
| 32 | cyclopropyl | H | 6-OMe, H | H | H | NHC(O)O-neopentyl |
| 33 | cyclopropyl | H | 6-OMe, H | H | H | NHC(O)NH-cyclopentyl |
| 34 | cyclopropyl | H | 6-OMe, H | H | H | NHC(O)NH-tBu |
| 35 | 1-methylcyclopropyl | H | 6-OMe, H | H | H | NHC(O)O-iPr |
| 36 | 1-methylcyclopropyl | H | 6-OMe, H | H | H | NHC(O)NH-cyclopentyl |
| 37 | 1-ethylcyclopropyl | H | 6-OMe, H | H | H | NHC(O)O-iPr |
| 38 | 1-ethylcyclopropyl | H | 6-OMe, H | H | H | NHC(O)NH-cyclopentyl |
| 39 | cyclopropyl | H | 6-OMe, H | H | H | NHC(O)OC(CH3)2CF3 |
| 40 | cyclopropyl | H | 6-OMe, H | H | H | NHC(O)OC(CH3)2CH2Cl |

TABLE 7-continued
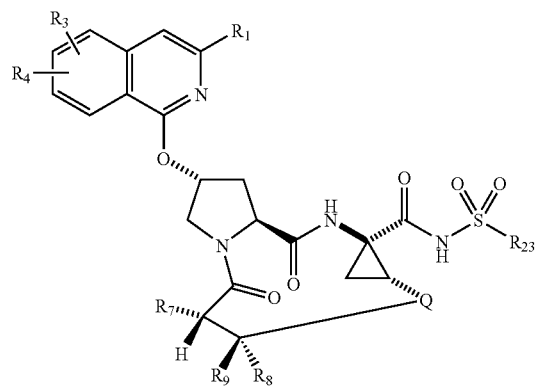
| | | | | | |
|---|---|---|---|---|---|
| 41 | cyclopropyl-Me | H | 6-OMe, H | H | H | NHC(O)O-iPr |
| 42 | cyclopropyl-Me | H | 6-OMe, H | H | H | NHC(O)O-neopentyl |
| 43 | cyclopropyl-Me | H | 6-OMe, H | H | H | NHC(O)NH-cyclopentyl |
| 44 | cyclopropyl-Et | H | 6-OMe, H | H | H | NHC(O)O-iPr |
| 45 | cyclopropyl-Et | H | 6-OMe, H | H | H | NHC(O)O-neopentyl |
| 46 | cyclopropyl-Et | H | 6-OMe, H | H | H | NHC(O)NH-cyclopentyl |
| 47 | cyclopropyl-Et | H | 6-OMe, H | H | H | NHC(O)O-tBu |
| 48 | cyclopropyl-Et | H | 6-OMe, H | H | H | NHC(O)O-tBu |
| 49 | cyclopropyl-Me | H | 6-OMe, H | H | H | NHC(O)O-tBu |

TABLE 7-continued
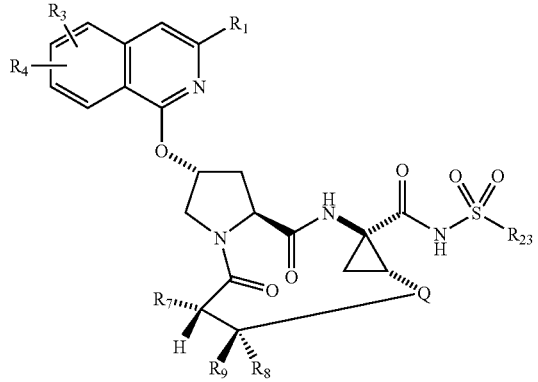

TABLE 7-continued
| 60 | 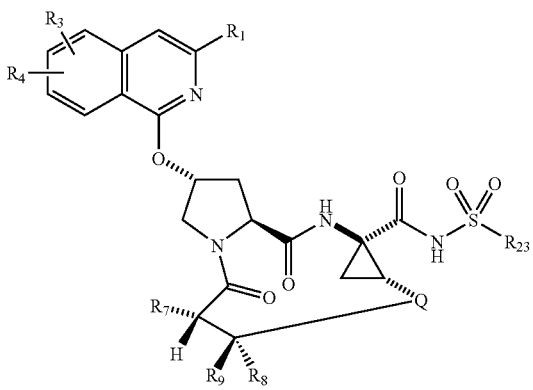 | 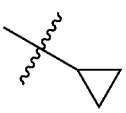 6-OMe, H | 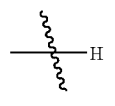 H | 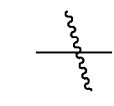 H | 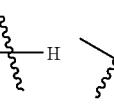 |
| --- | --- | --- | --- | --- | --- |
| 62 | 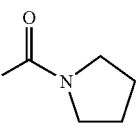 | 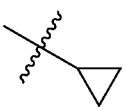 6-OMe, H | 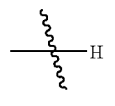 Me | 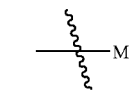 H | 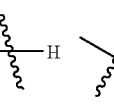 |
| 63 | 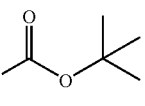 | 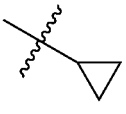 6-OMe, H | 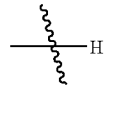 Me | 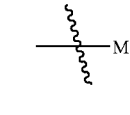 H | 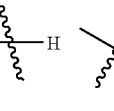 |
| 64 | 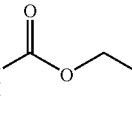 | 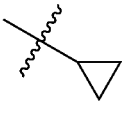 6-OMe, H | 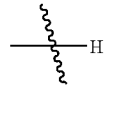 Me | 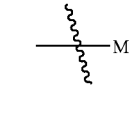 H | 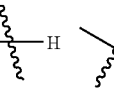 |
| 65 | 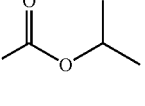 | 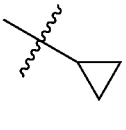 6-OMe, H | 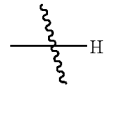 Me | 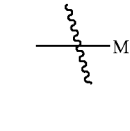 H | 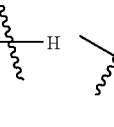 |
| 66 | 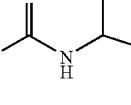 |  6-OMe, H | 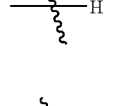 Me | 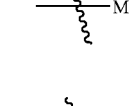 H |  |
| 67 | 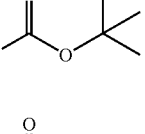 |  6-OMe, H | 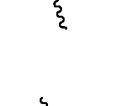 Me | 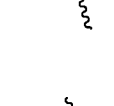 H |  |
| 68 | 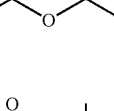 |  6-OMe, H | 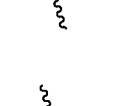 Me | 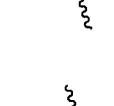 H |  |
| 69 | 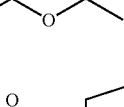 | 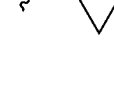 6-OMe, H |  Me |  H |  |

TABLE 7-continued

| # | R₇ | R₃,R₄ | R₈ | R₉ | R₂₃ |
|---|----|-------|----|----|-----|
| 70 | cyclopropyl-CH₂-Me | H | Me | H | NHC(O)O-tBu |
| 71 | cyclopropyl-CH₂-Me | 6-OMe, H | Me | H | NHC(O)O-CH₂C(Me)₃ |
| 72 | cyclopropyl-CH₂-Me | 6-OMe, H | Me | H | NHC(O)O-iPr |
| 73 | cyclopropyl-CH₂-Me | 6-OMe, H | Me | H | NHC(O)NH-cyclopentyl |
| 74 | cyclopropyl | 6-OMe, H | H | H | NHC(O)O-iPr |
| 75 | cyclopropyl | 6-OMe, H | H | H | NHC(O)O-CH₂C(Me)₃ |
| 76 | cyclopropyl | 6-OMe, 7-Cl | cyclobutyl | H | NHC(O)O-tBu |
| 77 | cyclopropyl | 5-OMe, H | H | H | NHC(O)O-tBu |
| 78 | cyclopropyl | 5-Cl, H | H | H | NHC(O)O-tBu |

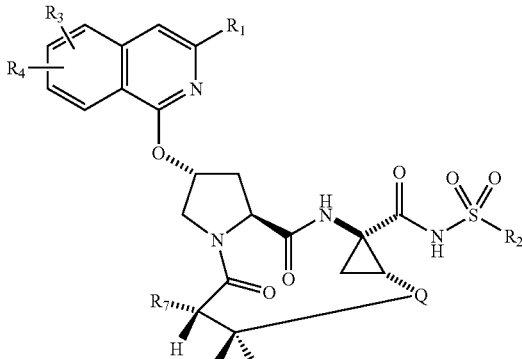

TABLE 7-continued

| # | | | | | |
|---|---|---|---|---|---|
| 91 | cyclopropyl | Ph | 6-OMe, H | H | H | NHC(O)O-tBu |
| 92 | cyclopropyl | Ph | 6-OMe, H | H | H | NHC(O)NH-tBu |
| 93 | cyclopropyl | Ph | 6-OMe, H | H | H | NHC(O)-pyrrolidinyl |
| 94 | cyclopropyl | Ph | 6-OMe, H | H | H | NHC(O)O-cyclopentyl |
| 95 | cyclopropyl | Ph | 6-OMe, H | H | H | NHC(O)O-neopentyl |
| 96 | cyclopropyl | Ph | 6-OMe, H | H | H | NHC(O)O-iPr |
| 97 | cyclopropyl | Ph | 6-OMe, H | H | H | NHC(O)O-tBu |
| 98 | cyclopropyl | Ph | 6-OMe, H | H | H | NHC(O)O-iPr |
| 99 | cyclopropyl | Ph | 6-OMe, H | H | H | NHC(O)O-cyclopentyl |

TABLE 7-continued

| | | | | | |
|---|---|---|---|---|---|
| 100 | cyclopropyl | Ph | 6-OMe, H | H | H | NHC(O)-pyrrolidine |
| 101 | cyclopropyl | Ph | 6-OMe, H | H | H | NHC(O)NH-cyclopentyl |
| 102 | cyclopropyl | Ph | 6-OMe, H | H | H | NHC(O)NH-t-Bu |
| 103 | cyclopropyl | Ph | 6-OMe, H | H | H | NHC(O)O-neopentyl |
| 104 | cyclopropyl | Ph | 6-OMe, H | H | H | NHC(S)NH-cyclopropyl |
| 105 | cyclopropyl | Ph | 6-OMe, H | H | H | NHC(O)NH-(4-CN-phenyl) |
| 106 | cyclopropyl | Ph | 6-OMe, H | H | H | NHC(O)-(2-oxoimidazolidin-1-yl) |

TABLE 7-continued
| | | | | | |
|---|---|---|---|---|---|
| 107 | 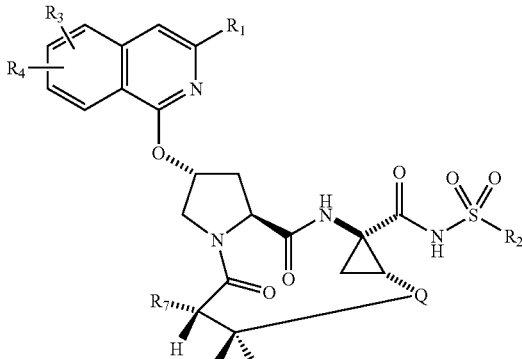 | 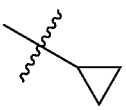 | 6-OMe, H | —H  —H | 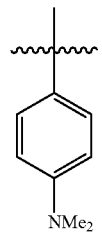 |
| 108 | 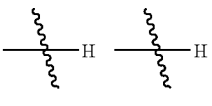 | 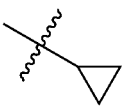 | 6-OMe, H | —H  —H | 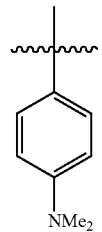 |
| 109 | 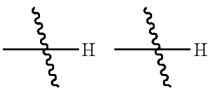 | 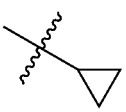 | 6-OMe, H | —H  —H | 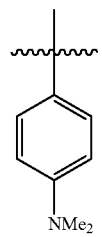 |
| 110 | 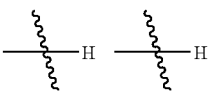 | 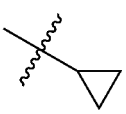 | 6-OMe, H | —H  —H | 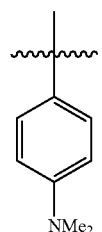 |
| 111 | 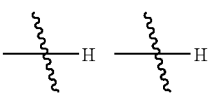 | 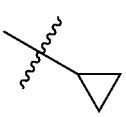 | 6-OMe, H | —H  —H | 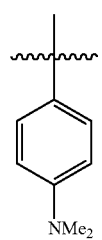 |

TABLE 7-continued

TABLE 7-continued

| # | | | | | |
|---|---|---|---|---|---|
| 118 | cyclopropyl | H, H | H | H | NHC(O)SEt |
| 119 | cyclopropyl | H, H | H | H | NHCHO |
| 120 | cyclopropyl | H, H | H | H | NH-CH=CH-C(O)CH₃ |
| 121 | cyclopropyl-Me | 6-OMe, H | H | H | NHC(O)O-tBu |
| 122 | cyclopropyl | H, H | H | H | NHC(O)OCH₂-(1-methylcyclopropyl) |
| 123 | cyclopropyl | H, H | H | H | NHC(O)OC(CH₃)₂C(O)CH₃ |
| 124 | cyclopropyl | H, H | H | H | NHC(O)OC(CH₃)₂CCl₃ |
| 125 | cyclopropyl | H, H | H | H | NHC(O)OC(CH₃)₂Et |
| 126 | cyclopropyl | H, H | H | H | NHC(O)NH-tBu |
| 127 | cyclopropyl | H, H | H | H | NHC(O)NH-cyclopentyl |

TABLE 7-continued

| # | | | | | | |
|---|---|---|---|---|---|---|
| 128 | cyclopropyl | H | H, H | H | H | NH-C(O)-NH-iPr |
| 129 | cyclopropyl | H | H, H | H | H | NH-C(O)-NH-C(CH3)2CH2C(CH3)3 |
| 130 | cyclopropyl | H | 5-Cl, H | H | H | NH-C(O)-O-tBu |
| 131 | cyclopropyl | H | 6-OMe, 7-Cl | H | H | NH-C(O)-O-tBu |
| 132 | cyclopropyl | H | 5-F, 6-OMe | H | H | NH-C(O)-O-tBu |
| 133 | cyclopropyl | H | 5-OMe, H | H | H | NH-C(O)-O-tBu |
| 134 | cyclopropyl | H | 5,6-dimethoxy | H | H | NH-C(O)-O-tBu |
| 135 | cyclopropyl | H | 6-OMe, H | H | H | NH-C(O)-NH-tBu |
| 136 | cyclopropyl | H | 6-OMe, H | H | H | NH-C(O)-NH-cyclopentyl |

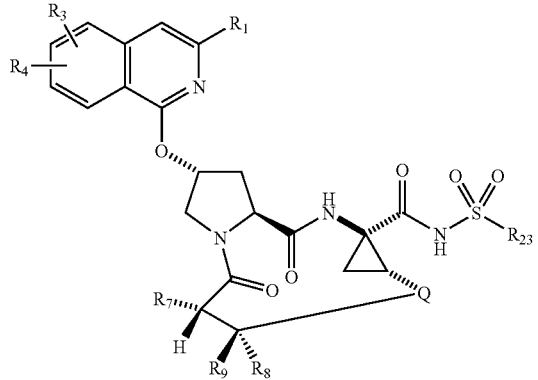

TABLE 7-continued
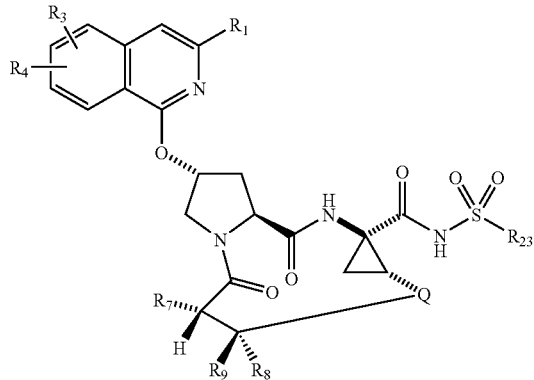

TABLE 7-continued
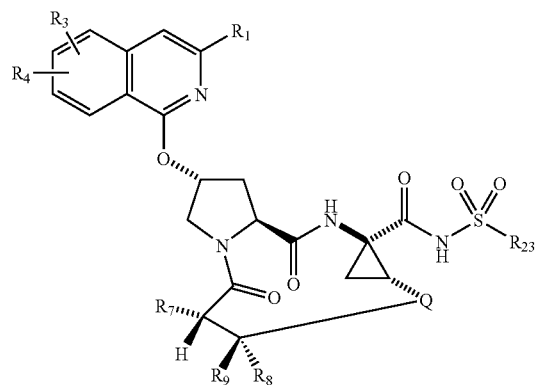
| | | | | |
|---|---|---|---|---|
| 5 | | | D | C |
| 6 | | | D | D |
| 7 | | | D | D |
| 8 | | | D | D |
| 9 | | | D | D |
| 10 | | | D | D |
| 11 | | | D | C |
| 12 | | | D | D |

TABLE 7-continued
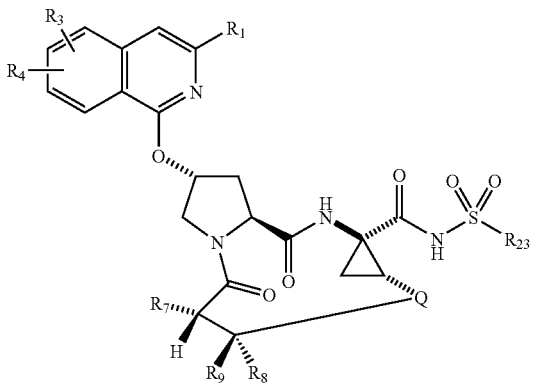
| | | | | |
|---|---|---|---|---|
| 13 | 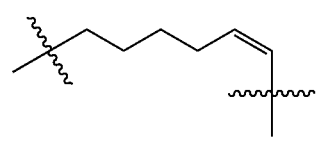 | | D | D |
| 14 | 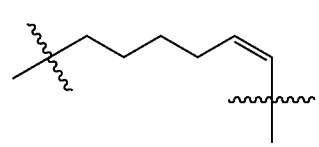 | | D | D |
| 15 | 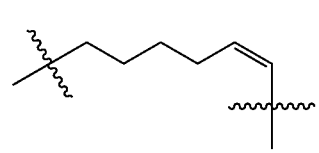 | | D | D |
| 16 | 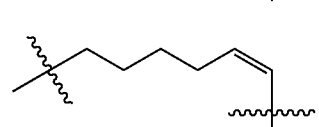 | | D | D |
| 17B | 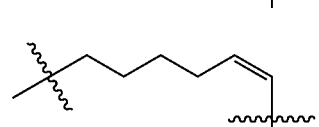 | | D | D |
| 18B | 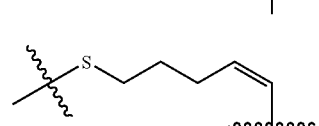 | | D | D |
| 19 | 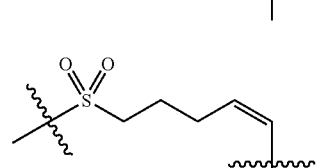 | | D | C |
| 20 | 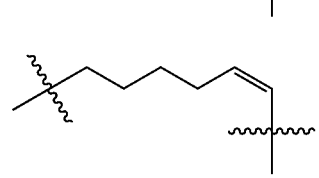 | | D | D |

TABLE 7-continued
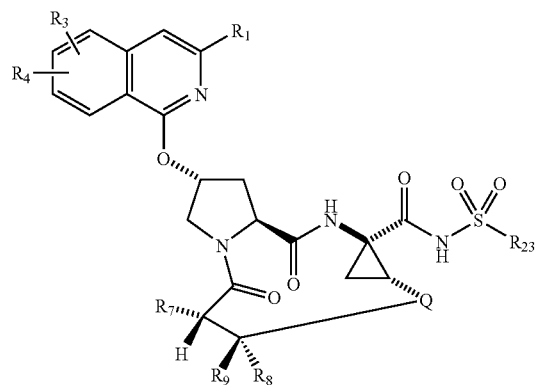
| | | | | |
|---|---|---|---|---|
| 21 | | | D | C |
| 22 | | | D | D |
| 23 | | | D | D |
| 24 | | | D | C |
| 25 | | | D | B |
| 26 | | | D | C |
| 28 | | | D | D |
| 29 | | | D | D |

TABLE 7-continued
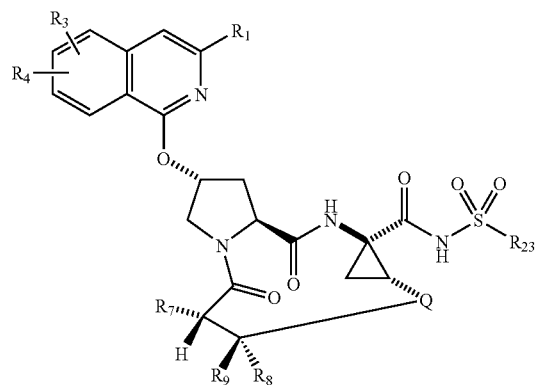
| | | | | |
|---|---|---|---|---|
| 30 | ~~~CH2-O-CH2-CH=CH~~~ | | D | D |
| 31 | ~~~CH2-O-CH2-CH=CH~~~ | | D | D |
| 32 | ~~~CH2-O-CH2-CH=CH~~~ | | D | D |
| 33 | ~~~CH2-O-CH2-CH=CH~~~ | | D | D |
| 34 | ~~~CH2-O-CH2-CH=CH~~~ | | D | D |
| 35 | ~~~CH2-O-CH2-CH=CH~~~ | | D | D |
| 36 | ~~~CH2-O-CH2-CH=CH~~~ | | D | D |
| 37 | ~~~CH2-O-CH2-CH=CH~~~ | | D | D |

TABLE 7-continued
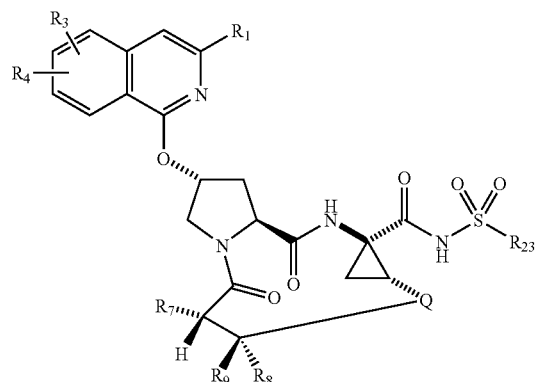
| | | | | |
|---|---|---|---|---|
| 38 | ~O~ | | D | D |
| 39 | ~O~ | | D | D |
| 40 | ~O~ | | D | C |
| 41 | ~S~ | | D | D |
| 42 | ~S~ | | D | D |
| 43 | ~S~ | | D | D |
| 44 | ~S~ | | D | D |
| 45 | ~S~ | | D | D |

TABLE 7-continued
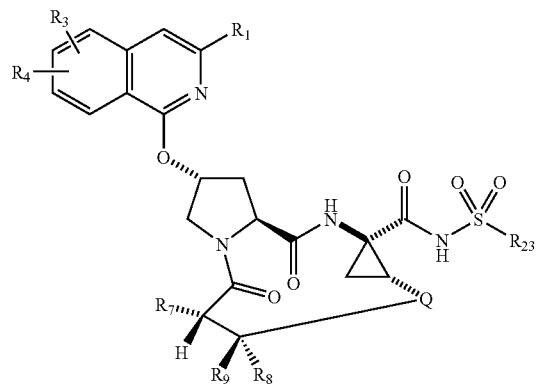
| | | | | |
|---|---|---|---|---|
| 46 | | S-CH2CH2CH=CH- | D | D |
| 47 | | S(O)-CH2CH2CH=CH- | D | D |
| 48 | | S(O)2-CH2CH2CH=CH- | D | C |
| 49 | | S(O)2-CH2CH2CH2CH=CH- | C | B |
| 50 | | -CH2CH2CH2CH2CH=CH- | D | D |
| 51 | | -CH2CH2CH2CH2CH=CH- | D | D |
| 52 | | -CH2CH2CH2CH2CH2CH=CH- | D | D |

TABLE 7-continued
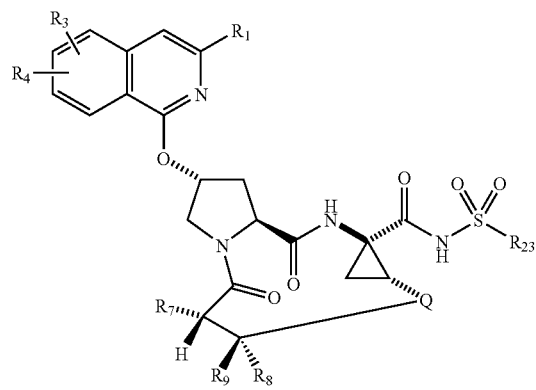
| | | | | |
|---|---|---|---|---|
| 53 | | | D | D |
| 54 | | | D | D |
| 55 | | | D | D |
| 56 | | | D | D |
| 57 | | | D | D |
| 58 | | | D | D |
| 59 | | | D | D |
| 60 | | | D | D |

TABLE 7-continued
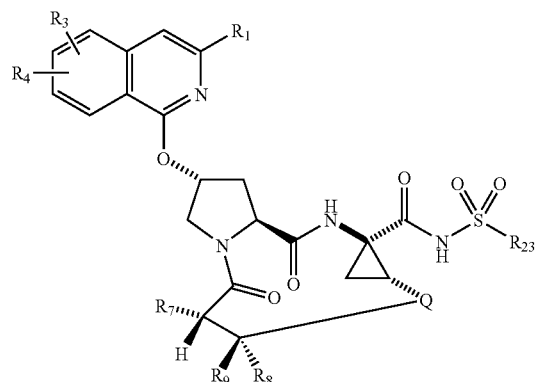
| | | | | |
|---|---|---|---|---|
| 62 | ⸝O⸝⸝⸝⸝⸝ | | D | C |
| 63 | ⸝O⸝⸝⸝⸝⸝ | | D | C |
| 64 | ⸝O⸝⸝⸝⸝⸝ | | D | C |
| 65 | ⸝O⸝⸝⸝⸝⸝ | | D | D |
| 66 | ⸝O⸝⸝⸝⸝⸝ | | D | C |
| 67 | ⸝O⸝⸝⸝⸝⸝ | | D | C |
| 68 | ⸝O⸝⸝⸝⸝⸝ | | D | C |
| 69 | ⸝O⸝⸝⸝⸝⸝ | | D | D |

TABLE 7-continued
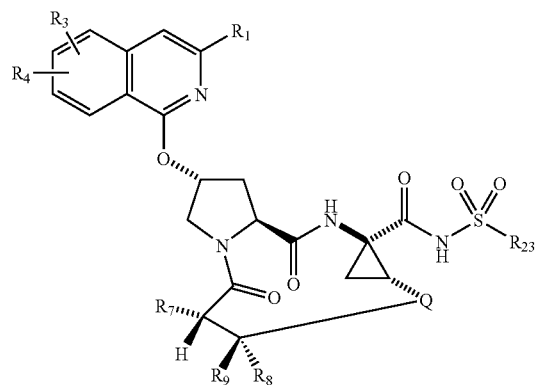
| | | | | |
|---|---|---|---|---|
| 70 | | | D | C |
| 71 | | | D | C |
| 72 | | | D | C |
| 73 | | | D | C |
| 74 | | | D | D |
| 75 | | | D | D |
| 76 | | | D | D |
| 77 | | | D | D |

TABLE 7-continued
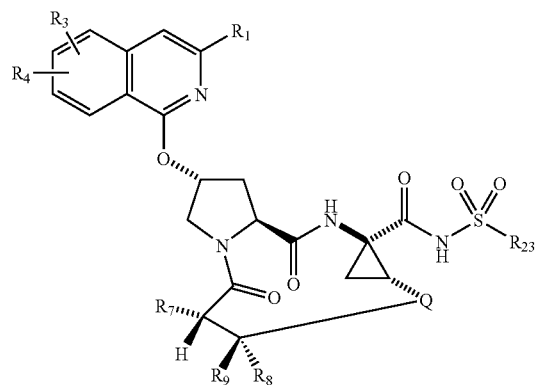
| | | | | |
|---|---|---|---|---|
| 78 | S-CH2CH2CH=CH- | | D | D |
| 80 | S-CH2CH2CH=CH- | | D | C |
| 81 | S-CH2CH2CH=CH- | | D | C |
| 82 | S-CH2CH2CH=CH- | | D | C |
| 83 | S-CH2CH2CH=CH- | | B | A |
| 85 | O-CH2CH2CH=CH- | | D | D |
| 86 | O-CH2CH2CH=CH- | | D | D |
| 87 | O-CH2CH2CH=CH- | | D | D |

TABLE 7-continued
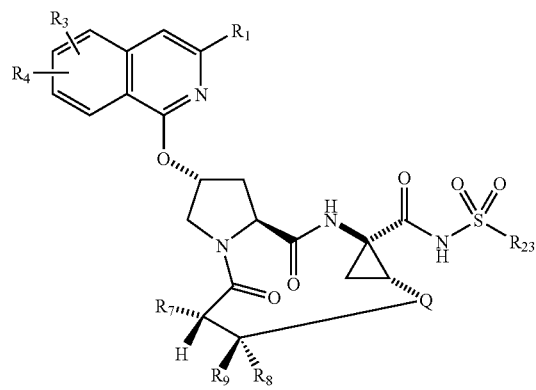
| | | | | |
|---|---|---|---|---|
| 88 | ~O~~~ | | D | D |
| 89 | ~O~~~ | | D | D |
| 90 | ~O~~~ | | D | D |
| 91 | ~O~~~ | | D | D |
| 92 | ~O~~~ | | D | D |
| 93 | ~O~~~ | | D | D |
| 94 | ~O~~~ | | D | D |
| 95 | ~O~~~ | | D | D |

TABLE 7-continued
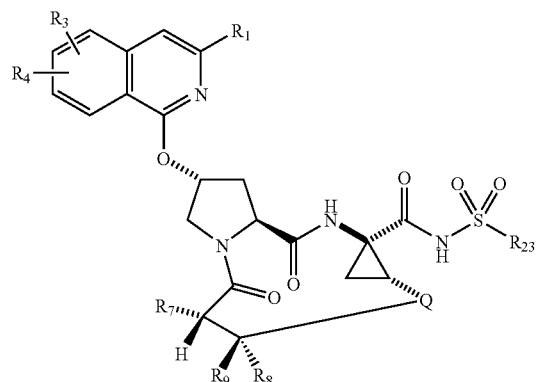
| | | | | |
|---|---|---|---|---|
| 96 | (structure) | | D | D |
| 97 | (structure) | | D | D |
| 98 | (structure) | | D | D |
| 99 | (structure) | | D | D |
| 100 | (structure) | | D | D |
| 101 | (structure) | | D | D |
| 102 | (structure) | | D | D |
| 103 | (structure) | | D | D |

TABLE 7-continued
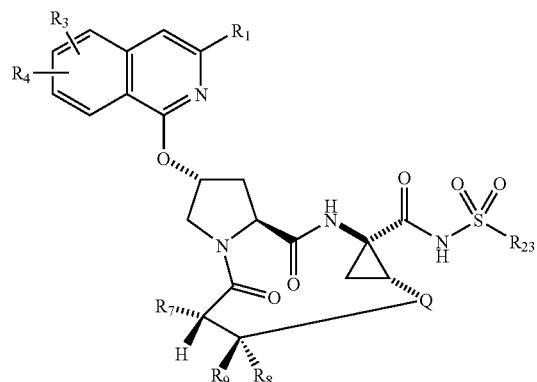
| 104 | 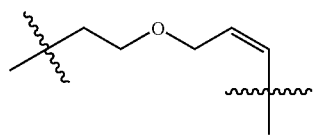 | D | C |
| 105 | 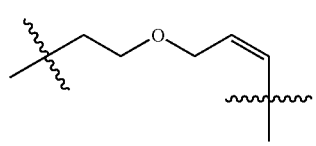 | D | C |
| 106 | 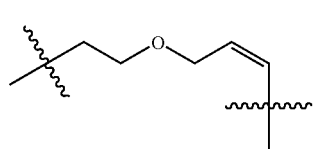 | D | B |
| 107 | 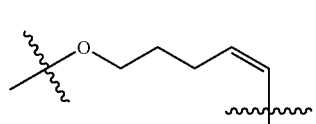 | D | D |
| 108 | 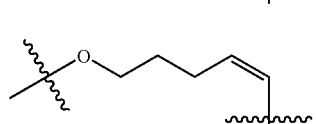 | D | D |
| 109 | 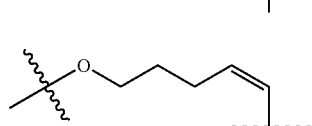 | D | D |
| 110 | 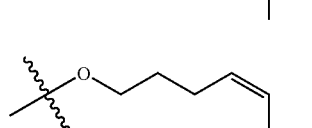 | D | D |
| 111 | 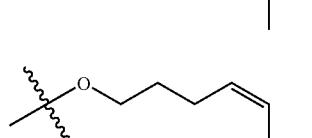 | D | D |

TABLE 7-continued
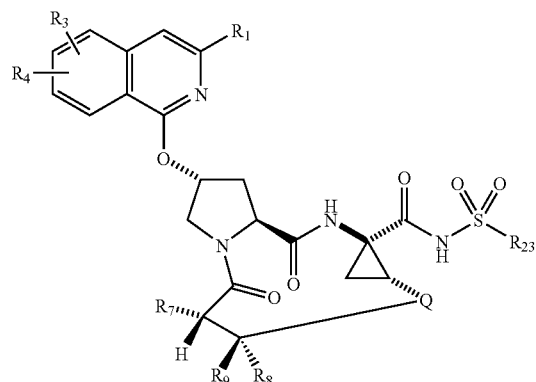
| | | | | |
|---|---|---|---|---|
| 112 | (CH2)2-O-CH2-CH=CH- | | D | D |
| 113 | (CH2)2-O-CH2-CH=CH- | | D | D |
| 114 | (CH2)2-O-CH2-CH=CH- | | D | D |
| 115 | S-(CH2)3-CH=CH- | | D | D |
| 116 | (CH2)4-CH=CH- | | D | D |
| 117 | S-(CH2)3-CH=CH- | | C | C |
| 118 | (CH2)4-CH=CH- | | D | D |
| 119 | (CH2)4-CH=CH- | | D | C |

TABLE 7-continued
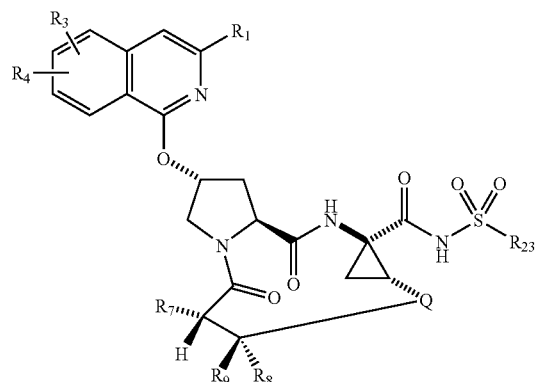
| | | | | |
|---|---|---|---|---|
| 120 | | | D | B |
| 121 | | | D | D |
| 122 | | | D | D |
| 123 | | | D | C |
| 124 | | | D | D |
| 125 | | | D | D |
| 126 | | | D | D |
| 127 | | | D | D |

TABLE 7-continued
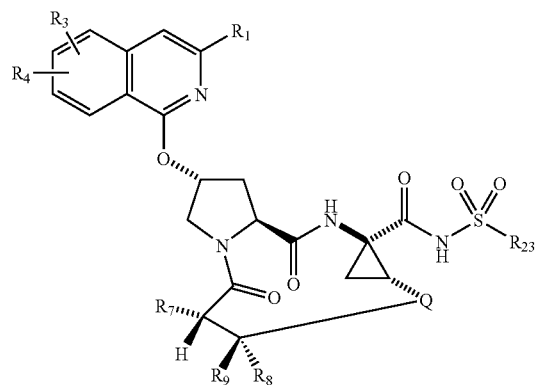
| 128 | | D | D |
| 129 | | D | D |
| 130 | | D | D |
| 131 | | D | D |
| 132 | | D | D |
| 133 | | D | D |
| 134 | | D | D |
| 135 | | D | D |

TABLE 7-continued
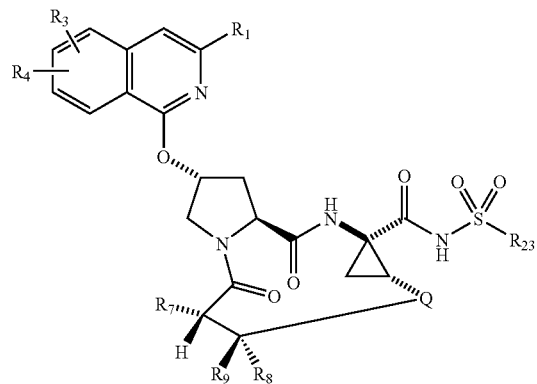
| | | | | |
|---|---|---|---|---|
| 136 | 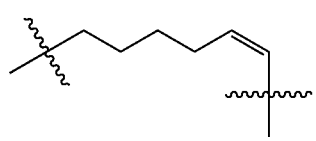 | | D | D |
| 137 | 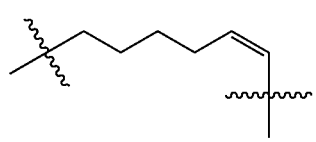 | | D | D |
| 138 | 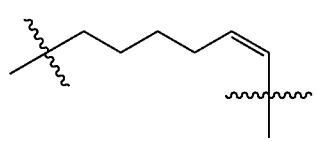 | | D | D |
| 139 | 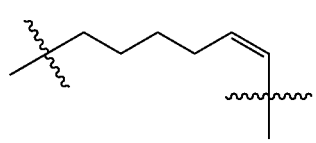 | | D | D |
| 141 | 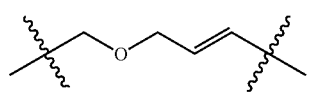 | | C | B |
| 142 | 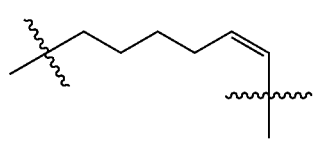 | | D | D |
| 145 | 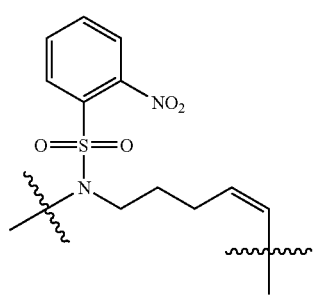 | | D | C |

TABLE 7-continued
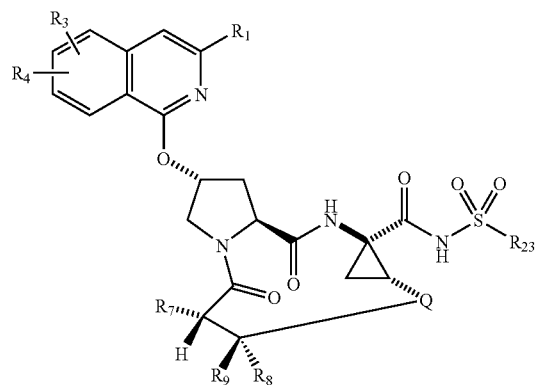
| | | | |
|---|---|---|---|
| 146 | 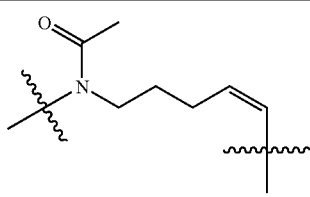 | D | B |
| 147 | 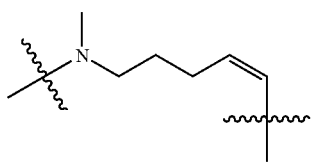 | D | D |
| 148 | 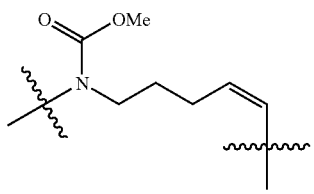 | D | C |
| 149 | 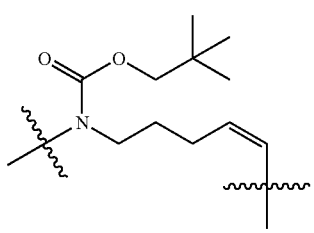 | D | C |
| 150 | 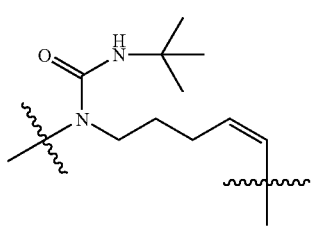 | D | C |
| 151 | 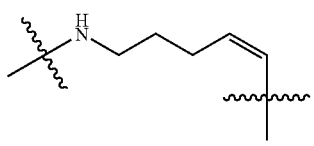 | D | C |

TABLE 7-continued

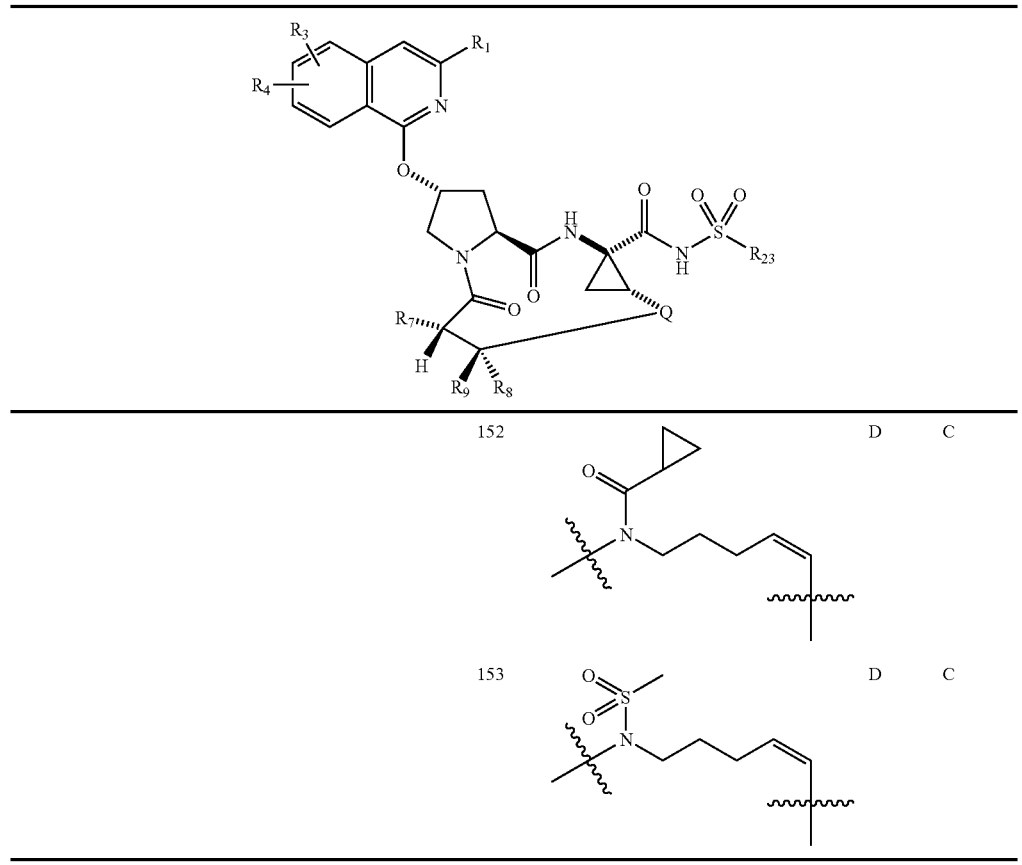

Combination Studies

Since clinical drug resistance often develops in viral infections following single-agent therapies, there is a need to assess the additive, antagonistic, or synergistic properties of combination therapies. We used the HCV replicon system, as described above, to assess the potential use of our NS3 protease macrocyclic inhibitor in combination therapies with Intron A and inhibitors targeting other HCV proteins. Three HCV antivirals, Intron A (recombinant Interferon alfa-2b) an HCV NS5A inhibitor having the following structure:

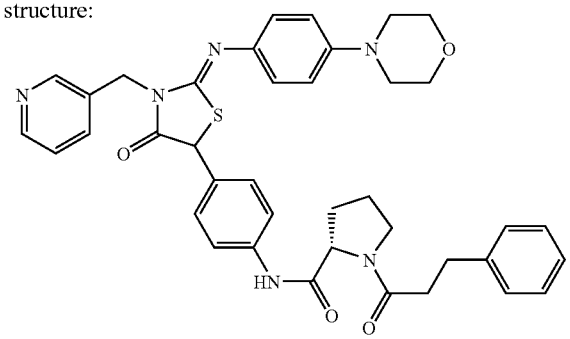

MS(ESI) m/z=691.2 (MH$^+$); HPLC rt 1.21 min; Purity (99%), and an NS5B replicase inhibitor (compound 2006; WO 03/010141), were tested in 2-drug combinations with the macrocyclic HCV NS3 protease inhibitor compound 28. In addition, compound 28 was also tested in 3-drug combinations with the NS5A and NS5B inhibitors.

For the experiments shown in Tables 8 and 9, inhibitors were tested at eleven concentrations each. 200× stock solutions of each inhibitor concentration were prepared by 2- or 3-fold dilution in DMSO prior to addition to cells/media. The drugs were tested as monotherapies and in combination with the NS3 protease inhibitor at various concentration ratios. Cells were exposed to compounds for 4 days and the amount of HCV inhibition was then determined using the FRET assay. The potential cytotoxicities of these combined agents were also analyzed in parallel by Alamar Blue staining. The $CC_{50}$ values for the compounds presented were greater than the highest tested inhibitor concentration. The degree of antagonism, additivity, or synergy was determined over a range of drug concentrations, and combination response curves were fit to assess the antiviral effects of the drug treatment combinations. The concentration ratios were analyzed using the method of Chou (Chou, Ting-Chao, and Rideout (Editors), (1991) *Synergism and Antagonism in Chemotherapy*, P. 61–101, Academic Press, New York). Tables 8 and 9 report the estimated $EC_{50}$ values for the compounds tested, as well as the combination indices (CI). All estimates were computed using SAS Proc NLIN, and a two-parameter logistic. All combination indices were tested for departure from additivity using isobologram methods. Asymptotic confidence intervals were also calculated for each of the combination indices. These intervals are used to test for departure from additivity by comparing the bounds to one—a lower bound of the interval greater than 1 indicates antagonism, an upper bound of less than 1 indicates synergism, and a value of 1 contained in the interval indicates additivity.

In addition to the combination index approach, above, the Universal Response Surface Approach (URSA) was also used to assess the antiviral effects of combinations of NS5A or NS5B inhibitors with the NS3 protease inhibitor. The experiments were conducted in a matrixed format with 8 concentrations of NS3 protease inhibitor crossed against 10 concentrations of NS5A or NS5B inhibitor on each of three plates. 200× stock solutions of each inhibitor concentration were prepared by 3-fold dilution in DMSO. Effects on replication were assessed in the HCV replicon system as described above. The data was analyzed using the URSA as described in Greco, Park and Rustum (Greco, Park, Sook, and Rustum (1990) *Application of a New Approach for the Quantitation of Drug Synergism to the Combination of cis-Diamminedichloroplatinum and 1-β-D-Arabinofuranosylcytosine*, Cancer Research, 50, 5318–5327). The interaction of the two drugs was assessed by using non-linear regression with a bisection algorithm. Seven parameters were estimated. These include the minimal response or response in the absence of drug, the maximal response or response in the presence of infinite drug, $EC_{50}$'s for the two drugs, slope parameters for the two drugs, and the drug interaction parameter α which provides the assessment of synergism, antagonism or additivity. Tables 10 and 11 present key estimated parameters and standard errors. Additivity is implied when α is equal to zero, synergy if the interaction parameter is larger than zero, and antagonism when the interaction parameter is less than zero. The confidence interval for the interaction parameter is also presented. This interval is used to test for departure from additivity by comparing the bounds to zero—a lower bound of the interval greater than zero indicates synergy, an upper bound of less than zero indicates antagonism, and a value of zero contained in the interval indicates additivity.

Compound 28

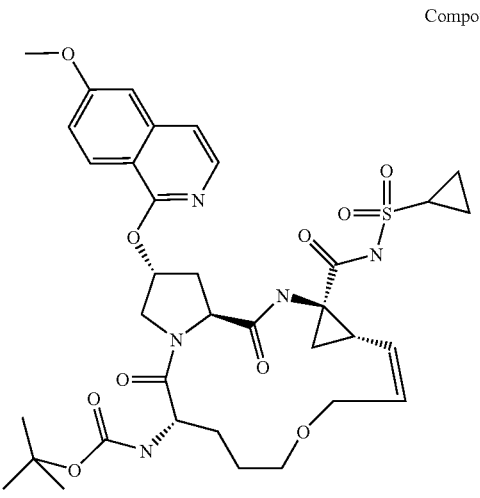

Protease Inhibitor

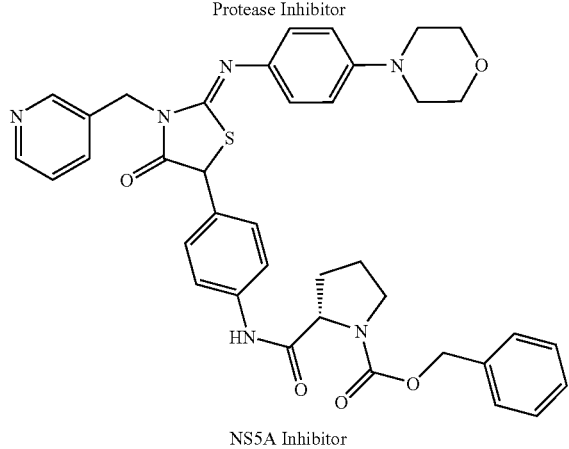

NS5A Inhibitor

-continued

Compound Y, WO 03/010141

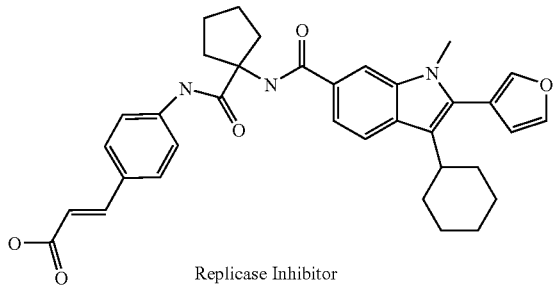

Replicase Inhibitor

Table 8 summarizes data from combinations of compound 28 with Intron A. $EC_{50}$ values for each monotherapy are also presented. In two experiments, combination of compound 28 with Intron-A yielded either synergistic or additivity effects at the 75%, 90, and 95% effective doses.

The effects of compound 28 in combination with the HCV NS5A inhibitor are summarized in Table 9. Synergy or additivity was observed in two experiments at the 75, 90, and 95% effective doses of compound 28. Importantly, no drug antagonism was observed at the 75, 90, or 95% effective doses when compound 28 was combined with the HCV NS5A inhibitor, or Interferon alfa-2b. Follow-up experiments using these same inhibitor combinations in the matrix format (Table 10) yielded results similar to the combination index experiments; additivity for the combination of the NS5A inhibitor with compound 28.

The matrix format was also used to examine the activity of combinations of the HCV NS5B inhibitor, with compound 28 (Table 11). In two experiments, overall additivity was observed.

Compound 28 was also tested in 3-drug combination experiments with the NS5A inhibitor and the NS5B inhibitor (Table 12). The starting concentrations for the mono-therapies consisted of a 0.667 μM solution of the NS5A inhibitor, a 0.3 μM solution of compound 28, and a 2.5 μM solution of the NS5B inhibitor. The starting concentration for the triple combination contained a mixture of ⅓ of each of the above concentrations. Dose response curves for all three mono-therapies and the triple combination therapy were obtained using 3-fold dilutions, and data analysis was carried out as described above for combination index experiments. Synergistic effects were observed using the triple combination. No drug antagonism was observed at the 75, 90, or 95% effective doses with the 3-drug combination.

These results demonstrate that combination treatment of replicon cells with the HCV NS3 protease inhibitor, compound 28 and Intron A, and/or inhibitors targeting HCV NS5A and/or NS5B, yield additive to synergistic antiviral effects. The ability to use these NS3 protease inhibitors in combination therapy can provide major advantages over single drug therapy for the treatment of HCV.

TABLE 8

Two Drug Combinations with Interferon alfa-2b

| Expt | NS3 protease inhibitor EC50, μM | Interferon alfa-2b EC50, units per ml | Molar ratio, NS3 protease inhibitor to Interferon alfa-2b | Combination Indices (confidence interval) 75% effective | 90% effective | 95% effective | Overall Result |
|---|---|---|---|---|---|---|---|
| 1 | 0.008 | 20 | 2:5 | 0.67 (0.53, 0.8) | 0.59 (0.4, 0.77) | 0.56 (0.33, 0.79) | Synergy |
|  |  |  | 1:1 | 0.57 (0.48, 0.66) | 0.5 (0.38, 0.62) | 0.46 (0.32, 0.61) | Synergy |
|  |  |  | 4:25 | 1.02 (0.88, 1.16) | 0.64 (0.5, 0.78) | 0.5 (0.36, 0.64) | Additivity at 75%; Synergy at 90, 95% |
| 2 | 0.01 | 51 | 2:5 | 0.59 (0.43, 0.74) | 0.38 (0.22, 0.54) | 0.28 (0.13, 0.43) | Synergy |
|  |  |  | 1:1 | 0.50 (0.44, 0.56) | 0.33 (0.27, 0.39) | 0.25 (0.19, 0.31) | Synergy |
|  |  |  | 4:25 | 1.03 (0.87, 1.19) | 0.65 (0.50, 0.81) | 0.48 (0.33, 0.63) | Additivity at 75%; Synergy at 90, 95% |

TABLE 9

Two Drug Combinations with an NS5A inhibitor

| Expt | NS3 protease inhibitor EC50, μM | NS5A inhibitor EC50, μM | Molar ratio, NS3 protease inhibitor to NS5A inhibitor | Combination Indices (confidence interval) 75% effective | 90% effective | 95% effective | Overall Result |
|---|---|---|---|---|---|---|---|
| 1 | 0.009 | 0.043 | 3:100 | 0.66 (0.47, 0.85) | 0.61 (0.35, 0.88) | 0.59 (0.27, 0.91) | Synergy |
|  |  |  | 3:250 | 0.57 (0.41, 0.73) | 0.62 (0.36, 0.89) | 0.66 (0.3, 1.02) | Additivity at 95%; Synergy at 75, 90% |
|  |  |  | 3:40 | 0.73 (0.55, 0.9) | 0.64 (0.43, 0.85) | 0.59 (0.34, 0.83) | Synergy |
| 2 | 0.011 | 0.005 | 1:5 | 1.1 (0.91, 1.3) | 1.15 (0.82, 1.47) | 1.18 (0.75, 1.61) | Additivity |
|  |  |  | 2:25 | 1.24 (1.0, 1.49) | 1.19 (0.81, 1.58) | 1.16 (0.67, 1.65) | Additivity |
|  |  |  | 1:2 | 1.0 (0.88, 1.14) | 0.83 (0.67, 1.0) | 0.73 (0.54, 0.92) | Additivit at 75%; Synergy at 90, 95% |

TABLE 10

Two Drug Combinations with an NS5A inhibitor: matrix studies

|  |  | Standard Error | Overall Result |
|---|---|---|---|
| Compound 28 EC50, μM | 0.009 | 0.52 |  |
| NS5A inhibitor EC50, μM | 0.008 | 0.46 |  |
| Interaction parameter alpha (confidence interval) | 0.63 (−0.09, 1.36) | 0.37 | Additivity |

TABLE 11

Two Drug Combinations with an NS5B inhibitor: matrix studies

| | Expt 1 | Standard Error | Overall Result | Expt 2 | Standard Error | Overall Result |
|---|---|---|---|---|---|---|
| Compound 28 EC50, μM | 0.015 | 0.53 | | 0.020 | 0.87 | |
| NS5B inhibitor EC50, μM | 0.059 | 2.63 | | 0.050 | 2.39 | |
| Interaction parameter alpha (confidence interval) | 0.47 (−0.05, 1.0) | 0.27 | Additivity | 0.31 (−0.22, 0.83) | 0.27 | Additivity |

TABLE 12

Three Drug Combination Studies

| Expt | NS3 Pr inhibitor EC50, μM | NS5A inhibitor EC50, μM | NS5B inhibitor EC50, μM | Molar ratio, NS3 protease inhibitor to NS5A inhibitor to NS5B inhibitor | NS5B inhibitor EC50, μM | Combination Indices (confidence interval) 75% effective | 90% effective | 95% effective | Overall Result |
|---|---|---|---|---|---|---|---|---|---|
| 1 | 0.008 | 0.005 | 0.052 | 9:20:75 | 0.052 | 0.78 (0.62, 0.94) | 0.7 (0.47, 0.93) | 0.65 (0.37, 0.93) | Synergy |
| 2 | 0.009 | 0.009 | 0.064 | 9:20:75 | 0.064 | 0.71 (0.6, 0.81) | 0.58 (0.44, 0.72) | 0.52 (0.36, 0.67) | Synergy |

Those skilled in the art will recognize that although the invention has been described above with respect to specific aspects, other aspects are intended to be within the scope of the claims which follow. All documents referenced herein are hereby incorporated by reference as if set out in full.

What is claimed is:

1. A compound of formula I:

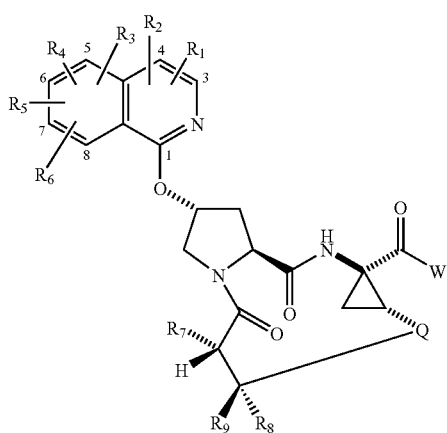

wherein:

(a) $R_1$, $R_2$, $R_3$, $R_4$, $R_5$ and $R_6$ are each independently H; $C_{1-6}$ alkyl; $C_{3-7}$ cycloalkyl; $C_{1-6}$ alkoxy; $C_{3-7}$ cycloalkoxy; halo-$C_{1-6}$ alkoxy; halo-$C_{1-6}$ alkyl; cyano; halo; hydroxyl; $C_{1-6}$ alkanoyl; nitro; amino; mono or di-($C_{1-6}$) alkyl amine; mono or di-($C_{3-7}$) cycloalkyl amine; mono or di-$C_{1-6}$ alkylamide; mono or di-($C_{3-7}$) cycloalkyl amide; carboxyl; ($C_{1-6}$) carboxyester; thiol; $C_{1-6}$ thioalkyl; $C_{1-6}$ alkylsulfoxide; $C_{1-6}$ alkylsulfone; $C_{1-6}$ alkylsulfonamide; $C_{6-10}$ aryl optionally substituted with Het; $C_{7-14}$ alkylaryl; $C_{6-10}$ aryloxy; $C_{7-14}$ alkylaryloxy; 4–7 membered monocyclic heteroaryloxy; or Het; said $R_1$ to $R_6$ optionally attached to the isoquinoline group by a $C_{1-6}$ alkyl linking group;

(b) $R_7$ is $NH_2$ or $-NR_{10}R_{11}$; wherein $R_{10}$ is $C_{1-6}$ alkyl, $C_{1-6}$ haloalkyl, C(O)—$NR_{12}R_{13}$, C(O)—$OR_{14}$, C(O)—$SR_{15}$, or —C(O)—$R_{16}$; $R_{11}$ is H, $C_{1-6}$ alkyl or $C_{1-6}$ haloalkyl, provided that if either $R_{12}$ or $R_{13}$ is H then $R_{11}$ is H; $R_{12}$ and $R_{13}$ are each independently H; $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; or aryl; and wherein $R_{12}$ and $R_{13}$ together with the nitrogen to which they are bonded can form a 4–7 membered heterocycle; $R_{14}$ and $R_{15}$ are each independently $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; aryl or Het; $R_{16}$ is H; $C_{1-6}$ alkyl, $C_{3-7}$ cycloalkyl or $C_{4-10}$ alkylcycloalkyl, each optionally substituted with halo, $C_{1-3}$ alkoxy, $C_{1-3}$ haloalkoxy, $C_{1-3}$ alkyl or $C_{1-3}$ haloalkyl; aryl or Het;

(c) $R_8$ and $R_9$ are each independently H or $C_{1-3}$ alkyl optionally substituted with halo, or $C_{1-3}$ alkoxy, or $C_{1-3}$ haloalkoxy;

(d) Q is a $C_{3-9}$ saturated or unsaturated chain optionally containing one to three heteroatoms independently selected from O, $S(O)_m$; wherein m is 0, 1 or 2, or NR$_{17}$, wherein R$_{17}$ is H; C$_{1-6}$ alkyl or C$_{1-6}$ cycloalkyl, each optionally substituted with halo, C$_{1-6}$ alkoxy, cyano or C$_{1-6}$ haloalkoxy; —C(O)—R$_{18}$, C(O)—OR$_{19}$, C(O)—NR$_{20}$R$_{21}$ or —SO$_2$R$_{22}$; R$_{18}$, R$_{20}$, and R$_{21}$ are each independently H; C$_{1-6}$ alkyl or C$_{1-6}$ cycloalkyl, each optionally substituted with halo, C$_{1-6}$ alkoxy, cyano or C$_{1-6}$ haloalkoxy; R$_{19}$ is C$_{1-6}$ alkyl or C$_{1-6}$ cycloalkyl, each optionally substituted with halo, C$_{1-6}$ alkoxy, cyano or C$_{1-6}$ haloalkoxy; R$_{22}$ is aryl, C$_{1-6}$ alkyl or C$_{1-6}$ cycloalkyl, each optionally substituted with halo, C$_{1-6}$ alkoxy, cyano or C$_{1-6}$ haloalkoxy; and (e) W is OH, —NH—SO$_n$—R$_{23}$, or NH—SO$_n$—R$_{24}$; wherein n is 1 or 2, R$_{23}$ is C$_{1-8}$ alkyl, C$_{4-10}$ alkylcycloalkyl, unsubstituted C$_{3-7}$ cycloalkyl, or cyclopropyl or cyclobutyl optionally substituted with C$_{7-9}$ alkylaryl or C$_{1-4}$ alkyl optionally substituted with halo, C$_{1-3}$ alkoxy, cyano, amine, mono or di-C$_{1-6}$ alkylamine, mono or di-C$_{1-6}$ alkylamide or carboxylate; and R$_{24}$ is C$_{6-10}$ aryl or Het;

or a pharmaceutically acceptable enantiomer, diastereomer, salt, solvate or prodrug thereof.

2. The compound of claim 1 wherein R$_1$ is bonded to the C$_3$ position and is selected from H; C$_{1-6}$ alkyl; C$_{3-7}$ cycloalkyl; C$_{1-6}$ alkoxy; C$_{3-7}$ cycloalkoxy; halo-C$_{1-6}$ alkoxy; halo-C$_{1-6}$ alkyl; cyano; halo; C$_{1-6}$ alkanoyl; mono or di-(C$_{1-6}$) alkyl amine; mono or di-C$_{1-6}$ alkylamide; carboxyl; C$_{6-10}$ aryl optionally substituted with Het; C$_{7-14}$ alkylaryl; C$_{6-10}$ aryloxy or Het.

3. The compound of claim 1 wherein R$_2$, R$_3$, and R$_4$ are bonded to the C$_4$, C$_5$ and C$_6$ positions, respectively, and are each independently selected from H; C$_{1-6}$ alkyl; C$_{3-7}$cycloalkyl; C$_{1-6}$ alkoxy; C$_{3-7}$ cycloalkoxy; halo-C$_{1-6}$ alkoxy; halo-C$_{1-6}$ alkyl; cyano; halo; hydroxyl; C$_{1-6}$ alkanoyl; mono or di-(C$_{1-6}$) alkyl amine; mono or di-(C$_{3-7}$) cycloalkyl amine; mono or di-C$_{1-6}$ alkylamide; mono or di-(C$_{3-7}$) cycloalkyl amide; carboxyl; C$_{6-10}$ aryl optionally substituted with Het; C$_{7-14}$ alkylaryl; C$_6$-l$_0$ aryloxy; or Het.

4. The compound of claim 1 wherein R$_5$ and R$_6$ are bonded to the C$_7$ and C$_8$ positions, respectively, and are each independently selected from H; C$_{1-3}$ alkyl; C$_{3-4}$ cycloalkyl; C$_{1-3}$ alkoxy; C$_{3-4}$ cycloalkoxy; halo-C$_{1-3}$ alkoxy; halo-C$_{1-3}$ alkyl; cyano; halo; hydroxyl; C$_{1-3}$ alkanoyl; mono or di-(C$_{1-3}$) alkyl amine; mono or di-(C$_{3-4}$) cycloalkyl amine; mono or di-C$_{1-3}$ alkylamide; mono or di-(C$_{3-4}$) cycloalkyl amide; or carboxyl.

5. The compound of claim 1 wherein Q is a C$_{3-9}$ saturated or unsaturated chain optionally containing one to three heteroatoms independently selected from O, S(O)$_m$; wherein m is 0, 1 or 2, or NR$_{17}$, wherein R$_{17}$ is H; C$_{1-6}$ alkyl, C$_{1-6}$ cycloalkyl, —C(O)—R$_{18}$, C(O)—OR$_{19}$, C(O)—NR$_{20}$R$_{21}$ or —SO$_2$R$_{22}$.

6. The compound of claim 5 wherein R$_{18}$, R$_{20}$, and R$_{21}$ are each independently H; C$_{1-6}$ alkyl or C$_{1-6}$ cycloalkyl; R$_{19}$ is C$_{1-6}$ alkyl or C$_{1-6}$ cycloalkyl; and R$_{22}$ is aryl, C$_{1-6}$ alkyl or C$_{1-6}$ cycloalkyl, each optionally substituted with halo.

7. The compound of claim 1 wherein W is OH, —NH—SO$_n$—R$_{23}$, or NH—SO$_n$—R$_{24}$ wherein n is 1 or 2, R$_{23}$ is unsubstituted C$_{3-7}$ cycloalkyl, or cyclopropyl or cyclobutyl optionally substituted with C$_{7-9}$ alkylaryl or C$_{1-4}$ alkyl; and R$_{24}$ is C$_{6-10}$ aryl or Het.

8. A compound of formula II:

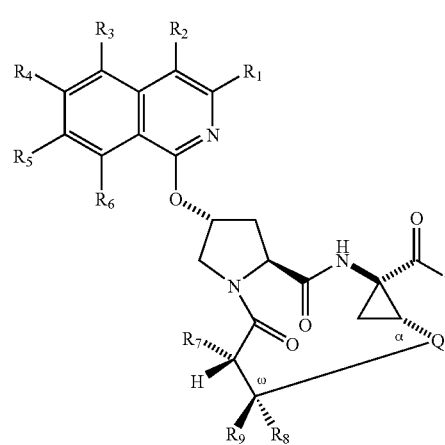

II wherein:
(a) R$_1$ is H; C$_{1-6}$ alkyl; C$_{3-7}$ cycloalkyl; C$_{1-6}$ alkoxy; C$_{3-7}$ cycloalkoxy; halo-C$_{1-6}$ alkoxy; halo-C$_{1-6}$ alkyl; cyano; halo; C$_{1-6}$ alkanoyl; mono or di-(C$_{1-6}$) alkyl amine; mono or di-C$_{1-6}$ alkylamide; carboxyl; C$_{6-10}$ aryl optionally substituted with Het; C$_{7-14}$ alkylaryl; C$_{6-10}$ aryloxy or Het; said R$_1$ optionally attached to the isoquinoline group by a C$_{1-6}$ alkyl linking group; R$_2$, R$_3$, and R$_4$ are each independently H; C$_{1-6}$ alkyl; C$_{3-7}$ cycloalkyl; C$_{1-6}$ alkoxy; C$_{3-7}$ cycloalkoxy; halo-C$_{1-6}$ alkoxy; halo-C$_{1-6}$ alkyl; cyano; halo; hydroxyl; C$_{1-6}$ alkanoyl; mono or di-(C$_{1-6}$) alkyl amine; mono or di-(C$_{3-7}$) cycloalkyl amine; mono or di-C$_{1-6}$ alkylamide; mono or di-(C$_{3-7}$) cycloalkyl amide; carboxyl; C$_{6-10}$ aryl optionally substituted with Het; C$_{7-14}$ alkylaryl; C$_{6-10}$ aryloxy; or Het; said R$_2$ to R$_4$ optionally attached to the isoquinoline group by a C$_{1-3}$ alkyl linking group; R$_5$ and R$_6$ are each independently H; C$_{1-3}$ alkyl; C$_{3-4}$ cycloalkyl; C$_{1-3}$ alkoxy; C$_{3-4}$ cycloalkoxy; halo-C$_{1-3}$ alkoxy; halo-C$_{1-3}$ alkyl; cyano; halo; hydroxyl; C$_{1-3}$ alkanoyl; mono or di-(C$_{1-3}$) alkyl amine; mono or di-(C$_{3-4}$) cycloalkyl amine; mono or di-C$_{1-3}$ alkylamide; mono or di-(C$_{3-4}$) cycloalkyl amide; or carboxyl;

(b) R$_7$ is NH$_2$ or —NR$_{10}$R$_{11}$; wherein R$_{10}$ is C$_{1-6}$ alkyl, C$_{1-6}$ haloalkyl, C(O)—NR$_{12}$R$_{13}$, C(O)—OR$_{14}$, or —C(O)—R$_{16}$; R$_{11}$ is H, C$_{1-6}$ alkyl or C$_{1-6}$ haloalkyl, provided that if either R$_{12}$ or R$_{13}$ is H then R$_{11}$ is H; R$_{12}$ and R$_{13}$ are each independently H; C$_{1-6}$ alkyl, C$_{3-7}$ cycloalkyl or C$_{4-10}$ alkylcycloalkyl, each optionally substituted with halo, C$_{1-3}$ alkoxy, C$_{1-3}$ haloalkoxy, C$_{1-3}$ alkyl or C$_{1-3}$ haloalkyl; and wherein R$_{12}$ and R$_{13}$ together with the nitrogen to which they are bonded can form a 4–7 membered heterocycle; R$_{14}$ and R$_{15}$ are each independently C$_{1-6}$ alkyl, C$_{3-7}$ cycloalkyl or C$_{4-10}$ alkylcycloalkyl, each optionally substituted with halo, C$_{1-3}$ alkoxy, C$_{1-3}$ haloalkoxy, C$_{1-3}$ alkyl or C$_{1-3}$ haloalkyl; R$_{16}$ is H; C$_{1-6}$ alkyl, C$_{3-7}$ cycloalkyl or C$_{4-10}$ alkylcycloalkyl, each optionally substituted with halo, C$_{1-3}$ alkoxy, C$_{1-3}$ haloalkoxy, C$_{1-3}$ alkyl or C$_{1-3}$ haloalkyl; aryl or Het;

(c) R$_8$ and R$_9$ are each independently H or C$_{1-3}$ alkyl optionally substituted with halo, or C$_{1-3}$ alkoxy, or C$_{1-3}$ haloalkoxy;

(d) Q is a C$_{3-9}$ saturated or unsaturated chain optionally containing one to three heteroatoms independently selected from O, S(O)$_m$; wherein m is 0, 1 or 2, or NR$_{17}$, wherein R$_{17}$ is H; C$_{1-6}$ alkyl, C$_{1-6}$ cycloalkyl, —C(O)—R$_{18}$, C(O)—OR$_{19}$, C(O)—NR$_{20}$R$_{21}$ or —SO$_2$R$_{22}$; R$_{18}$, R$_{20}$, and R$_2$, are each independently H; C$_{1-6}$ alkyl or C$_{1-6}$ cycloalkyl; R$_{19}$ is C$_{1-6}$ alkyl or C$_{1-6}$ cycloalkyl; R$_{22}$ is aryl, C$_{1-6}$ alkyl or C$_{1-6}$ cycloalkyl, each optionally substituted with halo; and (e) W is OH, —NH—SO$_n$—R$_{23}$ or NH—SO$_n$—R$_{24}$ wherein n is 1 or 2, R$_{23}$ is unsubstituted C$_{3-7}$ cycloalkyl, or cyclopropyl or cyclobutyl optionally substituted with C$_{7-9}$ alkylaryl or C$_{1-4}$ alkyl; and R$_{24}$ is C$_{6-10}$ aryl or Het;

or a pharmaceutically acceptable enantiomer, diastereomer, salt, solvate or prodrug thereof.

9. The compound of claim 8 wherein R$_1$ is H; C$_{1-3}$ alkoxy; mono or di-(C$_{1-6}$) alkyl amine; a 5 or 6 membered monocyclic heterocycle; or C$_{6-10}$ aryl optionally substituted with a 5 or 6 membered monocyclic heterocycle.

10. The compound of claim 8 wherein R$_2$, R$_3$, R$_4$ and R$_5$ are each independently H; C$_{1-6}$ alkoxy; halo-C$_{1-6}$ alkoxy; hydroxyl; or mono or di-(C$_{1-6}$) alkyl amine.

11. The compound of claim 8 wherein R$_7$ is NH$_2$ or —NHR$_{10}$; wherein R$_{10}$ is C(O)—NR$_{12}$R$_{13}$, or C(O)—OR$_{14}$; and R$_{12}$ and R$_{13}$ are C$_{1-6}$ alkyl optionally substituted with halo; and R$_{14}$ is C$_{1-6}$ alkyl or C$_{3-7}$ cycloalkyl optionally substituted with halo.

12. The compound of claim 8 wherein Q is a C$_{5-7}$ membered chain having one double bond optionally containing one heteroatom independently selected from O, S(O)$_m$; wherein m is 0, 1 or 2, or NR$_{17}$, wherein R$_{17}$ is H; C$_{1-6}$ alkyl or C$_{1-6}$ cycloalkyl.

13. The compound of claim 8 wherein Q has the following structure:

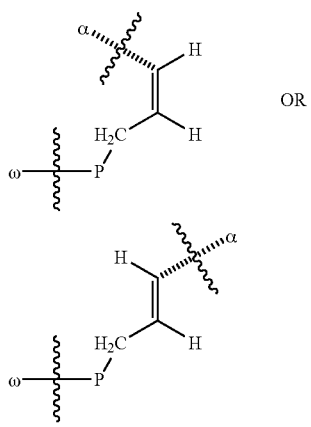

wherein P is a C$_3$ saturated chain optionally containing one heteroatom independently selected from O, S(O)$_m$; wherein m is 0, 1 or 2, or NR$_{17}$.

14. The compound of claim 8 wherein W is —NH—SO$_n$—R$_{23}$, wherein n is 1 or 2 and R$_{23}$ is unsubstituted C$_{3-7}$ cycloalkyl, or cyclopropyl or cyclobutyl optionally substituted with C$_{7-9}$ alkylaryl or C$_{1-4}$ alkyl.

15. The compound of claim 8 wherein W is NH—SO$_n$—R$_{24}$, wherein n is 1 or 2 and R$_{24}$ is Het.

16. The compound of claim 15 wherein said Het is selected from the group consisting of:

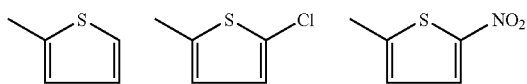

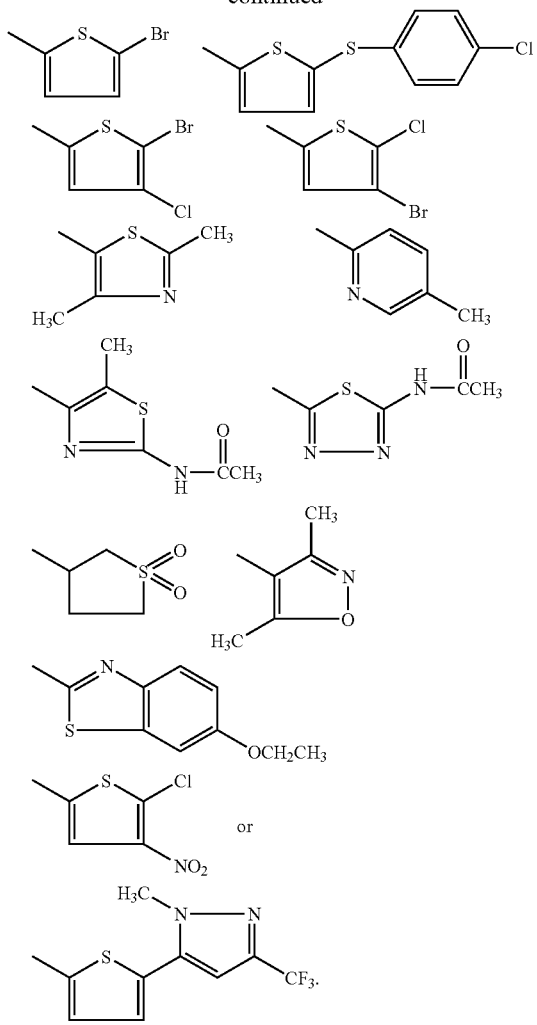

17. A compound of formula III:

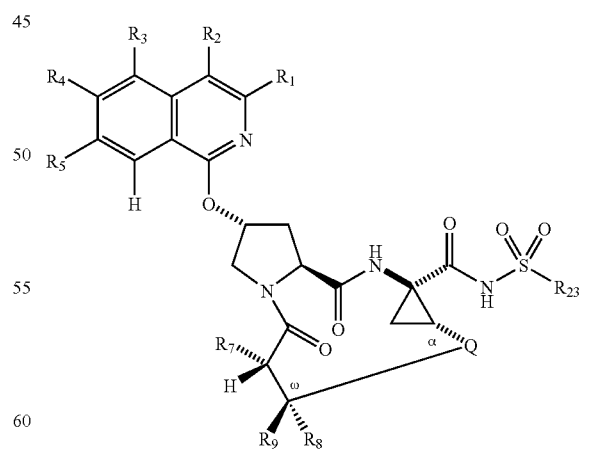

wherein:

(a) R$_1$ is H; C$_{1-3}$ alkoxy; di-(C$_{1-6}$) alkyl amine; a 5 or 6 membered monocyclic heterocycle; or C$_{6-10}$ aryl optionally substituted with a 5 or 6 membered monocyclic heterocycle; $R_2$, $R_3$, $R_4$ and $R_5$ are each independently H; $C_{1-3}$ alkoxy; halo; or di-$(C_{1-6})$ alkyl amine;

(b) $R_7$ is —$NHR_{10}$; wherein $R_{10}$ is $C(O)$—$NHR_{13}$, or $C(O)$—$OR_{14}$; $R_{13}$ and $R_{14}$ are $C_{1-6}$ alkyl;

(c) Q is a $C_{5-7}$ membered chain having one double bond optionally containing one heteroatom independently selected from O, $S(O)_m$; wherein m is 0, 1 or 2, or $NR_{17}$, wherein $R_{17}$ is H; $C_{1-6}$ alkyl or $C_{1-6}$ cycloalkyl; and (d) $R_{23}$ is unsubstituted $C_{3-7}$ cycloalkyl, or cyclopropyl or cyclobutyl optionally substituted with $C_{7-9}$ alkylaryl or $C_{1-4}$ alkyl;

or a pharmaceutically acceptable enantiomer, diastereomer, salt, solvate or prodrug thereof.

18. The compound of claim 17 wherein $R_1$ is selected from the group consisting of pyridine, morpholine, piperazine, oxazole, isoxazole, thiazole, imidazole, pyrrole and pyrazole.

19. The compound of claim 17 wherein $R_1$ is phenyl optionally substituted with one or more members selected from the group consisting of selected from the group consisting of $C_{1-3}$ alkoxy, halo, carboxyl, di-$(C_{1-3})$ alkyl amine, $C_{1-3}$ haloalkyl, trifluoromethyl, trifluoromethoxy and hydroxy.

20. The compound of claim 17 wherein $R_1$ is di-$(C_{1-3})$ alkyl amine.

21. The compound of claim 17 wherein $R_1$ is piperazine substituted with one or more members selected from the group consisting of $C_{1-3}$ alkyl, $C_{5-7}$ cycloalkyl or pyridine.

22. The compound of claim 17 wherein $R_2$ is chloro or fluoro.

23. The compound of claim 17 wherein $R_2$ is di-$(C_{1-3})$ alkyl amine or methoxy.

24. The compound of claim 17 wherein Q has a structure selected from the following:

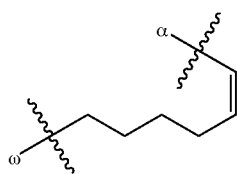

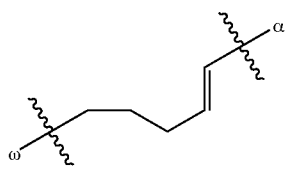

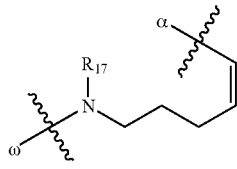

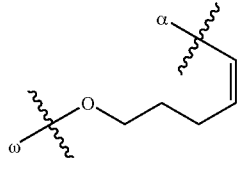

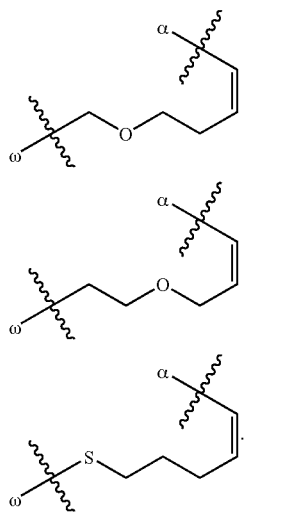

25. The compound of claim 17 wherein Q has a structure selected from the following:

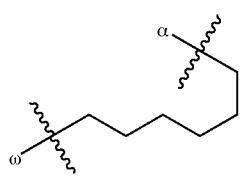

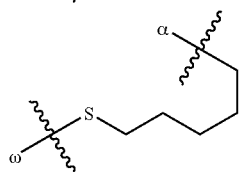

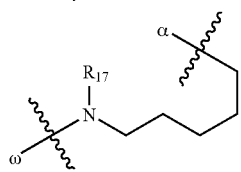

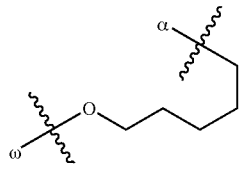

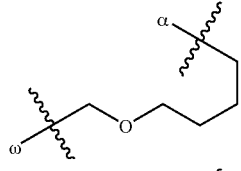

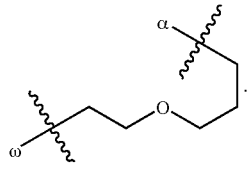

26. A compound selected from the group consisting of
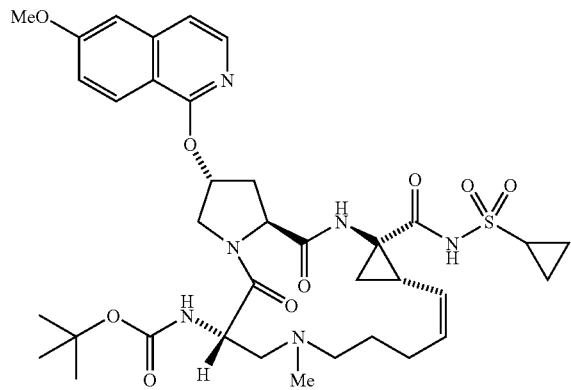
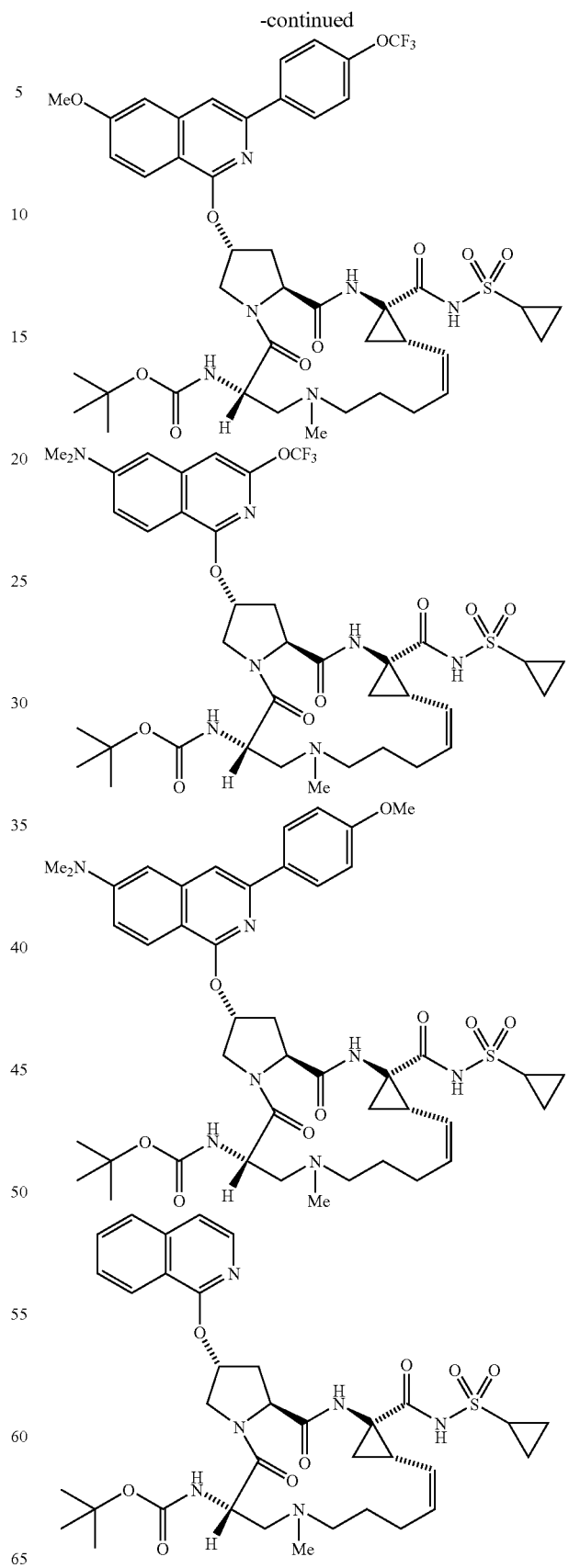

387 388
-continued -continued
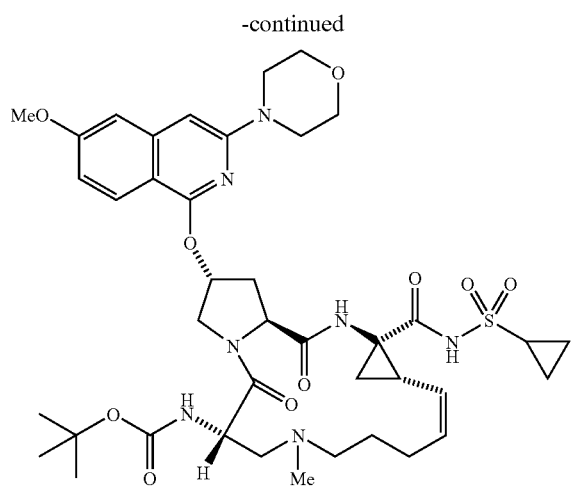
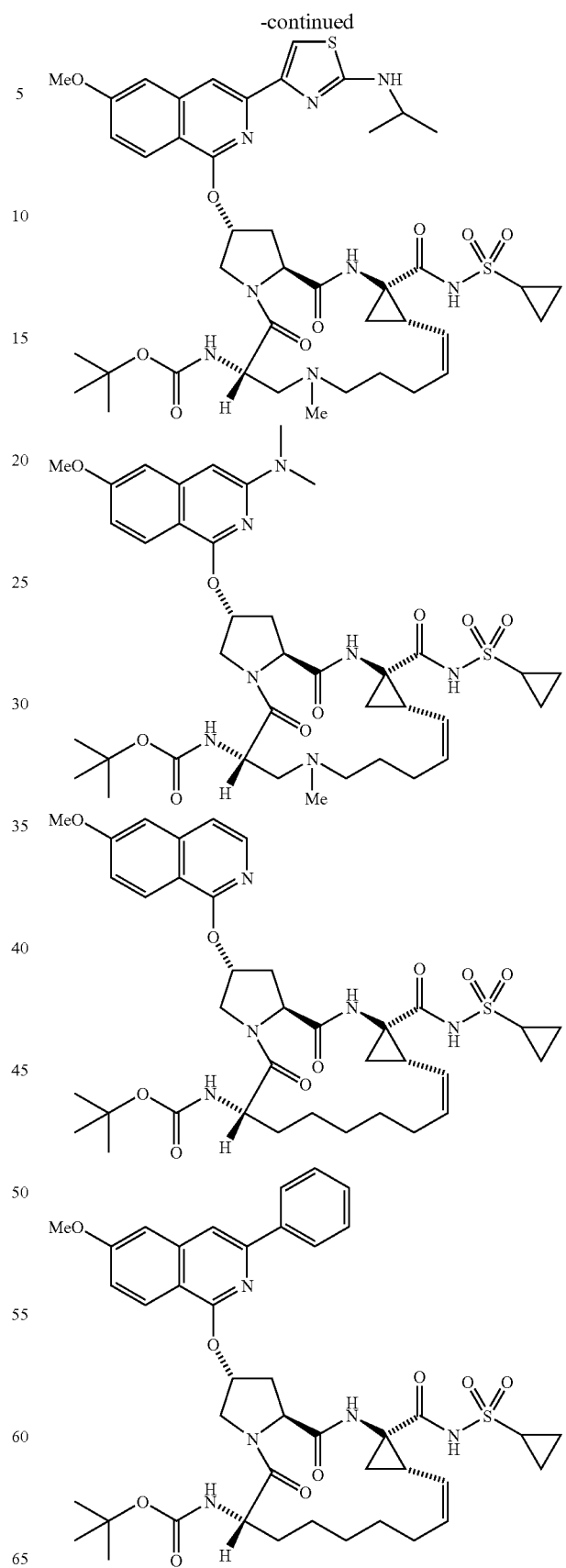

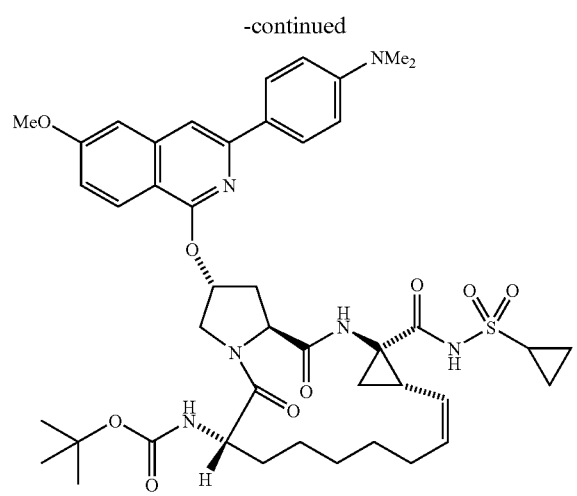
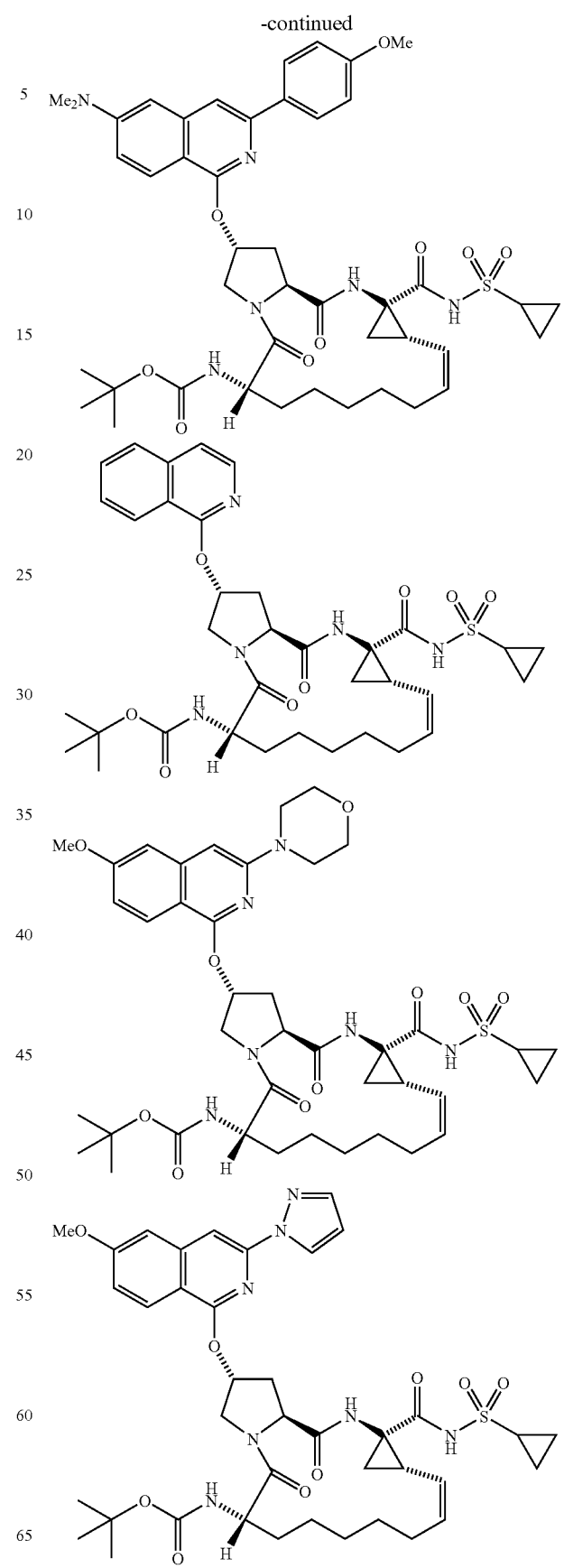

391
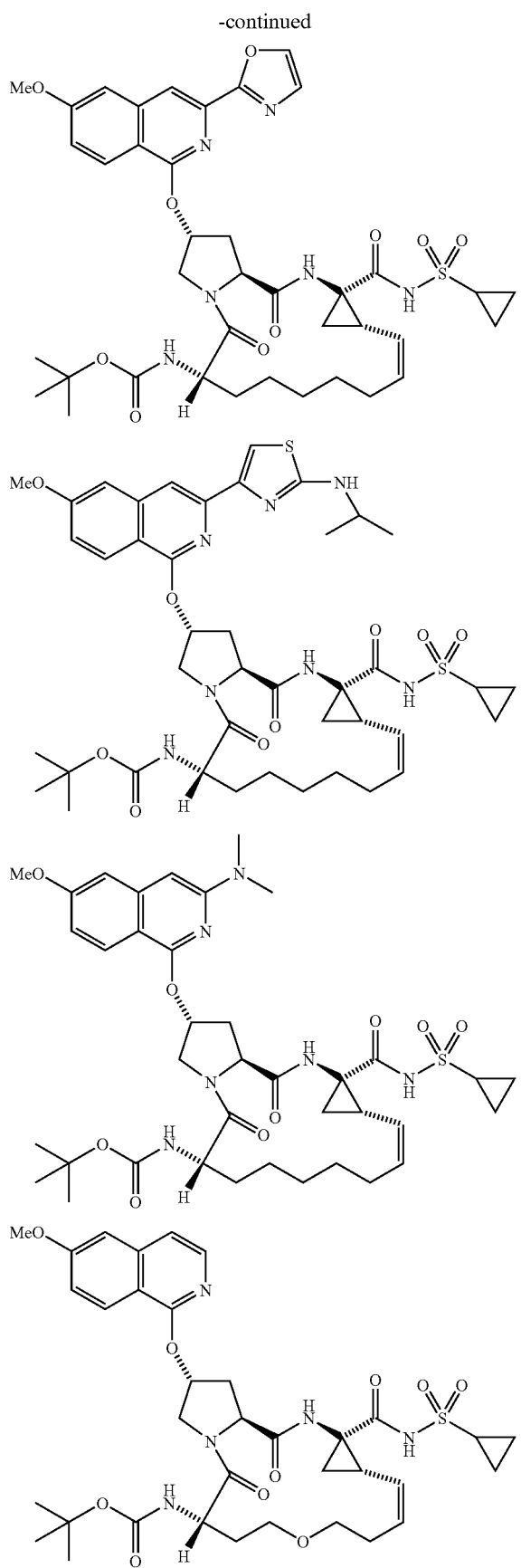
392
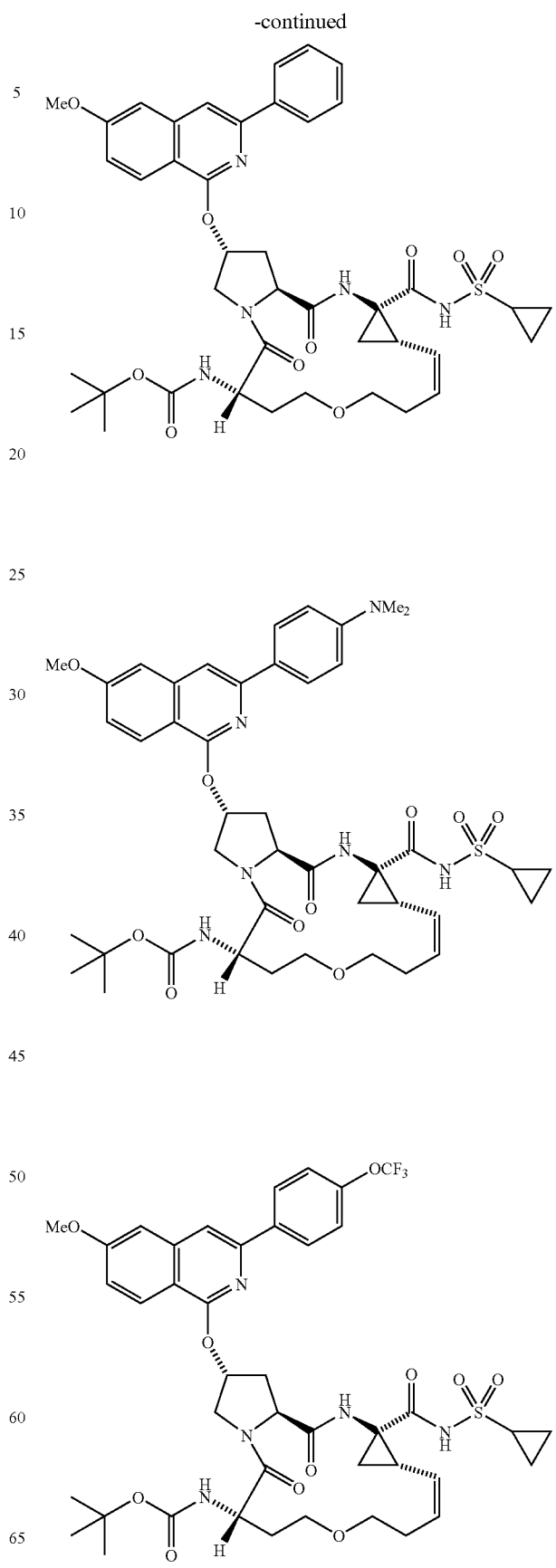

393
-continued
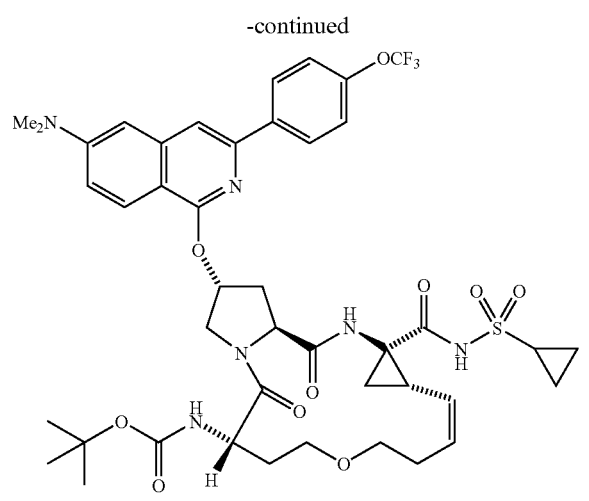
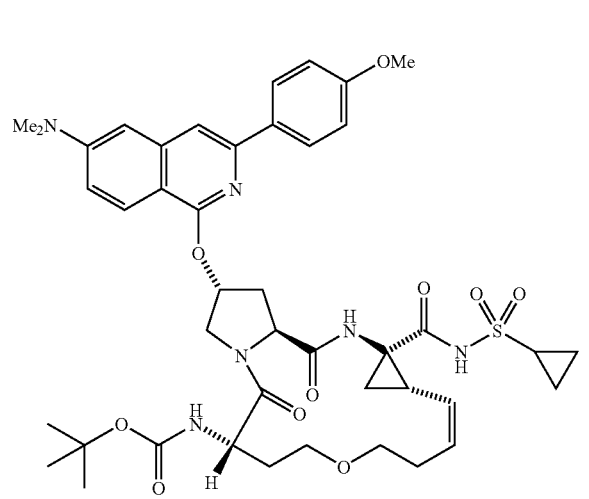
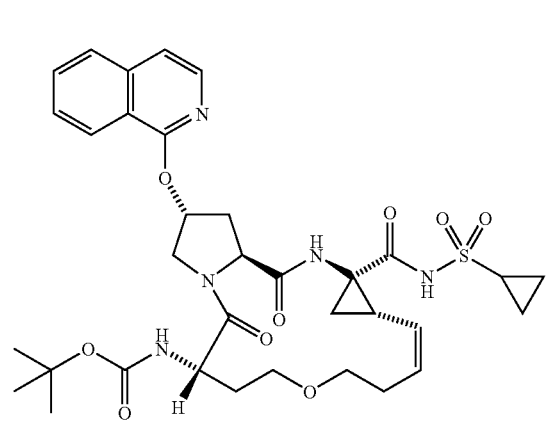
394
-continued
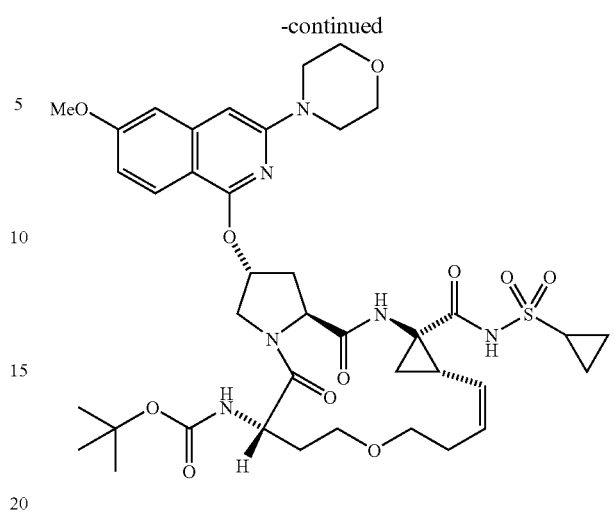
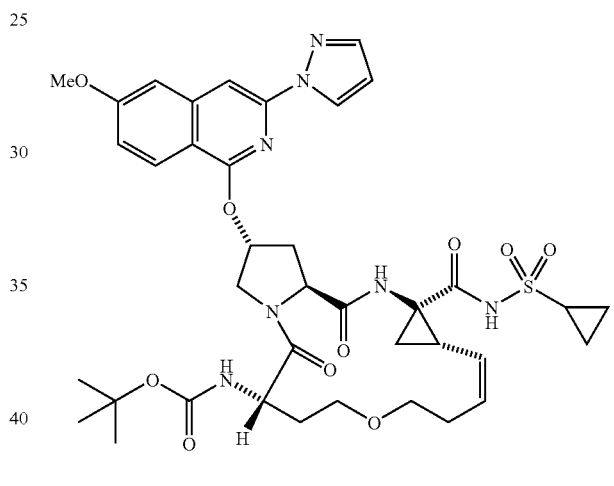
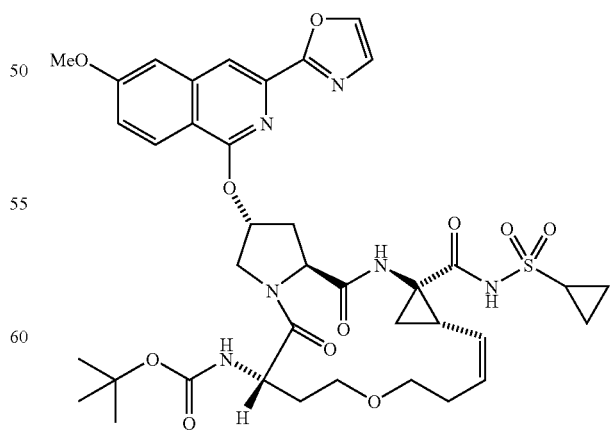

395
-continued
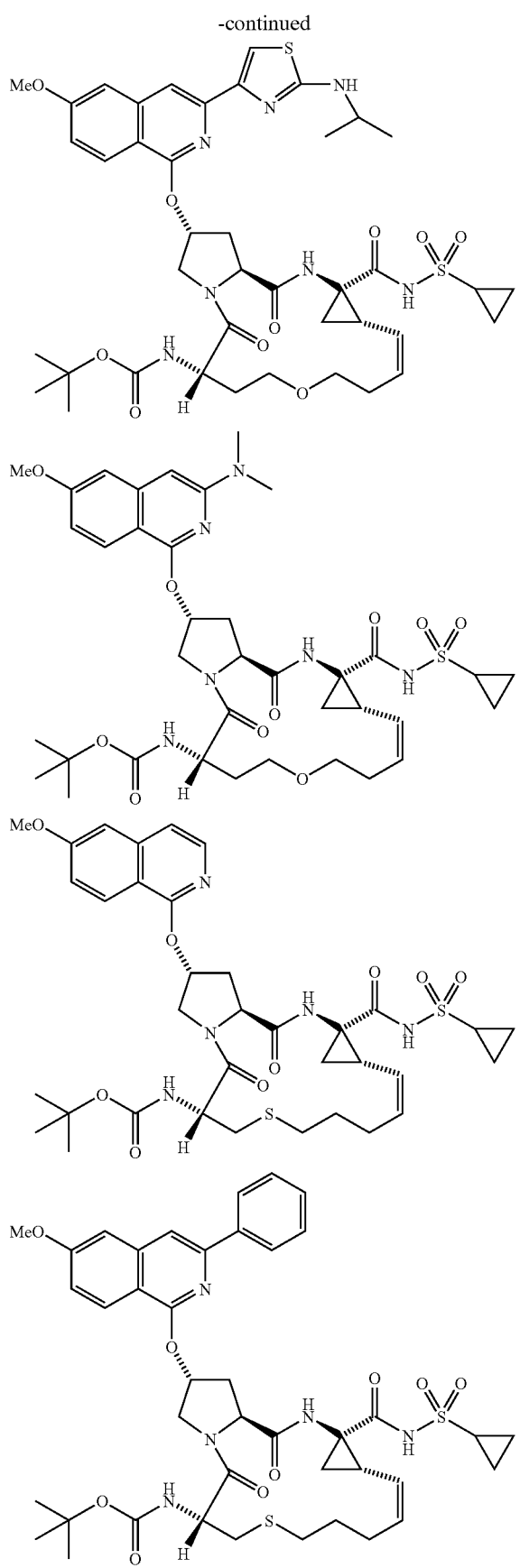
396
-continued
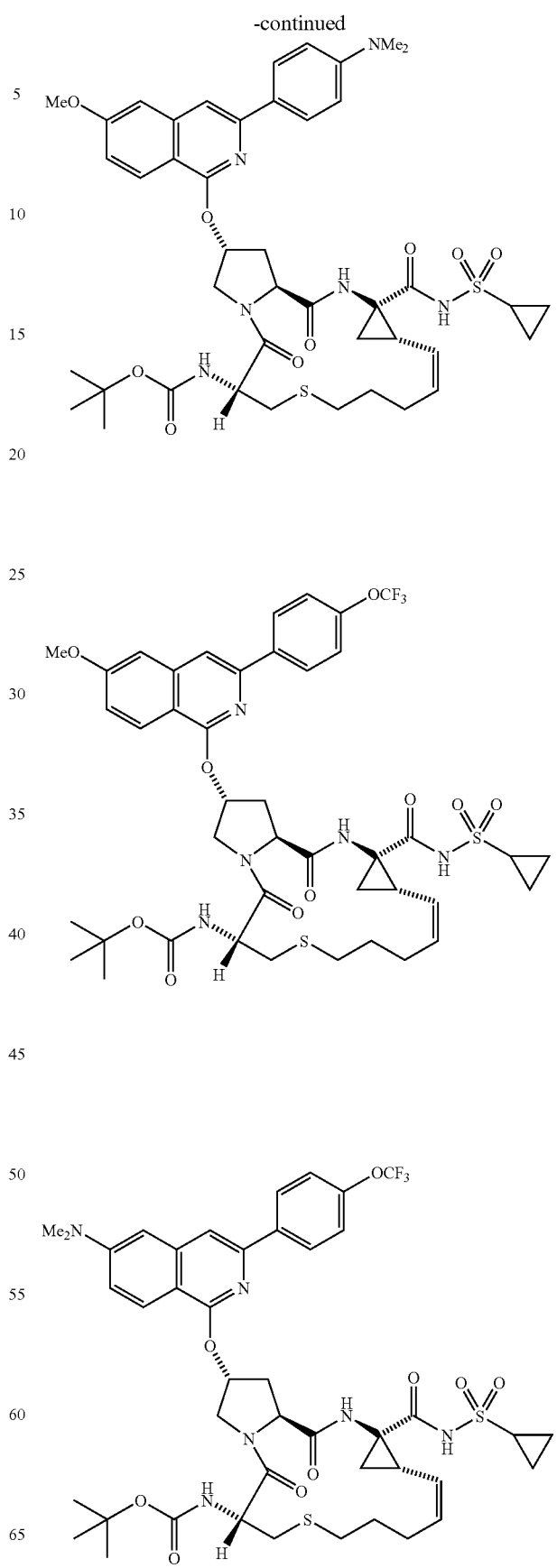

397
-continued
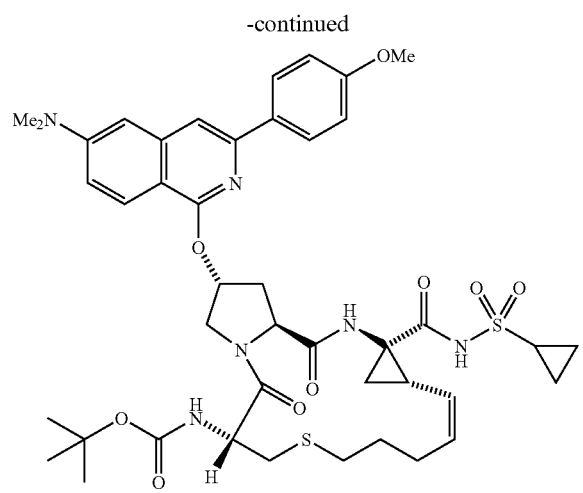
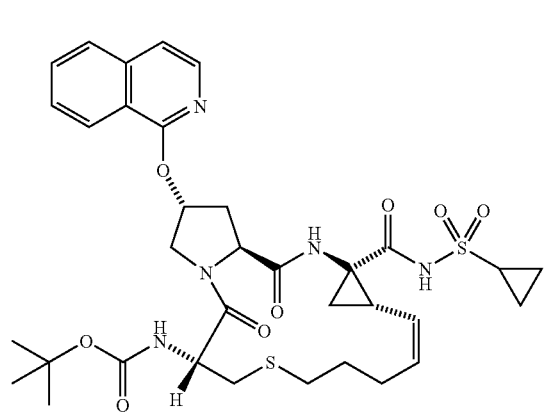
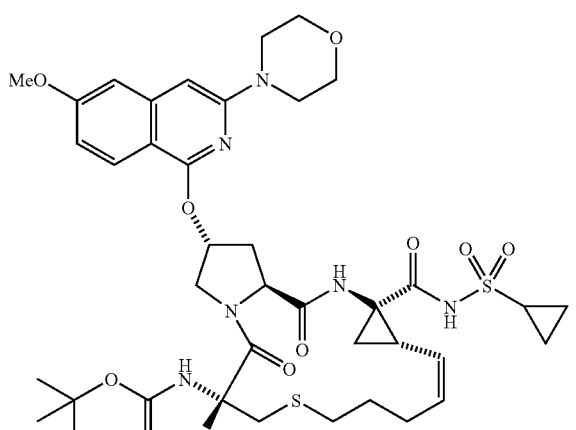
398
-continued
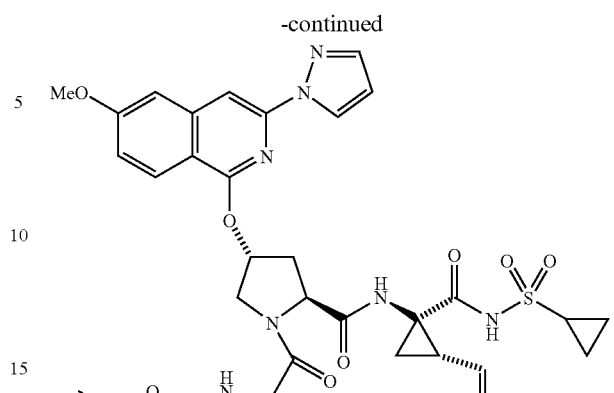
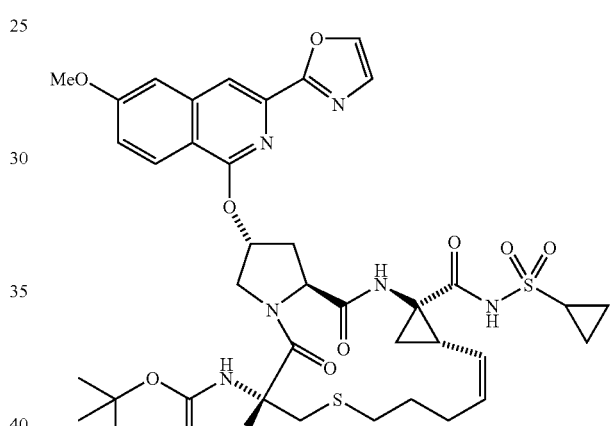
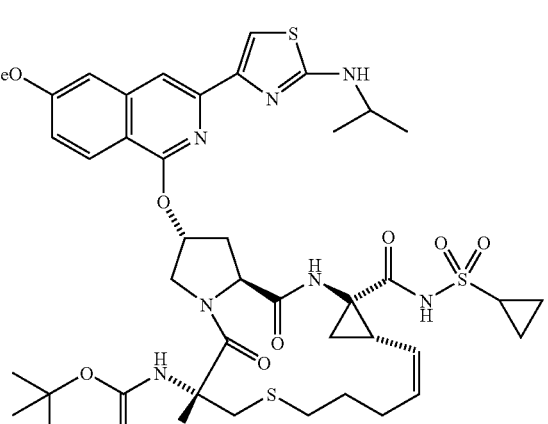

399
-continued
400
-continued
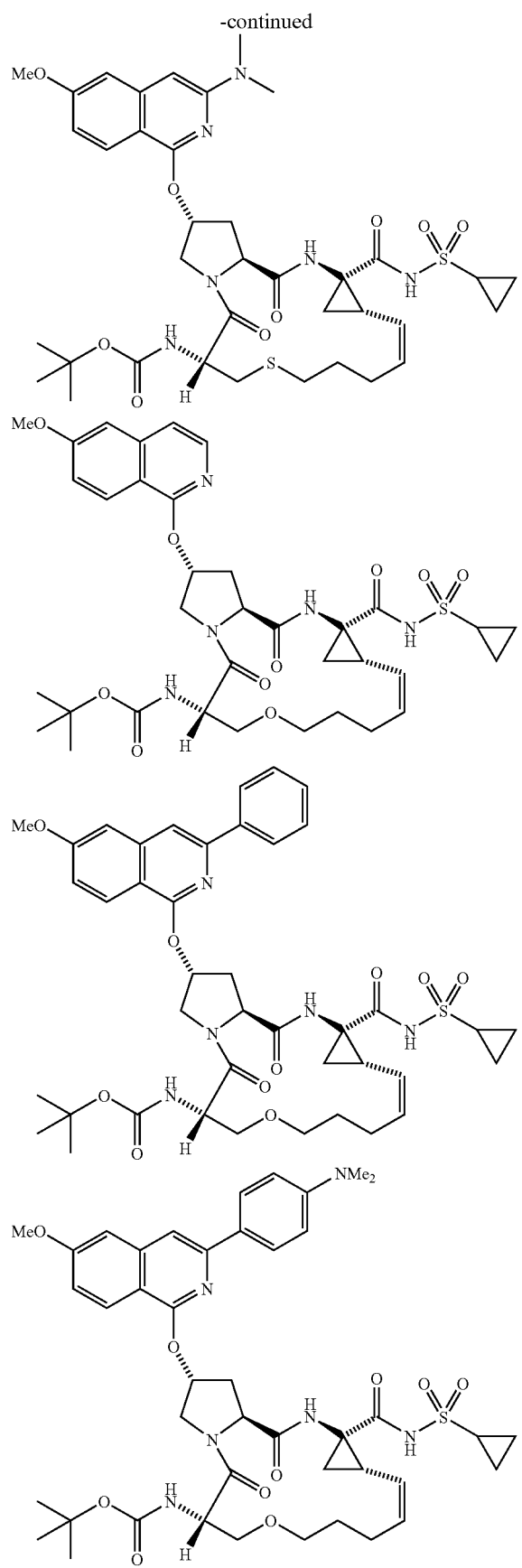
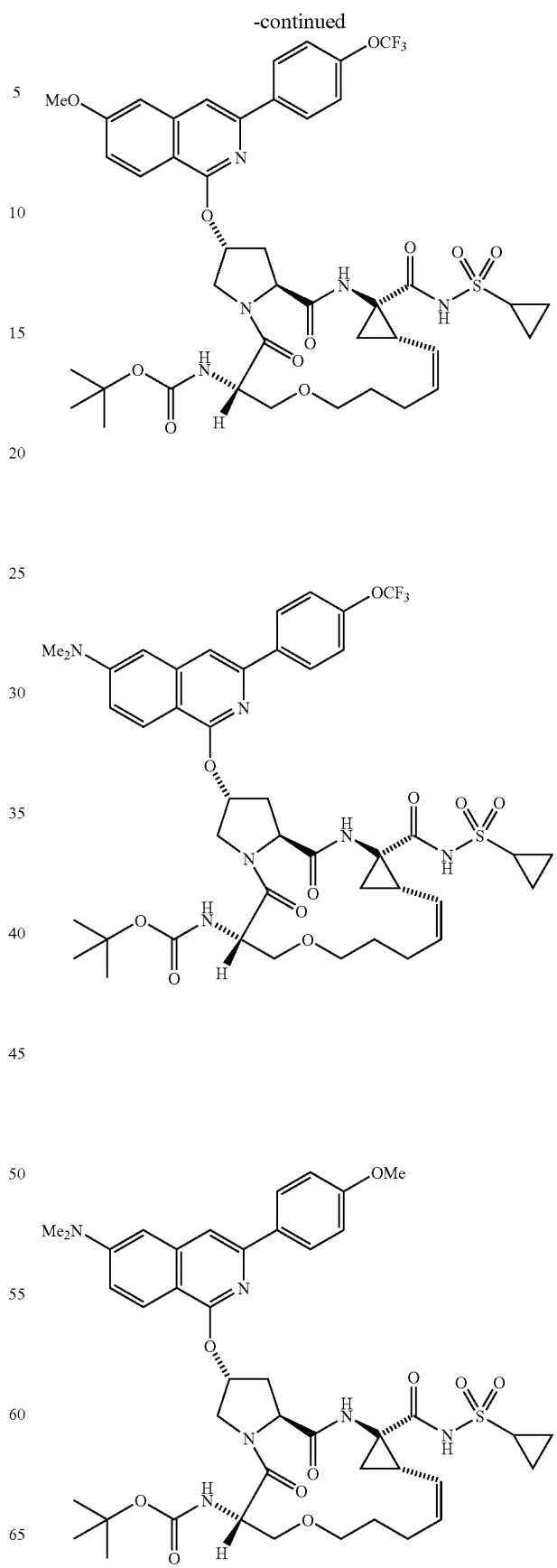

401
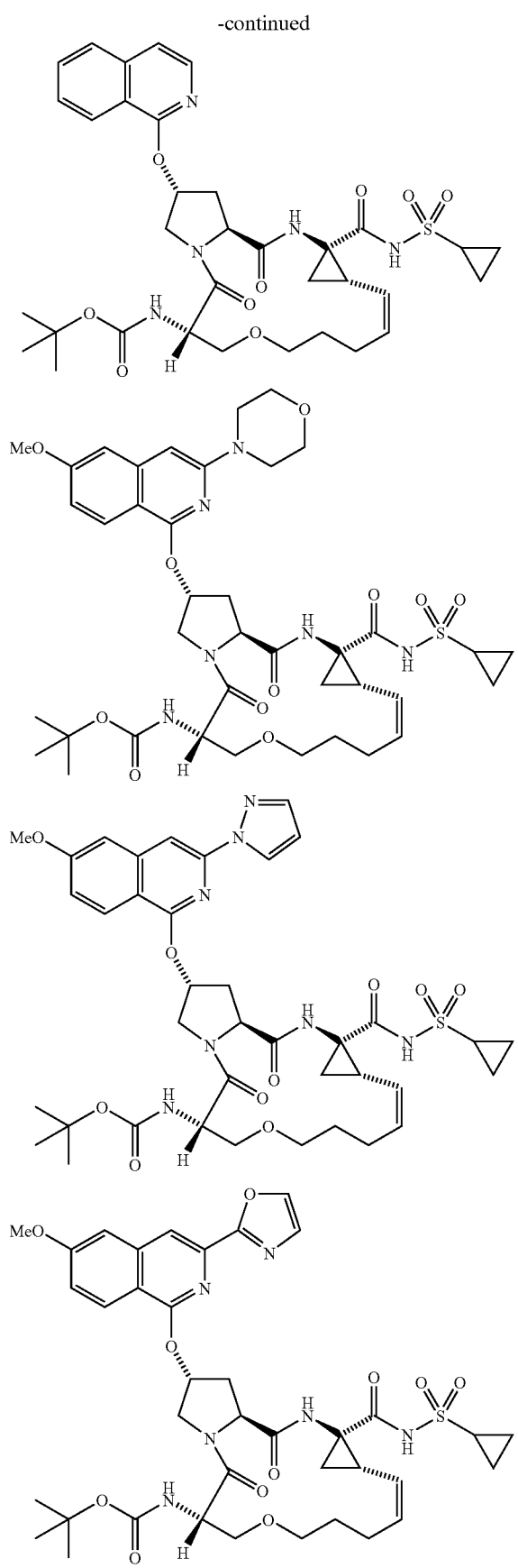
402
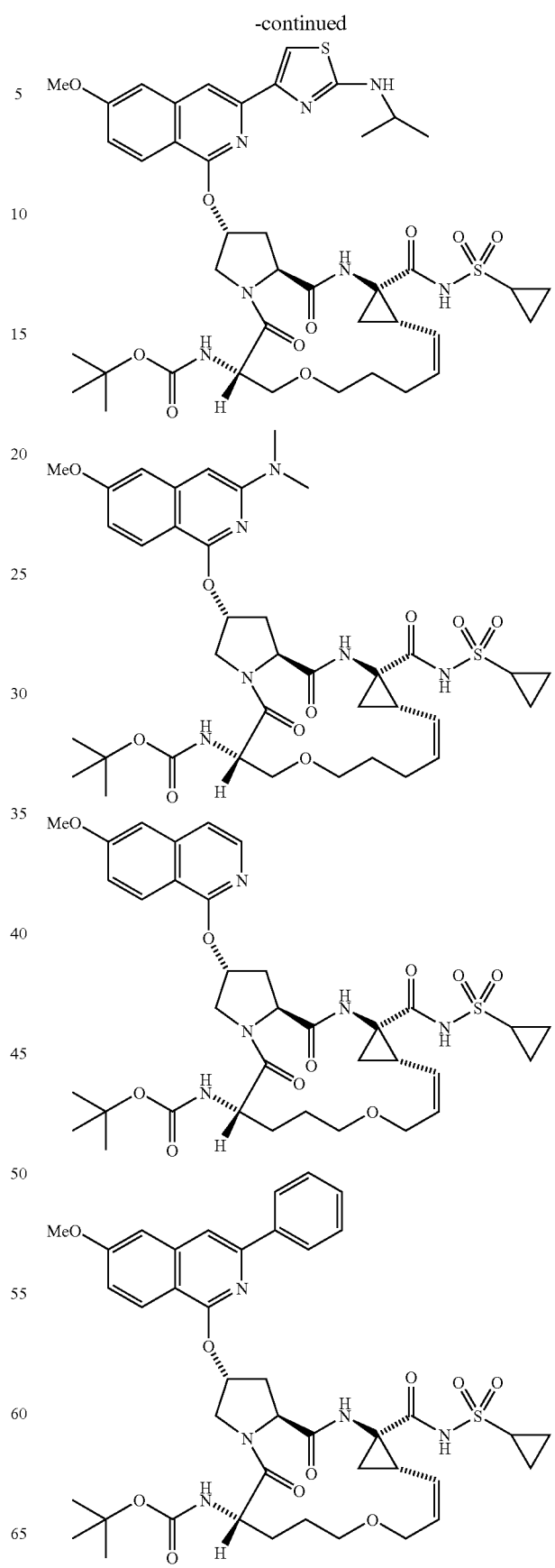

403
404
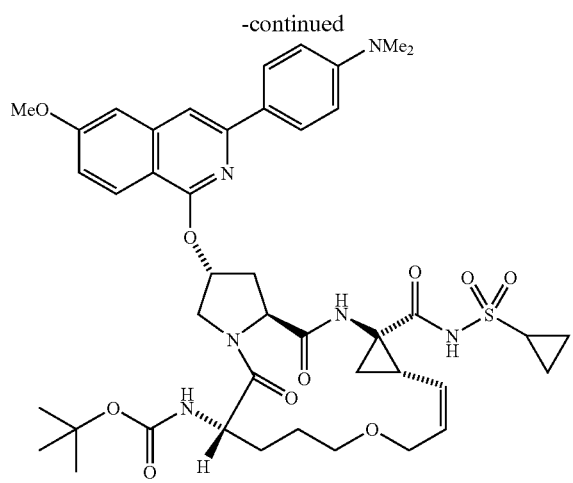
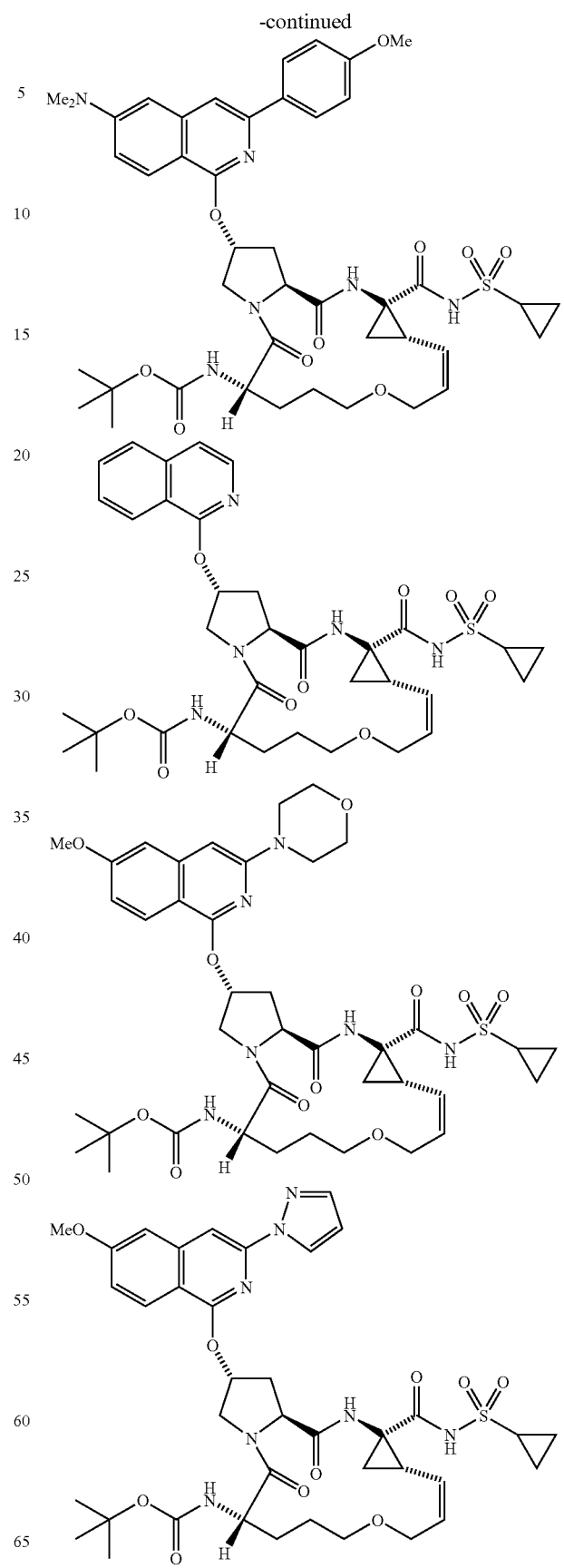

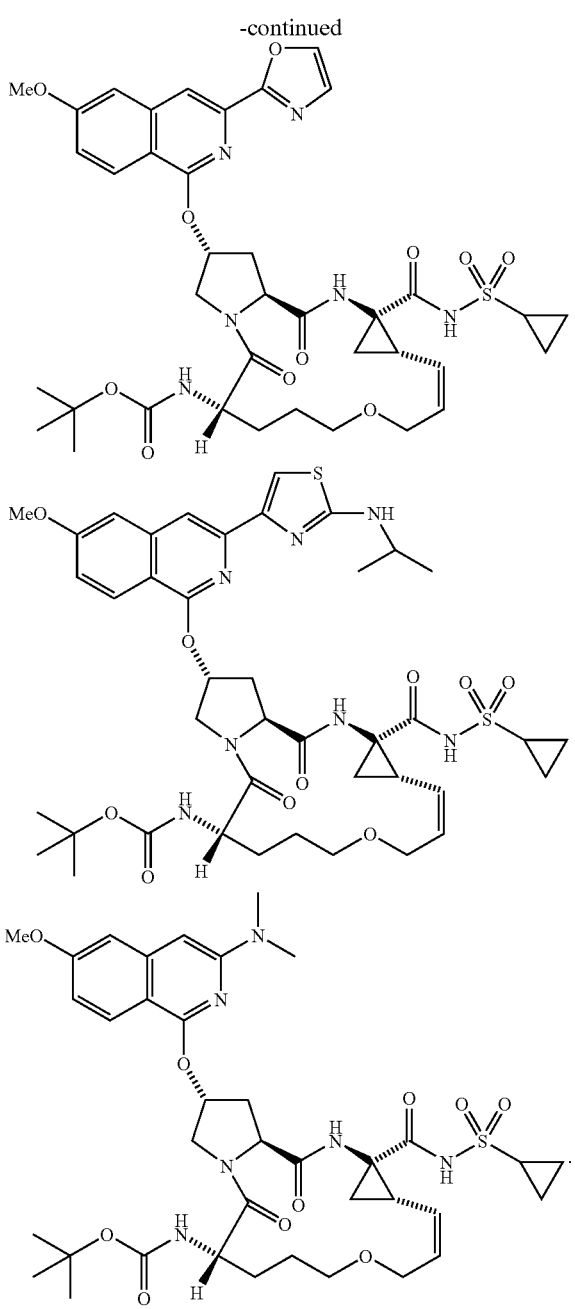

27. A composition comprising the compound of claim 1 and a pharmaceutically acceptable carrier.

28. The composition according to claim 27 further comprising a compound having anti-HCV activity.

29. The composition according to claim 28 wherein the compound having anti-HCV activity is an interferon.

30. The composition according to claim 29 wherein the interferon is selected from the group consisting of interferon alpha 2B, pegylated interferon alpha, consensus interferon, interferon alpha 2A, and lymphoblastiod interferon tau.

31. The composition according to claim 28 wherein the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

32. The composition according to the claim 28 further comprising an interferon and ribavirin.

33. The composition according to claim 28 wherein the compound having anti-HCV activity is a small molecule compound.

34. The composition according to claim 28 wherein the compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection.

35. A method of inhibiting the function of the HCV serine protease comprising contacting the HCV serine protease with the compound of claim 1.

36. A method of treating an HCV infection in a patient, comprising administering to the patient a therapeutically effective amount of the compound of claim 1, or a pharmaceutically acceptable enantiomer, diastereomer, solvate, prodrug or salt thereof.

37. The method according to claim 36 wherein the compound is effective to inhibit the function of the HCV serine protease.

38. The method according to claim 36 further comprising administering another compound having anti-HCV activity prior to, after or simultaneously with the compound of claim 1.

39. The method according to claim 38 wherein the other compound having anti-HCV activity is an interferon.

40. The method according to claim 39 wherein the interferon is selected from the group consisting of interferon alpha 2B, pegylated interferon alpha, consensus interferon, interferon alpha 2A, lymphoblastiod interferon tau.

41. The method according to claim 38 wherein the other compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

42. The method according to claim 38 wherein the compound having anti-HCV activity is a small molecule.

43. The method according to claim 42 wherein the compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection.

44. The method according to claim 38 wherein the other compound having anti-HCV activity is effective to inhibit the function of target in the HCV life cycle other than the HCV serine protease.

* * * * *